United States Patent
Pentelute et al.

(10) Patent No.: US 11,279,734 B2
(45) Date of Patent: Mar. 22, 2022

(54) SOLUTION-PHASE AFFINITY SELECTION OF INHIBITORS FROM COMBINATORIAL PEPTIDE LIBRARIES

(71) Applicant: Massachusetts Institute of Technology, Cambridge, MA (US)

(72) Inventors: Bradley L. Pentelute, Cambridge, MA (US); Faycal Touti, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 437 days.

(21) Appl. No.: 16/206,944

(22) Filed: Nov. 30, 2018

(65) Prior Publication Data

US 2019/0300576 A1  Oct. 3, 2019
US 2020/0308231 A9  Oct. 1, 2020

Related U.S. Application Data

(60) Provisional application No. 62/593,861, filed on Dec. 1, 2017.

(51) Int. Cl.

| C07K 7/64 | (2006.01) |
| A61K 38/00 | (2006.01) |
| C07K 1/22 | (2006.01) |
| C07K 7/08 | (2006.01) |
| C07K 14/00 | (2006.01) |
| G01N 33/68 | (2006.01) |
| A61P 35/00 | (2006.01) |
| C40B 30/04 | (2006.01) |
| A61P 31/12 | (2006.01) |

(52) U.S. Cl.
CPC .............. *C07K 7/64* (2013.01); *A61P 31/12* (2018.01); *A61P 35/00* (2018.01); *C07K 1/22* (2013.01); *C07K 7/08* (2013.01); *C07K 14/00* (2013.01); *C40B 30/04* (2013.01); *G01N 33/6845* (2013.01); *G01N 33/6848* (2013.01); *A61K 38/00* (2013.01); *G01N 2500/20* (2013.01)

(58) Field of Classification Search
CPC .................................. C07K 7/64; A61K 38/00
See application file for complete search history.

(56) References Cited

U.S. PATENT DOCUMENTS

| 2010/0130430 A1 | 5/2010 | Debnath et al. |
| 2012/0328692 A1 | 12/2012 | Lu et al. |
| 2013/0210743 A1 | 8/2013 | Guerlavais et al. |
| 2014/0113871 A1 | 4/2014 | Pentelute et al. |
| 2014/0308267 A1 | 10/2014 | Schmidt et al. |

FOREIGN PATENT DOCUMENTS

| WO | 2008/106507 A2 | 9/2008 |
| WO | 2016/049359 A1 | 3/2016 |
| WO | 2017/015630 A2 | 1/2017 |

OTHER PUBLICATIONS

Burgess et al., Clinical Overview of MDM2/X-Targeted Therapies. Front Oncol. Jan. 27, 2016;6:7. doi:10.3389/fonc.2016.00007. eCollection 2016.
Chang et al., Stapled α-helical peptide drug development: a potent dual inhibitor of MDM2 and MDMX for p53-dependent cancer therapy. Proc Natl Acad Sci USA. Sep. 3, 2013;110(36):E3445-54. doi: 10.1073/pnas.1303002110. Epub Aug. 14, 2013.
Cunningham et al., Peptides and peptidomimetics as regulators of protein-protein interactions. Curr Opin Struct Biol. Jun. 2017;44:59-66. doi: 10.1016/j.sbi.2016.12.009. Epub Jan. 4, 2017.
Grossmann et al., Inhibition of oncogenic Wnt signaling through direct targeting of β-catenin. Proc Natl Acad Sci USA. Oct. 30, 2012;109(44):17942-7. doi: 10.1073/pnas.1208396109. Epub Oct. 15, 2012.
Kussie et al., Structure of the MDM2 oncoprotein bound to the p53 tumor suppressor transactivation domain. Science. Nov. 8, 1996;274(5289):948-53.
Lautrette et al., Nitrogen Arylation for Macrocyclization of Unprotected Peptides. J Am Chem Soc. Jul. 13, 2016;138(27):8340-3. doi: 10.1021/jacs.6b03757. Epub Jun. 30, 2016.
Lin et al., Several hydrophobic amino acids in the p53 amino-terminal domain are required for transcriptional activation, binding to mdm-2 and the adenovirus 5 E1B 55-kD protein. Genes Dev. May 15, 1994;8(10):1235-46.
Milroy et al., Modulators of protein-protein interactions. Chem Rev. May 14, 2014;114(9):4695-748. doi:10.1021/cr400698c. Epub Apr. 15, 2014.
Pelay-Gimeno et al., Structure-Based Design of Inhibitors of Protein-Protein Interactions: Mimicking Peptide Binding Epitopes. Angew Chem Int Ed Engl. Jul. 27, 2015;54(31):8896-927. doi: 10.1002/anie.201412070. Epub Jun. 26, 2015.

(Continued)

*Primary Examiner* — Amber D Steele
(74) *Attorney, Agent, or Firm* — Wolf, Greenfield & Sacks, P.C.

(57) ABSTRACT

The present invention provides novel peptides (e.g., peptides, macrocyclic peptides, mini-proteins) that modulate protein-protein interactions or salts thereof, and methods of making and using the inventive peptides. In some embodiments, the peptides are high affinity inhibitors (e.g., $K_D$ of at most 100 nM, at most 10 nM, at most 1 nM) of a protein-protein interaction. In certain embodiments, these peptides interfere with p53-MDM2 binding interactions (e.g., by binding to MDM2 (GenBank® Gene ID: 4193)). In some embodiments, the peptides interfere with the dimerization of the C-terminal domain of the human immunodeficiency virus (HIV) capsid protein (C-CA), comprising residues 146-231 of the HIV capsid protein (e.g., by binding to the C-terminal domain of the HIV capsid protein (C-CA), thereby inhibiting the dimeric interface of HIV capsid protein, thereby inhibiting viral assembly). These inventive peptides were rapidly generated and identified using novel methods described herein comprising combinatorial peptide synthesis and/or solution affinity selection.

39 Claims, 114 Drawing Sheets

Specification includes a Sequence Listing.

(56) References Cited

OTHER PUBLICATIONS

Picksley et al., Immunochemical analysis of the interaction of p53 with MDM2;—fine mapping of the MDM2 binding site on p53 using synthetic peptides. Oncogene. Sep. 1994;9(9):2523-9.

Spokoyny et al., A perfluoroaryl-cysteine S(N)Ar chemistry approach to unprotected peptide stapling. J Am Chem Soc. Apr. 24, 2013;135(16):5946-9. doi: 10.1021/ja400119t. Epub Apr. 16, 2013.

Teveroni et al., Peptides and peptidomimetics in the p53/MDM2/MDM4 circuitry—a patent review. Expert Opin Ther Pat. Dec. 2016;26(12):1417-1429. Epub Sep. 20, 2016.

Vassilev et al., In vivo activation of the p53 pathway by small-molecule antagonists of MDM2. Science. Feb. 6, 2004;303(5659):844-8. Epub Jan. 2, 2004.

Walensky et al., Activation of apoptosis in vivo by a hydrocarbon-stapled BH3 helix. Science. Sep. 3, 2004;305(5689): 1466-70.

Zhan et al., An ultrahigh affinity d-peptide antagonist of MDM2. J Med Chem. Jul. 12, 2012;55(13):6237-41. doi: 10.1021/jm3005465. Epub Jun. 22, 2012.

Zhang et al., A cell-penetrating helical peptide as a potential HIV-1 inhibitor. J Mol Biol. May 2, 2008;378(3):565-80. doi:10.1016/j.jmb.2008.02.066. Epub Mar. 6, 2008.

Zhou et al., Structure-based design of high-affinity macrocyclic peptidomimetics to block the menin-mixed lineage leukemia 1 (MLL1) protein-protein interaction. J Med Chem. Feb. 14, 2013;56(3):1113-23. doi: 10.1021/jm3015298. Epub Jan. 17, 2013.

Li et al., Systematic mutational analysis of peptide inhibition of the p53-MDM2/MDMX interactions. J Mol Biol. Apr. 30, 2010;398(2):200-13. doi: 10.1016/j.jmb.2010.03.005. Epub Mar. 10, 2010. Author Manuscript, 23 pages.

Zondlo et al., Determinants of specificity of MDM2 for the activation domains of p53 and p65: proline27 disrupts the MDM2-binding motif of p53. Biochemistry. Oct. 3, 2006;45(39):11945-57.

Figure 2A

SEQ ID NO: 179
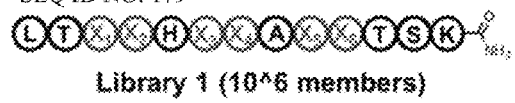
Library 1 (10^6 members)

SEQ ID NO: 9
Library 2 (1000 members)

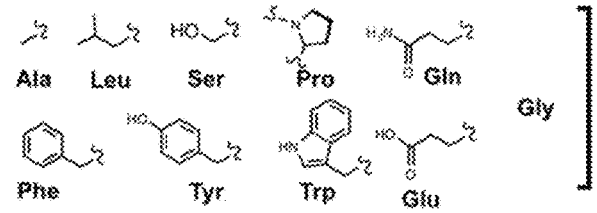

Figure 2B

| | | Library 1 binders | | | | | | | | | | | | | Kd MDM2 (nM) |
|---|---|---|---|---|---|---|---|---|---|---|---|---|---|---|---|
| SEQ ID NO: 2 | 1a | Bio-(PEG)₂- | Leu | Thr | *Phe* | *Gln* | His | *Phe* | *Trp* | Ala | *Glu* | *Leu* | Thr | Ser | Lys | -NH₂ | 45 |
| SEQ ID NO: 3 | 2a | Bio-(PEG)₂- | Leu | Thr | *Phe* | *Gln* | His | *Tyr* | *Trp* | Ala | *Glu* | *Leu* | Thr | Ser | Lys | -NH₂ | 62 |
| SEQ ID NO: 4 | 3a | Bio-(PEG)₂- | Leu | Thr | *Phe* | *Pro* | His | *Tyr* | *Trp* | Ala | *Glu* | *Leu* | Thr | Ser | Lys | -NH₂ | 80 |
| SEQ ID NO: 159 | 4a | Bio-(PEG)₂- | Leu | Thr | *Phe* | *Pro* | His | *Phe* | *Trp* | Ala | *Glu* | *Leu* | Thr | Ser | Lys | -NH₂ | 120 |

| | | Library 2 binders | | | | | | | | | | | | | Kd MDMX (nM) |
|---|---|---|---|---|---|---|---|---|---|---|---|---|---|---|---|
| SEQ ID NO: 7 | 5a | Bio-(PEG)₂- | Leu | Thr | *Phe* | Glu | His | Tyr | *Trp* | Ala | Gln | *Phe* | Thr | Ser | Lys | -NH₂ | 38 |
| SEQ ID NO: 8 | 6a | Bio-(PEG)₂- | Leu | Thr | *Phe* | Glu | His | Tyr | *Trp* | Ala | Gln | *Leu* | Thr | Ser | Lys | -NH₂ | 47 |
| SEQ ID NO: 66 | 7b | Ac- | Leu | Thr | *Phe* | Glu | His | Tyr | *Trp* | Ala | Gln | *Tyr* | Thr | Ser | Lys | -NH₂ | 490 |
| SEQ ID NO: 67 | 8b | Ac- | Leu | Thr | *Tyr* | Glu | His | Tyr | *Trp* | Ala | Gln | *Leu* | Thr | Ser | Lys | -NH₂ | 2700 |
| SEQ ID NO: 68 | 9b | Ac- | Leu | Thr | *Leu* | Glu | His | Tyr | *Trp* | Ala | Gln | *Leu* | Thr | Ser | Lys | -NH₂ | 6700 |

Figure 2E

| | | | | | | | | | | | | | | | Kd MDM2 (nM) |
|---|---|---|---|---|---|---|---|---|---|---|---|---|---|---|---|
| Library 3 binders | | | | | | | | | | | | | | | |
| (SEQ ID NO: 11) 10a | Biv-PEG- | Leu | Thr | F-f | Glu | His | Tyr | Hexa | Ala | Gln | Cba | Thr | Ser | Lys | -NH2 | 0.5 |
| (SEQ ID NO: 12) 11a | Biv-PEG- | Leu | Thr | F-f | Glu | His | Tyr | Trp | Ala | Gln | Cba | Thr | Ser | Lys | -NH2 | 2.0 |
| (SEQ ID NO: 14) 13a | Biv-PEG- | Leu | Thr | F-f | Glu | His | Tyr | Hexa | Ala | Gln | Cba | Thr | Ser | Lys | -NH2 | 2.9 |
| (SEQ ID NO: 24) 23a | Biv-PEG- | Leu | Thr | F-f | Glu | His | Tyr | Anta | Ala | Gln | Cba | Thr | Ser | Lys | -NH2 | 10 |
| (SEQ ID NO: 26) 25a | Biv-PEG- | Leu | Thr | F-f | Glu | His | Tyr | Hexa | Ala | Gln | F-f | Thr | Ser | Lys | -NH2 | 16 |

| | | | | | | | | | | | | | | Kd C-CA (nM) |
|---|---|---|---|---|---|---|---|---|---|---|---|---|---|---|
| Library 4 binders | | | | | | | | | | | | | | |
| (SEQ ID NO: 160) 30a | Ile | Thr | F-f | Glu | Asp | Cba | Leu | His | Tyr | Tyr | Gly | Pro | (Gly-Ser)2 | Lys(Bio) | -NH2 | 88 |
| (SEQ ID NO: 161) 31a | Ile | Thr | F-f | Glu | Asp | Cba | Leu | His | Dmf | Tyr | Gly | Pro | (Gly-Ser)2 | Lys-Bio | -NH2 | 120 |
| (SEQ ID NO: 162) 32a | Ile | Thr | F-f | Glu | Asp | Cba | Leu | His | Dmf | F-f | Gly | Pro | (Gly-Ser)2 | Lys-Bio | -NH2 | 140 |
| (SEQ ID NO: 69) 33a | Ile | Thr | Phe | Glu | Asp | Cba | Leu | His | Tyr | Tyr | Gly | Pro | (Gly-Ser)2 | Lys-Bio | -NH2 | 320 |
| (SEQ ID NO: 70) 37a | Ile | Thr | Phe | Glu | Asp | Leu | Leu | His | Tyr | Tyr | Gly | Pro | (Gly-Ser)2 | Lys-Bio | -NH2 | 2300 |

Figure 2F

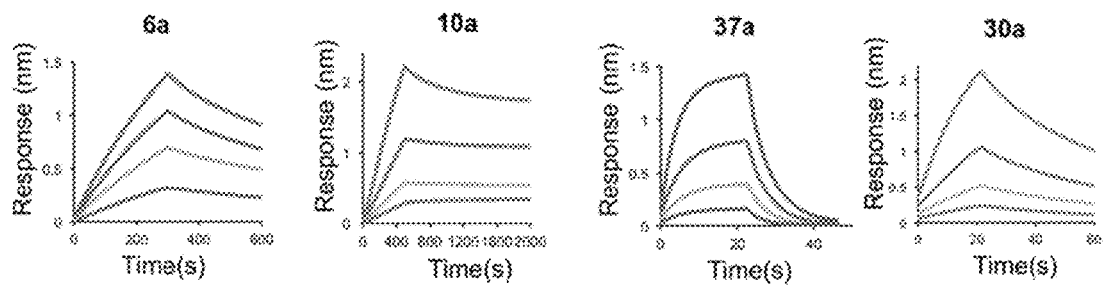

Figure 4C

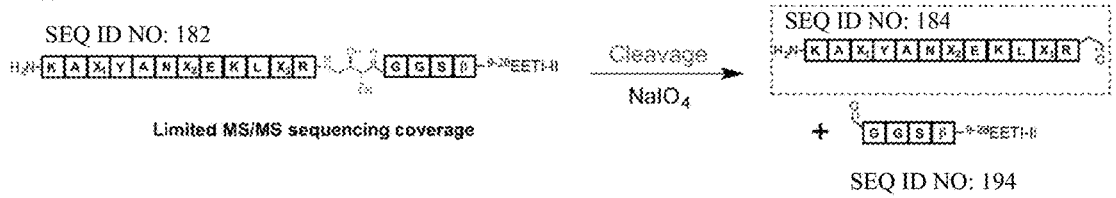

Figure 4D

| Library 5 select binders | | | | | | | | | | | | | | | | | | Kd MDM2 (nM) |
|---|---|---|---|---|---|---|---|---|---|---|---|---|---|---|---|---|---|---|
| (SEQ ID NO: 163) 43 | | Lys | Ala | Trp | Tyr | Ala | Asn | Hexa | Glu | Lys | Leu | Homol | Arg | Diol | Gly | Gly | Ser | β-Ala | 5-26EETI-II | -NH2 | 1 |
| (SEQ ID NO: 164) 44 | | Lys | Ala | Trp | Tyr | Ala | Asn | Hexa | Glu | Lys | Leu | Cha | Arg | Diol | Gly | Gly | Ser | β-Ala | 5-26EETI-II | -NH2 | 4.4 |
| (SEQ ID NO: 165) 45 | | Lys | Ala | Trp | Tyr | Ala | Asn | Cha | Glu | Lys | Leu | Leu | Arg | Diol | Gly | Gly | Ser | β-Ala | 5-26EETI-II | -NH2 | 8.1 |
| (SEQ ID NO: 166) 46 | | Lys | Ala | Trp | Tyr | Ala | Asn | Hexa | Glu | Lys | Leu | Hexa | Arg | Diol | Gly | Gly | Ser | β-Ala | 5-26EETI-II | -NH2 | 10.4 |
| (SEQ ID NO: 167) 47 | | Lys | Ala | Trp | Tyr | Ala | Asn | Hexa | Glu | Lys | Leu | Trp | Arg | Diol | Gly | Gly | Ser | β-Ala | 5-26EETI-II | -NH2 | 11.9 |
| (SEQ ID NO: 168) 53 | | Lys | Ala | Trp | Tyr | Ala | Asn | CF3 | Glu | Lys | Leu | Leu | Arg | Diol | Gly | Gly | Ser | β-Ala | 5-26EETI-II | -NH2 | 20 |
| (SEQ ID NO: 169) 54b | Ac- | Lys | Ala | Trp | Tyr | Ala | Asn | CF3 | Glu | Lys | Leu | Leu | Arg | | | | | | | -NH2 | 1.3 |

Figure 5

In solution competition assay: calibration curve

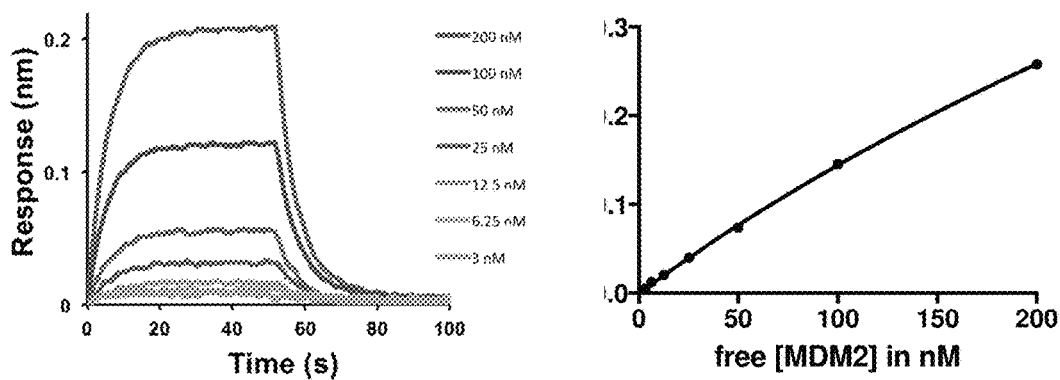

Figure 6

| Model binders | m/z (charge) | K_D (nM) | |
|---|---|---|---|
| pDI (6) — LTFEHYWAQLTSK | 541.6046 (+3) | 47 | SEQ ID NO: 8 |
| CAI (37) — ITFEDLLHYYGPK | 532.2693 (+3) | 2200 | SEQ ID NO: 185 |
| Flag-diol (57a) — GDYKDDDDK-...(Peg)₄-Biotin...K | 596.58 (+3) | 15 | SEQ ID NO: 186 |
| EETI-II (58) — GCPRILMRCKQDSDCLAGCVCGPNGFCG | 724.8087 (+4) | 1.2 | SEQ ID NO: 187 |
| EETI-II-diol (59) | 732.3007 (+4) | 0.93 | SEQ ID NO: 188 |
| pDI-Sulfone (60) — LTF-(HYWAQL)-SK | 652.8966 (+3) | 22 | SEQ ID NO: 189 |

*EETI-II (58)/Trypsin*

Figure 9B
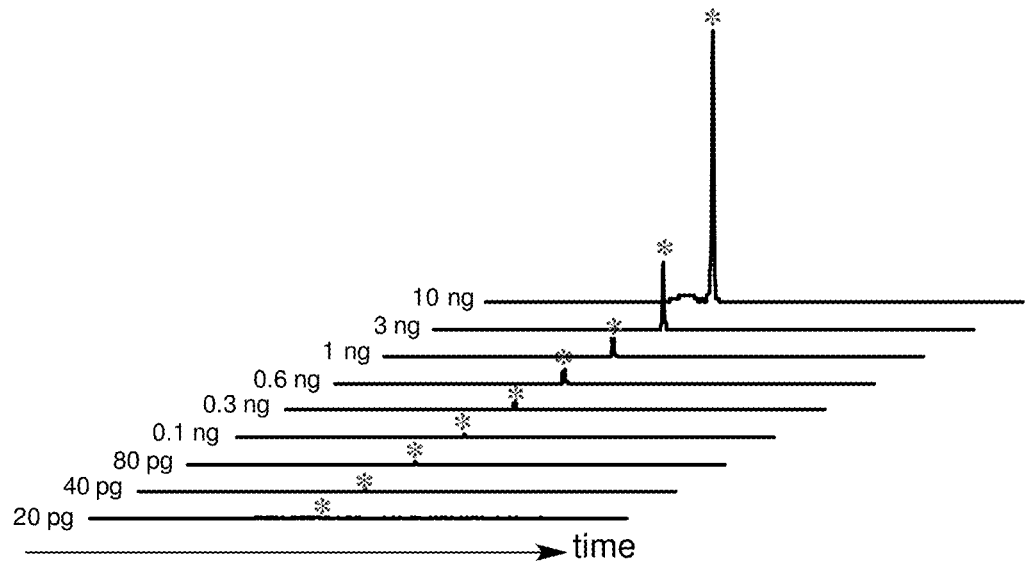
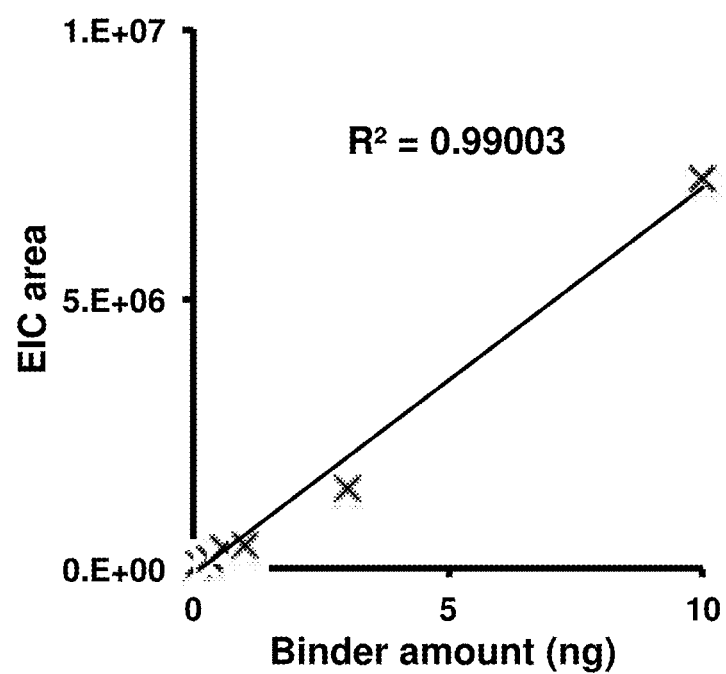

Figure 10A
*EETI-II-diol (59)/Trypsin*
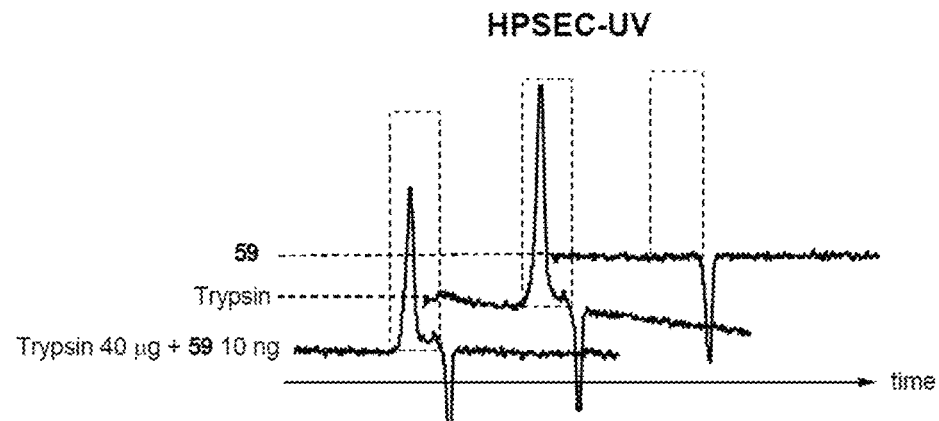
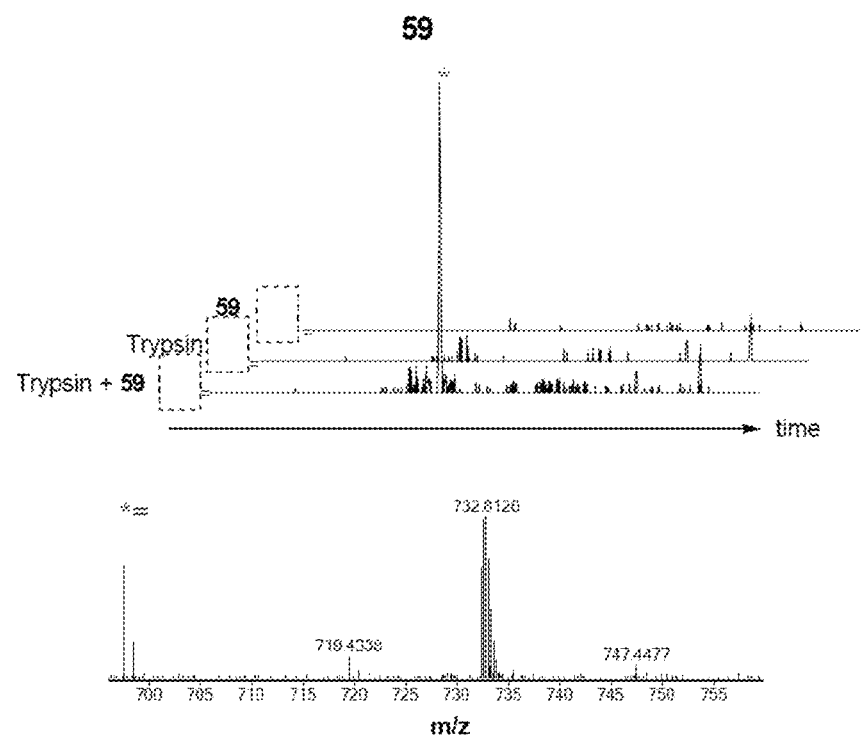

Figure 10B
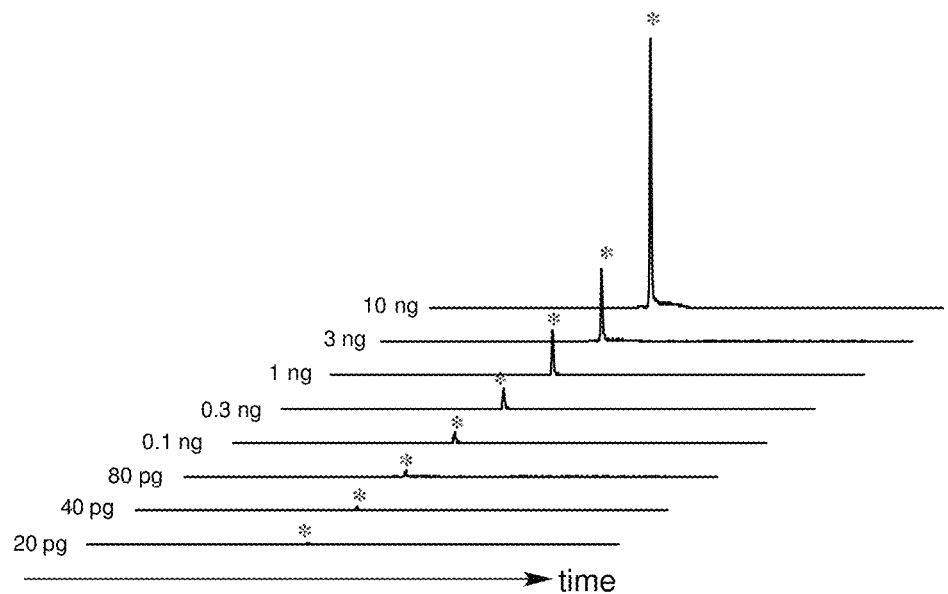
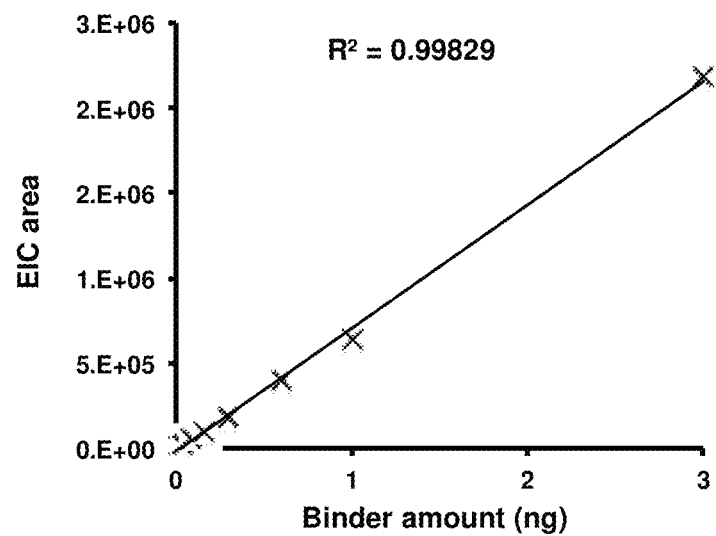

*Flag peptide (57a)/Flag antibody*

Figure 11B
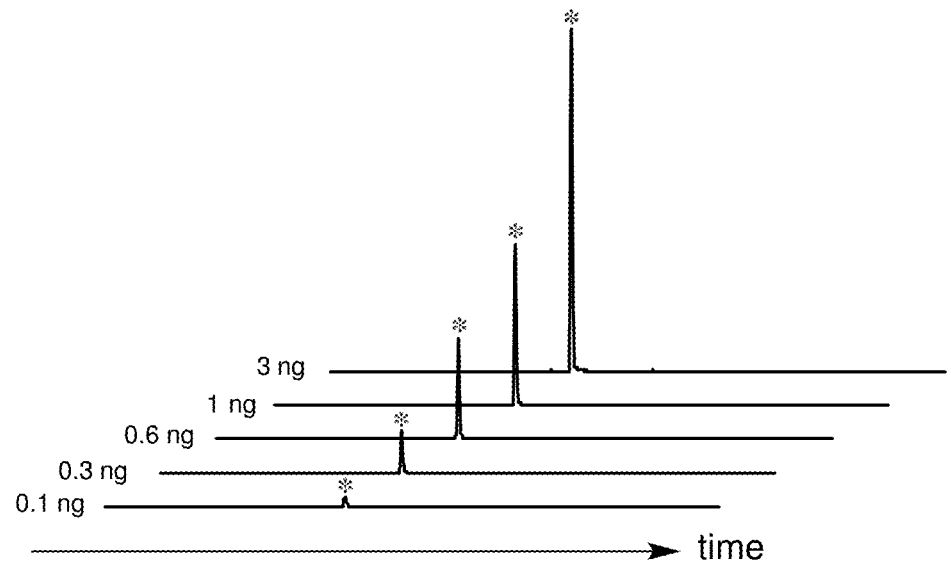
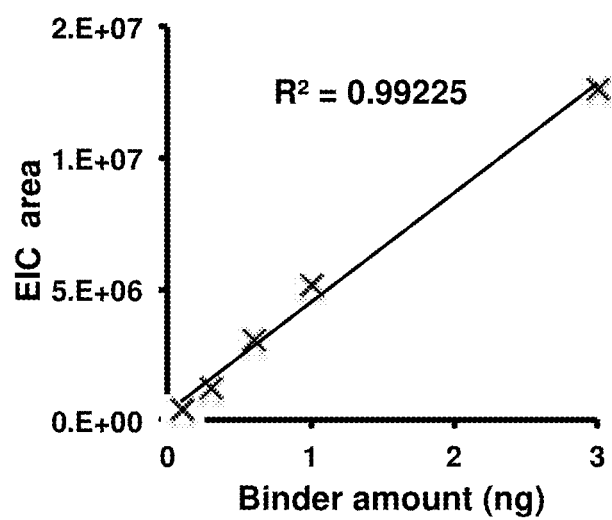

*pDI (6) /MDM2*

Figure 12B
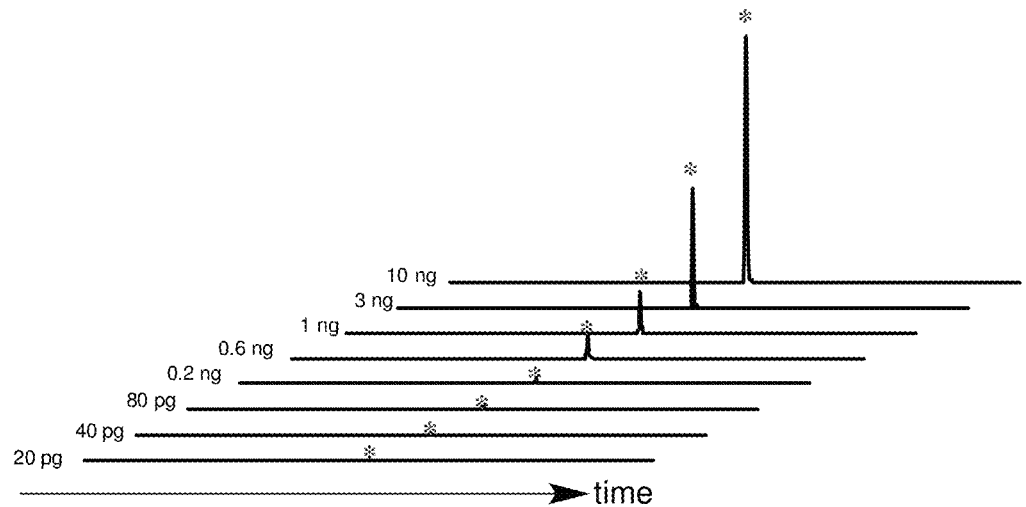
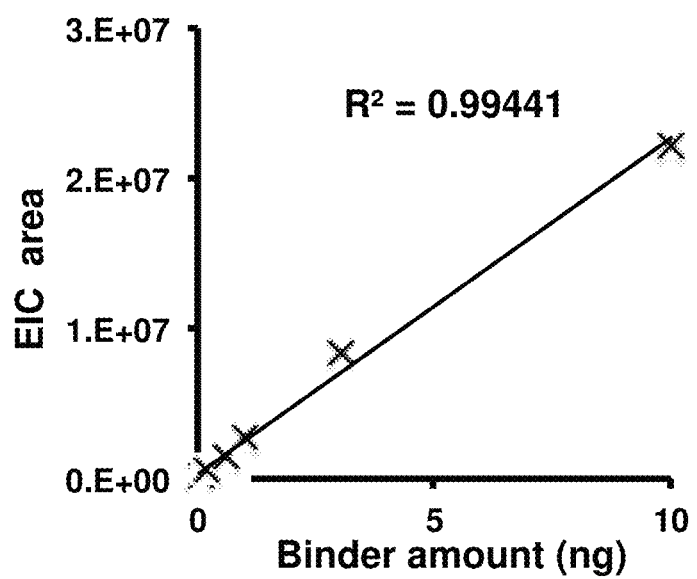

*PDI-Sulfone (60) /MDM2*

*CAI (37)/C-CA*

Figure 20
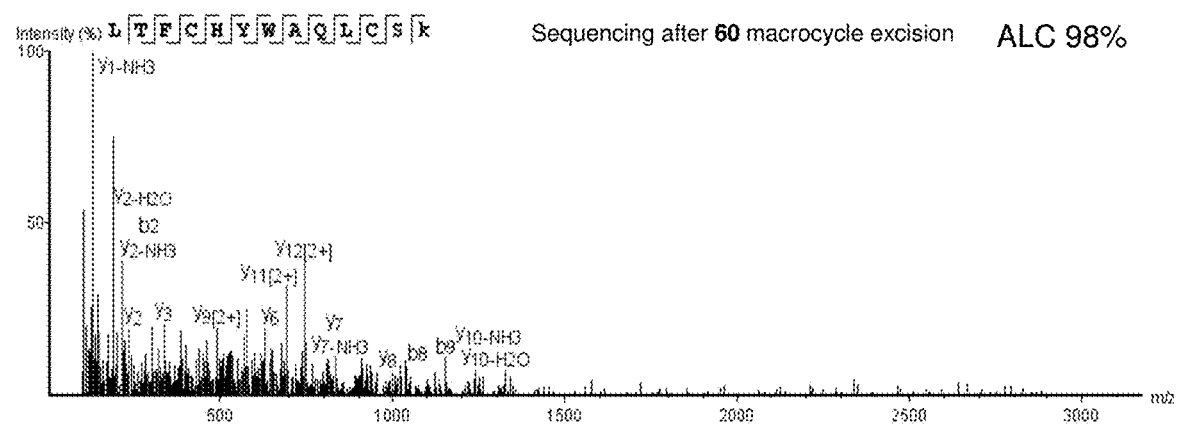
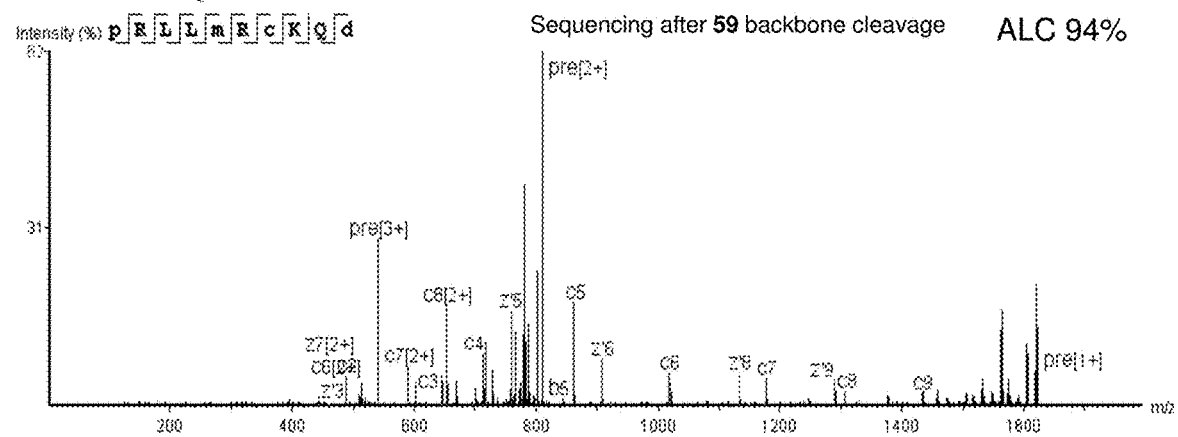

Figure 27
| Library 2 sequences | | | | | | | | | | | | | | m/z (+3) | RT (min) | ALC (%) |
|---|---|---|---|---|---|---|---|---|---|---|---|---|---|---|---|---|
| (SEQ ID NO: 71) 5 | Leu | Thr | *Phe* | Glu | His | Tyr | *Trp* | Ala | Gln | *Phe* | Thr | Ser | Lys | -NH2 | 552.94 | 14.1 | 99 |
| (SEQ ID NO: 72) 6 | Leu | Thr | *Phe* | Glu | His | Tyr | *Trp* | Ala | Gln | *Leu* | Thr | Ser | Lys | -NH2 | 541.61 | 14 | 99 |
| (SEQ ID NO: 73) 7 | Leu | Thr | *Phe* | Glu | His | Tyr | *Trp* | Ala | Gln | *Tyr* | Thr | Ser | Lys | -NH2 | 558.29 | 12.8 | 99 |
| (SEQ ID NO: 74) 8 | Leu | Thr | *Tyr* | Glu | His | Tyr | *Trp* | Ala | Gln | *Leu* | Thr | Ser | Lys | -NH2 | 546.95 | 12.4 | 93 |
| (SEQ ID NO: 75) 9 | Leu | Thr | *Leu* | Glu | His | Tyr | *Trp* | Ala | Gln | *Leu* | Thr | Ser | Lys | -NH2 | 530.28 | 13.7 | 99 |
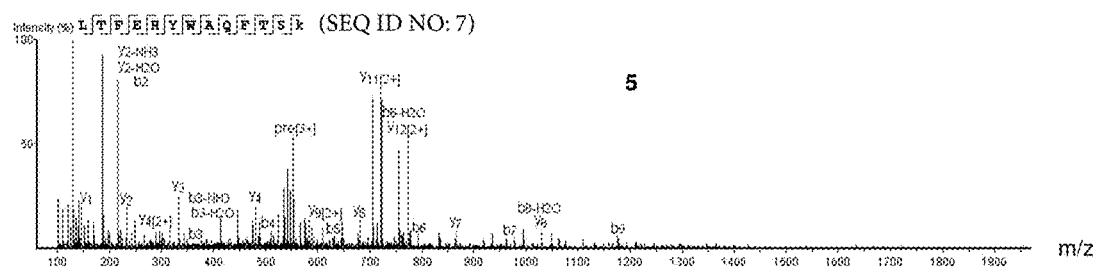
(SEQ ID NO: 7)
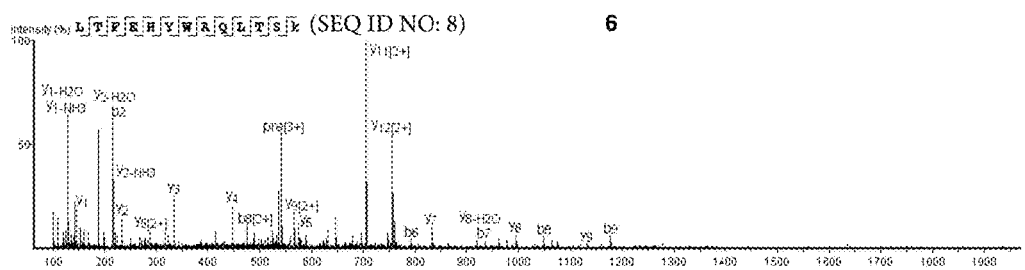
(SEQ ID NO: 8)

Figure 36

| Library 1 sequences | | | | | | | | | | | | | | ALC Score(%) |
|---|---|---|---|---|---|---|---|---|---|---|---|---|---|---|
| (SEQ ID NO: 76) 2 | Leu | Thr | Phe | Gln | His | Tyr | Trp | Ala | Glu | Leu | Thr | Ser | Lys | -NH2 | 95 |
| (SEQ ID NO: 77) | Leu | Thr | Phe | Gln | His | Tyr | Trp | Ala | Gly | Leu | Thr | Ser | Lys | -NH2 | 95 |
| (SEQ ID NO: 78) 1 | Leu | Thr | Phe | Gln | His | Phe | Trp | Ala | Glu | Leu | Thr | Ser | Lys | -NH2 | 93 |
| (SEQ ID NO: 79) 3 | Leu | Thr | Phe | Pro | His | Tyr | Trp | Ala | Glu | Leu | Thr | Ser | Lys | -NH2 | 91 |
| (SEQ ID NO: 80) | Leu | Thr | Phe | Pro | His | Tyr | Trp | Ala | Ala | Leu | Thr | Ser | Lys | -NH2 | 91 |
| (SEQ ID NO: 81) | Leu | Thr | Phe | Glu | His | Tyr | Trp | Ala | Ala | Leu | Thr | Ser | Lys | -NH2 | 90 |
| (SEQ ID NO: 82) | Leu | Thr | Phe | Ala | His | Glu | Trp | Ala | Leu | Leu | Thr | Ser | Lys | -NH2 | 89 |
| (SEQ ID NO: 83) | Leu | Thr | Phe | Glu | His | Glu | Trp | Ala | Leu | Leu | Thr | Ser | Lys | -NH2 | 88 |
| (SEQ ID NO: 84) | Leu | Thr | Phe | Phe | His | Tyr | Trp | Ala | Gln | Leu | Thr | Ser | Lys | -NH2 | 88 |
| (SEQ ID NO: 85) | Leu | Thr | Phe | Ser | His | Tyr | Trp | Ala | Ser | Leu | Thr | Ser | Lys | -NH2 | 86 |
| (SEQ ID NO: 86) | Leu | Thr | Phe | Glu | His | Glu | Trp | Ala | Gln | Leu | Thr | Ser | Lys | -NH2 | 86 |
| (SEQ ID NO: 87) | Leu | Thr | Phe | Glu | His | Tyr | Trp | Ala | Ala | Leu | Thr | Ser | Lys | -NH2 | 84 |
| (SEQ ID NO: 88) | Leu | Thr | Phe | Pro | His | Tyr | Trp | Ala | Gln | Leu | Thr | Ser | Lys | -NH2 | 84 |
| (SEQ ID NO: 89) | Leu | Thr | Phe | Gln | His | Tyr | Trp | Ala | Ser | Leu | Thr | Ser | Lys | -NH2 | 83 |
| (SEQ ID NO: 90) | Leu | Thr | Phe | Gln | His | Phe | Trp | Ala | Glu | Leu | Thr | Ser | Lys | -NH2 | 83 |
| (SEQ ID NO: 91) | Leu | Thr | Phe | Phe | His | Tyr | Trp | Ala | Gly | Leu | Thr | Ser | Lys | -NH2 | 81 |
| (SEQ ID NO: 92) 4 | Leu | Thr | Phe | Pro | His | Phe | Trp | Ala | Glu | Leu | Thr | Ser | Lys | -NH2 | 80 |
| (SEQ ID NO: 93) | Leu | Thr | Phe | Phe | His | Ala | Trp | Ala | Glu | Leu | Thr | Ser | Lys | -NH2 | 80 |

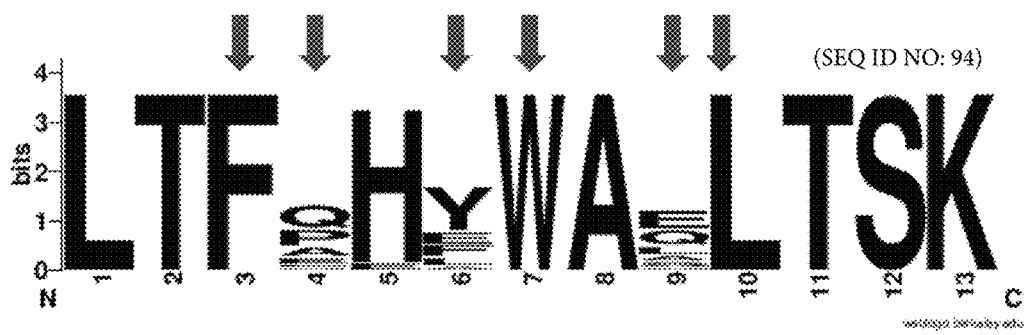

Figure 41

| | Library 3 usual stringency select sequences | | | | | | | | | | | | | | Kd MDM2 (nM) |
|---|---|---|---|---|---|---|---|---|---|---|---|---|---|---|---|
| (SEQ ID NO: 95) 38a | Bio-(PEG)₄- | Leu | Thr | Ff | Glu | His | Tyr | Hexa | Ala | Gln | *Leu* | Thr | Ser | Lys | -NH2 | 58 |
| (SEQ ID NO: 96) 39a | Bio-(PEG)₄- | Leu | Thr | F₅f | Glu | His | Tyr | Homof | Ala | Gln | Cba | Thr | Ser | Lys | -NH2 | 140 |
| (SEQ ID NO: 97) 40a | Bio-(PEG)₄- | Leu | Thr | F₅f | Glu | His | Tyr | CF₃f | Ala | Gln | *Leu* | Thr | Ser | Lys | -NH2 | 160 |
| (SEQ ID NO: 98) 41a | Bio-(PEG)₄- | Leu | Thr | Ff | Glu | His | Tyr | Homof | Ala | Gln | Anan | Thr | Ser | Lys | -NH2 | 220 |
| (SEQ ID NO: 99) 42a | Bio-(PEG)₄- | Leu | Thr | NH₂f | Glu | His | Tyr | *Trp* | Ala | Gln | Cba | Thr | Ser | Lys | -NH2 | 530 |

Figure 48

| | | | | | | | | | | | | | | | | Kd MDM2 (nM) | Kd MDMX (nM) |
|---|---|---|---|---|---|---|---|---|---|---|---|---|---|---|---|---|---|
| | | Library 3 resynthesized sequences | | | | | | | | | | | | | | | |
| (SEQ ID NO: 11) | 10a | Bio-(PEG)- | Leu | Thr | F₃f | Glu | His | Tyr | Hexa | Ala | Gln | Cba | Thr | Ser | Lys | -NH2 | 0.5 | 26 |
| (SEQ ID NO: 172) | 10b | Ac- | Leu | Thr | F₃f | Glu | His | Tyr | Hexa | Ala | Gln | Cba | Thr | Ser | Lys | -NH2 | 0.8 | |
| (SEQ ID NO: 12) | 11a | Bio-(PEG)- | Leu | Thr | F₃f | Glu | His | Tyr | Trp | Ala | Gln | Cba | Thr | Ser | Lys | -NH2 | 2.0 | 33 |
| (SEQ ID NO: 173) | 11b | Ac- | Leu | Thr | F₃f | Glu | His | Tyr | Trp | Ala | Gln | Cba | Thr | Ser | Lys | -NH2 | 1 | |
| (SEQ ID NO: 13) | 12a | Bio-(PEG)- | Leu | Thr | Ff | Glu | His | Tyr | Hexa | Ala | Gln | Cba | Thr | Ser | Lys | -NH2 | 2.1 | |
| (SEQ ID NO: 14) | 13a | Bio-(PEG)- | Leu | Thr | Ff | Glu | His | Tyr | Hexa | Ala | Gln | Cba | Thr | Ser | Lys | -NH2 | 2.9 | |
| (SEQ ID NO: 15) | 14a | Bio-(PEG)- | Leu | Thr | F₃f | Glu | His | Tyr | Hexa | Ala | Gln | Ff | Thr | Ser | Lys | -NH2 | 3.2 | |
| (SEQ ID NO: 16) | 15a | Bio-(PEG)- | Leu | Thr | F₃f | Glu | His | Tyr | Hexa | Ala | Gln | Ff | Thr | Ser | Lys | -NH2 | 3.8 | |
| (SEQ ID NO: 17) | 16a | Bio-(PEG)- | Leu | Thr | F₃f | Glu | His | Tyr | Hexa | Ala | Gln | Cba | Thr | Ser | Lys | -NH2 | 5.6 | |
| (SEQ ID NO: 18) | 17a | Bio-(PEG)- | Leu | Thr | F₃f | Glu | His | Tyr | Hexa | Ala | Gln | Hexa | Thr | Ser | Lys | -NH2 | 6.3 | |
| (SEQ ID NO: 19) | 18a | Bio-(PEG)- | Leu | Thr | F₃f | Glu | His | Tyr | Hexa | Ala | Gln | F₃f | Thr | Ser | Lys | -NH2 | 7.6 | |
| (SEQ ID NO: 20) | 19a | Bio-(PEG)- | Leu | Thr | F₃f | Glu | His | Tyr | Trp | Ala | Gln | Hexa | Thr | Ser | Lys | -NH2 | 8.0 | |
| (SEQ ID NO: 21) | 20a | Bio-(PEG)- | Leu | Thr | F₃f | Glu | His | Tyr | Trp | Ala | Gln | Cba | Thr | Ser | Lys | -NH2 | 8.9 | |
| (SEQ ID NO: 22) | 21a | Bio-(PEG)- | Leu | Thr | F₃f | Glu | His | Tyr | Hexa | Ala | Gln | Homof | Thr | Ser | Lys | -NH2 | 8.9 | |
| (SEQ ID NO: 23) | 22a | Bio-(PEG)- | Leu | Thr | F₃f | Glu | His | Tyr | Anta | Ala | Gln | Cba | Thr | Ser | Lys | -NH2 | 10 | |
| (SEQ ID NO: 24) | 23a | Bio-(PEG)- | Leu | Thr | F₃f | Glu | His | Tyr | Hexa | Ala | Gln | F₃f | Thr | Ser | Lys | -NH2 | 15 | |
| (SEQ ID NO: 25) | 24a | Bio-(PEG)- | Leu | Thr | F₃f | Glu | His | Tyr | Hexa | Ala | Gln | F₃f | Thr | Ser | Lys | -NH2 | 16 | |
| (SEQ ID NO: 26) | 25a | Bio-(PEG)- | Leu | Thr | F₃f | Glu | His | Tyr | Trp | Ala | Gln | F₃f | Thr | Ser | Lys | -NH2 | 20 | |
| (SEQ ID NO: 27) | 26a | Bio-(PEG)- | Leu | Thr | F₃f | Glu | His | Tyr | Trp | Ala | Gln | F₃f | Thr | Ser | Lys | -NH2 | 23 | |
| (SEQ ID NO: 28) | 27a | Bio-(PEG)- | Leu | Thr | F₃f | Glu | His | Tyr | Napa | Ala | Gln | Cba | Thr | Ser | Lys | -NH2 | 24 | |
| (SEQ ID NO: 29) | 28a | Bio-(PEG)- | Leu | Thr | F₃f | Glu | His | Tyr | Napa | Ala | Gln | Ff | Thr | Ser | Lys | -NH2 | 63 | |
| (SEQ ID NO: 100) | 29a | Bio-(PEG)- | Leu | Thr | Dmf | Glu | His | Tyr | CF₃f | Ala | Gln | Dmf | Thr | Ser | Lys | -NH2 | >800 | |
| (SEQ ID NO: 8) | 6a | Bio-(PEG)- | Leu | Thr | Phe | Glu | His | Tyr | Trp | Ala | Gln | Leu | Thr | Ser | Lys | -NH2 | 47 | 83 |

Figure 71

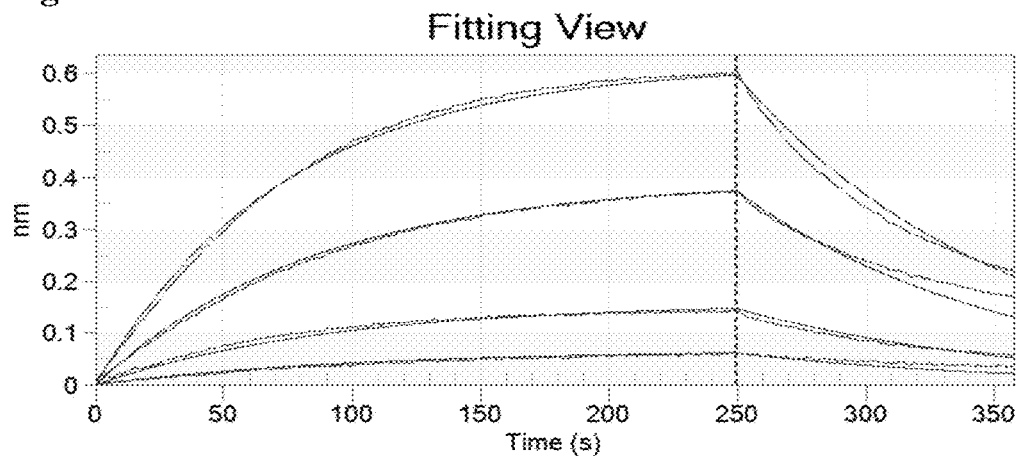

Figure 72

| Library 4 resynthesized binders | | | | | | | | | | | | | | | Kd C-CA (nM) |
|---|---|---|---|---|---|---|---|---|---|---|---|---|---|---|---|
| (SEQ ID NO: 142)30a | Ile | Thr | $F_{2}f$ | Glu | Asp | Cba | Leu | His | Tyr | Tyr | Gly | Pro | (Gly-Ser)$_8$ | Lys-Bio | -NH2 | 88 |
| (SEQ ID NO: 143)31a | Ile | Thr | $F_{2}f$ | Glu | Asp | Cba | Leu | His | Dmf | Tyr | Gly | Pro | (Gly-Ser)$_8$ | Lys-Bio | -NH2 | 120 |
| (SEQ ID NO: 144)32a | Ile | Thr | $F_{2}f$ | Glu | Asp | Cba | Leu | His | Dmf | $F_{2}f$ | Gly | Pro | (Gly-Ser)$_8$ | Lys-Bio | -NH2 | 140 |
| (SEQ ID NO: 101)33a | Ile | Thr | Phe | Glu | Asp | Cba | Leu | His | Tyr | Tyr | Gly | Pro | (Gly-Ser)$_8$ | Lys-Bio | -NH2 | 320 |
| (SEQ ID NO: 102)34a | Ile | Thr | $F_{2}f$ | Glu | Asp | Cba | Leu | Leu | His | Dmf | $F_{2}f$ | Gly | Pro | (Gly-Ser)$_8$ | Lys-Bio | -NH2 | 400 |
| (SEQ ID NO: 103)35a | Ile | Thr | $F_{2}f$ | Glu | Asp | Leu | Leu | His | Dmf | Tyr | Gly | Pro | (Gly-Ser)$_8$ | Lys-Bio | -NH2 | 480 |
| (SEQ ID NO: 104)36a | Ile | Thr | $F_{2}f$ | Glu | Asp | Leu | Leu | His | Tyr | Tyr | Gly | Pro | (Gly-Ser)$_8$ | Lys-Bio | -NH2 | 1200 |
| (SEQ ID NO: 105)37a | Ile | Thr | Phe | Glu | Asp | Leu | Leu | His | Tyr | Tyr | Gly | Pro | (Gly-Ser)$_8$ | Lys-Bio | -NH2 | 2300 |

Figure 73

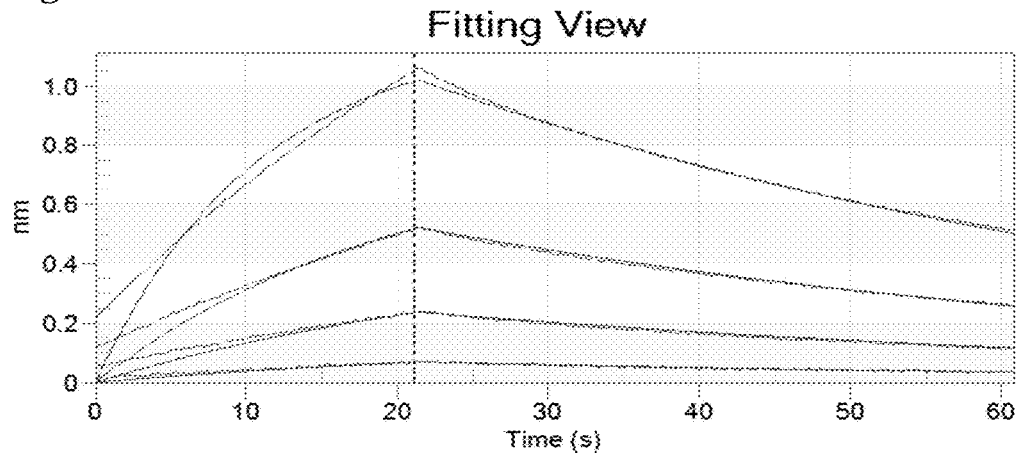

Figure 82

| | | | | | | | | | | | | | | | | Kd MDM2 (nM) | IC50 (µM) SJSA-1 |
|---|---|---|---|---|---|---|---|---|---|---|---|---|---|---|---|---|---|
| \multicolumn{16}{|l|}{Select macrocyclic inhibitors based on library 3 binders} | | |
| (SEQ ID NO: 35) 10a-M | Bio-(PEG)₂- | Leu | Thr | F₃f | R8 | Glu | Tyr | Hexa | Ala | Gln | Cba | S5 | Ser | (Ala)₂ | -NH2 | 5 | N.A |
| (SEQ ID NO: 171) 10b-M | Ac- | Leu | Thr | F₃f | R8 | Glu | Tyr | Hexa | Ala | Gln | Cba | S5 | Ser | (Ala)₂ | -NH2 | 8.7 | 2.4 |
| (SEQ ID NO: 174) 10b-M unclosed | Ac- | Leu | Thr | F₃f | R8 | Glu | Tyr | Hexa | Ala | Gln | Cba | S5 | Ser | (Ala)₂ | -NH2 | 75 | 17 |
| (SEQ ID NO: 106) 10b-M scramble | Ac- | Leu | Thr | Hexa | R8 | Glu | Tyr | Cba | Ala | Gln | F₃f | S5 | Ser | (Ala)₂ | -NH2 | >10000 | >20 |
| (SEQ ID NO: 36) 10b-S1 | Ac- | Leu | Thr | F₃f | Dap | Glu | Tyr | Hexa | Ala | Gln | Cba | Dap | Ser | (Ala)₂ | -NH2 | 30 | >20 |
| (SEQ ID NO: 37) 10b-S4 | Ac- | Leu | Thr | F₃f | Lys | Glu | Tyr | Hexa | Ala | Gln | Cba | Lys | Ser | (Ala)₂ | -NH2 | 298 | >20 |
| (SEQ ID NO: 38) 11b-M | Ac- | Leu | Thr | F₃f | R8 | Glu | Phe | Trp | Ala | Gln | Cba | S5 | Ser | (Ala)₂ | -NH2 | 4.1 | 3.2 |
| (SEQ ID NO: 39) 11a-S1 | Bio-(PEG)₂- | Leu | Thr | F₃f | Dap | Glu | Phe | Trp | Ala | Gln | Cba | Dap | Ser | (Ala)₂ | -NH2 | 2.5 | N.A |
| (SEQ ID NO: 40) 11b-S1 | Ac- | Leu | Thr | F₃f | Dap | Glu | Tyr | Trp | Ala | Gln | Cba | Dap | Ser | (Ala)₂ | -NH2 | 1.2 | 7.8 |
| (SEQ ID NO: 107) 11b-S1 scramble | Ac- | Leu | Thr | Trp | Dap | Glu | Tyr | Cba | Ala | Gln | F₃f | Dap | Ser | (Ala)₂ | -NH2 | >1000 | >20 |
| (SEQ ID NO: 41) 11b-S4 | Ac- | Leu | Thr | F₃f | Lys | Glu | Tyr | Trp | Ala | Glu | Cba | Lys | Ser | (Ala)₂ | -NH2 | 162 | >20 |
| (SEQ ID NO: 108) 22b-M | Ac- | Leu | Thr | F₃f | R8 | Glu | Tyr | Anta | Ala | Glu | Cba | S5 | Ser | (Ala)₂ | -NH2 | >1000 | >20 |
| (SEQ ID NO: 109) 22b-S1 | Ac- | Leu | Thr | F₃f | Dap | Glu | Tyr | Anta | Ala | Glu | Cba | Dap | Ser | (Ala)₂ | -NH2 | >1000 | >20 |
| (SEQ ID NO: 110) 22b-S4 | Ac- | Leu | Thr | F₃f | Lys | Glu | Tyr | Anta | Ala | Glu | Cba | Lys | Ser | (Ala)₂ | -NH2 | >1000 | >20 |
| (SEQ ID NO: 176) 27b-M | Ac- | Leu | Thr | F₃f | R8 | Glu | Tyr | Napa | Ala | Glu | Cba | S5 | Ser | (Ala)₂ | -NH2 | 3.6 | 2.7 |
| (SEQ ID NO: 111) 27b-S1 | Ac- | Leu | Thr | F₃f | Dap | Glu | Tyr | Napa | Ala | Glu | Cba | Dap | Ser | (Ala)₂ | -NH2 | 460 | >20 |
| (SEQ ID NO: 112) 27b-S4 | Ac- | Leu | Thr | F₃f | Lys | Glu | Tyr | Napa | Ala | Glu | Cba | Lys | Ser | (Ala)₂ | -NH2 | >1000 | >20 |
| (SEQ ID NO: 42) ATSP-7041 | Ac- | Leu | Thr | Phe | R8 | Glu | Tyr | Trp | Ala | Glu | Cba | S5 | Ser | (Ala)₂ | -NH2 | 1.2 | 3.0 |
| Nutlin-3 | | | | | | | | | | | | | | | | 52 | 1.9 |

Figure 101
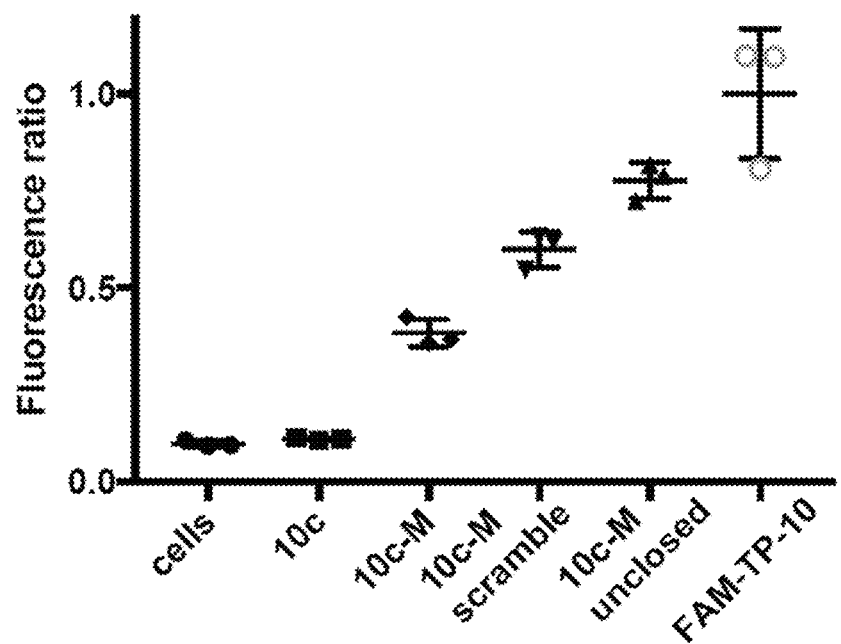
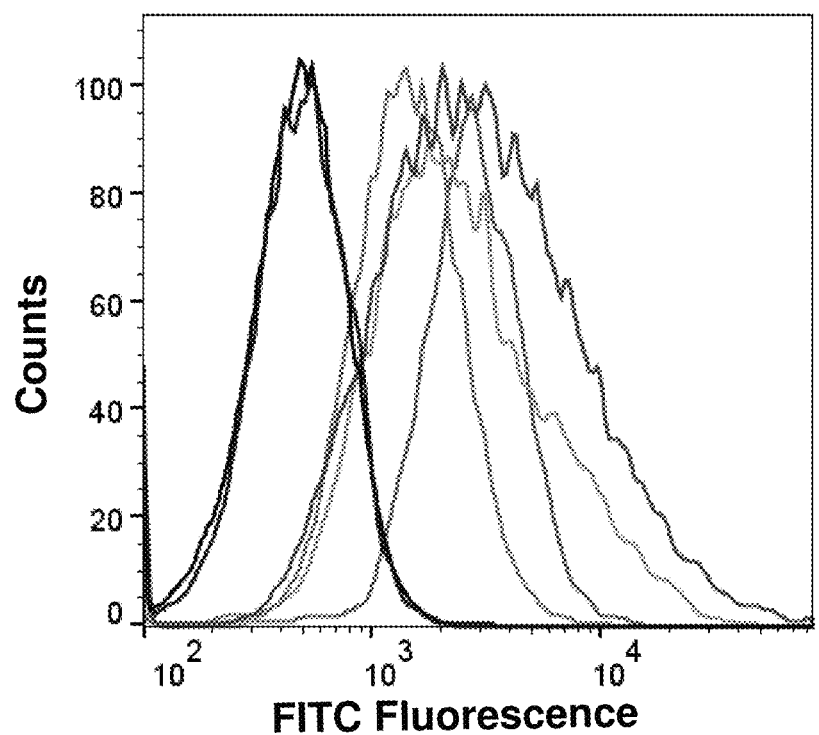

Figure 107
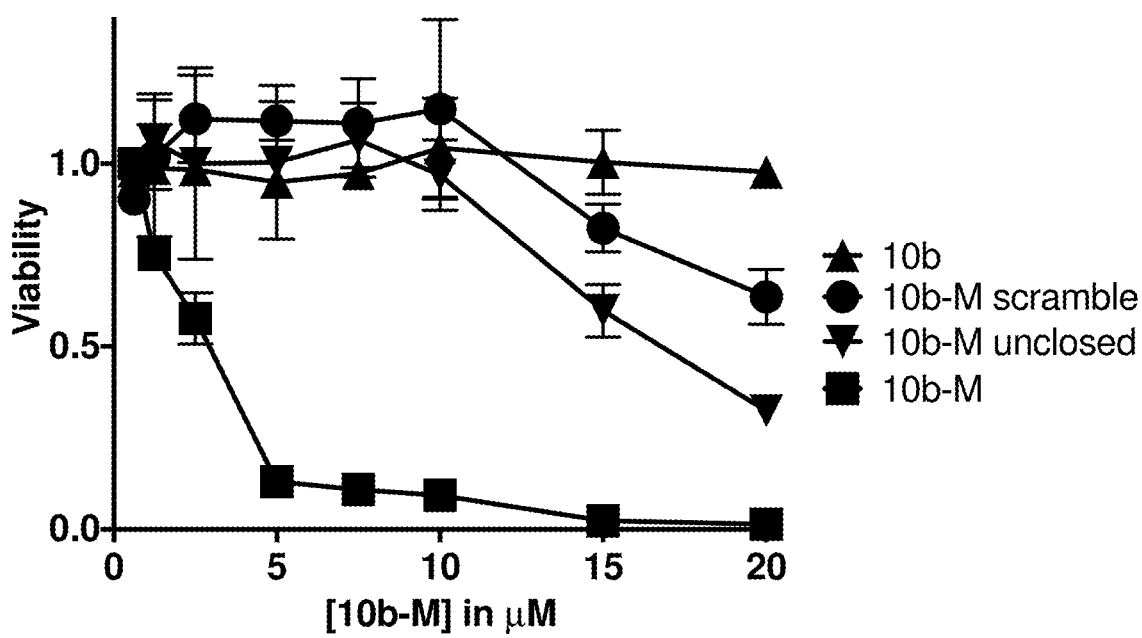
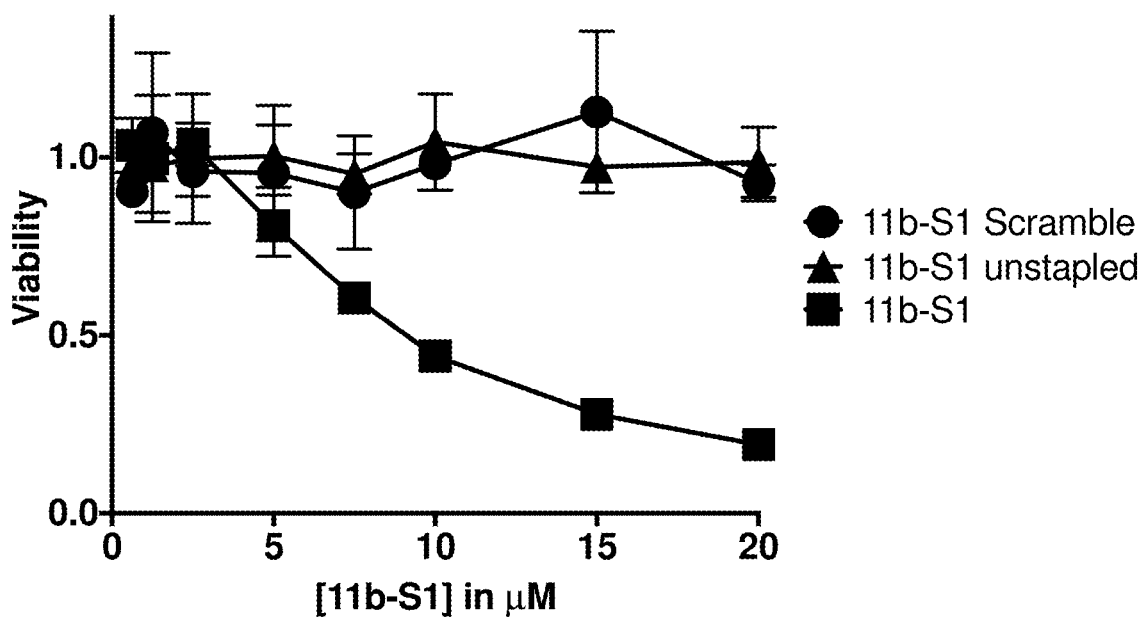

Figure 118

| | | Affinity selected sequence | | | | | | | | | | | | | |
|---|---|---|---|---|---|---|---|---|---|---|---|---|---|---|---|
| (SEQ ID NO: 48) | 60 | | Leu | Thr | *Phe* | Cys | His | Tyr | *Trp* | Ala | Gln | *Leu* | Cys | Ser | Lys | -NH2 | |
| | | Resynthesis and validation | | | | | | | | | | | | | | | Kd MDM2 (nM) |
| | | *Perflurorosulfone macrocyclized* | | | | | | | | | | | | | | | |
| (SEQ ID NO: 49) | 60a | Biotin-(PEG)$_4$- | Leu | Thr | *Phe* | Cys(ar) | His | Tyr | *Trp* | Ala | Gln | *Leu* | Cys(ar) | Ser | Lys | -NH2 | 24 |
| (SEQ ID NO: 175) | 60b | Ac- | Leu | Thr | *Phe* | Cys(ar) | His | Tyr | *Trp* | Ala | Gln | *Leu* | Cys(ar) | Ser | Lys | -NH2 | 22 |
| (SEQ ID NO: 65) | 61a | Biotin-(PEG)$_4$- | Leu | Thr | *Phe* | Cys(ar) | His | Tyr | *Trp* | Ala | Gln | *Phe* | Cys(ar) | Ser | Lys | -NH2 | 310 |
| | | *Decafluorobiphenyl macrocyclized* | | | | | | | | | | | | | | | |
| (SEQ ID NO: 116) | 62a | Biotin-(PEG)$_4$- | Leu | Thr | *Phe* | Cys | His | Tyr | *Trp* | Ala | Gln | *Leu* | Cys(ar) | Ser | Lys | -NH2 | > 1000 |

Figure 125

| | Library 5 decoded sequences after capture and cleavage | | | | | | | | | | | | ALC (%) | m/z (+3) | Binder | m/z (+5) | mass difference |
|---|---|---|---|---|---|---|---|---|---|---|---|---|---|---|---|---|---|
| (SEQ ID NO: 117) | Lys | Ala | Trp | Tyr | Ala | Asn | Hexa | Glu | Lys | Leu | Trp | Arg | -NH-CH$_2$-CH=N-OMe | 94 | 563.99 | 47 | 789.96 | 2255.8 |
| (SEQ ID NO: 118) | Lys | Ala | Trp | Tyr | Ala | Asn | CF$_3$f | Glu | Lys | Leu | Leu | Arg | -NH-CH$_2$-CH=N-OMe | 92 | 559.64 | 53 | 787.36 | 2255.8 |
| (SEQ ID NO: 119) | Lys | Ala | Trp | Tyr | Ala | Asn | Hexa | Glu | Lys | Leu | Leu | Arg | -NH-CH$_2$-CH=N-OMe | 90 | 539.66 | | 775.36 | 2255.8 |
| (SEQ ID NO: 120) | Lys | Ala | Trp | Tyr | Ala | Asn | Hexa | Glu | Lys | Leu | Cha | Arg | -NH-CH$_2$-CH=N-OMe | 89 | 553.00 | 44 | 783.37 | 2255.8 |
| (SEQ ID NO: 121) | Lys | Ala | Trp | Tyr | Ala | Asn | Hexa | Glu | Lys | Leu | F$_5$f | Arg | -NH-CH$_2$-CH=N-OMe | 89 | 562.98 | | 789.35 | 2255.8 |
| (SEQ ID NO: 122) | Lys | Ala | Trp | Tyr | Ala | Asn | Cha | Glu | Lys | Leu | Leu | Arg | -NH-CH$_2$-CH=N-OMe | 89 | 538.99 | 45 | 774.95 | 2255.8 |
| (SEQ ID NO: 123) | Lys | Ala | Trp | Tyr | Ala | Asn | Hexa | Glu | Lys | Leu | Cba | Arg | -NH-CH$_2$-CH=N-OMe | 88 | 543.66 | 51 | 777.76 | 2255.8 |
| (SEQ ID NO: 124) | Lys | Ala | Trp | Tyr | Ala | Asn | CF$_3$f | Glu | Lys | Leu | Homol | Arg | -NH-CH$_2$-CH=N-OMe | 87 | 564.31 | | 790.15 | 2255.8 |
| (SEQ ID NO: 125) | Lys | Ala | Trp | Tyr | Ala | Asn | Hexa | Glu | Lys | Leu | Homol | Arg | -NH-CH$_2$-CH=N-OMe | 86 | 544.33 | 43 | 778.16 | 2255.8 |
| (SEQ ID NO: 126) | Lys | Ala | Trp | Tyr | Ala | Asn | Hepa | Glu | Lys | Leu | Homol | Arg | -NH-CH$_2$-CH=N-OMe | 86 | 549.00 | 49 | 780.97 | 2255.8 |
| (SEQ ID NO: 127) | Lys | Ala | Trp | Tyr | Ala | Asn | CF$_3$f | Glu | Lys | Leu | Cba | Arg | -NH-CH$_2$-CH=N-OMe | 85 | 563.84 | | 789.75 | 2255.8 |
| (SEQ ID NO: 128) | Lys | Ala | Trp | Tyr | Ala | Asn | Hexa | Glu | Lys | Leu | Hexa | Arg | -NH-CH$_2$-CH=N-OMe | 85 | 553.68 | 46 | 783.77 | 2255.8 |
| (SEQ ID NO: 129) | Lys | Ala | Trp | Tyr | Ala | Asn | CF$_3$f | Glu | Lys | Leu | F$_5$f | Arg | -NH-CH$_2$-CH=N-OMe | 84 | 582.95 | | 801.34 | 2255.8 |
| (SEQ ID NO: 130) | Lys | Ala | Trp | Tyr | Ala | Asn | Hepa | Glu | Lys | Leu | Cha | Arg | -NH-CH$_2$-CH=N-OMe | 84 | 557.66 | 52 | 786.17 | 2255.8 |
| (SEQ ID NO: 131) | Lys | Ala | Trp | Tyr | Ala | Asn | Hepa | Glu | Lys | Leu | Cba | Arg | -NH-CH$_2$-CH=N-OMe | 81 | 548.33 | 48 | 780.56 | 2255.8 |
| (SEQ ID NO: 132) | Lys | Ala | Trp | Tyr | Ala | Asn | Hepa | Glu | Lys | Leu | F$_5$f | Arg | -NH-CH$_2$-CH=N-OMe | 80 | 567.65 | | 792.16 | 2255.8 |
| (SEQ ID NO: 133) | Lys | Ala | Trp | Tyr | Ala | Asn | Hepa | Glu | Lys | Leu | Hexa | Arg | -NH-CH$_2$-CH=N-OMe | 79 | 558.35 | 51 | 786.57 | 2255.8 |
| (SEQ ID NO: 134) | Lys | Ala | Trp | Tyr | Ala | Asn | CF$_3$f | Glu | Lys | Leu | Cha | Arg | -NH-CH$_2$-CH=N-OMe | 75 | 572.98 | | 795.35 | 2255.8 |

Figure 126

| | | Library 5 resynthesized binders | | | | | | | | | | | | | | | | Kd MDM2 (nM) |
|---|---|---|---|---|---|---|---|---|---|---|---|---|---|---|---|---|---|---|
| (SEQ ID NO: 147) | 43 | NH2- | Lys | Ala | Trp | Tyr | Ala | Asn | Hexa | Glu | Lys | Leu | Homol | Arg | Diol | Gly | Gly | Ser | β-Ala | 9-28EETI-II | 1 |
| (SEQ ID NO: 148) | 44 | NH2- | Lys | Ala | Trp | Tyr | Ala | Asn | Hexa | Glu | Lys | Leu | Cha | Arg | Diol | Gly | Gly | Ser | β-Ala | 9-28EETI-II | 4.4 |
| (SEQ ID NO: 149) | 45 | NH2- | Lys | Ala | Trp | Tyr | Ala | Asn | Cha | Glu | Lys | Leu | Leu | Arg | Diol | Gly | Gly | Ser | β-Ala | 9-28EETI-II | 8.1 |
| (SEQ ID NO: 150) | 46 | NH2- | Lys | Ala | Trp | Tyr | Ala | Asn | Hexa | Glu | Lys | Leu | Hexa | Arg | Diol | Gly | Gly | Ser | β-Ala | 9-28EETI-II | 10.4 |
| (SEQ ID NO: 151) | 47 | NH2- | Lys | Ala | Trp | Tyr | Ala | Asn | Hexa | Glu | Lys | Leu | Trp | Arg | Diol | Gly | Gly | Ser | β-Ala | 9-28EETI-II | 11.0 |
| (SEQ ID NO: 152) | 48 | NH2- | Lys | Ala | Trp | Tyr | Ala | Asn | Hepa | Glu | Lys | Leu | Cba | Arg | Diol | Gly | Gly | Ser | β-Ala | 9-28EETI-II | 13 |
| (SEQ ID NO: 153) | 49 | NH2- | Lys | Ala | Trp | Tyr | Ala | Asn | Hepa | Glu | Lys | Leu | Homol | Arg | Diol | Gly | Gly | Ser | β-Ala | 9-28EETI-II | 15 |
| (SEQ ID NO: 154) | 50 | NH2- | Lys | Ala | Trp | Tyr | Ala | Asn | Hepa | Glu | Lys | Leu | Hexa | Arg | Diol | Gly | Gly | Ser | β-Ala | 9-28EETI-II | 17 |
| (SEQ ID NO: 155) | 51 | NH2- | Lys | Ala | Trp | Tyr | Ala | Asn | Hexa | Glu | Lys | Leu | Cba | Arg | Diol | Gly | Gly | Ser | β-Ala | 9-28EETI-II | 23 |
| (SEQ ID NO: 156) | 52 | NH2- | Lys | Ala | Trp | Tyr | Ala | Asn | Hepa | Glu | Lys | Leu | Cha | Arg | Diol | Gly | Gly | Ser | β-Ala | 9-28EETI-II | 26 |
| (SEQ ID NO: 157) | 53 | NH2- | Lys | Ala | Trp | Tyr | Ala | Asn | CF$_3$f | Glu | Lys | Leu | Leu | Arg | Diol | Gly | Gly | Ser | β-Ala | 9-28EETI-II | 20 |
| (SEQ ID NO: 158) | 54b | Ac- | Lys | Ala | Trp | Tyr | Ala | Asn | CF$_3$f | Glu | Lys | Leu | Leu | Arg | | | | | | | 1.3 |
| (SEQ ID NO: 135) | 55 | NH2- | Lys | Ala | Trp | Tyr | Ala | Asn | Leu | Glu | Lys | Leu | CF$_3$f | Arg | Diol | Gly | Gly | Ser | β-Ala | 9-28EETI-II | > 1000 nM |
| (SEQ ID NO: 136) | 56 | NH2- | Lys | Ala | Ala | Tyr | Ala | Asn | Ala | Glu | Lys | Leu | Ala | Arg | Diol | Gly | Gly | Ser | β-Ala | 9-28EETI-II | > 1000 nM |

63a: Biotin-(Peg)4-(Gly-Ser)6-Ser-Gln-Glu-Thr-Phe-Ser-Asp-Leu-Trp-Lys-Leu-Leu-Pro-Glu-Asn-CONH2

(SEQ ID NO: 137)

6: Leu-Thr-Phe-Glu-His-Tyr-Trp-Ala-Gln-Leu-Thr-Ser-Lys-CONH$_2$
(SEQ ID NO: 72)

Figure 142
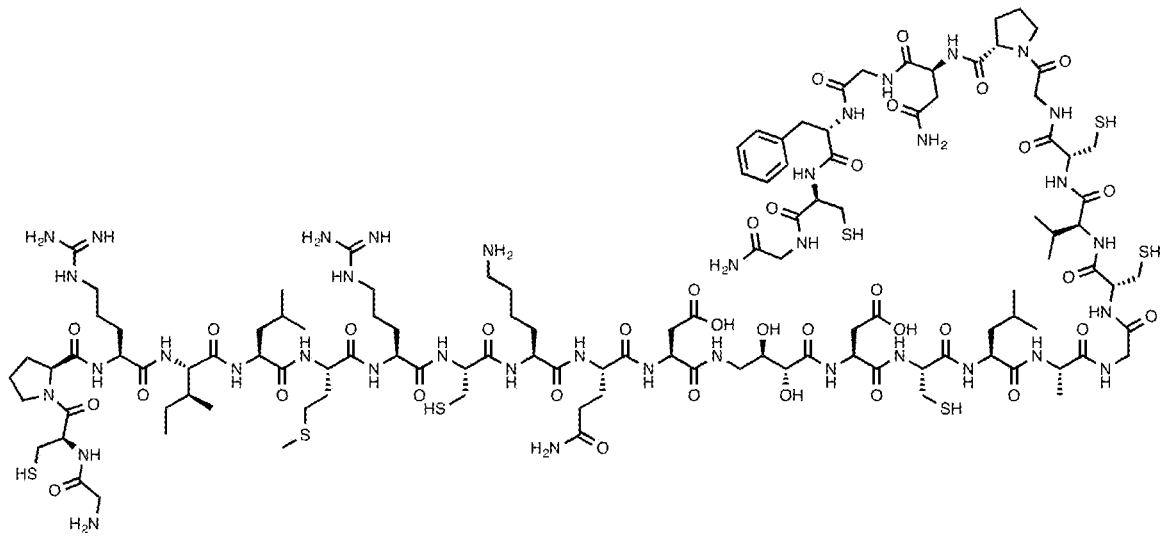
59: Gly-Cys*-Pro-Arg-Ile-Met-Arg-Cys*-Lys-Gln-Asp-Diol-Asp-Cys*-Leu-Ala-Gly-Cys*-Val-Cys*-Gly-Pro-Asn-GLy-Phe-Cys*-Gly-CONH$_2$
(SEQ ID NO: 138)
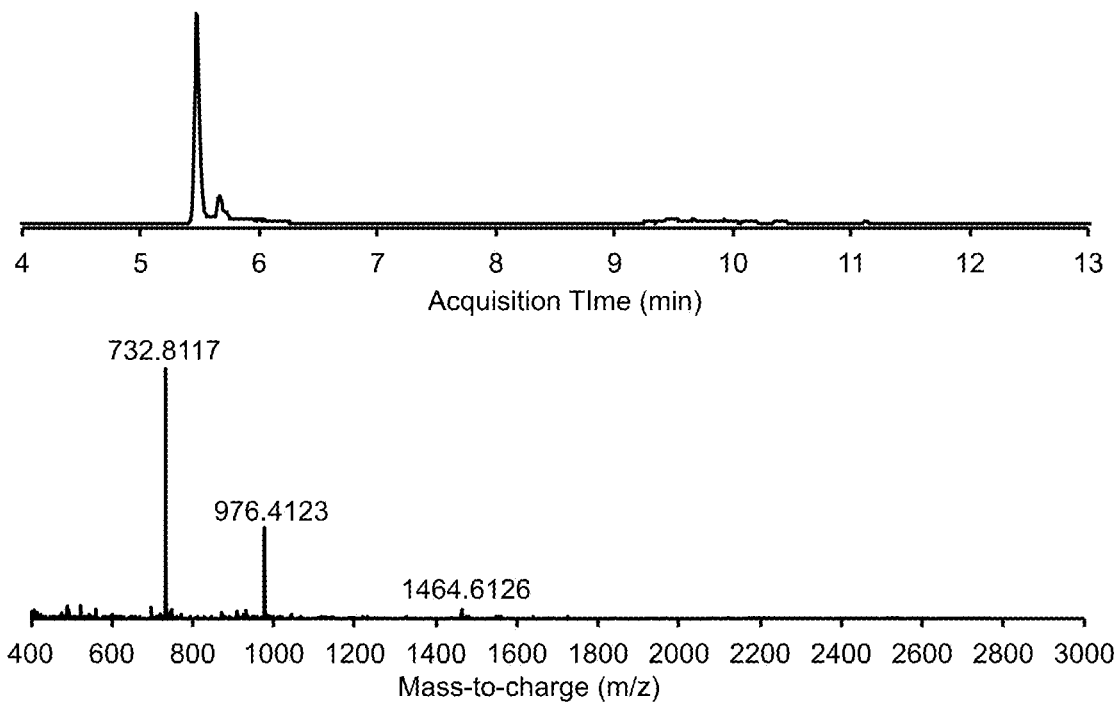

1a:Biotin-(Peg)$_4$-Leu-Thr-Phe-Gln-His-Phe-Trp-Ala-Glu-Leu-Thr-Ser-Lys-CONH$_2$ (SEQ ID NO: 2)

5a:Biotin-(Peg)₄-Leu-Thr-Phe-Gln-His-Tyr-Trp-Ala-Gln-Phe-Thr-Ser-Lys-CONH₂
(SEQ ID NO: 7)

10a: Biotin-(Peg)₄-Leu-Thr-F₂f-Glu-His-Tyr-Hexa-Ala-Gln-Cba-Thr-Ser-Lys
(SEQ ID NO: 11)

11b: Ac-Leu-Thr-F₃f-Glu-His-Tyr-Trp-Ala-Gln-Cba-Thr-Ser-Lys-CONH₂
(SEQ ID NO: 12)

Figure 147
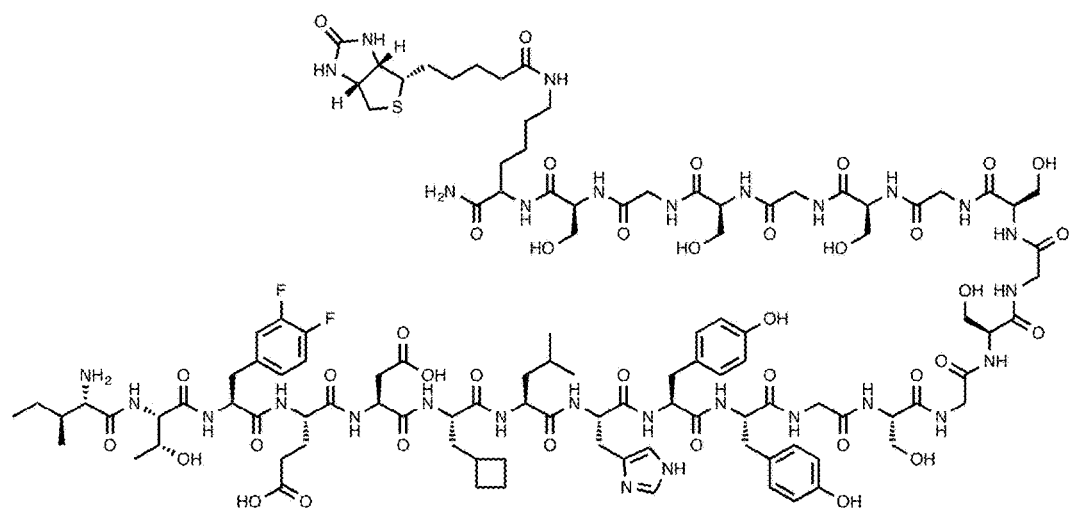
30a: Ile-Thr-F₂f-Glu-Asp-Cba-Leu-His-Tyr-Tyr-(Gly-Ser)₆-Lys(Biotin)-CONH₂
(SEQ ID NO: 170)
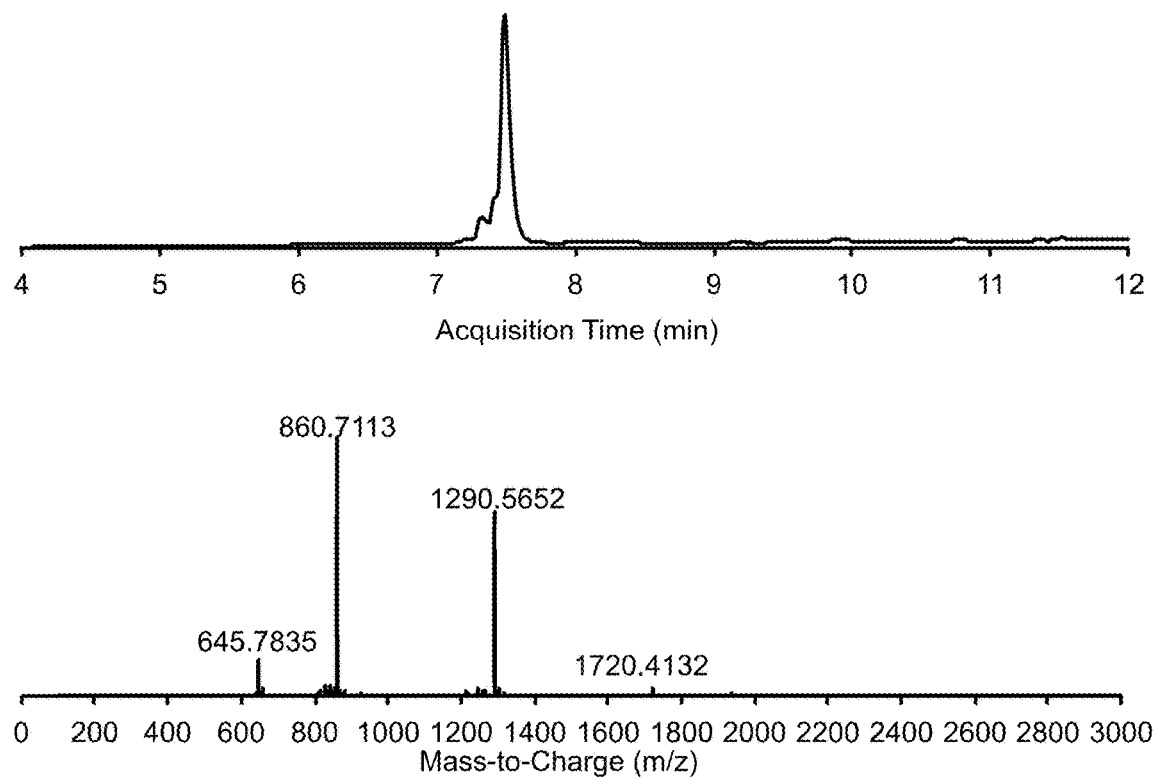

Figure 148
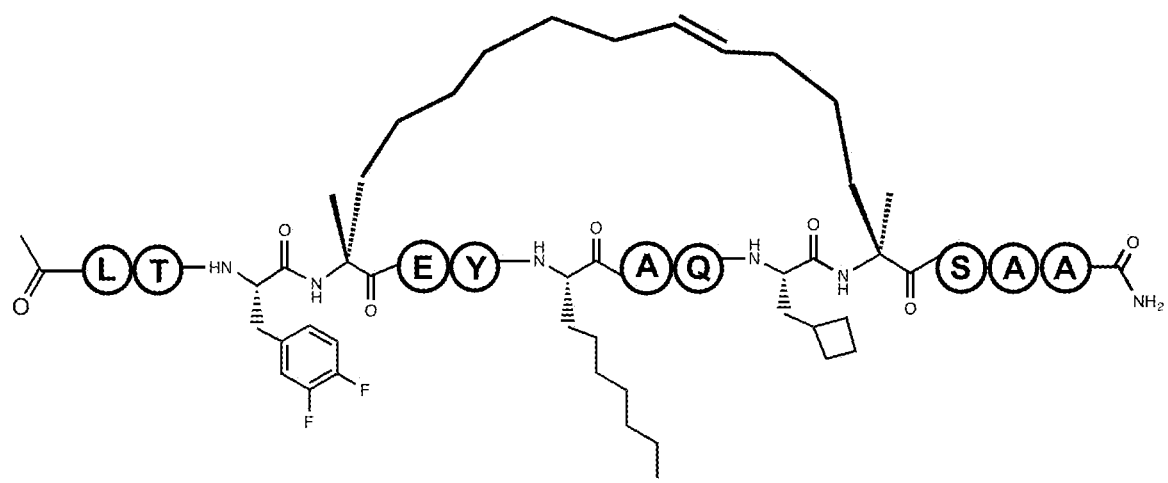
10b-M: Ac-Leu-Thr-F₃fR8-Glu-Tyr-Hexa-Ala-Gln-Cba-S5-Ser-Ala-Ala-CONH₂
(SEQ ID NO: 171)
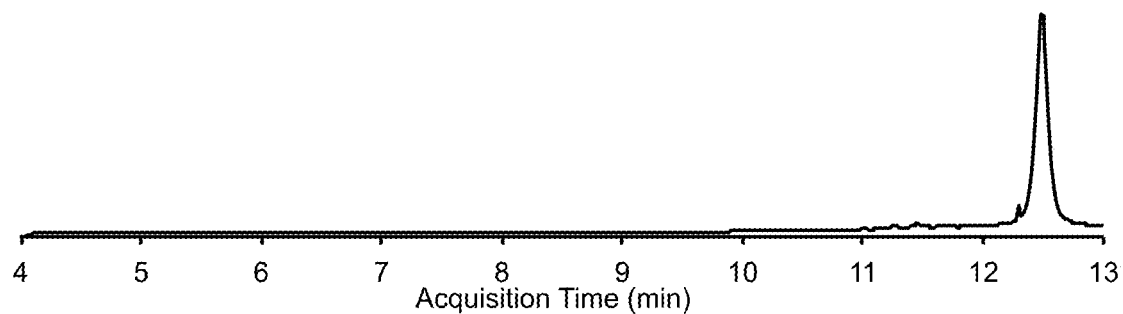
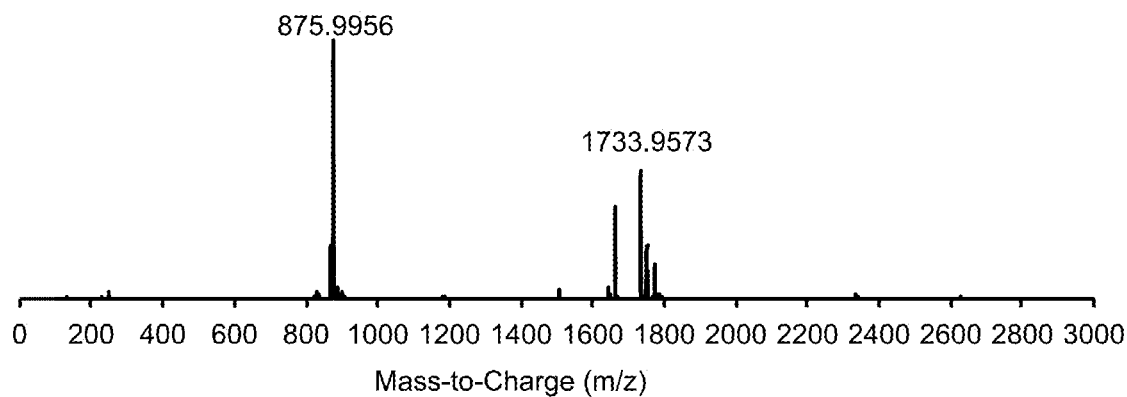

Figure 149
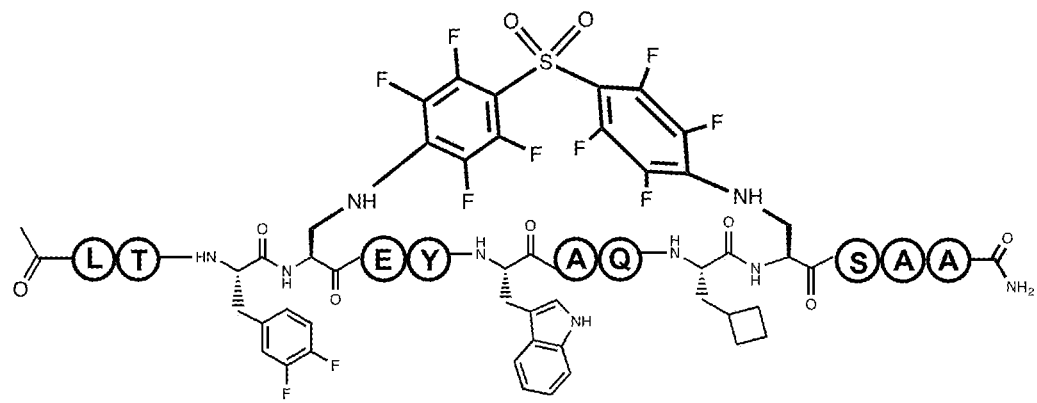
11b-S1:Ac-Leu-Thr-F₂f-Dap(sulfone)-Glu-Tyr-Trp-Ala-Gln-Cba-Dap(Sulfone)-Ser-Ala-Ala-CONH₂
(SEQ ID NO: 40)
TIC
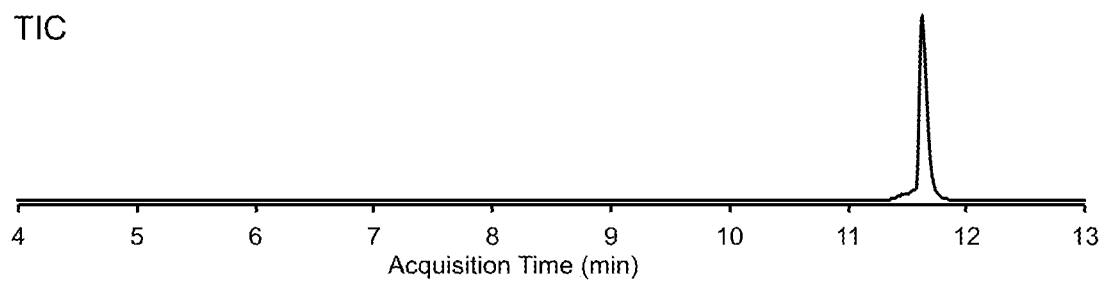
UVC
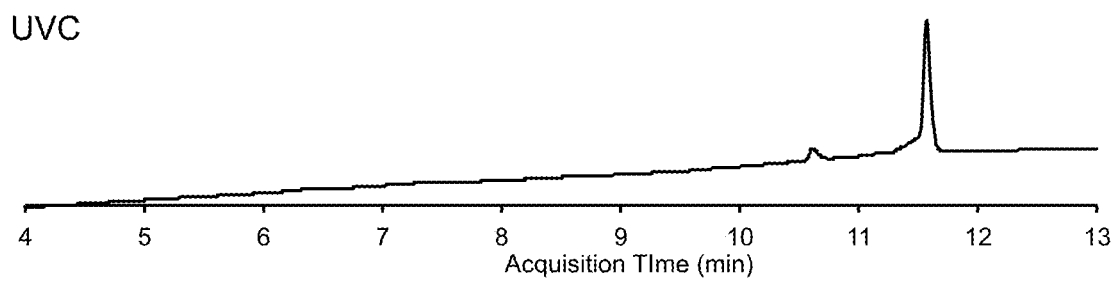

11c-S1: FITC-Leu-Thr-F₃f-Dap(sulfone)-Glu-Tyr-Trp-Ala-Gln-Cba-Dap(Sulfone)-Ser-Ala-Ala-CONH₂

(SEQ ID NO: 140)

Figure 152
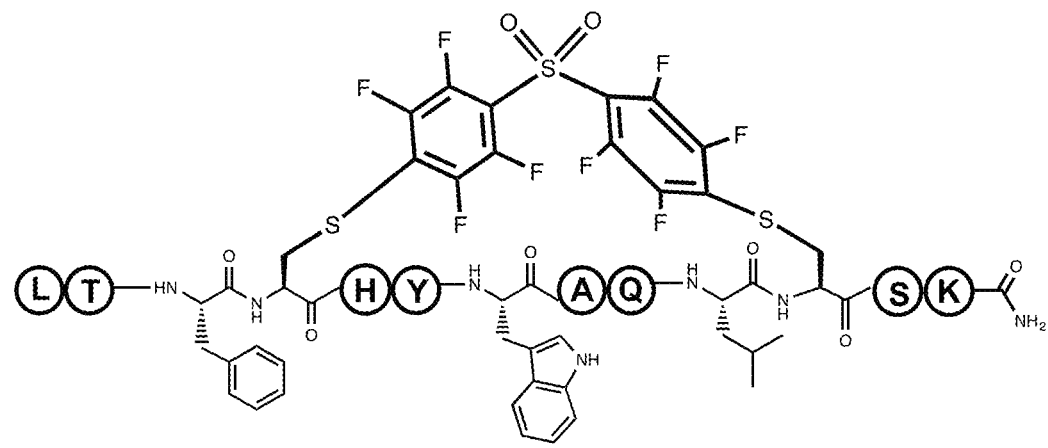
60: Leu-Thr-Phe-Cys(sulfone)-Glu-Tyr-Trp-Ala-Gln-Leu-Cys(Sulfone)-Ser-Ala-Ala-CONH$_2$
(SEQ ID NO: 141)
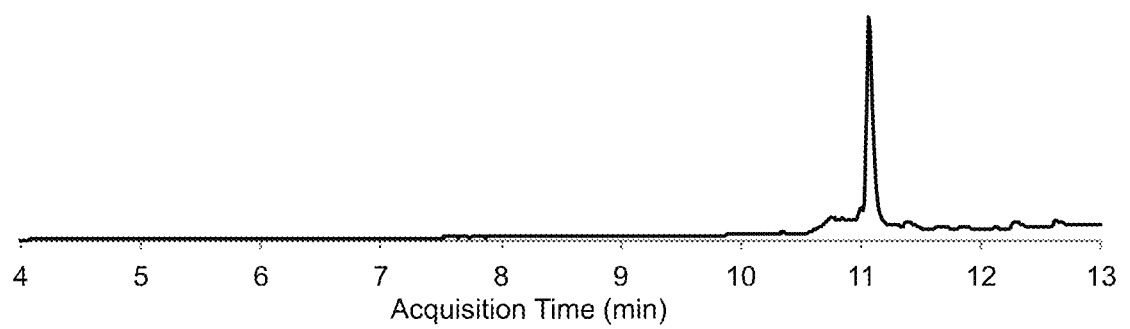
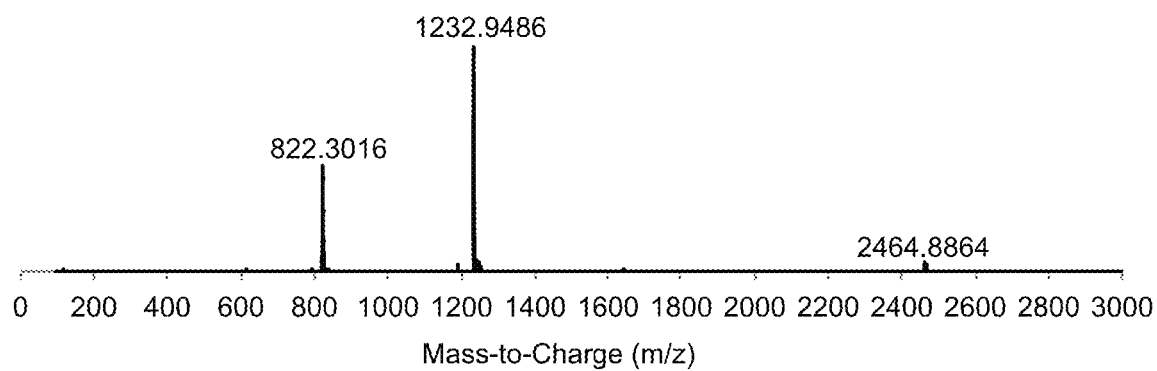

Figure 153
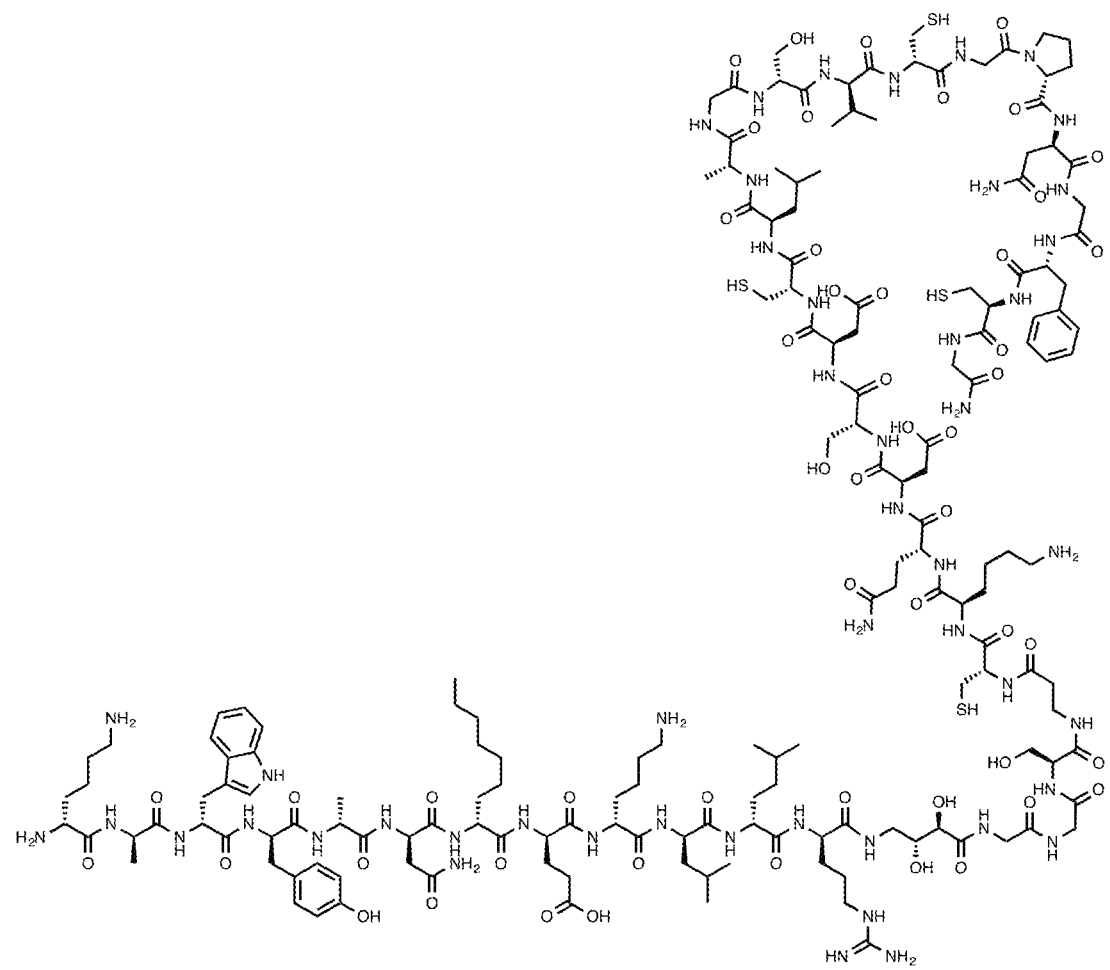
43: Lys-Ala-Trp-Tyr-Ala-Asn-Hexa-Glu-Lys-Leu-Homo-Arg-Did-Gly-Gly-Ser-βAla-Cys*-Lys-Gln-Asp-Ser-Asp-Cys*-Leu-Ala-Gly-Ser-Val-Cys*-Gly-Pro-Asn-Gly-Phe-Cys*-Gly-CONH$_2$ (SEQ ID NO: 177)
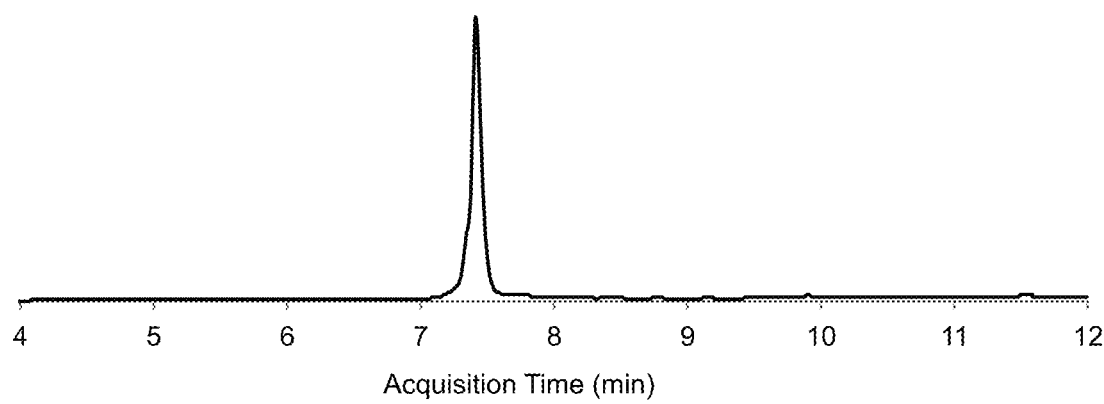

SEQUENCE LISTING

<160> NUMBER OF SEQ ID NOS: 202

<210> SEQ ID NO 1

```
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: X may be Gln, Pro, or Glu
<220> FEATURE:
<221> NAME/KEY: misc_feature
<222> LOCATION: (6)..(6)
<223> OTHER INFORMATION: X may be Phe, Tyr, or Glu
<220> FEATURE:
<221> NAME/KEY: misc_feature
<222> LOCATION: (9)..(9)
<223> OTHER INFORMATION: X may be Glu, Gln, Ala, or Leu

<400> SEQUENCE: 1

Leu Thr Phe Xaa His Xaa Trp Ala Xaa Leu Thr Ser Lys
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 2

Leu Thr Phe Gln His Phe Trp Ala Glu Leu Thr Ser Lys
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 3

Leu Thr Phe Gln His Tyr Trp Ala Glu Leu Thr Ser Lys
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 4

Leu Thr Phe Pro His Tyr Trp Ala Glu Leu Thr Ser Lys
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 5

Leu Thr Phe Pro His Phe Trp Ala Glu Leu Thr Ser Lys
1               5                   10

<210> SEQ ID NO 6
<211> LENGTH: 13
<212> TYPE: PRT
```

```
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (10)..(10)
<223> OTHER INFORMATION: X may be Phe or Leu

<400> SEQUENCE: 6

Leu Thr Phe Glu His Tyr Trp Ala Gln Xaa Thr Ser Lys
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 7

Leu Thr Phe Glu His Tyr Trp Ala Gln Phe Thr Ser Lys
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 8

Leu Thr Phe Glu His Tyr Trp Ala Gln Leu Thr Ser Lys
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X may be Ff, F2f, F3f, or Phe
<220> FEATURE:
<221> NAME/KEY: misc_feature
<222> LOCATION: (7)..(7)
<223> OTHER INFORMATION: X may be Hexa, Trp, Napha, or Anta
<220> FEATURE:
<221> NAME/KEY: misc_feature
<222> LOCATION: (10)..(10)
<223> OTHER INFORMATION: X may be Cba, Cha, Ff, F2f, F3f, F5f, Hexa,
      Homof, or Leu

<400> SEQUENCE: 9

Leu Thr Xaa Glu His Tyr Xaa Ala Gln Xaa Thr Ser Lys
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is Ff
<220> FEATURE:
<221> NAME/KEY: misc_feature
<222> LOCATION: (7)..(7)
```

```
<223> OTHER INFORMATION: X is Hexa

<400> SEQUENCE: 10

Leu Thr Xaa Glu His Tyr Xaa Ala Gln Leu Thr Ser Lys
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (10)..(10)
<223> OTHER INFORMATION: X is Cba

<400> SEQUENCE: 11

Leu Thr Xaa Glu His Tyr Xaa Ala Gln Xaa Thr Ser Lys
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (10)..(10)
<223> OTHER INFORMATION: X is Cba

<400> SEQUENCE: 12

Leu Thr Xaa Glu His Tyr Trp Ala Gln Xaa Thr Ser Lys
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is Ff
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (10)..(10)
<223> OTHER INFORMATION: X is Cha

<400> SEQUENCE: 13

Leu Thr Xaa Glu His Tyr Xaa Ala Gln Xaa Thr Ser Lys
1               5                   10
```

```
<210> SEQ ID NO 14
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is Ff
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (10)..(10)
<223> OTHER INFORMATION: X is Cba

<400> SEQUENCE: 14

Leu Thr Xaa Glu His Tyr Xaa Ala Gln Xaa Thr Ser Lys
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F3f
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (10)..(10)
<223> OTHER INFORMATION: X is Ff

<400> SEQUENCE: 15

Leu Thr Xaa Glu His Tyr Xaa Ala Gln Xaa Thr Ser Lys
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (10)..(10)
<223> OTHER INFORMATION: X is Ff

<400> SEQUENCE: 16

Leu Thr Xaa Glu His Tyr Xaa Ala Gln Xaa Thr Ser Lys
1               5                   10

<210> SEQ ID NO 17
<211> LENGTH: 13
<212> TYPE: PRT
<213> ORGANISM: Artificial Sequence
```

```
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F3f
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (10)..(10)
<223> OTHER INFORMATION: X is Cha

<400> SEQUENCE: 17

Leu Thr Xaa Glu His Tyr Xaa Ala Gln Xaa Thr Ser Lys
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F3f
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (10)..(10)
<223> OTHER INFORMATION: X is Hexa

<400> SEQUENCE: 18

Leu Thr Xaa Glu His Tyr Xaa Ala Gln Xaa Thr Ser Lys
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (10)..(10)
<223> OTHER INFORMATION: X is F3f

<400> SEQUENCE: 19

Leu Thr Xaa Glu His Tyr Xaa Ala Gln Xaa Thr Ser Lys
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
```

```
<222> LOCATION: (3)..(3)
<223> OTHER INFORMATION: X is F2f
<220> FEATURE:
<221> NAME/KEY: misc_feature
<222> LOCATION: (10)..(10)
<223> OTHER INFORMATION: X is Hexa

<400> SEQUENCE: 20

Leu Thr Xaa Glu His Tyr Trp Ala Gln Xaa Thr Ser Lys
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F3f
<220> FEATURE:
<221> NAME/KEY: misc_feature
<222> LOCATION: (10)..(10)
<223> OTHER INFORMATION: X is Cha

<400> SEQUENCE: 21

Leu Thr Xaa Glu His Tyr Trp Ala Gln Xaa Thr Ser Lys
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (10)..(10)
<223> OTHER INFORMATION: X is Homof

<400> SEQUENCE: 22

Leu Thr Xaa Glu His Tyr Xaa Ala Gln Xaa Thr Ser Lys
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F3f
<220> FEATURE:
<221> NAME/KEY: misc_feature
<222> LOCATION: (7)..(7)
<223> OTHER INFORMATION: X is Anta
<220> FEATURE:
<221> NAME/KEY: misc_feature
<222> LOCATION: (10)..(10)
<223> OTHER INFORMATION: X is Cba

<400> SEQUENCE: 23
```

```
Leu Thr Xaa Glu His Tyr Xaa Ala Gln Xaa Thr Ser Lys
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F3f
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (10)..(10)
<223> OTHER INFORMATION: X is F3f

<400> SEQUENCE: 24

Leu Thr Xaa Glu His Tyr Xaa Ala Gln Xaa Thr Ser Lys
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F3f
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (10)..(10)
<223> OTHER INFORMATION: X is F5f

<400> SEQUENCE: 25

Leu Thr Xaa Glu His Tyr Xaa Ala Gln Xaa Thr Ser Lys
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (10)..(10)
<223> OTHER INFORMATION: X is F2f

<400> SEQUENCE: 26

Leu Thr Xaa Glu His Tyr Trp Ala Gln Xaa Thr Ser Lys
1               5                   10

<210> SEQ ID NO 27
<211> LENGTH: 13
<212> TYPE: PRT
```

```
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (10)..(10)
<223> OTHER INFORMATION: X is F3f

<400> SEQUENCE: 27

Leu Thr Xaa Glu His Tyr Trp Ala Gln Xaa Thr Ser Lys
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (7)..(7)
<223> OTHER INFORMATION: X is Napa
<220> FEATURE:
<221> NAME/KEY: misc_feature
<222> LOCATION: (10)..(10)
<223> OTHER INFORMATION: X is Cba

<400> SEQUENCE: 28

Leu Thr Xaa Glu His Tyr Xaa Ala Gln Xaa Thr Ser Lys
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (7)..(7)
<223> OTHER INFORMATION: X is Napa
<220> FEATURE:
<221> NAME/KEY: misc_feature
<222> LOCATION: (10)..(10)
<223> OTHER INFORMATION: X is Ff

<400> SEQUENCE: 29

Leu Thr Xaa Glu His Tyr Xaa Ala Gln Xaa Thr Ser Lys
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
```

```
<221> NAME/KEY: misc_feature
<222> LOCATION: (6)..(6)
<223> OTHER INFORMATION: X is Cba
<220> FEATURE:
<221> NAME/KEY: misc_feature
<222> LOCATION: (9)..(9)
<223> OTHER INFORMATION: X may be Tyr or Dmf
<220> FEATURE:
<221> NAME/KEY: misc_feature
<222> LOCATION: (10)..(10)
<223> OTHER INFORMATION: X may be Tyr or F2f

<400> SEQUENCE: 30

Ile Thr Xaa Glu Asp Xaa Leu His Xaa Xaa Gly Pro
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (6)..(6)
<223> OTHER INFORMATION: X is Cba

<400> SEQUENCE: 31

Ile Thr Xaa Glu Asp Xaa Leu His Tyr Tyr Gly Pro
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (6)..(6)
<223> OTHER INFORMATION: X is Cba
<220> FEATURE:
<221> NAME/KEY: misc_feature
<222> LOCATION: (9)..(9)
<223> OTHER INFORMATION: X is Dmf

<400> SEQUENCE: 32

Ile Thr Xaa Glu Asp Xaa Leu His Xaa Tyr Gly Pro
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (6)..(6)
<223> OTHER INFORMATION: X is Cba
<220> FEATURE:
```

```
<221> NAME/KEY: misc_feature
<222> LOCATION: (9)..(9)
<223> OTHER INFORMATION: X is Dmf
<220> FEATURE:
<221> NAME/KEY: misc_feature
<222> LOCATION: (10)..(10)
<223> OTHER INFORMATION: X is F2f

<400> SEQUENCE: 33

Ile Thr Xaa Glu Asp Xaa Leu His Xaa Xaa Gly Pro
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X may be F2f or Phe
<220> FEATURE:
<221> NAME/KEY: misc_feature
<222> LOCATION: (4)..(4)
<223> OTHER INFORMATION: X may be R8 or Dap or a portion of a cross-link
     or staple
<220> FEATURE:
<221> NAME/KEY: misc_feature
<222> LOCATION: (6)..(6)
<223> OTHER INFORMATION: X may be Tyr or Phe
<220> FEATURE:
<221> NAME/KEY: misc_feature
<222> LOCATION: (7)..(7)
<223> OTHER INFORMATION: X may be Hexa, Napha, or Trp
<220> FEATURE:
<221> NAME/KEY: misc_feature
<222> LOCATION: (9)..(9)
<223> OTHER INFORMATION: X may be Gln or Glu
<220> FEATURE:
<221> NAME/KEY: misc_feature
<222> LOCATION: (10)..(10)
<223> OTHER INFORMATION: X is Cba
<220> FEATURE:
<221> NAME/KEY: misc_feature
<222> LOCATION: (11)..(11)
<223> OTHER INFORMATION: X may be S5 or Dap or a portion of a cross-link
     or staple

<400> SEQUENCE: 34

Leu Thr Xaa Xaa Glu Xaa Xaa Ala Xaa Xaa Xaa Ser Ala Ala
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (4)..(4)
<223> OTHER INFORMATION: X is R8
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (10)..(10)
<223> OTHER INFORMATION: X is Cba
```

```
<220> FEATURE:
<221> NAME/KEY: misc_feature
<222> LOCATION: (11)..(11)
<223> OTHER INFORMATION: X is S5

<400> SEQUENCE: 35

Leu Thr Xaa Xaa Glu Tyr Xaa Ala Gln Xaa Xaa Ser Ala Ala
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (4)..(4)
<223> OTHER INFORMATION: X is Dap
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (10)..(10)
<223> OTHER INFORMATION: X is Cba
<220> FEATURE:
<221> NAME/KEY: misc_feature
<222> LOCATION: (11)..(11)
<223> OTHER INFORMATION: X is Dap

<400> SEQUENCE: 36

Leu Thr Xaa Xaa Glu Tyr Xaa Ala Gln Xaa Xaa Ser Ala Ala
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (10)..(10)
<223> OTHER INFORMATION: X is Cba

<400> SEQUENCE: 37

Leu Thr Xaa Lys Glu Tyr Xaa Ala Gln Xaa Lys Ser Ala Ala
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
```

```
<220> FEATURE:
<221> NAME/KEY: misc_feature
<222> LOCATION: (4)..(4)
<223> OTHER INFORMATION: X is R8
<220> FEATURE:
<221> NAME/KEY: misc_feature
<222> LOCATION: (10)..(10)
<223> OTHER INFORMATION: X is Cba
<220> FEATURE:
<221> NAME/KEY: misc_feature
<222> LOCATION: (11)..(11)
<223> OTHER INFORMATION: X is S5

<400> SEQUENCE: 38

Leu Thr Xaa Xaa Glu Phe Trp Ala Gln Xaa Xaa Ser Ala Ala
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (4)..(4)
<223> OTHER INFORMATION: X is Dap
<220> FEATURE:
<221> NAME/KEY: misc_feature
<222> LOCATION: (10)..(10)
<223> OTHER INFORMATION: X is Cba
<220> FEATURE:
<221> NAME/KEY: misc_feature
<222> LOCATION: (11)..(11)
<223> OTHER INFORMATION: X is Dap

<400> SEQUENCE: 39

Leu Thr Xaa Xaa Glu Phe Trp Ala Gln Xaa Xaa Ser Ala Ala
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (4)..(4)
<223> OTHER INFORMATION: X is Dap(sulfone)
<220> FEATURE:
<221> NAME/KEY: misc_feature
<222> LOCATION: (10)..(10)
<223> OTHER INFORMATION: X is Cba
<220> FEATURE:
<221> NAME/KEY: misc_feature
<222> LOCATION: (11)..(11)
<223> OTHER INFORMATION: X is Dap

<400> SEQUENCE: 40

Leu Thr Xaa Xaa Glu Tyr Trp Ala Gln Xaa Xaa Ser Ala Ala
1               5                   10

<210> SEQ ID NO 41
<211> LENGTH: 14
```

```
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (10)..(10)
<223> OTHER INFORMATION: X is Cba

<400> SEQUENCE: 41

Leu Thr Xaa Lys Glu Tyr Trp Ala Glu Xaa Lys Ser Ala Ala
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: X is R8
<220> FEATURE:
<221> NAME/KEY: misc_feature
<222> LOCATION: (10)..(10)
<223> OTHER INFORMATION: X is Cba
<220> FEATURE:
<221> NAME/KEY: misc_feature
<222> LOCATION: (11)..(11)
<223> OTHER INFORMATION: X is S5

<400> SEQUENCE: 42

Leu Thr Phe Xaa Glu Tyr Trp Ala Glu Xaa Xaa Ser Ala Ala
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (4)..(4)
<223> OTHER INFORMATION: X is R8
<220> FEATURE:
<221> NAME/KEY: misc_feature
<222> LOCATION: (7)..(7)
<223> OTHER INFORMATION: X is Napa
<220> FEATURE:
<221> NAME/KEY: misc_feature
<222> LOCATION: (10)..(10)
<223> OTHER INFORMATION: X is Cba

<400> SEQUENCE: 43

Leu Thr Xaa Xaa Glu Tyr Xaa Ala Glu Xaa Lys Ser Ala Ala
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Synthetic polypeptide
```

```
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (4)..(4)
<223> OTHER INFORMATION: X may be Cys or S5 or portion of a cross-link
      or staple
<220> FEATURE:
<221> NAME/KEY: misc_feature
<222> LOCATION: (6)..(6)
<223> OTHER INFORMATION: X may be Cba or Leu
<220> FEATURE:
<221> NAME/KEY: misc_feature
<222> LOCATION: (8)..(8)
<223> OTHER INFORMATION: X may be Cys or S5 or a portion of a cross-link
      or staple
<220> FEATURE:
<221> NAME/KEY: misc_feature
<222> LOCATION: (9)..(9)
<223> OTHER INFORMATION: X may be Tyr or Dmf
<220> FEATURE:
<221> NAME/KEY: misc_feature
<222> LOCATION: (10)..(10)
<223> OTHER INFORMATION: X may be Tyr or F2f

<400> SEQUENCE: 44

Ile Thr Xaa Xaa Asp Xaa Leu Xaa Xaa Xaa Gly Pro
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (6)..(6)
<223> OTHER INFORMATION: X is Cba

<400> SEQUENCE: 45

Ile Thr Xaa Cys Asp Xaa Leu Cys Tyr Tyr Gly Pro
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (4)..(4)
<223> OTHER INFORMATION: X is S5
<220> FEATURE:
<221> NAME/KEY: misc_feature
<222> LOCATION: (6)..(6)
<223> OTHER INFORMATION: X is Cba
<220> FEATURE:
<221> NAME/KEY: misc_feature
<222> LOCATION: (8)..(8)
<223> OTHER INFORMATION: X is S5

<400> SEQUENCE: 46
```

Ile Thr Xaa Xaa Asp Xaa Leu Xaa Tyr Tyr Gly Pro
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: X may be Cys or Cys(ar) or a portion of a
      cross-link or staple
<220> FEATURE:
<221> NAME/KEY: misc_feature
<222> LOCATION: (11)..(11)
<223> OTHER INFORMATION: X may be Cys or Cys(ar) or a portion of a
      cross-link or staple

<400> SEQUENCE: 47

Leu Thr Phe Xaa His Tyr Trp Ala Gln Leu Xaa Ser Lys
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 48

Leu Thr Phe Cys His Tyr Trp Ala Gln Leu Cys Ser Lys
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: X is Cys(ar)
<220> FEATURE:
<221> NAME/KEY: misc_feature
<222> LOCATION: (11)..(11)
<223> OTHER INFORMATION: X is Cys(ar)

<400> SEQUENCE: 49

Leu Thr Phe Xaa His Tyr Trp Ala Gln Leu Xaa Ser Lys
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X may be Hexa, Hepa, Cha, or CF3f
<220> FEATURE:
<221> NAME/KEY: misc_feature
<222> LOCATION: (11)..(11)
<223> OTHER INFORMATION: X may be Homol, Cha, Cba, Leu, Hexa, or Trp

<400> SEQUENCE: 50

Lys Ala Trp Tyr Ala Asn Xaa Glu Lys Leu Xaa Arg

<210> SEQ ID NO 51
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (11)..(11)
<223> OTHER INFORMATION: X is Homol

<400> SEQUENCE: 51

Lys Ala Trp Tyr Ala Asn Xaa Glu Lys Leu Xaa Arg
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (11)..(11)
<223> OTHER INFORMATION: X is Cha

<400> SEQUENCE: 52

Lys Ala Trp Tyr Ala Asn Xaa Glu Lys Leu Xaa Arg
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feaure
<222> LOCATION: (7)..(7)
<223> OTHER INFORMATION: X is Cha

<400> SEQUENCE: 53

Lys Ala Trp Tyr Ala Asn Xaa Glu Lys Leu Leu Arg
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (11)..(11)
<223> OTHER INFORMATION: X is Hexa

<400> SEQUENCE: 54

Lys Ala Trp Tyr Ala Asn Xaa Glu Lys Leu Xaa Arg
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hexa

<400> SEQUENCE: 55

Lys Ala Trp Tyr Ala Asn Xaa Glu Lys Leu Trp Arg
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hepa
<220> FEATURE:
<221> NAME/KEY: misc_feature
<222> LOCATION: (11)..(11)
<223> OTHER INFORMATION: X is Cba

<400> SEQUENCE: 56

Lys Ala Trp Tyr Ala Asn Xaa Glu Lys Leu Xaa Arg
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hepa
<220> FEATURE:
<221> NAME/KEY: misc_feature
<222> LOCATION: (11)..(11)
<223> OTHER INFORMATION: X is Homol

<400> SEQUENCE: 57

Lys Ala Trp Tyr Ala Asn Xaa Glu Lys Leu Xaa Arg
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hepa
<220> FEATURE:
<221> NAME/KEY: misc_feature
<222> LOCATION: (11)..(11)
<223> OTHER INFORMATION: X is Hexa

<400> SEQUENCE: 58

```
Lys Ala Trp Tyr Ala Asn Xaa Glu Lys Leu Xaa Arg
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (11)..(11)
<223> OTHER INFORMATION: X is Cba

<400> SEQUENCE: 59

Lys Ala Trp Tyr Ala Asn Xaa Glu Lys Leu Xaa Arg
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hepa
<220> FEATURE:
<221> NAME/KEY: misc_feature
<222> LOCATION: (11)..(11)
<223> OTHER INFORMATION: X is Cha

<400> SEQUENCE: 60

Lys Ala Trp Tyr Ala Asn Xaa Glu Lys Leu Xaa Arg
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is CF3f

<400> SEQUENCE: 61

Lys Ala Trp Tyr Ala Asn Xaa Glu Lys Leu Leu Arg
1               5                   10

<210> SEQ ID NO 62
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X may be F2f or Phe
<220> FEATURE:
<221> NAME/KEY: misc_feature
<222> LOCATION: (4)..(4)
<223> OTHER INFORMATION: X may be a non-canonical alpha-amino acid
      (e.g., R8 or Dap) or a portion of a cross-link or staple
```

```
<220> FEATURE:
<221> NAME/KEY: misc_feature
<222> LOCATION: (6)..(6)
<223> OTHER INFORMATION: X may be Tyr or Phe
<220> FEATURE:
<221> NAME/KEY: misc_feature
<222> LOCATION: (7)..(7)
<223> OTHER INFORMATION: X may be Hexa, Napha, or Trp
<220> FEATURE:
<221> NAME/KEY: misc_feature
<222> LOCATION: (9)..(9)
<223> OTHER INFORMATION: X may be Gln or Glu
<220> FEATURE:
<221> NAME/KEY: misc_feature
<222> LOCATION: (10)..(10)
<223> OTHER INFORMATION: X is Cba
<220> FEATURE:
<221> NAME/KEY: misc_feature
<222> LOCATION: (11)..(11)
<223> OTHER INFORMATION: X may be a non-canonical alpha-amino acid
      (e.g., S5 or Dap) or a portion of a cross-link or staple
<220> FEATURE:
<221> NAME/KEY: misc_feature
<222> LOCATION: (13)..(14)
<223> OTHER INFORMATION: X may be absent

<400> SEQUENCE: 62

Leu Thr Xaa Xaa Glu Xaa Xaa Ala Xaa Xaa Xaa Ser Ala Ala
1               5                   10

<210> SEQ ID NO 63
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X may be F2f or Phe
<220> FEATURE:
<221> NAME/KEY: misc_feature
<222> LOCATION: (4)..(4)
<223> OTHER INFORMATION: X may be is R8 or Dap or a portion of a cross-
      link or staple
<220> FEATURE:
<221> NAME/KEY: misc_feature
<222> LOCATION: (6)..(6)
<223> OTHER INFORMATION: X may be Tyr or Phe
<220> FEATURE:
<221> NAME/KEY: misc_feature
<222> LOCATION: (7)..(7)
<223> OTHER INFORMATION: X may be Hexa, Napha, or Trp
<220> FEATURE:
<221> NAME/KEY: misc_feature
<222> LOCATION: (9)..(9)
<223> OTHER INFORMATION: X may be Gln or Glu
<220> FEATURE:
<221> NAME/KEY: misc_feature
<222> LOCATION: (10)..(10)
<223> OTHER INFORMATION: X is Cba
<220> FEATURE:
<221> NAME/KEY: misc_feature
<222> LOCATION: (11)..(11)
<223> OTHER INFORMATION: X may be S5 or Dap or a portion of a cross-link
      or staple
<220> FEATURE:
<221> NAME/KEY: misc_feature
<222> LOCATION: (13)..(14)
<223> OTHER INFORMATION: may be absent

<400> SEQUENCE: 63

Leu Thr Xaa Xaa Glu Xaa Xaa Ala Xaa Xaa Xaa Ser Ala Ala
1               5                   10
```

```
<210> SEQ ID NO 64
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: X is Cys or Cys(ar) or a portion of a cross-
      link or staple
<220> FEATURE:
<221> NAME/KEY: misc_feature
<222> LOCATION: (11)..(11)
<223> OTHER INFORMATION: X is Cys or Cys(ar) or a portion of a cross-
      link or staple

<400> SEQUENCE: 64

Leu Thr Phe Xaa His Tyr Trp Ala Gln Phe Xaa Ser Lys
1               5                   10

<210> SEQ ID NO 65
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: X is Cys(ar)
<220> FEATURE:
<221> NAME/KEY: misc_feature
<222> LOCATION: (11)..(11)
<223> OTHER INFORMATION: X is Cys(ar)

<400> SEQUENCE: 65

Leu Thr Phe Xaa His Tyr Trp Ala Gln Phe Xaa Ser Lys
1               5                   10

<210> SEQ ID NO 66
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 66

Leu Thr Phe Glu His Tyr Trp Ala Gln Tyr Thr Ser Lys
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 67

Leu Thr Tyr Glu His Tyr Trp Ala Gln Leu Thr Ser Lys
1               5                   10

<210> SEQ ID NO 68
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 68
```

Leu Thr Leu Glu His Tyr Trp Ala Gln Leu Thr Ser Lys
1               5                   10

<210> SEQ ID NO 69
<211> LENGTH: 25
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (6)..(6)
<223> OTHER INFORMATION: X is Cba

<400> SEQUENCE: 69

Ile Thr Phe Glu Asp Xaa Leu His Tyr Tyr Gly Pro Gly Ser Gly Ser
1               5                   10                  15

Gly Ser Gly Ser Gly Ser Gly Ser Lys
            20                  25

<210> SEQ ID NO 70
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 70

Ile Thr Phe Glu Asp Leu Leu His Tyr Tyr Gly Pro Gly Ser Gly Ser
1               5                   10                  15

Gly Ser Gly Ser Gly Ser Gly Ser Lys
            20                  25

<210> SEQ ID NO 71
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 71

Leu Thr Phe Glu His Tyr Trp Ala Gln Phe Thr Ser Lys
1               5                   10

<210> SEQ ID NO 72
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 72

Leu Thr Phe Glu His Tyr Trp Ala Gln Leu Thr Ser Lys
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 73

Leu Thr Phe Glu His Tyr Trp Ala Gln Tyr Thr Ser Lys
1               5                   10

```
<210> SEQ ID NO 74
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 74

Leu Thr Tyr Glu His Tyr Trp Ala Gln Leu Thr Ser Lys
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 75

Leu Thr Leu Glu His Tyr Trp Ala Gln Leu Thr Ser Lys
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 76

Leu Thr Phe Gln His Tyr Trp Ala Glu Leu Thr Ser Lys
1               5                   10

<210> SEQ ID NO 77
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 77

Leu Thr Phe Gln His Tyr Trp Ala Gly Leu Thr Ser Lys
1               5                   10

<210> SEQ ID NO 78
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 78

Leu Thr Phe Gln His Phe Trp Ala Glu Leu Thr Ser Lys
1               5                   10

<210> SEQ ID NO 79
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 79

Leu Thr Phe Pro His Tyr Trp Ala Glu Leu Thr Ser Lys
1               5                   10

<210> SEQ ID NO 80
```

```
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 80

Leu Thr Phe Pro His Tyr Trp Ala Ala Leu Thr Ser Lys
1               5                   10

<210> SEQ ID NO 81
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 81

Leu Thr Phe Glu His Tyr Trp Ala Ala Leu Thr Ser Lys
1               5                   10

<210> SEQ ID NO 82
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 82

Leu Thr Phe Ala His Glu Trp Ala Leu Leu Thr Ser Lys
1               5                   10

<210> SEQ ID NO 83
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 83

Leu Thr Phe Glu His Glu Trp Ala Leu Leu Thr Ser Lys
1               5                   10

<210> SEQ ID NO 84
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 84

Leu Thr Phe Phe His Tyr Trp Ala Gln Leu Thr Ser Lys
1               5                   10

<210> SEQ ID NO 85
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 85

Leu Thr Phe Ser His Tyr Trp Ala Ser Leu Thr Ser Lys
1               5                   10

<210> SEQ ID NO 86
<211> LENGTH: 13
```

```
<212> TYPE: PRT
<213> ORGANISM: Artificial Sequence
<220> FEATURE:
<223> OTHER INFORMATION: Synthetic polypeptide

<400> SEQUENCE: 86

Leu Thr Phe Glu His Glu Trp Ala Gln Leu Thr Ser Lys
1               5                   10

<210> SEQ ID NO 87
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 87

Leu Thr Phe Glu His Tyr Trp Ala Ala Leu Thr Ser Lys
1               5                   10

<210> SEQ ID NO 88
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 88

Leu Thr Phe Pro His Tyr Trp Ala Gln Leu Thr Ser Lys
1               5                   10

<210> SEQ ID NO 89
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 89

Leu Thr Phe Gln His Tyr Trp Ala Ser Leu Thr Ser Lys
1               5                   10

<210> SEQ ID NO 90
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 90

Leu Thr Phe Gln His Phe Trp Ala Glu Leu Thr Ser Lys
1               5                   10

<210> SEQ ID NO 91
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 91

Leu Thr Phe Phe His Tyr Trp Ala Gly Leu Thr Ser Lys
1               5                   10

<210> SEQ ID NO 92
<211> LENGTH: 13
<212> TYPE: PRT
```

```
<213> ORGANISM: Artificial Sequence
<220> FEATURE:
<223> OTHER INFORMATION: Synthetic polypeptide

<400> SEQUENCE: 92

Leu Thr Phe Pro His Phe Trp Ala Glu Leu Thr Ser Lys
1               5                   10

<210> SEQ ID NO 93
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 93

Leu Thr Phe Phe His Ala Trp Ala Glu Leu Thr Ser Lys
1               5                   10

<210> SEQ ID NO 94
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: X may be Gln, Pro, Ala, Glu, Phe, or Ser
<220> FEATURE:
<221> NAME/KEY: misc_feature
<222> LOCATION: (6)..(6)
<223> OTHER INFORMATION: X may be Phe, Tyr, Glu, or Ala
<220> FEATURE:
<221> NAME/KEY: misc_feature
<222> LOCATION: (9)..(9)
<223> OTHER INFORMATION: X may be Glu, Gly, Ala, Leu, Gln, or Ser

<400> SEQUENCE: 94

Leu Thr Phe Xaa His Xaa Trp Ala Xaa Leu Thr Ser Lys
1               5                   10

<210> SEQ ID NO 95
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is Ff
<220> FEATURE:
<221> NAME/KEY: misc_feature
<222> LOCATION: (7)..(7)
<223> OTHER INFORMATION: X is Hexa

<400> SEQUENCE: 95

Leu Thr Xaa Glu His Tyr Xaa Ala Gln Leu Thr Ser Lys
1               5                   10

<210> SEQ ID NO 96
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F3f
```

<220> FEATURE:
<221> NAME/KEY: misc_feature
<222> LOCATION: (7)..(7)
<223> OTHER INFORMATION: X is Homof
<220> FEATURE:
<221> NAME/KEY: misc_feature
<222> LOCATION: (10)..(10)
<223> OTHER INFORMATION: X is Cba

<400> SEQUENCE: 96

Leu Thr Xaa Glu His Tyr Xaa Ala Gln Xaa Thr Ser Lys
1               5                   10

<210> SEQ ID NO 97
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (7)..(7)
<223> OTHER INFORMATION: X is CF3f

<400> SEQUENCE: 97

Leu Thr Xaa Glu His Tyr Xaa Ala Gln Leu Thr Ser Lys
1               5                   10

<210> SEQ ID NO 98
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is Ff
<220> FEATURE:
<221> NAME/KEY: misc_feature
<222> LOCATION: (7)..(7)
<223> OTHER INFORMATION: X is Homof
<220> FEATURE:
<221> NAME/KEY: misc_feature
<222> LOCATION: (10)..(10)
<223> OTHER INFORMATION: X is Anon

<400> SEQUENCE: 98

Leu Thr Xaa Glu His Tyr Xaa Ala Gln Xaa Thr Ser Lys
1               5                   10

<210> SEQ ID NO 99
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is NH2f
<220> FEATURE:
<221> NAME/KEY: misc_feature
<222> LOCATION: (10)..(10)
<223> OTHER INFORMATION: X is Cba

<400> SEQUENCE: 99

Leu Thr Xaa Glu His Tyr Trp Ala Gln Xaa Thr Ser Lys

<210> SEQ ID NO 100
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is Dmf
<220> FEATURE:
<221> NAME/KEY: misc_feature
<222> LOCATION: (7)..(7)
<223> OTHER INFORMATION: X is CF3f
<220> FEATURE:
<221> NAME/KEY: misc_feature
<222> LOCATION: (10)..(10)
<223> OTHER INFORMATION: X is Dmf

<400> SEQUENCE: 100

Leu Thr Xaa Glu His Tyr Xaa Ala Gln Xaa Thr Ser Lys
1               5                   10

<210> SEQ ID NO 101
<211> LENGTH: 25
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (6)..(6)
<223> OTHER INFORMATION: X is Cba

<400> SEQUENCE: 101

Ile Thr Phe Glu Asp Xaa Leu His Tyr Tyr Gly Pro Gly Ser Gly Ser
1               5                   10                  15

Gly Ser Gly Ser Gly Ser Gly Ser Lys
            20                  25

<210> SEQ ID NO 102
<211> LENGTH: 25
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (9)..(9)
<223> OTHER INFORMATION: X is Dmf
<220> FEATURE:
<221> NAME/KEY: misc_feature
<222> LOCATION: (10)..(10)
<223> OTHER INFORMATION: X is F2f

<400> SEQUENCE: 102

Ile Thr Xaa Glu Asp Leu Leu His Xaa Xaa Gly Pro Gly Ser Gly Ser
1               5                   10                  15

Gly Ser Gly Ser Gly Ser Gly Ser Lys
            20                  25

<210> SEQ ID NO 103
<211> LENGTH: 25
<212> TYPE: PRT

<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (9)..(9)
<223> OTHER INFORMATION: X is Dmf

<400> SEQUENCE: 103

Ile Thr Xaa Glu Asp Leu Leu His Xaa Tyr Gly Pro Gly Ser Gly Ser
1               5                   10                  15

Gly Ser Gly Ser Gly Ser Gly Ser Lys
            20                  25

<210> SEQ ID NO 104
<211> LENGTH: 25
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f

<400> SEQUENCE: 104

Ile Thr Xaa Glu Asp Leu Leu His Tyr Tyr Gly Pro Gly Ser Gly Ser
1               5                   10                  15

Gly Ser Gly Ser Gly Ser Gly Ser Lys
            20                  25

<210> SEQ ID NO 105
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 105

Ile Thr Phe Glu Asp Leu Leu His Tyr Tyr Gly Pro Gly Ser Gly Ser
1               5                   10                  15

Gly Ser Gly Ser Gly Ser Gly Ser Lys
            20                  25

<210> SEQ ID NO 106
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is Hexa
<220> FEATURE:
<221> NAME/KEY: misc_feature
<222> LOCATION: (4)..(4)
<223> OTHER INFORMATION: X is R8
<220> FEATURE:
<221> NAME/KEY: misc_feature
<222> LOCATION: (7)..(7)
<223> OTHER INFORMATION: X is Cba
<220> FEATURE:
<221> NAME/KEY: misc_feature
<222> LOCATION: (10)..(10)
<223> OTHER INFORMATION: X is F2f -continued

```
<220> FEATURE:
<221> NAME/KEY: misc_feature
<222> LOCATION: (11)..(11)
<223> OTHER INFORMATION: X is S5

<400> SEQUENCE: 106

Leu Thr Xaa Xaa Glu Tyr Xaa Ala Gln Xaa Xaa Ser Ala Ala
1               5                   10

<210> SEQ ID NO 107
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: X is Dap
<220> FEATURE:
<221> NAME/KEY: misc_feature
<222> LOCATION: (7)..(7)
<223> OTHER INFORMATION: X is Cba
<220> FEATURE:
<221> NAME/KEY: misc_feature
<222> LOCATION: (10)..(10)
<223> OTHER INFORMATION: X is F2f
<220> FEATURE:
<221> NAME/KEY: misc_feature
<222> LOCATION: (11)..(11)
<223> OTHER INFORMATION: X is Dap

<400> SEQUENCE: 107

Leu Thr Trp Xaa Glu Tyr Xaa Ala Gln Xaa Xaa Ser Ala Ala
1               5                   10

<210> SEQ ID NO 108
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (4)..(4)
<223> OTHER INFORMATION: X is R8
<220> FEATURE:
<221> NAME/KEY: misc_feature
<222> LOCATION: (7)..(7)
<223> OTHER INFORMATION: X is Anta
<220> FEATURE:
<221> NAME/KEY: misc_feature
<222> LOCATION: (10)..(10)
<223> OTHER INFORMATION: X is Cba
<220> FEATURE:
<221> NAME/KEY: misc_feature
<222> LOCATION: (11)..(11)
<223> OTHER INFORMATION: X is S5

<400> SEQUENCE: 108

Leu Thr Xaa Xaa Glu Tyr Xaa Ala Glu Xaa Xaa Ser Ala Ala
1               5                   10

<210> SEQ ID NO 109
<211> LENGTH: 14
<212> TYPE: PRT
<213> ORGANISM: Artificial Sequence
<220> FEATURE:
<223> OTHER INFORMATION: Synthetic polypeptide
```

-continued

```
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (4)..(4)
<223> OTHER INFORMATION: X is Dap
<220> FEATURE:
<221> NAME/KEY: misc_feature
<222> LOCATION: (7)..(7)
<223> OTHER INFORMATION: X is Anta
<220> FEATURE:
<221> NAME/KEY: misc_feature
<222> LOCATION: (10)..(10)
<223> OTHER INFORMATION: X is Cba
<220> FEATURE:
<221> NAME/KEY: misc_feature
<222> LOCATION: (11)..(11)
<223> OTHER INFORMATION: X is Dap

<400> SEQUENCE: 109

Leu Thr Xaa Xaa Glu Tyr Xaa Ala Glu Xaa Xaa Ser Ala Ala
1               5                   10

<210> SEQ ID NO 110
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (7)..(7)
<223> OTHER INFORMATION: X is Anta
<220> FEATURE:
<221> NAME/KEY: misc_feature
<222> LOCATION: (10)..(10)
<223> OTHER INFORMATION: X is Cba

<400> SEQUENCE: 110

Leu Thr Xaa Lys Glu Tyr Xaa Ala Glu Xaa Lys Ser Ala Ala
1               5                   10

<210> SEQ ID NO 111
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (4)..(4)
<223> OTHER INFORMATION: X is Dap
<220> FEATURE:
<221> NAME/KEY: misc_feature
<222> LOCATION: (7)..(7)
<223> OTHER INFORMATION: X is Napa
<220> FEATURE:
<221> NAME/KEY: misc_feature
<222> LOCATION: (10)..(10)
<223> OTHER INFORMATION: X is Cba
<220> FEATURE:
<221> NAME/KEY: misc_feature
<222> LOCATION: (11)..(11)
<223> OTHER INFORMATION: X is Dap
```

<400> SEQUENCE: 111

Leu Thr Xaa Xaa Glu Tyr Xaa Ala Glu Xaa Xaa Ser Ala Ala
1               5                   10

<210> SEQ ID NO 112
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (7)..(7)
<223> OTHER INFORMATION: X is Napa
<220> FEATURE:
<221> NAME/KEY: misc_feature
<222> LOCATION: (10)..(10)
<223> OTHER INFORMATION: X is Cba

<400> SEQUENCE: 112

Leu Thr Xaa Lys Glu Tyr Xaa Ala Glu Xaa Lys Ser Ala Ala
1               5                   10

<210> SEQ ID NO 113
<211> LENGTH: 25
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (6)..(6)
<223> OTHER INFORMATION: X is Cba
<220> FEATURE:
<221> NAME/KEY: misc_feature
<222> LOCATION: (9)..(9)
<223> OTHER INFORMATION: X is Dmf
<220> FEATURE:
<221> NAME/KEY: misc_feature
<222> LOCATION: (10)..(10)
<223> OTHER INFORMATION: X is F2f

<400> SEQUENCE: 113

Ile Thr Xaa Cys Asp Xaa Leu Cys Xaa Xaa Gly Pro Gly Ser Gly Ser
1               5                   10                  15

Gly Ser Gly Ser Gly Ser Gly Ser Lys
            20                  25

<210> SEQ ID NO 114
<211> LENGTH: 25
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (4)..(4)
<223> OTHER INFORMATION: X is S5
<220> FEATURE:
<221> NAME/KEY: misc_feature

```
<222> LOCATION: (8)..(8)
<223> OTHER INFORMATION: X is S5
<220> FEATURE:
<221> NAME/KEY: misc_feature
<222> LOCATION: (9)..(9)
<223> OTHER INFORMATION: X is Dmf
<220> FEATURE:
<221> NAME/KEY: misc_feature
<222> LOCATION: (10)..(10)
<223> OTHER INFORMATION: X is F2f

<400> SEQUENCE: 114

Ile Thr Xaa Xaa Asp Leu Leu Xaa Xaa Xaa Gly Pro Gly Ser Gly Ser
1               5                   10                  15

Gly Ser Gly Ser Gly Ser Gly Ser Lys
            20                  25

<210> SEQ ID NO 115
<211> LENGTH: 25
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: X is S5
<220> FEATURE:
<221> NAME/KEY: misc_feature
<222> LOCATION: (8)..(8)
<223> OTHER INFORMATION: X is S5

<400> SEQUENCE: 115

Ile Thr Phe Xaa Asp Leu Leu Xaa Tyr Tyr Gly Pro Gly Ser Gly Ser
1               5                   10                  15

Gly Ser Gly Ser Gly Ser Gly Ser Lys
            20                  25

<210> SEQ ID NO 116
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (11)..(11)
<223> OTHER INFORMATION: X is Cys(ar)

<400> SEQUENCE: 116

Leu Thr Phe Cys His Tyr Trp Ala Gln Leu Xaa Ser Lys
1               5                   10

<210> SEQ ID NO 117
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hexa

<400> SEQUENCE: 117

Lys Ala Trp Tyr Ala Asn Xaa Glu Lys Leu Trp Arg
1               5                   10

<210> SEQ ID NO 118
```

```
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is CF3f

<400> SEQUENCE: 118

Lys Ala Trp Tyr Ala Asn Xaa Glu Lys Leu Leu Arg
1               5                   10

<210> SEQ ID NO 119
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hexa

<400> SEQUENCE: 119

Lys Ala Trp Tyr Ala Asn Xaa Glu Lys Leu Leu Arg
1               5                   10

<210> SEQ ID NO 120
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (11)..(11)
<223> OTHER INFORMATION: X is Cha

<400> SEQUENCE: 120

Lys Ala Trp Tyr Ala Asn Xaa Glu Lys Leu Xaa Arg
1               5                   10

<210> SEQ ID NO 121
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (11)..(11)
<223> OTHER INFORMATION: X is F2f

<400> SEQUENCE: 121

Lys Ala Trp Tyr Ala Asn Xaa Glu Lys Leu Xaa Arg
1               5                   10

<210> SEQ ID NO 122
<211> LENGTH: 12
<212> TYPE: PRT
<213> ORGANISM: Artificial Sequence
```

```
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Cha

<400> SEQUENCE: 122

Lys Ala Trp Tyr Ala Asn Xaa Glu Lys Leu Leu Arg
1               5                   10

<210> SEQ ID NO 123
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (11)..(11)
<223> OTHER INFORMATION: X is Cba

<400> SEQUENCE: 123

Lys Ala Trp Tyr Ala Asn Xaa Glu Lys Leu Xaa Arg
1               5                   10

<210> SEQ ID NO 124
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is CF3f
<220> FEATURE:
<221> NAME/KEY: misc_feature
<222> LOCATION: (11)..(11)
<223> OTHER INFORMATION: X is Homol

<400> SEQUENCE: 124

Lys Ala Trp Tyr Ala Asn Xaa Glu Lys Leu Xaa Arg
1               5                   10

<210> SEQ ID NO 125
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (11)..(11)
<223> OTHER INFORMATION: X is Homol

<400> SEQUENCE: 125

Lys Ala Trp Tyr Ala Asn Xaa Glu Lys Leu Xaa Arg
1               5                   10

<210> SEQ ID NO 126
<211> LENGTH: 12
<212> TYPE: PRT
```

```
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hepa
<220> FEATURE:
<221> NAME/KEY: misc_feature
<222> LOCATION: (11)..(11)
<223> OTHER INFORMATION: X is Homol

<400> SEQUENCE: 126

Lys Ala Trp Tyr Ala Asn Xaa Glu Lys Leu Xaa Arg
1               5                   10

<210> SEQ ID NO 127
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is CF3f
<220> FEATURE:
<221> NAME/KEY: misc_feature
<222> LOCATION: (11)..(11)
<223> OTHER INFORMATION: X is Cba

<400> SEQUENCE: 127

Lys Ala Trp Tyr Ala Asn Xaa Glu Lys Leu Xaa Arg
1               5                   10

<210> SEQ ID NO 128
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (11)..(11)
<223> OTHER INFORMATION: X is Hexa

<400> SEQUENCE: 128

Lys Ala Trp Tyr Ala Asn Xaa Glu Lys Leu Xaa Arg
1               5                   10

<210> SEQ ID NO 129
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is CF3f
<220> FEATURE:
<221> NAME/KEY: misc_feature
<222> LOCATION: (11)..(11)
<223> OTHER INFORMATION: X is F2f

<400> SEQUENCE: 129

Lys Ala Trp Tyr Ala Asn Xaa Glu Lys Leu Xaa Arg
1               5                   10
```

```
<210> SEQ ID NO 130
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hepa
<220> FEATURE:
<221> NAME/KEY: misc_feature
<222> LOCATION: (11)..(11)
<223> OTHER INFORMATION: X is Cha

<400> SEQUENCE: 130

Lys Ala Trp Tyr Ala Asn Xaa Glu Lys Leu Xaa Arg
1               5                   10

<210> SEQ ID NO 131
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hepa
<220> FEATURE:
<221> NAME/KEY: misc_feature
<222> LOCATION: (11)..(11)
<223> OTHER INFORMATION: X is Cba

<400> SEQUENCE: 131

Lys Ala Trp Tyr Ala Asn Xaa Glu Lys Leu Xaa Arg
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hepa
<220> FEATURE:
<221> NAME/KEY: misc_feature
<222> LOCATION: (11)..(11)
<223> OTHER INFORMATION: X is F2f

<400> SEQUENCE: 132

Lys Ala Trp Tyr Ala Asn Xaa Glu Lys Leu Xaa Arg
1               5                   10

<210> SEQ ID NO 133
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hepa
<220> FEATURE:
<221> NAME/KEY: misc_feature
<222> LOCATION: (11)..(11)
<223> OTHER INFORMATION: X is Hexa
```

<400> SEQUENCE: 133

Lys Ala Trp Tyr Ala Asn Xaa Glu Lys Leu Xaa Arg
1               5                   10

<210> SEQ ID NO 134
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is CF3f
<220> FEATURE:
<221> NAME/KEY: misc_feature
<222> LOCATION: (11)..(11)
<223> OTHER INFORMATION: X is Cha

<400> SEQUENCE: 134

Lys Ala Trp Tyr Ala Asn Xaa Glu Lys Leu Xaa Arg
1               5                   10

<210> SEQ ID NO 135
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (11)..(11)
<223> OTHER INFORMATION: X is CF3f
<220> FEATURE:
<221> NAME/KEY: misc_feature
<222> LOCATION: (13)..(13)
<223> OTHER INFORMATION: X is Diol
<220> FEATURE:
<221> NAME/KEY: mod_res
<222> LOCATION: (17)..(17)
<223> OTHER INFORMATION: bAla

<400> SEQUENCE: 135

Lys Ala Trp Tyr Ala Asn Leu Glu Lys Leu Xaa Arg Xaa Gly Gly Ser
1               5                   10                  15
Ala

<210> SEQ ID NO 136
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (13)..(13)
<223> OTHER INFORMATION: X is Diol
<220> FEATURE:
<221> NAME/KEY: mod_res
<222> LOCATION: (17)..(17)
<223> OTHER INFORMATION: bAla

<400> SEQUENCE: 136

Lys Ala Ala Tyr Ala Asn Ala Glu Lys Leu Ala Arg Xaa Gly Gly Ser
1               5                   10                  15
Ala

<210> SEQ ID NO 137

```
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 137

Gly Ser Gly Ser Gly Ser Gly Ser Gly Ser Gly Ser Gln Glu Thr
1               5                   10                  15

Phe Ser Asp Leu Trp Lys Leu Leu Pro Glu Asn
            20                  25

<210> SEQ ID NO 138
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (12)..(12)
<223> OTHER INFORMATION: X is Diol

<400> SEQUENCE: 138

Gly Cys Pro Arg Ile Met Arg Cys Lys Gln Asp Xaa Asp Cys Leu Ala
1               5                   10                  15

Gly Cys Val Cys Gly Pro Asn Gly Phe Cys Gly
            20                  25

<210> SEQ ID NO 139
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (4)..(4)
<223> OTHER INFORMATION: X is R8
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (10)..(10)
<223> OTHER INFORMATION: X is Cba
<220> FEATURE:
<221> NAME/KEY: misc_feature
<222> LOCATION: (11)..(11)
<223> OTHER INFORMATION: X is S5

<400> SEQUENCE: 139

Leu Thr Xaa Xaa Glu Tyr Xaa Ala Gln Xaa Xaa Ser Ala Ala
1               5                   10

<210> SEQ ID NO 140
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
```

```
<221> NAME/KEY: misc_feature
<222> LOCATION: (4)..(4)
<223> OTHER INFORMATION: X is Dap (sulfone)
<220> FEATURE:
<221> NAME/KEY: misc_feature
<222> LOCATION: (10)..(10)
<223> OTHER INFORMATION: X is Cba
<220> FEATURE:
<221> NAME/KEY: misc_feature
<222> LOCATION: (11)..(11)
<223> OTHER INFORMATION: X is Dap

<400> SEQUENCE: 140

Leu Thr Xaa Xaa Glu Tyr Trp Ala Gln Xaa Xaa Ser Ala Ala
1               5                   10

<210> SEQ ID NO 141
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: Cys(sulfone)
<220> FEATURE:
<221> NAME/KEY: misc_feature
<222> LOCATION: (11)..(11)
<223> OTHER INFORMATION: Cys(sulfone)

<400> SEQUENCE: 141

Leu Thr Phe Cys Glu Tyr Trp Ala Gln Leu Cys Ser Ala Ala
1               5                   10

<210> SEQ ID NO 142
<211> LENGTH: 25
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (6)..(6)
<223> OTHER INFORMATION: X is Cba

<400> SEQUENCE: 142

Ile Thr Xaa Glu Asp Xaa Leu His Tyr Tyr Gly Pro Gly Ser Gly Ser
1               5                   10                  15

Gly Ser Gly Ser Gly Ser Gly Ser Lys
            20                  25

<210> SEQ ID NO 143
<211> LENGTH: 25
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (6)..(6)
<223> OTHER INFORMATION: X is Cba
<220> FEATURE:
<221> NAME/KEY: misc_feature
```

<222> LOCATION: (9)..(9)
<223> OTHER INFORMATION: X is Dmf

<400> SEQUENCE: 143

Ile Thr Xaa Glu Asp Xaa Leu His Xaa Tyr Gly Pro Gly Ser Gly Ser
1               5                   10                  15

Gly Ser Gly Ser Gly Ser Gly Ser Lys
            20                  25

<210> SEQ ID NO 144
<211> LENGTH: 25
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (6)..(6)
<223> OTHER INFORMATION: X is Cba
<220> FEATURE:
<221> NAME/KEY: misc_feature
<222> LOCATION: (9)..(9)
<223> OTHER INFORMATION: X is Dmf
<220> FEATURE:
<221> NAME/KEY: misc_feature
<222> LOCATION: (10)..(10)
<223> OTHER INFORMATION: X is F2f

<400> SEQUENCE: 144

Ile Thr Xaa Glu Asp Xaa Leu His Xaa Xaa Gly Pro Gly Ser Gly Ser
1               5                   10                  15

Gly Ser Gly Ser Gly Ser Gly Ser Lys
            20                  25

<210> SEQ ID NO 145
<211> LENGTH: 25
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (6)..(6)
<223> OTHER INFORMATION: X is Cba

<400> SEQUENCE: 145

Ile Thr Xaa Cys Asp Xaa Leu Cys Tyr Tyr Gly Pro Gly Ser Gly Ser
1               5                   10                  15

Gly Ser Gly Ser Gly Ser Gly Ser Lys
            20                  25

<210> SEQ ID NO 146
<211> LENGTH: 25
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:

```
<221> NAME/KEY: misc_feature
<222> LOCATION: (4)..(4)
<223> OTHER INFORMATION: X is S5
<220> FEATURE:
<221> NAME/KEY: misc_feature
<222> LOCATION: (6)..(6)
<223> OTHER INFORMATION: X is Cba
<220> FEATURE:
<221> NAME/KEY: misc_feature
<222> LOCATION: (8)..(8)
<223> OTHER INFORMATION: X is S5

<400> SEQUENCE: 146

Ile Thr Xaa Xaa Asp Xaa Leu Xaa Tyr Tyr Gly Pro Gly Ser Gly Ser
1               5                   10                  15

Gly Ser Gly Ser Gly Ser Gly Ser Lys
            20                  25

<210> SEQ ID NO 147
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (11)..(11)
<223> OTHER INFORMATION: X is Homo1
<220> FEATURE:
<221> NAME/KEY: misc_feature
<222> LOCATION: (13)..(13)
<223> OTHER INFORMATION: X is Diol
<220> FEATURE:
<221> NAME/KEY: mod_res
<222> LOCATION: (17)..(17)
<223> OTHER INFORMATION: bAla

<400> SEQUENCE: 147

Lys Ala Trp Tyr Ala Asn Xaa Glu Lys Leu Xaa Arg Xaa Gly Gly Ser
1               5                   10                  15
Ala

<210> SEQ ID NO 148
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (11)..(11)
<223> OTHER INFORMATION: X is Cha
<220> FEATURE:
<221> NAME/KEY: misc_feature
<222> LOCATION: (13)..(13)
<223> OTHER INFORMATION: X is Diol
<220> FEATURE:
<221> NAME/KEY: mod_res
<222> LOCATION: (17)..(17)
<223> OTHER INFORMATION: bAla

<400> SEQUENCE: 148

Lys Ala Trp Tyr Ala Asn Xaa Glu Lys Leu Xaa Arg Xaa Gly Gly Ser
1               5                   10                  15
```

Ala

```
<210> SEQ ID NO 149
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Cha
<220> FEATURE:
<221> NAME/KEY: misc_feature
<222> LOCATION: (13)..(13)
<223> OTHER INFORMATION: X is Diol
<220> FEATURE:
<221> NAME/KEY: mod_res
<222> LOCATION: (17)..(17)
<223> OTHER INFORMATION: bAla

<400> SEQUENCE: 149

Lys Ala Trp Tyr Ala Asn Xaa Glu Lys Leu Leu Arg Xaa Gly Gly Ser
1               5                   10                  15

Ala

<210> SEQ ID NO 150
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (11)..(11)
<223> OTHER INFORMATION: X is Hexa
<220> FEATURE:
<221> NAME/KEY: misc_feature
<222> LOCATION: (13)..(13)
<223> OTHER INFORMATION: X is Diol
<220> FEATURE:
<221> NAME/KEY: mod_res
<222> LOCATION: (17)..(17)
<223> OTHER INFORMATION: bAla

<400> SEQUENCE: 150

Lys Ala Trp Tyr Ala Asn Xaa Glu Lys Leu Xaa Arg Xaa Gly Gly Ser
1               5                   10                  15

Ala

<210> SEQ ID NO 151
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (13)..(13)
<223> OTHER INFORMATION: X is Diol
<220> FEATURE:
<221> NAME/KEY: mod_res
<222> LOCATION: (17)..(17)
```

<223> OTHER INFORMATION: bAla

<400> SEQUENCE: 151

Lys Ala Trp Tyr Ala Asn Xaa Glu Lys Leu Trp Arg Xaa Gly Gly Ser
1               5                   10                  15

Ala

<210> SEQ ID NO 152
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hepa
<220> FEATURE:
<221> NAME/KEY: misc_feature
<222> LOCATION: (11)..(11)
<223> OTHER INFORMATION: X is Cba
<220> FEATURE:
<221> NAME/KEY: misc_feature
<222> LOCATION: (13)..(13)
<223> OTHER INFORMATION: X is Diol
<220> FEATURE:
<221> NAME/KEY: mod_res
<222> LOCATION: (17)..(17)
<223> OTHER INFORMATION: bAla

<400> SEQUENCE: 152

Lys Ala Trp Tyr Ala Asn Xaa Glu Lys Leu Xaa Arg Xaa Gly Gly Ser
1               5                   10                  15

Ala

<210> SEQ ID NO 153
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hepa
<220> FEATURE:
<221> NAME/KEY: misc_feature
<222> LOCATION: (11)..(11)
<223> OTHER INFORMATION: X is Homol
<220> FEATURE:
<221> NAME/KEY: misc_feature
<222> LOCATION: (13)..(13)
<223> OTHER INFORMATION: X is Diol
<220> FEATURE:
<221> NAME/KEY: mod_res
<222> LOCATION: (17)..(17)
<223> OTHER INFORMATION: bAla

<400> SEQUENCE: 153

Lys Ala Trp Tyr Ala Asn Xaa Glu Lys Leu Xaa Arg Xaa Gly Gly Ser
1               5                   10                  15

Ala

<210> SEQ ID NO 154
<211> LENGTH: 17
<212> TYPE: PRT
<213> ORGANISM: Artificial Sequence
<220> FEATURE:
<223> OTHER INFORMATION: Synthetic polypeptide
<220> FEATURE:

```
<221> NAME/KEY: misc_feature
<222> LOCATION: (7)..(7)
<223> OTHER INFORMATION: X is Hepa
<220> FEATURE:
<221> NAME/KEY: misc_feature
<222> LOCATION: (11)..(11)
<223> OTHER INFORMATION: X is Hexa
<220> FEATURE:
<221> NAME/KEY: misc_feature
<222> LOCATION: (13)..(13)
<223> OTHER INFORMATION: X is Diol
<220> FEATURE:
<221> NAME/KEY: mod_res
<222> LOCATION: (17)..(17)
<223> OTHER INFORMATION: bAla

<400> SEQUENCE: 154

Lys Ala Trp Tyr Ala Asn Xaa Glu Lys Leu Xaa Arg Xaa Gly Gly Ser
1               5                   10                  15

Ala

<210> SEQ ID NO 155
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (11)..(11)
<223> OTHER INFORMATION: X is Cba
<220> FEATURE:
<221> NAME/KEY: misc_feature
<222> LOCATION: (13)..(13)
<223> OTHER INFORMATION: X is Diol
<220> FEATURE:
<221> NAME/KEY: mod_res
<222> LOCATION: (17)..(17)
<223> OTHER INFORMATION: bAla

<400> SEQUENCE: 155

Lys Ala Trp Tyr Ala Asn Xaa Glu Lys Leu Xaa Arg Xaa Gly Gly Ser
1               5                   10                  15

Ala

<210> SEQ ID NO 156
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hepa
<220> FEATURE:
<221> NAME/KEY: misc_feature
<222> LOCATION: (11)..(11)
<223> OTHER INFORMATION: X is Cha
<220> FEATURE:
<221> NAME/KEY: misc_feature
<222> LOCATION: (13)..(13)
<223> OTHER INFORMATION: X is Diol
<220> FEATURE:
<221> NAME/KEY: mod_res
<222> LOCATION: (17)..(17)
<223> OTHER INFORMATION: bAla

<400> SEQUENCE: 156
```

```
Lys Ala Trp Tyr Ala Asn Xaa Glu Lys Leu Xaa Arg Xaa Gly Gly Ser
1               5                   10                  15

Ala

<210> SEQ ID NO 157
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is CF3f
<220> FEATURE:
<221> NAME/KEY: misc_feature
<222> LOCATION: (13)..(13)
<223> OTHER INFORMATION: X is Diol
<220> FEATURE:
<221> NAME/KEY: mod_res
<222> LOCATION: (17)..(17)
<223> OTHER INFORMATION: bAla

<400> SEQUENCE: 157

Lys Ala Trp Tyr Ala Asn Xaa Glu Lys Leu Leu Arg Xaa Gly Gly Ser
1               5                   10                  15

Ala

<210> SEQ ID NO 158
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is CF3f

<400> SEQUENCE: 158

Lys Ala Trp Tyr Ala Asn Xaa Glu Lys Leu Leu Arg
1               5                   10

<210> SEQ ID NO 159
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 159

Leu Thr Phe Pro His Phe Trp Ala Glu Leu Thr Ser Lys
1               5                   10

<210> SEQ ID NO 160
<211> LENGTH: 25
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (6)..(6)
<223> OTHER INFORMATION: X is Cba
```

```
<400> SEQUENCE: 160

Ile Thr Xaa Glu Asp Xaa Leu His Tyr Tyr Gly Pro Gly Ser Gly Ser
1               5                   10                  15

Gly Ser Gly Ser Gly Ser Gly Ser Lys
            20                  25

<210> SEQ ID NO 161
<211> LENGTH: 25
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (6)..(6)
<223> OTHER INFORMATION: X is Cba
<220> FEATURE:
<221> NAME/KEY: misc_feature
<222> LOCATION: (9)..(9)
<223> OTHER INFORMATION: X is Dmf

<400> SEQUENCE: 161

Ile Thr Xaa Glu Asp Xaa Leu His Xaa Tyr Gly Pro Gly Ser Gly Ser
1               5                   10                  15

Gly Ser Gly Ser Gly Ser Gly Ser Lys
            20                  25

<210> SEQ ID NO 162
<211> LENGTH: 25
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (6)..(6)
<223> OTHER INFORMATION: X is Cba
<220> FEATURE:
<221> NAME/KEY: misc_feature
<222> LOCATION: (9)..(9)
<223> OTHER INFORMATION: X is Dmf
<220> FEATURE:
<221> NAME/KEY: misc_feature
<222> LOCATION: (10)..(10)
<223> OTHER INFORMATION: X is F2f

<400> SEQUENCE: 162

Ile Thr Xaa Glu Asp Xaa Leu His Xaa Xaa Gly Pro Gly Ser Gly Ser
1               5                   10                  15

Gly Ser Gly Ser Gly Ser Gly Ser Lys
            20                  25

<210> SEQ ID NO 163
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hexa
```

```
<220> FEATURE:
<221> NAME/KEY: misc_feature
<222> LOCATION: (11)..(11)
<223> OTHER INFORMATION: X is Homol
<220> FEATURE:
<221> NAME/KEY: misc_feature
<222> LOCATION: (13)..(13)
<223> OTHER INFORMATION: X is Diol
<220> FEATURE:
<221> NAME/KEY: MOD_RES
<222> LOCATION: (17)..(17)
<223> OTHER INFORMATION: bAla

<400> SEQUENCE: 163

Lys Ala Trp Tyr Ala Asn Xaa Glu Lys Leu Xaa Arg Xaa Gly Gly Ser
1               5                   10                  15

Ala

<210> SEQ ID NO 164
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (11)..(11)
<223> OTHER INFORMATION: X is Cha
<220> FEATURE:
<221> NAME/KEY: misc_feature
<222> LOCATION: (13)..(13)
<223> OTHER INFORMATION: X is Diol
<220> FEATURE:
<221> NAME/KEY: mod_res
<222> LOCATION: (17)..(17)
<223> OTHER INFORMATION: bAla

<400> SEQUENCE: 164

Lys Ala Trp Tyr Ala Asn Xaa Glu Lys Leu Xaa Arg Xaa Gly Gly Ser
1               5                   10                  15

Ala

<210> SEQ ID NO 165
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Cha
<220> FEATURE:
<221> NAME/KEY: misc_feature
<222> LOCATION: (13)..(13)
<223> OTHER INFORMATION: X is Diol
<220> FEATURE:
<221> NAME/KEY: mod_res
<222> LOCATION: (17)..(17)
<223> OTHER INFORMATION: bAla

<400> SEQUENCE: 165

Lys Ala Trp Tyr Ala Asn Xaa Glu Lys Leu Leu Arg Xaa Gly Gly Ser
1               5                   10                  15

Ala
```

-continued

```
<210> SEQ ID NO 166
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (11)..(11)
<223> OTHER INFORMATION: X is Hexa
<220> FEATURE:
<221> NAME/KEY: misc_feature
<222> LOCATION: (13)..(13)
<223> OTHER INFORMATION: X is Diol
<220> FEATURE:
<221> NAME/KEY: mod_res
<222> LOCATION: (17)..(17)
<223> OTHER INFORMATION: bAla

<400> SEQUENCE: 166

Lys Ala Trp Tyr Ala Asn Xaa Glu Lys Leu Xaa Arg Xaa Gly Gly Ser
1               5                   10                  15

Ala

<210> SEQ ID NO 167
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (13)..(13)
<223> OTHER INFORMATION: X is Diol
<220> FEATURE:
<221> NAME/KEY: mod_res
<222> LOCATION: (17)..(17)
<223> OTHER INFORMATION: bAla

<400> SEQUENCE: 167

Lys Ala Trp Tyr Ala Asn Xaa Glu Lys Leu Trp Arg Xaa Gly Gly Ser
1               5                   10                  15

Ala

<210> SEQ ID NO 168
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is CF3f
<220> FEATURE:
<221> NAME/KEY: misc_feature
<222> LOCATION: (13)..(13)
<223> OTHER INFORMATION: X is Diol
<220> FEATURE:
<221> NAME/KEY: mod_res
<222> LOCATION: (17)..(17)
<223> OTHER INFORMATION: bAla

<400> SEQUENCE: 168
```

```
Lys Ala Trp Tyr Ala Asn Xaa Glu Lys Leu Leu Arg Xaa Gly Gly Ser
1               5                   10                  15

Ala

<210> SEQ ID NO 169
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is CF3f

<400> SEQUENCE: 169

Lys Ala Trp Tyr Ala Asn Xaa Glu Lys Leu Leu Arg
1               5                   10

<210> SEQ ID NO 170
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (6)..(6)
<223> OTHER INFORMATION: X is Cba

<400> SEQUENCE: 170

Ile Thr Xaa Glu Asp Xaa Leu His Tyr Tyr Gly Ser Gly Ser Gly Ser
1               5                   10                  15

Gly Ser Gly Ser Gly Ser Lys
            20

<210> SEQ ID NO 171
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (4)..(4)
<223> OTHER INFORMATION: X is R8
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (10)..(10)
<223> OTHER INFORMATION: X is Cba
<220> FEATURE:
<221> NAME/KEY: misc_feature
<222> LOCATION: (11)..(11)
<223> OTHER INFORMATION: X is S5

<400> SEQUENCE: 171

Leu Thr Xaa Xaa Glu Tyr Xaa Ala Gln Xaa Xaa Ser Ala Ala
1               5                   10
```

```
<210> SEQ ID NO 172
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (10)..(10)
<223> OTHER INFORMATION: X is Cba

<400> SEQUENCE: 172

Leu Thr Xaa Glu His Tyr Xaa Ala Gln Xaa Thr Ser Lys
1               5                   10

<210> SEQ ID NO 173
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (10)..(10)
<223> OTHER INFORMATION: X is Cba

<400> SEQUENCE: 173

Leu Thr Xaa Glu His Tyr Trp Ala Gln Xaa Thr Ser Lys
1               5                   10

<210> SEQ ID NO 174
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (4)..(4)
<223> OTHER INFORMATION: X is R8
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (10)..(10)
<223> OTHER INFORMATION: X is Cba
<220> FEATURE:
<221> NAME/KEY: misc_feature
<222> LOCATION: (11)..(11)
<223> OTHER INFORMATION: X is S5

<400> SEQUENCE: 174

Leu Thr Xaa Xaa Glu Tyr Xaa Ala Gln Xaa Xaa Ser Ala Ala
1               5                   10
```

```
<210> SEQ ID NO 175
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: X is Cys(ar)
<220> FEATURE:
<221> NAME/KEY: misc_feature
<222> LOCATION: (11)..(11)
<223> OTHER INFORMATION: X is Cys(ar)

<400> SEQUENCE: 175

Leu Thr Phe Xaa His Tyr Trp Ala Gln Leu Xaa Ser Lys
1               5                   10

<210> SEQ ID NO 176
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: X is F2f
<220> FEATURE:
<221> NAME/KEY: misc_feature
<222> LOCATION: (4)..(4)
<223> OTHER INFORMATION: X is R8
<220> FEATURE:
<221> NAME/KEY: misc_feature
<222> LOCATION: (7)..(7)
<223> OTHER INFORMATION: X is Napa
<220> FEATURE:
<221> NAME/KEY: misc_feature
<222> LOCATION: (10)..(10)
<223> OTHER INFORMATION: X is Cba
<220> FEATURE:
<221> NAME/KEY: misc_feature
<222> LOCATION: (11)..(11)
<223> OTHER INFORMATION: X is S5

<400> SEQUENCE: 176

Leu Thr Xaa Xaa Glu Tyr Xaa Ala Glu Xaa Xaa Ser Ala Ala
1               5                   10

<210> SEQ ID NO 177
<211> LENGTH: 37
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: X is Hexa
<220> FEATURE:
<221> NAME/KEY: misc_feature
<222> LOCATION: (11)..(11)
<223> OTHER INFORMATION: X is Homol
<220> FEATURE:
<221> NAME/KEY: misc_feature
<222> LOCATION: (13)..(13)
<223> OTHER INFORMATION: X is Diol
<220> FEATURE:
<221> NAME/KEY: mod_res
<222> LOCATION: (17)..(17)
<223> OTHER INFORMATION: bAla

<400> SEQUENCE: 177
```

```
Lys Ala Trp Tyr Ala Asn Xaa Glu Lys Leu Xaa Arg Xaa Gly Gly Ser
1               5                   10                  15

Ala Cys Lys Gln Asp Ser Asp Cys Leu Ala Gly Ser Val Cys Gly Pro
            20                  25                  30

Asn Gly Phe Cys Gly
            35

<210> SEQ ID NO 178
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: REPEAT
<222> LOCATION: (1)..(2)
<223> OTHER INFORMATION: May be repeated up to 12 times

<400> SEQUENCE: 178

Gly Ser Lys
1

<210> SEQ ID NO 179
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: Xaa may be Ala, Leu, Ser, Pro, Gln, Gly, Phe,
      Tyr, Trp, Glu
<220> FEATURE:
<221> NAME/KEY: misc_feature
<222> LOCATION: (6)..(7)
<223> OTHER INFORMATION: Xaa may be Ala, Leu, Ser, Pro, Gln, Gly, Phe,
      Tyr, Trp, Glu
<220> FEATURE:
<221> NAME/KEY: misc_feature
<222> LOCATION: (9)..(10)
<223> OTHER INFORMATION: Xaa may be Ala, Leu, Ser, Pro, Gln, Gly, Phe,
      Tyr, Trp, Glu

<400> SEQUENCE: 179

Leu Thr Xaa Xaa His Xaa Xaa Ala Xaa Xaa Thr Ser Lys
1               5                   10

<210> SEQ ID NO 180
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa may be Ff, F2f, F3f, F5f, Phe, Trp, Leu,
      Tyr, Hexa, Napha, Anta, Cba, Cha, Hexa, Homof
<220> FEATURE:
<221> NAME/KEY: misc_feature
<222> LOCATION: (6)..(6)
<223> OTHER INFORMATION: Xaa may be Ff, F2f, F3f, F5f, Phe, Trp, Leu,
      Tyr, Hexa, Napha, Anta, Cba, Cha, Hexa, Homof
<220> FEATURE:
<221> NAME/KEY: misc_feature
<222> LOCATION: (9)..(10)
<223> OTHER INFORMATION: Xaa may be Ff, F2f, F3f, F5f, Phe, Trp, Leu,
      Tyr, Hexa, Napha, Anta, Cba, Cha, Hexa, Homof

<400> SEQUENCE: 180
```

```
Ile Thr Xaa Glu Asp Xaa Leu His Xaa Xaa Gly Pro Lys
1               5                   10
```

<210> SEQ ID NO 181
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa may be F2f, Lys, Phe
<220> FEATURE:
<221> NAME/KEY: NON_CONS
<222> LOCATION: (3)..(4)
<220> FEATURE:
<221> NAME/KEY: misc_feature
<222> LOCATION: (6)..(6)
<223> OTHER INFORMATION: Xaa may be Hexa, Ala, Trp
<220> FEATURE:
<221> NAME/KEY: NON_CONS
<222> LOCATION: (9)..(10)
<220> FEATURE:
<221> NAME/KEY: misc_feature
<222> LOCATION: (9)..(9)
<223> OTHER INFORMATION: Xaa may be Cba, Lys

<400> SEQUENCE: 181

```
Leu Thr Xaa Glu Tyr Xaa Ala Gln Xaa Ser Ala Ala
1               5                   10
```

<210> SEQ ID NO 182
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: MOD_RES
<222> LOCATION: (16)..(16)
<223> OTHER INFORMATION: Beta-ala

<400> SEQUENCE: 182

```
Lys Ala Xaa Tyr Ala Asn Xaa Glu Lys Leu Xaa Arg Gly Gly Ser Ala
1               5                   10                  15
```

<210> SEQ ID NO 183
<211> LENGTH: 20
<212> TYPE: PRT
<213> ORGANISM: Artificial Sequence
<220> FEATURE:
<223> OTHER INFORMATION: Synthetic

<400> SEQUENCE: 183

```
Cys Lys Gln Asp Ser Asp Cys Leu Ala Gly Ser Val Cys Gly Pro Asn
1               5                   10                  15

Gly Phe Cys Gly
            20
```

```
<210> SEQ ID NO 184
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 184

Lys Ala Xaa Tyr Ala Asn Xaa Glu Lys Leu Xaa Arg
1               5                   10

<210> SEQ ID NO 185
<211> LENGTH: 13
<212> TYPE: PRT
<213> ORGANISM: Artificial Sequence
<220> FEATURE:
<223> OTHER INFORMATION: Synthetic

<400> SEQUENCE: 185

Ile Thr Phe Glu Asp Leu Leu His Tyr Tyr Gly Pro Lys
1               5                   10

<210> SEQ ID NO 186
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: NON_CONS
<222> LOCATION: (9)..(10)

<400> SEQUENCE: 186

Gly Asp Tyr Lys Asp Asp Asp Asp Lys Lys
1               5                   10

<210> SEQ ID NO 187
<211> LENGTH: 28
<212> TYPE: PRT
<213> ORGANISM: Artificial Sequence
<220> FEATURE:
<223> OTHER INFORMATION: Synthetic

<400> SEQUENCE: 187

Gly Cys Pro Arg Ile Leu Met Arg Cys Lys Gln Asp Ser Asp Cys Lys
1               5                   10                  15

Ala Gly Cys Val Cys Gly Pro Asn Gly Phe Cys Gly
            20                  25

<210> SEQ ID NO 188
<211> LENGTH: 27
<212> TYPE: PRT
<213> ORGANISM: Artificial Sequence
<220> FEATURE:
<223> OTHER INFORMATION: Synthetic
<220> FEATURE:
```

```
<221> NAME/KEY: NON_CONS
<222> LOCATION: (12)..(13)

<400> SEQUENCE: 188

Gly Cys Pro Arg Ile Leu Met Arg Cys Lys Gln Asp Asp Cys Leu Ala
1               5                   10                  15

Gly Cys Val Cys Gly Pro Asn Gly Phe Cys Gly
            20                  25

<210> SEQ ID NO 189
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: NON_CONS
<222> LOCATION: (3)..(4)
<220> FEATURE:
<221> NAME/KEY: NON_CONS
<222> LOCATION: (9)..(10)

<400> SEQUENCE: 189

Leu Thr Phe His Tyr Trp Ala Gln Leu Ser Lys
1               5                   10

<210> SEQ ID NO 190
<211> LENGTH: 13
<212> TYPE: PRT
<213> ORGANISM: Artificial Sequence
<220> FEATURE:
<223> OTHER INFORMATION: Synthetic

<400> SEQUENCE: 190

Gly Cys Pro Arg Ile Leu Met Arg Cys Lys Gln Asp Lys
1               5                   10

<210> SEQ ID NO 191
<211> LENGTH: 12
<212> TYPE: PRT
<213> ORGANISM: Artificial Sequence
<220> FEATURE:
<223> OTHER INFORMATION: Synthetic

<400> SEQUENCE: 191

Gly Cys Pro Arg Ile Leu Met Arg Cys Lys Gln Asp
1               5                   10

<210> SEQ ID NO 192
<211> LENGTH: 15
<212> TYPE: PRT
<213> ORGANISM: Artificial Sequence
<220> FEATURE:
<223> OTHER INFORMATION: Synthetic

<400> SEQUENCE: 192

Asp Cys Leu Ala Gly Cys Val Cys Gly Pro Asn Gly Phe Cys Gly
1               5                   10                  15

<210> SEQ ID NO 193
<211> LENGTH: 10
<212> TYPE: PRT
<213> ORGANISM: Artificial Sequence
<220> FEATURE:
<223> OTHER INFORMATION: Synthetic

<400> SEQUENCE: 193
```

Pro Arg Leu Leu Met Arg Cys Lys Gln Asp
1               5                   10

<210> SEQ ID NO 194
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Beta-ala

<400> SEQUENCE: 194

Gly Gly Ser Ala
1

<210> SEQ ID NO 195
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa may be F2f
<220> FEATURE:
<221> NAME/KEY: misc_feature
<222> LOCATION: (6)..(6)
<223> OTHER INFORMATION: Xaa may be anta
<220> FEATURE:
<221> NAME/KEY: misc_feature
<222> LOCATION: (9)..(9)
<223> OTHER INFORMATION: Xaa may be Cba

<400> SEQUENCE: 195

Leu Thr Xaa Glu Tyr Xaa Ala Gln Xaa Ser Ala Ala
1               5                   10

<210> SEQ ID NO 196
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa may be F2f
<220> FEATURE:
<221> NAME/KEY: misc_feature
<222> LOCATION: (6)..(6)
<223> OTHER INFORMATION: Xaa may be Nalpha
<220> FEATURE:
<221> NAME/KEY: misc_feature
<222> LOCATION: (9)..(9)
<223> OTHER INFORMATION: Xaa may be Cba

<400> SEQUENCE: 196

Leu Thr Xaa Glu Tyr Xaa Ala Gln Xaa Ser Ala Ala
1               5                   10

<210> SEQ ID NO 197
<211> LENGTH: 13
<212> TYPE: PRT
<213> ORGANISM: Artificial Sequence
<220> FEATURE:
<223> OTHER INFORMATION: Synthetic

<400> SEQUENCE: 197

```
Gly Ser Gly Ser Gly Ser Gly Ser Gly Ser Leu
1               5                   10

<210> SEQ ID NO 198
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa may be Ala, Leu, Ser, Pro, Gln, Gly, Phe,
      Tyr, Trp, Glu
<220> FEATURE:
<221> NAME/KEY: NON_CONS
<222> LOCATION: (3)..(4)
<220> FEATURE:
<221> NAME/KEY: misc_feature
<222> LOCATION: (5)..(5)
<223> OTHER INFORMATION: Xaa may be Ala, Leu, Ser, Pro, Gln, Gly, Phe,
      Tyr, Trp, Glu
<220> FEATURE:
<221> NAME/KEY: misc_feature
<222> LOCATION: (7)..(8)
<223> OTHER INFORMATION: Xaa may be Ala, Leu, Ser, Pro, Gln, Gly, Phe,
      Tyr, Trp, Glu
<220> FEATURE:
<221> NAME/KEY: NON_CONS
<222> LOCATION: (9)..(10)

<400> SEQUENCE: 198

Ile Thr Xaa Asp Xaa Leu Xaa Xaa Gly Ser
1               5                   10

<210> SEQ ID NO 199
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 199

Leu Thr Xaa Cys His Tyr Xaa Ala Gln Xaa Cys Ser Lys
1               5                   10

<210> SEQ ID NO 200
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: NON_CONS
<222> LOCATION: (3)..(4)
<220> FEATURE:
<221> NAME/KEY: misc_feature
```

```
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: NON_CONS
<222> LOCATION: (10)..(11)

<400> SEQUENCE: 200

Leu Thr Xaa His Tyr Xaa Ala Gln Xaa Ser Lys
1               5                   10

<210> SEQ ID NO 201
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: NON_CONS
<222> LOCATION: (6)..(7)
<220> FEATURE:
<221> NAME/KEY: NON_CONS
<222> LOCATION: (11)..(12)
<220> FEATURE:
<221> NAME/KEY: MOD_RES
<222> LOCATION: (15)..(15)
<223> OTHER INFORMATION: Beta-ala

<400> SEQUENCE: 201

Lys Ala Trp Tyr Ala Asn Glu Lys Leu Leu Arg Gly Gly Ser Ala Cys
1               5                   10                  15

Lys Gln Asp Ser Asp Cys Ser Leu Ala Gly Ser Val Cys Gly Pro Asn
            20                  25                  30

Gly Phe Cys Gly
        35

<210> SEQ ID NO 202
<211> LENGTH: 10
<212> TYPE: PRT
<213> ORGANISM: Artificial Sequence
<220> FEATURE:
<223> OTHER INFORMATION: Synthetic

<400> SEQUENCE: 202

Trp Tyr Ala Asn Phe Glu Lys Leu Leu Arg
1               5                   10
```

SOLUTION-PHASE AFFINITY SELECTION OF INHIBITORS FROM COMBINATORIAL PEPTIDE LIBRARIES

RELATED APPLICATIONS

This application claims priority under 35 U.S.C. § 119(e) to U.S. Provisional patent application, U.S. Ser. No. 62/593,861, filed Dec. 1, 2017, the entire contents of which is incorporated herein by reference.

GOVERNMENT SUPPORT

This invention was made with Government support under Grant No. N66001-14-2-4058 awarded by the Space and Naval Warfare Systems Center (SPAWAR). The Government has certain rights in this invention.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Sep. 15, 2021 is named M092570613US01-SUBSEQ-PJH and is 5300 bytes in size.

BACKGROUND OF THE INVENTION

Drugging protein-protein interactions (PPIs) has become a major center of focus in drug discovery. However, simple methods allowing for the rapid generation of scaffolds containing non-proteinogenic side chains, which would broaden the peptide structure and function space and would therefore facilitate the discovery of potent peptide-based PPI inhibitors, are lacking.

Over the past 10 years, PPIs have been recognized as key targets in drug discovery [1]. In this regard peptide binders have the potential to play an important role in guiding the design of novel small molecule inhibitors and in serving themselves as the basis for the discovery of promising peptide-based drug candidates [2]. Peptide binders have recently gained momentum [3] in part thanks to the development of performing chemical toolboxes allowing for the synthesis of some potent macrocyclic peptidomimetics with improved pharmacological properties [4].

The use of non-canonical amino acids dramatically increases the opportunities for structural diversity, an important pre-requisite for the discovery of potent PPI inhibitors [1], [2], [3]. Non-canonical amino acids can also be used to enhance the metabolic stability and fine-tune physicochemical properties of peptide-derived inhibitors [3]. So far, implementing these non-canonical amino acids in the discovery process of peptide inhibitors has been relying on time consuming systematic studies [5], in silico guided efforts [6] and display based combinatorial approaches [7]. The latter are extremely attractive but are either not yet amenable to the use of large repertoires of non-canonical amino acids [8] or may suffer in their conventional format from screen complexity and false positives [9].

SUMMARY OF THE INVENTION

Some aspects of the present disclosure include a peptide, or a salt thereof, comprising a sequence of the formula (I) LTFX$_1$HX$_2$WAX$_3$LTSK (SEQ ID NO: 1), wherein X$_1$ is Gln, Pro, or Glu; X$_2$ is Phe, Tyr, or Glu; and X$_3$ is Glu, Gln, Ala, or Leu. In some embodiments, the sequence of the formula (I) is selected from the group consisting of SEQ ID NOs: 2-5.

Some aspects of the present disclosure include a peptide, or a salt thereof, comprising a sequence of the formula (II) LTFEHYWAQX$_1$TSK (SEQ ID NO: 6), wherein X$_1$ is Phe or Leu. In some embodiments, the sequence of the formula (I1) is selected from the group consisting of SEQ ID NOs: 7 and 8.

Some aspects of the present disclosure include a peptide, or a salt thereof, comprising a sequence of the formula (III) LTX$_1$EHYX$_2$AQX$_3$TSK (SEQ ID NO: 9), wherein X$_1$ is Ff, F$_2$f, F$_3$f, or Phe: X$_2$ is Hexa, Trp, Napha, or Anta; and X$_3$ is Cba, Cha, Ff, F$_2$f, F$_3$f, F$_5$f, Hexa, Homof, or Leu. In some embodiments, the sequence of the formula (III) is selected from the group consisting of SEQ ID NOs: 10-29.

Some aspects of the present disclosure include a peptide, or a salt thereof, comprising a sequence of the formula (IV) IT(F$_2$f)ED(Cba)LHX$_1$X$_2$GP (SEQ ID NO: 30), wherein X$_1$ is Tyr or Dmf and X$_2$ is Tyr or F$_2$f. In some embodiments, the C-terminal end of the sequence of formula (IV) is covalently bound to a portion of the peptide having (GS)$_n$K (SEQ ID NO: 178) on its N-terminal end, where n is an integer from 0 to 12. In other embodiments, the sequence of the formula (IV) is selected from the group consisting of SEQ ID NOs: 31-33.

Some aspects of the present disclosure include a peptide or macrocyclic peptide, or a salt thereof, comprising a sequence of the formula (V) LTX$_1$X$_2$EX$_3$X$_4$AX$_5$(Cba)X$_6$SAA (SEQ ID NO: 34), wherein X$_1$ is F$_2$f or Phe; X$_2$ is R8 or Dap or a portion of a cross-link or staple; X$_3$ is Tyr or Phe; X$_4$ is Hexa, Napha, or Trp; X$_5$ is Gln or Glu; and X$_6$ is S5 or Dap or a portion of a cross-link or staple. In some embodiments, the side chain of X$_2$ and the side chain of X$_6$ are joined together by a linker. In other embodiments, the sequence of the formula (V) is selected from the group consisting of SEQ ID NOs: 35-43.

Some aspects of the present disclosure include a peptide or macrocyclic peptide, or a salt thereof, comprising a sequence of the formula (VI) IT(F$_2$f)X$_1$DX$_2$LX$_3$X$_4$X$_5$GP (SEQ ID NO: 44), wherein X$_1$ is Cys or S5 or a portion of a cross-link or staple; X$_2$ is Cba or Leu; X$_3$ is Cys or S5 or a portion of a cross-link or staple: X$_4$ is Tyr or Dmf: and X$_5$ is Tyr or F$_2$f. In some embodiments, the side chain of X$_1$ and the side chain of X$_3$ are joined together by a linker. In other embodiments, the C-terminal end of the sequence of formula (VI) is covalently bound to a portion of the peptide having (GS)$_n$K (SEQ ID NO: 178) on its N-terminal end, where n is an integer from 0 to 12. In other embodiments, the sequence of the formula (VI) is selected from the group consisting of SEQ ID NOs: 45 and 46.

Some aspects of the present disclosure include a peptide or macrocyclic peptide, or a salt thereof, comprising a sequence of the formula (VII) LTFX$_1$HYWAQLX$_2$SK (SEQ ID NO: 47), wherein X$_1$ is Cys or Cys(ar) or a portion of a cross-link or staple; and X$_2$ is Cys or Cys(ar) or a portion of a cross-link or staple. In some embodiments, the side chain of the first Cys(ar) and the side chain of the second Cys(ar) are joined together by a linker. In other embodiments, the sequence of the formula (VII) is selected from the group consisting of SEQ ID NOs: 48 and 49.

In some embodiments, the linker of the presently disclosed peptide or macrocyclic peptide comprises optionally substituted alkylene, alkenylene, alkynylene, optionally substituted carbocyclylene, heterocyclylene, arylene, or heteroarylene, or a combination thereof.

Some aspects of the present disclosure include a peptide or mini-protein, or a salt thereof, comprising a sequence of the formula (VIII) KAWYANX$_1$EKLX$_2$R (SEQ ID NO: 50), wherein X$_1$ is Hexa, Hepa, Cha, or CF$_3$f and X$_2$ is Homol, Cha, Cba, Leu, Hexa, or Trp. In some embodiments, all amino acids in the mini-protein are of the D-configuration. In other aspects, the sequence of the formula (VIII) is selected from the group consisting of SEQ ID NOs: 51-61.

In some embodiments, the presently disclosure the peptide, mini-protein, or macrocyclic peptide comprises one or more vicinal diols along the backbone of the peptide, mini-protein or macrocyclic peptide. In other embodiments, the presently disclosed peptide, macrocyclic peptide, or mini-protein comprises a biotinylated N-terminus. In other embodiments, the presently disclosed peptide, macrocyclic peptide, or mini-protein comprises an acetylated N-terminus. In other embodiments, the presently disclosed peptide, macrocyclic peptide, or mini-protein comprises a biotinylated C-terminus. In other embodiments, the presently disclosed peptide, macrocyclic peptide, or mini-protein comprises an amidated C-terminus.

In some embodiments, the presently disclosed peptide, macrocyclic peptide, or mini-protein has up to 20 amino acids. In other embodiments, the presently disclosed peptide, macrocyclic peptide, or mini-protein has from 20 to 30 amino acids. In other embodiments, the presently disclosed peptide, macrocyclic peptide, or mini-protein has from 30 to 40 amino acids. In other embodiments, the presently disclosed peptide, macrocyclic peptide, or mini-protein has from 40 to 50 amino acids. In other embodiments, the presently disclosed peptide, macrocyclic peptide, or mini-protein has from 50 to 100 amino acids.

In some embodiments, the sequence of the presently disclosed peptide, macrocyclic peptide, or mini-protein has is modified by 1 amino acid relative to its respective known peptide. In other embodiments, the sequence is modified by 2 amino acids relative to its respective known peptide. In other embodiments, the sequence is modified by 3 amino acids relative to its respective known peptide. In other embodiments, the sequence is modified by 4 amino acids relative to its respective known peptide.

Some aspects of the present disclosure include a pharmaceutical composition comprising a presently disclosed peptide, a macrocyclic peptide, or a mini-protein of any preceding claim.

Some aspects of the present disclosure include a method of treating cancer in a subject in need thereof comprising administering a presently disclosed peptide, a macrocyclic peptide, and/or a mini-protein.

Other aspects of the present disclosure include a method of disrupting a p53-MDM2 interaction using a presently disclosed peptide, a macrocyclic peptide, or a mini-protein.

Some aspects of the present disclosure include a method of treating or preventing HIV in a subject in need thereof comprising administering a presently disclosed peptide or a macrocyclic peptide.

Other aspects of the present disclosure include a method of preventing an HIV capsid from forming using a presently disclosed peptide or a macrocyclic peptide.

Some aspects of the present disclosure include a method of identifying one or more modulators for inhibiting a protein-protein interaction (PPI), the method comprising incubating a peptide library with a protein target in solution under suitable conditions to form a mixture comprising one or more peptide-protein target complexes; fractionating the mixture comprising the one or more peptide-protein target complexes using high-pressure size exclusion chromatography (HPSEC) into a plurality of fractions; selecting a protein fraction of the plurality of fractions, comprising one or more peptide-protein target complexes, wherein the protein target was eluted; and analyzing the protein fraction directly by liquid chromatography-tandem mass spectrometry (LC-MS/MS) to obtain one or more peptide sequences, wherein each peptide sequence is the sequence of a modulator.

Some aspects of the present disclosure include a method of identifying one or more modulators for inhibiting a protein-protein interaction (PPI), the method comprising incubating a peptide library with a protein target in solution under suitable conditions to form a mixture comprising one or more peptide-protein target complexes; fractionating the mixture comprising the one or more peptide-protein target complexes using high-pressure size exclusion chromatography (HPSEC) into a plurality of fractions; selecting a protein fraction of the plurality of fractions, comprising one or more peptide-protein target complexes, wherein the protein target was eluted; subjecting the protein fraction to chemical conditions to form a linearized fraction having one or more linearized modulators; and analyzing the linearized fraction by LC-MS/MS to obtain one or more peptide sequences, wherein each peptide sequence is the sequence of a modulator.

In some embodiments of the presently disclosed method, the mixture comprises L-arginine. In other embodiments of the presently disclosed method, a mobile phase for HPSEC comprises L-arginine. In some embodiments, the presently disclosed method further comprises synthesizing the peptide library having at least 1000 members using a split and pool technique by randomizing one or more residues in a peptide sequence. In other embodiments, the presently disclosed method further comprises re-synthesizing the binder using the decoded binder sequence. In other embodiments, the presently disclosed method further comprises validating binding of the binder to the protein target using an assay.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

Definitions

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987.

The compounds of the present invention (e.g., amino acids, and peptides, e.g., unstapled peptides, stapled peptides, macrocyclic peptides, mini-proteins, and salts thereof) may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention.

Where an isomer/enantiomer is preferred, it may, in some embodiments, be provided substantially free of the corresponding enantiomer, and may also be referred to as "optically enriched." "Optically enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, *E. L. Stereochemistry of Carbon Compounds* (McGraw-Hill, N Y, 1962); Wilen, S. H. *Tables of Resolving Agents and Optical Resolutions* p. 268 (E. L. Eliel, Ed., Univ. of Notre Dame Press, Notre Dame, Ind. 1972).

"Stapling" or "hydrocarbon-stapling," as used herein, may refer to a process by which to amino acids side chains in a peptide are used in order to covalently link one part of a peptide chain to another. For example, stapling may involve a process by which two terminally unsaturated amino acid side chains in a peptide chain react with each other in the presence of a ring closing metathesis catalyst to generate a C=C double bonded cross-link between the two amino acids (a "staple"). Stapling engenders constraint on a secondary structure, such as an alpha helical structure. The length and geometry of the cross-link can be optimized to improve the yield of the desired secondary structure content. The constraint provided can, for example, prevent the secondary structure to unfold and/or can reinforce the shape of the secondary structure, and thus makes the secondary structure more stable. Stapling may occur between two non-consecutive amino acids in a peptide chain. In certain embodiments, stapling may occur at i,i+3, i,i+4, and/or i,i+7 positions of the polypeptide.

An "unstapled" polypeptide or amino acid sequence is a polypeptide or sequence comprising at least two amino acids having sites of terminal unsaturation capable of undergoing ring closing metathesis to generate a cross-link between the two amino acids, thereby providing a "stapled" polypeptide. After the unstapled polypeptide is synthesized the polypeptide is contacted with a ring closing metathesis (RCM) catalyst to promote stapling of the polypeptide (Bernal et al., J. Am. Chem. Soc. 2007, 129, 2456-2457). In certain embodiments, the RCM catalyst is a ruthenuim catalyst. Suitable RCM catalysts are described in, for example, Grubbs et al., *Acc. Chem. Res.* 1995, 28, 446-452; U.S. Pat. No. 5,811,515; Schrock et al., Organometallics (1982) 1 1645; Gallivan et al., *Tetrahedron Letters* (2005) 46:2577-2580; Furstner et al., J. Am. Chem. Soc. (1999) 121:9453; and *Chem. Eur. J.* (2001) 7:5299.

The compounds of the present invention (e.g., amino acids, and unstapled, partially stapled, and stapled polypeptides) may exist in particular geometric or stereoisomeric forms. The present invention contemplates all such compounds, including cis- and trans-isomers, R- and S-enantiomers, diastereomers, (D)- and (L)-isomers, the racemic mixtures thereof, and other mixtures thereof, as falling within the scope of the invention.

It will be appreciated that the compounds of the present invention, as described herein, may be substituted with any number of substituents or functional moieties. In general, the term "substituted" whether preeceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include substitution with all permissible substituents of organic compounds, any of the substituents described herein (for example, aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, etc.), and any combination thereof (for example, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like) that results in the formation of a stable moiety. The present invention contemplates any and all such combinations in order to arrive at a stable substituent/moiety. Additional examples of generally applicable substitutents are illustrated by the specific embodiments shown in the Examples, which are described herein. For purposes of this invention, heteroatoms such as nitrogen may have hydrogen substituents and/or any suitable substituent as described herein which satisfy the valencies of the heteroatoms and results in the formation of a stable moiety.

As used herein, substituent names which end in the suffix "-ene" refer to a biradical derived from the removal of two hydrogen atoms from the substitutent. Thus, for example, acyl is acylene; alkyl is alkylene; alkeneyl is alkenylene; alkynyl is alkynylene; heteroalkyl is heteroalkylene, heteroalkenyl is heteroalkenylene, heteroalkynyl is heteroalkynylene, aryl is arylene, and heteroaryl is heteroarylene.

The term "acyl," as used herein, refers to a group having the general formula —C(=O)R$^A$, —C(=O)OR$^A$, —C(=O)—O—C(=O)R$^A$, —C(=O)SR$^A$, —C(=O)N(R$^A$)$_2$, —C(=S)R$^A$, —C(=S)N(R$^A$)$_2$, and —C(=S)S(R$^A$), —C(=NR$^A$)R$^A$, —C(=NR$^A$)OR$^A$, —C(=NR$^A$)SR$^A$, and —C(=NR$^A$)N(R$^A$)$_2$, wherein R$^A$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^A$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "acyloxy" refers to a "substituted hydroxyl" of the formula (—OR$^t$), wherein R$_t$ is an optionally substituted acyl group, as defined herein, and the oxygen moiety is directly attached to the parent molecule.

The term "acylene," as used herein, refers to an acyl group having the general formulae: —R$^O$—(C=X$^1$)—R$^O$—, —R$^O$—X$^2$(C=X$^1$)—R$^O$—, or —R$^O$—X$^2$(C=X$^1$)X$^3$—R$^O$—, where X$_1$, X$^2$, and X$^3$ is, independently, oxygen, sulfur, or NR$^r$, wherein R$^r$ is hydrogen or aliphatic, and R$^O$ is an optionally substituted alkylene, alkenylene, alkynylene, heteroalkylene, heteroalkenylene, or heteroalkynylene group, as defined herein. Exemplary acylene groups wherein R$^O$ is alkylene includes —(CH$_2$)$_T$—O(C=O)—(CH$_2$)$_T$—; —(CH$_2$)$_T$—NR$^r$(C=O)$_T$; —(CH$_2$)$_T$—; —(CH$_2$)$_T$—O(C=NR$^r$)—(CH$_2$)$_T$—; —(CH$_2$)$_T$—NR(C=NR$^r$)—(CH$_2$)$_T$—; —(CH$_2$)$_T$—(C=O)—(CH$_2$)$_T$—; —(CH$_2$)$_T$—(C=NR$^r$)—(CH$_2$)$_T$—; —(CH$_2$)$_T$—S(C=S)—(CH$_2$)$_T$—; —(CH$_2$)$_T$—NR$^r$(C=S)—(CH$_2$)$_T$—; (CH$_2$)$_T$—S(C=NR$^r$)—(CH$_2$)$_T$—; —(CH$_2$)$_T$—O(C=S)—(CH$_2$)$_T$—; —(CH$_2$)$_T$—(C=S)—(CH$_2$)$_T$—; or —(CH$_2$)$_T$—S(C=O)—(CH$_2$)$_T$—, and the like, which may bear one or more substituents; and wherein each instance of xx is, independently, an integer between 0 to 20. Acylene groups may be cyclic or acyclic, branched or unbranched, substituted or unsubstituted. Acylene substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkyl," as used herein, refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms. In another embodiment, the alkyl group employed contains 1-15 carbon atoms. In another embodiment, the alkyl group employed contains 1-10 carbon atoms. In another embodiment, the alkyl group employed contains 1-8 carbon atoms. In another embodiment, the alkyl group employed contains 1-5 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substitutents. Alkyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkylene," as used herein, refers to a biradical derived from an alkyl group, as defined herein, by removal of two hydrogen atoms. Alkylene groups may be cyclic or acyclic, branched or unbranched, substituted or unsubstituted. Alkylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkenyl," as used herein, denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms. In some embodiments, the alkenyl group employed in the invention contains 2-15 carbon atoms. In another embodiment, the alkenyl group employed contains 2-10 carbon atoms. In still other embodiments, the alkenyl group contains 2-8 carbon atoms. In yet another embodiments, the alkenyl group contains 2-5 carbons. Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkenylene," as used herein, refers to a biradical derived from an alkenyl group, as defined herein, by removal of two hydrogen atoms. Alkenylene groups may be cyclic or acyclic, branched or unbranched, substituted or unsubstituted. Alkenylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkynyl," as used herein, refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms. In some embodiments, the alkynyl group employed in the invention contains 2-15 carbon atoms. In another embodiment, the alkynyl group employed contains 2-10 carbon atoms. In still other embodiments, the alkynyl group contains 2-8 carbon atoms. In still other embodiments, the alkynyl group contains 2-5 carbon atoms. Representative alkynyl groups include, but are not limited to, ethynyl, 2-propynyl (propargyl), 1-propynyl, and the like, which may bear one or more substituents. Alkynyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkynylene," as used herein, refers to a biradical derived from an alkynylene group, as defined herein, by removal of two hydrogen atoms. Alkynylene groups may be cyclic or acyclic, branched or unbranched, substituted or unsubstituted. Alkynylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "amino," as used herein, refers to a group of the formula ($—NH_2$). A "substituted amino" refers either to a mono-substituted amine ($—NHR^h$) of a disubstituted amine ($—NR^h_2$), wherein the $R^h$ substituent is any substitutent as described herein that results in the formation of a stable moiety (e.g., a suitable amino protecting group; aliphatic, alkyl, alkenyl, alkynyl, heteroaliphatic, heterocyclic, aryl, heteroaryl, acyl, amino, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). In certain embodiments, the $R^h$ substituents of the di-substituted amino group ($—NR^h_2$) form a 5- to 6-membered hetereocyclic ring.

The term "aliphaticamino," refers to a "substituted amino" of the formula ($—NR^h_2$), wherein $R^h$ is, independently, a hydrogen or an optionally substituted aliphatic group, as defined herein, and the amino moiety is directly attached to the parent molecule.

The term "aliphaticoxy," refers to a "substituted hydroxyl" of the formula ($—OR^i$), wherein $R^i$ is an optionally substituted aliphatic group, as defined herein, and the oxygen moiety is directly attached to the parent molecule.

The term "alkyloxy" refers to a "substituted hydroxyl" of the formula ($—OR^i$), wherein $R^i$ is an optionally substituted alkyl group, as defined herein, and the oxygen moiety is directly attached to the parent molecule.

The term "alkylthioxy" refers to a "substituted thiol" of the formula ($—SR^r$), wherein $R^r$ is an optionally substituted alkyl group, as defined herein, and the sulfur moiety is directly attached to the parent molecule.

The term "alkylamino" refers to a "substituted amino" of the formula ($—NR^h_2$), wherein $R^h$ is, independently, a hydrogen or an optionally substituted alkyl group, as defined herein, and the nitrogen moiety is directly attached to the parent molecule.

The term "aryl," as used herein, refer to stable aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic $C_4$-$C_{20}$ aromatic ring system having one, two, or three aromatic rings which include, but not limited to, phenyl, biphenyl, naphthyl, and the like, which may bear one or more substituents. Aryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "arylene," as used herein refers to an aryl biradical derived from an aryl group, as defined herein, by removal of two hydrogen atoms. Arylene groups may be substituted or unsubstituted. Arylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). Additionally, arylene groups may be incorporated as a linker group into an alkylene, alkenylene, alkynylene, heteroalkylene, heteroalkenylene, or heteroalkynylene group, as defined herein.

The term "cyano," as used herein, refers to a group of the formula (—CN).

The terms "halo" and "halogen" as used herein refer to an atom selected from fluorine (fluoro, —F), chlorine (chloro, —Cl), bromine (bromo, —Br), and iodine (iodo, —I).

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl," as used herein, refers to an alkyl moiety, as defined herein, which contain one or more oxygen, sulfur, nitrogen, phosphorus, or silicon atoms, e.g., in place of carbon atoms.

The term "heteroalkylene," as used herein, refers to a biradical derived from an heteroalkyl group, as defined herein, by removal of two hydrogen atoms. Heteroalkylene groups may be cyclic or acyclic, branched or unbranched, substituted or unsubstituted. Heteroalkylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkenyl," as used herein, refers to an alkenyl moiety, as defined herein, which contain one or more oxygen, sulfur, nitrogen, phosphorus, or silicon atoms, e.g., in place of carbon atoms. 1

The term "heteroalkenylene," as used herein, refers to a biradical derived from an heteroalkenyl group, as defined herein, by removal of two hydrogen atoms. Heteroalkenylene groups may be cyclic or acyclic, branched or unbranched, substituted or unsubstituted.

The term "heteroalkynyl," as used herein, refers to an alkynyl moiety, as defined herein, which contain one or more oxygen, sulfur, nitrogen, phosphorus, or silicon atoms, e.g., in place of carbon atoms.

The term "heteroalkynylene," as used herein, refers to a biradical derived from an heteroalkynyl group, as defined herein, by removal of two hydrogen atoms. Heteroalkynylene groups may be cyclic or acyclic, branched or unbranched, substituted or unsubstituted.

The term "heterocyclic," "heterocycles," or "heterocyclyl," as used herein, refers to a cyclic heteroaliphatic group. A heterocyclic group refers to a non-aromatic, partially unsaturated or fully saturated, 3- to 10-membered ring system, which includes single rings of 3 to 8 atoms in size, and bi- and tricyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocycyl groups include, but are not limited to, a bi- or tricyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroaryl," as used herein, refer to stable aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyyrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroarylene," as used herein, refers to a biradical derived from an heteroaryl group, as defined herein, by removal of two hydrogen atoms. Heteroarylene groups may be substituted or unsubstituted. Additionally, heteroarylene groups may be incorporated as a linker group into an alkylene, alkenylene, alkynylene, heteroalkylene, heteroalkenylene, or heteroalkynylene group, as defined herein. Heteroarylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "hydroxy," or "hydroxyl," as used herein, refers to a group of the formula (—OH). A "substituted hydroxyl" refers to a group of the formula (—$OR^i$), wherein $R^i$ can be any substitutent which results in a stable moiety (e.g., a suitable hydroxyl protecting group; aliphatic, alkyl, alkenyl, alkynyl, heteroaliphatic, heterocyclic, aryl, heteroaryl, acyl, nitro, alkylaryl, arylalkyl, and the like, each of which may or may not be further substituted).

As used herein, the term "resin" refers to a resin useful for solid phase synthesis. Solid phase synthesis is a well-known synthetic technique; see generally, Atherton, E., Sheppard, R. C. *Solid Phase Peptide Synthesis: A Practical Approach*, IRL Press, Oxford, England, 1989, and Stewart J. M., Young, J. D. *Solid Phase Peptide Synthesis*, 2nd edition, Pierce Chemical Company, Rockford, 1984, the entire contents of each of which are hereby incorporated herein by reference. Exemplary resins which may be employed by the present invention include, but are not limited to:

(1) alkenyl resins (e.g., REM resin, vinyl sulfone polymer-bound resin, vinyl-polystyrene resin);

(2) amine functionalized resins (e.g., amidine resin, N-(4-Benzyloxybenzyl)hydroxylamine polymer bound, (aminomethyl)polystyrene, polymer bound (R)-(+)-a-methylbenzylamine, 2-Chlorotrityl Knorr resin, 2-N-Fmoc-Aminodibenzocyclohepta-1,4-diene, polymer-bound resin, 4-[4-(1-Fmoc-aminoethyl)-2-methoxy-5-nitrophenoxy] butyramidomethyl-polystyrene resin, 4-Benzyloxybenzylamine, polymer-bound, 4-Carboxybenzenesulfonamide, polymer-bound, Bis(tert-butoxycarbonyl) thiopseudourea, polymer-bound, Dimethylaminomethyl-polystyrene, Fmoc-3-amino-3-(2-nitrophenyl)propionic acid, polymer-bound, N-Methyl aminomethylated polystyrene, PAL resin, Sieber amide resin, tert-Butyl N-(2-mercaptoethyl)carbamate, polymer-bound, Triphenylchloromethane-4-carboxamide polymer bound);

(3) benzhydrylamine (BHA) resins (e.g., 2-Chlorobenzhydryl chloride, polymer-bound, HMPB-benzhydrylamine polymer bound, 4-Methylbenzhydrol, polymer-bound, Benzhydryl chloride, polymer-bound, Benzhydrylamine polymer-bound);

(4) Br-functionalized resins (e.g., 4-(Benzyloxy)benzyl bromide polymer bound, 4-Bromopolystyrene, Brominated PPOA resin, Brominated Wang resin, Bromoacetal, polymer-bound, Bromopolystyrene, HypoGel® 200 Br, Polystyrene A-Br for peptide synthesis, Selenium bromide, polymer-bound, TentaGel HL-Br, TentaGel MB-Br, TentaGel S-Br, TentaGel S-Br):

(5) Chloromethyl resins (e.g., 5-[4-(Chloromethyl)phenyl]pentyl]styrene, polymer-bound, 4-(Benzyloxy)benzyl chloride polymer bound, 4-Methoxybenzhydryl chloride, polymer-bound);

(6) CHO functionalized resins (e.g., (4-Formyl-3-methoxyphenoxymethyl)polystyrene, (4-Formyl-3-methoxyphenoxymethyl)polystyrene, 3-Benzyloxybenzaldehyde, polymer-bound, 4-Benzyloxy-2,6-dimethoxybenzaldehyde,polymer-bound, Formylpolystyrene, HypoGel® 200 CHO, Indole resin, Polystyrene A-CH(OEt)$_2$, TentaGel HL-CH(OEt)$_2$);

(7) Cl-functionalized resins (e.g., Benzoyl chloride polymer bound, (Chloromethyl)polystyrene, Merrifield's resin);

(8) CO₂H functionalized resins (e.g., Carboxyethylpolystryrene, HypoGel® 200 COOH, Polystyrene AM-COOH, TentaGel HL-COOH, TentaGel MB-COOH, TentaGel S-COOH);

(9) Hypo-Gel resins (e.g., HypoGel® 200 FMP, HypoGel® 200 PHB, HypoGel® 200 Trt-OH, HypoGel® 200 HMB);

(10) I-functionalized resins (e.g., 4-Iodophenol, polymer-bound, Iodopolystyrene); Janda-Jels™ (JandaJel₂-Rink amide, JandaJel-NH₂, JandaJel-Cl, JandaJel-4-Mercaptophenol, JandaJel-OH, JandaJel-1-(3-Dimethylaminopropyl)-3-ethylcarbodiimide, JandaJel-1,3,4,6,7,8-hexahydro-2H-pyrimido-[1,2-a] pyrimidine, JandaJel-morpholine, JandaJel-polypyridine, JandaJel-Triphenylphosphine, JandaJel-Wang);

(11) MBHA resins (3[4'-(Hydroxymethyl)phenoxy] propionic acid-4-methylbenzhydrylamine resin, 4-(Hydroxymethyl)phenoxyacetic acid polymer-bound to MBHA resin, HMBA-4-methylbenzhydrylamine polymer bound, 4-Methylbenzhydrylamine hydrochloride polymer bound Capacity (amine));

(12) NH₂ functionalized resins ((Aminomethyl)polystyrene, (Aminomethyl)polystyrene, HypoGel® 200 NH2, Polystyrene AM-NH₂, Polystyrene Microspheres 2-aminoethylated, Polystyrol Microspheres 2-bromoethylated, Polystyrol Microspheres 2-hydroxyethylated, TentaGel HL-NH2, Tentagel M Br, Tentagel M NH₂, Tentagel M OH, TentaGel MB-NH₂, TentaGel S-NH₂, TentaGel S-NH₂);

(13) OH-functionalized resins (e.g., 4-Hydroxymethylbenzoic acid, polymer-bound, Hydroxymethyl Resins, OH-functionalized Wang Resins);

(14) oxime resins (e.g., 4-Chlorobenzophenone oxime polymer bound, Benzophenone oxime polymer bound, 4-Methoxybenzophenone oxime polymer bound);

(15) PEG resins (e.g., ethylene glycol polymer bound);

(16) Boc-/Blz peptide synthesis resins (e.g., Boc-Lys(Boc)-Lys[Boc-Lys(Boc)]-Cys(Acm)-b-Ala-O-PAM resin, Boc-Lys(Fmoc)-Lys[Boc-Lys(Fmoc)]-b-Ala-O-Pam resin, Boc-Lys(Boc)-Lys[Boc-Lys(Boc)]-Lys{Boc-Lys(Boc)-Lys[Boc-Lys(Boc)]}-b-Ala-O-PAM resin, Boc-Lys(Fmoc)-Lys[Boc-Lys(Fmoc)]-Lys(Boc-Lys(Fmoc)-Lys[Boc-Lys(Fmoc)])-b-Ala-O-PAM resin, Boc-Lys(Boc)-Lys[Boc-Lys(Boc)]-Lys{Boc-Lys(Boc)-Lys[Boc-Lys(Boc)]}-Cys(Acm)-b-Ala-O-PAM resin, Preloaded PAM resins);

(17) Fmoc-/t-Bu peptide synthesis resins (e.g., Fmoc-Lys(Fmoc)-Lys[Fmoc-Lys(Fmoc)]-b-Ala-O-Wang resin, Fmoc-Lys(Fmoc)-Lys[Fmoc-Lys(Fmoc)]-Lys{Fmoc-Lys(Fmoc)-Lys[Fmoc-Lys(Fmoc)]}-b-Ala-O-Wang resin, Preloaded TentaGel® S Trityl Resins, Preloaded TentaGel® Resins, Preloaded Trityl Resins, Preloaded Wang Resins, Trityl Resins Preloaded with Amino Alcohols);

(19) thiol functionalized resins (e.g., HypoGel® 200 S-Trt, Polystyrene AM-S-Trityl, TentaGel HL-S-Trityl, TentaGel MB-S-Trityl, TentaGel S-S-Trityl); and

(20) Wang resins (e.g., Fmoc-Ala-Wang resin, Fmoc-Arg(Pbf)-Wang resin, Fmoc-Arg(Pmc)-Wang resin, Fmoc-Asn(Trt)-Wang resin, Fmoc-Asp(OtBu)-Wang resin, Fmoc-Cys(Acm)-Wang resin, Fmoc-Cys(StBu)-Wang resin, Fmoc-Cys(Trt) Wang resin, Fmoc-Gln(Trt)-Wang resin, Fmoc-Glu(OtBu)-Wang resin, Fmoc-Gly-Wang resin, Fmoc-His(Trt)-Wang resin, Fmoc-Ile-Wang resin, Fmoc-Leu-Wang resin, Fmoc-Lys(Boc)-Wang resin, Fmoc-Met-Wang resin, Fmoc-D-Met-Wang resin, Fmoc-Phe-Wang resin, Fmoc-Pro-Wang resin, Fmoc-Ser(tBu)-Wang resin, Fmoc-Ser(Trt)-Wang resin, Fmoc-Thr(tBu)-Wang resin, Fmoc-Trp(Boc) Wang resin, Fmoc-Trp-Wang resin, Fmoc-Tyr(tBu)-Wang resin, Fmoc-Val-Wang resin).

A "suitable amino-protecting group," as used herein, is well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-<dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo) benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

A "suitable carboxylic acid protecting group," or "protected carboxylic acid," as used herein, are well known in the art and include those described in detail in Greene (1999). Examples of suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

A "suitable hydroxyl protecting group" as used herein, is well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference. Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis (4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl) ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

A "suitable thiol protecting group," as used herein, are well known in the art and include those described in detail in *Protecting Groups in Organic Synthesis*, T. W. Greene and P. G. M. Wuts, 3' edition, John Wiley & Sons, 1999, the entirety of which is incorporated herein by reference. Examples of suitably protected thiol groups further include, but are not limited to, thioesters, carbonates, sulfonates allyl thioethers, thioethers, silyl thioethers, alkyl thioethers, arylalkyl thioethers, and alkyloxyalkyl thioethers. Examples of suitable ester groups include formates, acetates, proprionates, pentanoates, crotonates, and benzoates. Specific examples of suitable ester groups include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxycrotonate, benzoate, p-benylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl groups include trimethylsilyl, triethylsilyl, t-butyldimethylsilyl, t-butyldiphenylsilyl, triisopropylsilyl ether, and other trialkylsilyl ethers. Examples of suitable alkyl groups include methyl, benzyl, p-methoxybenzyl, 3,4-dimethoxybenzyl, trityl, t-butyl, and allyl ether, or derivatives thereof. Examples of suitable arylalkyl groups include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

The term "thio," or "thiol," as used herein, refers to a group of the formula (—SH). A "substituted thiol" refers to a group of the formula (—SR), wherein R can be any substitute that results in the formation of a stable moiety (e.g., a suitable thiol protecting group; aliphatic, alkyl, alkenyl, alkynyl, heteroaliphatic, heterocyclic, aryl, heteroaryl, acyl, sulfinyl, sulfonyl, cyano, nitro, alkylaryl, arylalkyl, and the like, each of which may or may not be further substituted).

The term "thiooxo," as used herein, refers to a group of the formula (=S).

As used herein, a "pharmaceutically acceptable form thereof" includes any pharmaceutically acceptable salts, prodrugs, tautomers, isomers, isotopically enriched derivatives, and/or polymorphs of a peptide of the present invention, as defined herein.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the peptides of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "prodrug" refers to a derivative of a parent peptide that requires transformation within the body in order to release the parent peptide. In certain cases, a prodrug has improved physical and/or delivery properties over the parent peptide. Prodrugs are typically designed to enhance pharmaceutically and/or pharmacokinetically based properties associated with the parent peptide. The advantage of a prodrug can lie in its physical properties, such as enhanced water solubility for parenteral administration at physiological pH compared to the parent peptide, or it enhances absorption from the digestive tract, or it may enhance drug stability for long-term storage. In recent years several types of bioreversible derivatives have been exploited for utilization in designing prodrugs. Using esters as a prodrug type for peptides containing a carboxyl or hydroxyl functionality is known in the art as described, for example, in "*The Organic Chemistry of Drug Design and Drug Interaction*" Richard Silverman, published by Academic Press (1992).

As used herein, the term "tautomer" includes two or more interconvertable peptides resulting from at least one formal migration of a hydrogen atom and at least one change in valency (e.g., a single bond to a double bond, a triple bond to a double bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol; amide-to-imide; lactam-to-lactim; enamine-to-imine; and enamine-to-(a different) enamine tautomerizations.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, an isomer/enantiomer may, in some embodiments, be provided substantially free of the corresponding enantiomer, and may also be referred to as "optically enriched." "Optically-enriched," as used herein, means that the peptide is made up of a significantly greater proportion of one enantiomer. In certain embodiments, the peptide of the present invention is made up of at least about 90% by weight of a preferred enantiomer. In other embodiments, the peptide is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, N Y, 1962); Wilen, S. H. *Tables of Resolving Agents and Optical Resolutions* p. 268 (E. L. Eliel, Ed., Univ. of Notre Dame Press, Notre Dame, Ind. 1972).

As used herein, "polymorph" refers to a crystalline inventive peptide existing in more than one crystalline form/structure. When polymorphism exists as a result of difference in crystal packing it is called packing polymorphism. Polymorphism can also result from the existence of different conformers of the same molecule in conformational polymorphism. In pseudopolymorphism the different crystal types are the result of hydration or solvation.

The term "amino acid" refers to a molecule containing both an amino group and a carboxyl group. Amino acids include alpha-amino acids and beta-amino acids, the structures of which are depicted below. In certain embodiments, an amino acid is an alpha amino acid.

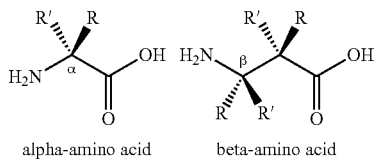

alpha-amino acid     beta-amino acid

Suitable amino acids include, without limitation, natural alpha-amino acids such as D- and L-isomers of the 20 common naturally occurring alpha-amino acids found in peptides (e.g., A, R, N, C, D, Q, E, G, H, I, L, K, M, F, P, S, T, W, Y, V), as provided in Table 1 depicted below), non-canonical alpha-amino acids (as depicted in Tables 2 and 3 below), natural beta-amino acids (e.g., beta-alanine), and unnnatural beta-amino acids.

Amino acids used in the construction of peptides of the present invention may be prepared by organic synthesis, or obtained by other routes, such as, for example, degradation of or isolation from a natural source. In certain embodiments of the present invention, the formula $X_n$ where n is an integer corresponds to the natural and/or non-canonical amino acids having the following formulae:

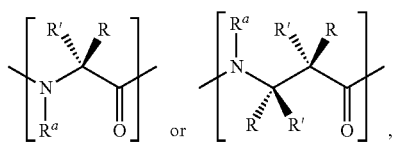

wherein R and R' correspond a suitable amino acid side chain, as defined below and herein, and $R^a$ is as defined below and herein.

TABLE 1

| Exemplary natural | Suitable amino acid side chains | |
|---|---|---|
| alpha-amino acids | R | R' |
| L-Alanine (A) | —CH$_3$ | —H |
| L-Arginine (R) | —CH$_2$CH$_2$CH$_2$—NHC(=NH)NH$_2$ | —H |
| L-Asparagine (N) | —CH$_2$C(=O)NH$_2$ | —H |
| L-Aspartic acid (D) | —CH$_2$CO$_2$H | —H |
| L-Cysteine (C) | —CH$_2$SH | —H |
| L-Glutamic acid (E) | —CH$_2$CH$_2$CO$_2$H | —H |
| L-Glutamine (Q) | —CH$_2$CH$_2$C(=O)NH$_2$ | —H |
| Glycine (G) | —H | —H |
| L-Histidine (H) | —CH$_2$-2-(1H-imidazole) | —H |
| L-Isoleucine (I) | -sec-butyl | —H |
| L-Leucine (L) | -iso-butyl | —H |
| L-Lysine (K) | —CH$_2$CH$_2$CH$_2$CH$_2$NH$_2$ | —H |
| L-Methionine (M) | —CH$_2$CH$_2$SCH$_3$ | —H |
| L-Phenylalanine (F) | —CH$_2$Ph | —H |
| L-Proline (P) | -2-(pyrrolidine) | —H |
| L-Serine (S) | —CH$_2$OH | —H |
| L-Threonine (T) | —CH$_2$CH(OH)(CH$_3$) | —H |
| L-Tryptophan (W) | —CH$_2$-3-(1H-indole) | —H |
| L-Tyrosine (Y) | —CH$_2$-(p-hydroxyphenyl) | —H |
| L-Valine (V) | -isopropyl | —H |

TABLE 2

| Exemplary non-canonical | Suitable amino acid side chains | |
|---|---|---|
| alpha-amino acids | R | R' |
| D-Alanine | —H | —CH$_3$ |
| D-Arginine | —H | —CH$_2$CH$_2$CH$_2$—NHC(=NH)NH$_2$ |
| D-Asparagine | —H | —CH$_2$C(=O)NH$_2$ |
| D-Aspartic acid | —H | —CH$_2$CO$_2$H |
| D-Cysteine | —H | —CH$_2$SH |
| D-Glutamic acid | —H | —CH$_2$CH$_2$CO$_2$H |
| D-Glutamine | —H | —CH$_2$CH$_2$C(=O)NH$_2$ |
| D-Histidine | —H | —CH$_2$-2-(1H-imidazole) |
| D-Isoleucine | —H | -sec-butyl |
| D-Leucine | —H | -iso-butyl |
| D-Lysine | —H | —CH$_2$CH$_2$CH$_2$CH$_2$NH$_2$ |
| D-Methionine | —H | —CH$_2$CH$_2$SCH$_3$ |
| D-Phenylalanine | —H | —CH$_2$Ph |
| D-Proline | —H | -2-(pyrrolidine) |
| D-Serine | —H | —CH$_2$OH |
| D-Threonine | —H | —CH$_2$CH(OH)(CH$_3$) |
| D-Tryptophan | —H | —CH$_2$-3-(1H-indole) |
| D-Tyrosine | —H | —CH$_2$-(p-hydroxyphenyl) |
| D-Valine | —H | -isopropyl |
| Di-vinyl | —CH=CH$_2$ | —CH=CH$_2$ |

| Exemplary non-canonical alpha-amino acids | R and R' are equal to: | |
|---|---|---|
| α-methyl-Alanine (Aib) | —CH$_3$ | —CH$_3$ |
| α-methyl-Arginine | —CH$_3$ | —CH$_2$CH$_2$CH$_2$—NHC(=NH)NH$_2$ |
| α-methyl-Asparagine | —CH$_3$ | —CH$_2$C(=O)NH$_2$ |
| α-methyl-Aspartic acid | —CH$_3$ | —CH$_2$CO$_2$H |
| α-methyl-Cysteine | —CH$_3$ | —CH$_2$SH |

TABLE 2-continued

| | | |
|---|---|---|
| α-methyl-Glutamic acid | —CH$_3$ | —CH$_2$CH$_2$CO$_2$H |
| α-methyl-Glutamine | —CH$_3$ | —CH$_2$CH$_2$C(=O)NH$_2$ |
| α-methyl-Histidine | —CH$_3$ | —CH$_2$-2-(1H-imidazole) |
| α-methyl-Isoleucine | —CH$_3$ | -sec-butyl |
| α-methyl-Leucine | —CH$_3$ | -iso-butyl |
| α-methyl-Lysine | —CH$_3$ | —CH$_2$CH$_2$CH$_2$CH$_2$NH$_2$ |
| α-methyl-Methionine | —CH$_3$ | —CH$_2$CH$_2$SCH$_3$ |
| α-methyl-Phenylalanine | —CH$_3$ | —CH$_2$Ph |
| α-methyl-Proline | —CH$_3$ | -2-(pyrrolidine) |
| α-methyl-Serine | —CH$_3$ | —CH$_2$OH |
| α-methyl-Threonine | —CH$_3$ | —CH$_2$CH(OH)(CH$_3$) |
| α-methyl-Tryptophan | —CH$_3$ | —CH$_2$-3-(1H-indole) |
| α-methyl-Tyrosine | —CH$_3$ | —CH$_2$-(p-hydroxyphenyl) |
| α-methyl-Valine | —CH$_3$ | -isopropyl |
| Di-vinyl | —CH=CH$_2$ | —CH=CH$_2$ |
| Norleucine | —H | —CH$_2$CH$_2$CH$_2$CH$_3$ |

TABLE 3

| Exemplary non-canonical alpha-amino acids | Suitable amino acid side chains R and R' is equal to hydrogen or —CH$_3$, and: |
|---|---|
| Terminally unsaturated alpha-amino acids and bis alpha-amino acids(e.g., modified cysteine, modified lysine, modified tryptophan, modified serine, modified threonine, modified proline, modified histidine, modified alanine, and the like). | —(CH$_2$)$_g$—S—(CH$_2$)$_g$CH=CH$_2$, <br> —(CH$_2$)$_g$—O—(CH$_2$)$_g$CH=CH$_2$, <br> —(CH$_2$)$_g$—NH—(CH$_2$)$_g$CH=CH$_2$, <br> —(CH$_2$)$_g$—(C=O)—S—(CH$_2$)$_g$CH=CH$_2$, <br> —(CH$_2$)$_g$—(C=O)—O—(CH$_2$)$_g$CH=CH$_2$, <br> —(CH$_2$)$_g$—(C=O)—NH—(CH$_2$)$_g$CH=CH$_2$, <br> —CH$_2$CH$_2$CH$_2$CH$_2$—NH—(CH$_2$)$_g$CH=CH$_2$, <br> —(C$_6$H$_5$)—p—O—(CH$_2$)$_g$CH=CH$_2$, <br> —CH(CH$_3$)—O—(CH$_2$)$_g$CH=CH$_2$, <br> —CH$_2$CH(—O—CH=CH$_2$)(CH$_3$), <br> -histidine-N((CH$_2$)$_g$CH=CH$_2$), <br> -tryptophan-N((CH$_2$)$_g$CH=CH$_2$), and <br> —(CH$_2$)$_{g+1}$(CH=CH$_2$), <br> wherein: <br> each instance of g is, independently, 0 to 10. |

Exemplary non-canonical alpha-amino acids

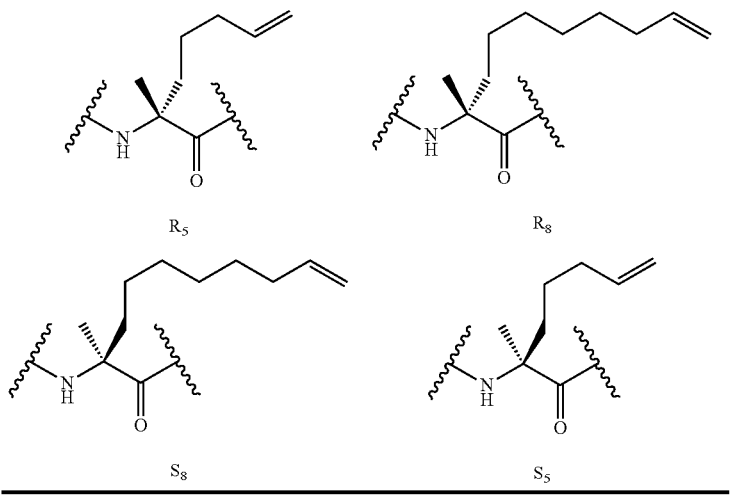

There are many known non-canonical amino acids any of which may be included in the peptides of the present invention. See for example, S. Hunt, *The Non-Protein Amino Acids: In Chemistry and Biochemistry of the Amino Acids*, edited by G. C. Barrett, Chapman and Hall, 1985. Some examples of non-canonical amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-1-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and para-substituted phenylalanines (e.g., substituted with —C(=O)C$_6$H$_5$; —CF$_3$; —CN; -halo; —NO$_2$; CH$_3$), disubstituted phenylalanines, substituted tyrosines (e.g., further substituted with —C(=O)C$_6$H$_5$; —CF$_3$; —CN; -halo, —NO$_2$; CH$_3$), and statine. Additionally, the amino acids suitable for use in the present invention may be derivatized to include amino acid residues that are hydroxylated, phosphorylated, sulfonated, acylated, and glycosylated, to name a few.

The term "amino acid side chain" refers to a group attached to the alpha- or beta-carbon of an amino acid. A "suitable amino acid side chain" includes, but is not limited to, any of the suitable amino acid side chains as defined above, and as provided in Tables 1 to 3.

For example, suitable amino acid side chains include methyl (as the alpha-amino acid side chain for alanine is methyl), 4-hydroxyphenylmethyl (as the alpha-amino acid side chain for tyrosine is 4-hydroxyphenylmethyl) and thiomethyl (as the alpha-amino acid side chain for cysteine is thiomethyl), etc. A "terminally unsaturated amino acid side chain" refers to an amino acid side chain bearing a terminal unsaturated moiety, such as a substituted or unsubstituted, double bond (e.g., olefinic) or a triple bond (e.g., acetylenic), that participates in crosslinking reaction with other terminal unsaturated moieties in the polypeptide chain. In certain embodiments, a "terminally unsaturated amino acid side chain" is a terminal olefinic amino acid side chain. In certain embodiments, a "terminally unsaturated amino acid side chain" is a terminal acetylenic amino acid side chain. In certain embodiments, the terminal moiety of a "terminally unsaturated amino acid side chain" is not further substituted. Terminally unsaturated amino acid side chains include, but are not limited to, side chains as depicted in Table 3.

A "peptide" or "polypeptide" comprises a polymer of amino acid residues linked together by peptide (amide) bonds. The term(s), as used herein, refers to proteins, polypeptides, and peptide of any size, structure, or function. Typically, a peptide or polypeptide will be at least three amino acids long. A peptide or polypeptide may refer to an individual protein or a collection of proteins. Inventive proteins preferably contain only natural amino acids, although non-natural amino acids (i.e., peptides that do not occur in nature but that can be incorporated into a polypeptide chain) and/or amino acid analogs as are known in the art may alternatively be employed. Also, one or more of the amino acids in a peptide or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A peptide or polypeptide may also be a single molecule or may be a multi-molecular complex, such as a protein. A peptide or polypeptide may be just a fragment of a naturally occurring protein or peptide. A peptide or polypeptide may be naturally occurring, recombinant, or synthetic, or any combination thereof. As used herein "dipeptide" refers to two covalently linked amino acids.

BRIEF DESCRIPTION OF THE DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIG. 1A: Large non-canonical peptide libraries were rapidly synthesized using split and pool technique by randomizing residues within a peptide sequence. These libraries were then (1) bound to a protein target in solution where stringency could be conveniently tuned. The binding mixture was subjected (2) to high-pressure size exclusion chromatography (HPSEC) for the high performance resolution of protein-binder complexes (in burgundy) from unbound library fraction (in yellow) and therefore for the selection of binders in the protein fraction. The breakthrough fraction (or protein fraction) was then (3) directly analyzed in the case of linear binders or subjected to chemical conditions to linearize complex peptide binders before LC-MS/MS analysis. The decoded sequences were then (4) resynthesized and modified for their validation using binding or functional assays.

FIGS. 2A-2F: Rapid combinatorial mapping of pDI (6) key binding residues and affinity selection of potent non-canonical inhibitors of $^{25-109}$MDM2 and C-CA proteins. FIG. 2A) Combinatorial mapping of pDI (6) binding hotspots, library design. Represented are 6's randomized residues using L-configured (circles) natural amino acids. FIG. 2B) Affinity selected sequences from Library 1 and 2 at different stringencies (sequences 1 to 9) were validated after resynthesis and biotinylation or acetylation (peptides 1a to 6a and 7b to 9b) using bio-layer interferometry (BLI). In bold italic are represented randomized residues, and those that were varied compared to sequence 6. FIG. 2C) Expanding linear inhibitor hotspots to non-canonical amino acids. Library 3 was designed around 6 while Library 4 was designed around CAI (37) inhibitor. Depicted are randomized residues using non-canonical amino acids (abbreviations for each monomer are indicated in bold). FIG. 2D) Affinity selection from Library 3 at higher stringency using 6 as a soluble competitive inhibitor. Starting with more than 300 selected sequences, stringency was maximally increased by adding 6 and by lowering MDM2 concentrations altogether, yielding one sequence above MS/MS threshold (sequence 10). FIG. 2E) Validation of non-canonical binders from Library 3 (sequences 10 to 29) and 4 (sequence 30 to 37) after resynthesis and biotinylation (10a to 29a and 30a to 37a, FIGS. 48 and 72) or acetylation (10b and 11b, FIG. 48) using Bio Layer Interferometry (BLI). In bold italic are represented randomized residues and those that were mutated compared to 6 and 37. FIG. 2F) Exemplary BLI traces illustrating improved affinity of non-canonical containing peptide binders compared to canonical reference peptides. For 6a traces correspond to 20 nM, 30 nM, 40 nM, and 50 nM MDM2 and 10a 1.25 nM, 2.5 nM, 5 nM, and 10 nM MDM2. For 37a traces correspond to 313 nM, 625 nM, 1250 nM, and 2500 nM C-CA and 30a 37.5 nM, 75 nM, 150 nM, and 300 nM C-CA.

FIG. 3A) Macrocyclization schemes of select Library 3 non-canonical sequences Xa or Xb using established i and i+7 macrocyclization chemistries (where X is the sequence number and Xa or Xb designate respectively N-terminal biotinylation or acetylation). Peptide sequences were modified for macrocyclization, using metathesis (Xa-M or Xb-M) or nitrogen arylation (Sn) of lysine (Xa-S4 or Xb-S4) or diamino propionic acid (Xa-S1 or Xb-S1) side chains. FIG. 3B) MDM2 binding affinities of select non-canonical macrocyclic peptides based on sequences 10 and 11. Binding affinities were determined using immobilized assay for biotinylated peptides (10a-M and 11a-S1) or estimated in solution for acetylated constructs (10b-M, 10b-S1, 10b-S4, 11b-S1 and 11b-S4) using BLI. FIG. 3C) Chemical structures of biologically tested non-canonical macrocyclic peptides and select controls. FIG. 3l)) Confocal microscopy imaging of MDM2 overexpressing SJSA-1 cells treated with 10b-M, 11b-S1 and their unstapled controls (10 μM, 126× magnification). Cell membrane (WGA staining) and fluorescence (for FITC labeled peptides) are shown. FIG. 3E) P53 activation in SJSA-1 cells was evaluated by Western blot analysis. Cells were treated for 12 hours with either macrocyclic MDM2 binders or controls (10 μM), and electrophoresed lysates were stained for MDM2, P21, and the loading control GAPDH. Macrocyclic binders I1b-S1 and 10b-M upregulated MDM2 and P21 markers relative to controls. This experiment was performed two times with similar results; upregulation of MDM2 and p21 by incubation of SJSA-1 cells with 11b-S1 and 10b-M was confirmed in at least three independent experiments. FIG. 3F) Cell viability responses of SJSA-1 cells to treatment with macrocyclic constructs and their controls.

FIGS. 4A-4D: Affinity selection of highly potent knottin derived and D-configured mini-protein binders of MDM2. FIG. 4A) Scaffold design was based on a D-configured minimal folding motif derived from EETI-II and a D-configured loop binding MDM2. Disulfide bridges are figured in yellow and randomized residues within binding loop are depicted, fixed regions are figured. FIG. 4B) D-configured mini-protein-based Library 5 was designed around D-PMI-β (54b) hotspots. Randomized residues are depicted and monomer set exclusively comprises D-configured residues (squares). FIG. 4C) In solution strategy for mini-protein binding loop sequencing. A diol was included between the cystine stabilized β-sheet domain and the randomized region and, upon oxidative cleavage by periodate yielded the short and efficiently sequenced binding peptide (dotted rectangle). FIG. 4D) Sequences of high affinity binders to MDM2 based on this non-canonical scaffold. All resynthesized and folded peptides were validated by estimating binding in solution using BLI and were found to have nanomolar affinities for MDM2.

FIG. 5: Calibration curve corresponding to binding response at equilibrium (in nm)=f(free [MDM2] in nM) Based on the binding (nm) values, the concentration of "free" MDM2 was interpolated for each sample using the calibration curve. The following equation was used to generate fitted curves: $[y]=0.5*[(b-Kd-[X])+(([X]+Kd-b)^2+4b*Kd)^(0.5)]$ where y is "free" MDM2 in nM, X is the acetylated peptide inhibitor in nM, Kd is the dissociation constant, and b is ymax.

FIG. 6: Exploration of HPSEC assay using model binders. Chemical characteristics of used model binders to establish affinity selection platform. Model binders spanned linear, macrocyclic and folded peptide structures. Retention times were determined using C3 column and LC-MS method A. Affinities for their respective binding targets were determined in this study using BLI (for 6 using 6a, 37 using 37a, 57a and for 60 using 60a), or Trypsin inhibition assay[6] (for 59 and 60). 59 was obtained by mutating $^3$Ser into a diol amino acid in EETI-II (58) sequence. This mutation did not disrupt folding nor binding of 59 to trypsin. Compound 60 was obtained by the perfluorosulfone macrocyclization of pDI-cysteine peptide.

FIG. 9B: Using LC-MS method A serial dilutions of pure 58 (*) were analyzed and EIC peak area=f (58 amounts) was plotted to determine linear range. The thus obtained calibration curve was used to determine selection yield in the collected protein fraction.

FIG. 10A: Protein fraction retention times (dashed boxes) were collected and subsequently analyzed using LC-MS method A. EETI-H-diol (59) is marked with a (*) and was only detected in the protein fraction for the Trypsin+59 condition. Bottom, MS spectrum confirming 59 identity (asterisk).

FIG. 10B: Using LC-MS method A serial dilutions of pure 59 (*) were analyzed and EIC peak area=f(59 amounts) was plotted to determine linear range. The thus obtained calibration curve was used to determine selection yield in the collected protein fraction. Serial dilutions of 59 were analyzed using LC-MS and extract ion peak area=f (59 amounts) was plotted to obtain a calibration curve and estimate selection yield.

FIG. 11B: Using LC-MS method A serial dilutions of pure 57a (*) were analyzed and EIC peak area=f (57 amounts) was plotted to determine linear range. Thus the obtained calibration curve was used to determine selection yield in the collected protein fraction.

FIG. 12B: Using LC-MS method A serial dilutions of pure 6 (*) were analyzed and EIC peak area=f (6 amounts) was plotted to determine linear range. The obtained calibration curve was used to determine selection yield in the collected protein fraction.

FIG. 20: Linearization of complex binders was used for full sequence coverage using LC-MS/MS analysis. De novo sequencing using PEAKS software, after 60 excision and 59 backbone cleavage. Top, MS/MS fragmentation (CID) spectra corresponding to sequencing of 60 after affinity selection (100 ng scale) and excision as described in FIG. 18. Bottom, MS/MS fragmentation (ETD) spectra corresponding to sequencing of 59 binding sequence after affinity selection (4 µg scale) and excision as described in FIG. 19. Trypsin binding sequence was found to be oxidized at $^7$Met (+16 Da) and $^1$Gly-$^2$Cys (amidomethyl) was set as a fixed PTM to allow for higher sequence coverage. Finally $^{12}$D was found to bear the expected PTM corresponding to diol oxidative cleavage.

FIG. 36: Affinity selected sequences from Library 1 in usual stringency conditions shared a conserved (F, W, L) triad motif. Top, list of decoded sequences with ALC scores >75%. Sequences 1 to 4 were found to be nanomolar binders to MDM2 after resynthesis (vide infra) and N-terminal biotinylation (peptides 1a to 4a, FIG. 2B). In bold italic are represented randomized residues, and shown are the residues modified compared to reference 6. Bottom, schematic representation of amino acid frequencies as a function of residue positioning using WEBLOGO software. Arrows indicate randomized residues in Library 1.

FIG. 41: Randomly selected binders, with high ALC scores, following affinity selection from library 3 had lower or equivalent affinities to 6. Library 3 (75 µg, ~ 45 µM) was added to MDM2 (50 µg, 20 µM) in 100 µL final volume of mobile phase supplemented with L-arginine pH 7.5. The solution was mixed by pipetting and left to stand for 1 hour at room temperature before size exclusion chromatography. Sequences with high decoding scores were randomly picked for resynthesis. These sequences were found to bind MDM2 with lower or equivalent affinities to 6. In bold italic are represented randomized residues, and shown are the residues modified compared to 6.

FIG. 48: Binding sequences discovered at high stringency were resynthesized and found to have higher affinity than 6a for MDM2. Library 3 (75 µg, ~45 µM) was added to MDM2 (50 µg, 20 µM) in 95 µL final volume of mobile phase supplemented with L-arginine pH 7.5. After 10 minutes, 5 µL of concentrated 6 in 20% DMSO (final concentration 100 µM) was added and the solution was mixed by pipetting and left to stand for 1 hour at room temperature before size exclusion chromatography. 20 efficiently decoded sequences featuring non-canonical residues (sequence 10 to 29) were resynthesized and validated (10a to 29a, 10b and 11b). In bold italic are represented randomized residues, and shown are the residues modified compared to 6. All resynthesized biotinylated (10a to 29a) peptides were found to bind MDM2 except 29a which had a low ALC score (Data not shown). All binders except 28a, were found to have improved affinity for MDM2 compared to reference 6a. High affinity sequences 10 and 11 were further validated using in solution competition (peptide 10b and 11b) confirming the low nanomolar affinity of these sequences. The potential for dual MDM2 and MDMX was also illustrated for 10a and 11a.

FIG. 71: Global fitting of association and dissociation curves of various concentrations of SUMO-$^{25-109}$ MDM2 (40 nM, 20 nM, 10 nM and 5 nM) with biotin labeled peptide 28a immobilized to streptavidin sensors. The $K_D$ was found to be 96 nM±0.5 nM. Coefficient of determination $R^2$=0.9972.

FIG. 72: Binding sequences discovered at high stringency were resynthesized and found to have higher affinity than 37a for C-CA. Library 4 (300 μg, ~1.9 mM) was added to C-CA (250 μg, 100 μM) in 100 μL final volume of mobile phase (25 mM, 50 mM NaCl, pH 7.5). The solution was mixed by pipetting and left to stand for 1 hour at room temperature before HPSEC using shorter BIO-SEC-3, 7.8*50 mm. All resynthesized C-terminally biotinylated peptides were found to bind to C-CA. In bold italic are represented randomized residues, and shown are the residues modified compared to reference 37.

FIG. 73: Global fitting of association and dissociation curves of various concentrations of SUMO-C-CA (300 nM, 150 nM, 75 nM and 37.5 nM) with biotin labeled peptide 30a immobilized to streptavidin sensors. The Ku was found to be 88 nM±5 nM. Coefficient of determination $R^2$=0.9916.

FIG. 82: Modification and macrocyclization of Library 3 non-canonical sequences were used for the discovery of potent macrocyclic inhibitors. Select sequences were macrocyclized using ring closing methathesis (RCM) and nitrogen arylation stapling of lysine and Dap (diamino propionic acid) side chains. In bold italic are represented hotspot residues. Depicted are non-canonical modified hotspots compared to 6. Represented are residues that were modified to allow for macrocyclization. 4 sequences from Library 3 were macrocyclized including 10 and 11 which were high affinity binding sequences to MDM2 (FIG. 48). 4 macrocyclic constructs were found to bind MDM2 with low nanomolar affinity (10b-M, 11b-M, 11b-S1, 27b-M) and demonstrated cell-killing properties against MDM2 overexpressing SJSA-1 cells. Anthracene containing (sequence 22) macrocyclic peptides did not bind MDM2, while perfluorosulfone stapling of lysine side chains systematically weakened or abrogated binding (10b-S4, 11b-S4 and 22b-S4). Macrocyclic controls derived from sequences 10 and 11 were also synthesized (10b-M scramble, 10b-M unclosed, 11b-S1 scramble, FIG. 81) and evaluated for binding and cell-killing.

FIG. 101: Flow cytometry analysis confirmed cellular loading with FITC labeled non-canonical peptides in RCM series. Intracellular loading of RCM constructs (10 μM) and controls (FIGS. 3C and 8I) was assessed by FACS. Cell impermeant Trypan blue was used to quench extracellular fluorescence. Mean fluorescence was normalized to FAM-TP-10 a fluorescein labeled cell-penetrating peptide[3]. The horizontal bar represents the mean of three measurements (n=3) within the same experiment. Error bars represent standard deviation of the mean. Each peptide was assayed three times. This experiment was performed one time.

FIG. 107: High affinity sequences from Library 3 yielded two potent low nanomolar macrocyclic inhibitors that killed SJSA-1 cells. Macrocyclic peptides 10b-M and 11b-S1 were tested along with their unstapled (respectively 10b, 10b-M unclosed and 11b-unstapled) and their scrambled analogs (FIGS. 3C and 81-82).

Figure 113:
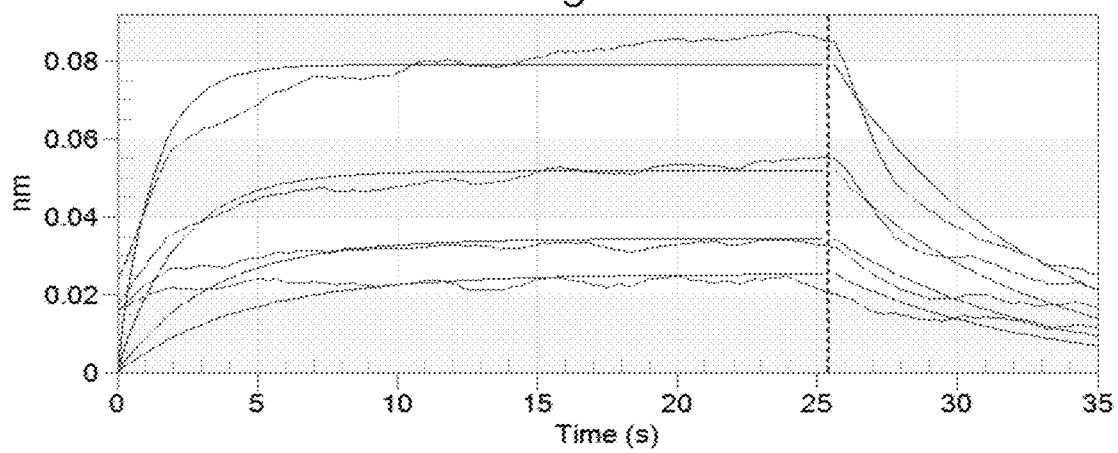

FIG. 113: Global fitting of association and dissociation curves of various concentrations of SUMO-C-CA (2500 nM, 1250 nM, 613 nM and 307 nM) with biotin labeled peptide 32a-M immobilized to streptavidin sensors. The $K_D$ was found to be 1.1 µM±0.1 µM. Coefficient of determination $R^2$=0.95.

Figure 114:
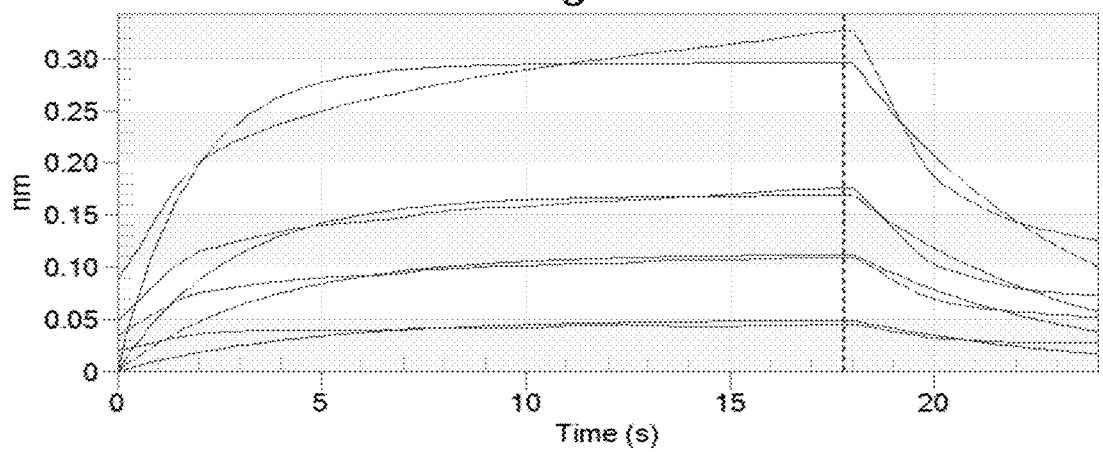

FIG. 114: Global fitting of association and dissociation curves of various concentrations of SUMO-C-CA (10000 nM, 5000 nM, 2500 nM and 1250 nM) with biotin labeled peptide NYAD (37a-M) immobilized to streptavidin sensors. The $K_D$ was found to be 5.8 µM±0.7 µM. Coefficient of determination $R^2$=0.97.

Figure 115:
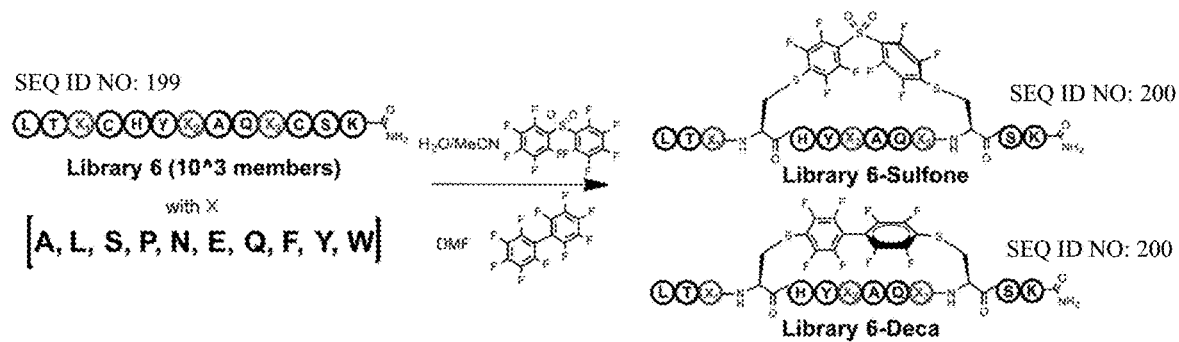

FIG. 115: Library 6-Sulfone and Library 6-Deca were prepared for the study of mutational tolerance of macrocyclized pDI-cysteine hot spots. Library 6 was designed similarly to Library 2 and aimed at demonstrating the feasibility of preparing and screening in solution perfluoroaryl macrocyclized peptide libraries. Decafluoro biphenyl electrophile in DMF or perfluorosulfone electrophile in a mixture of water/acetonitrile were used to rapidly prepare macrocyclic libraries in solution.

Figure 116:
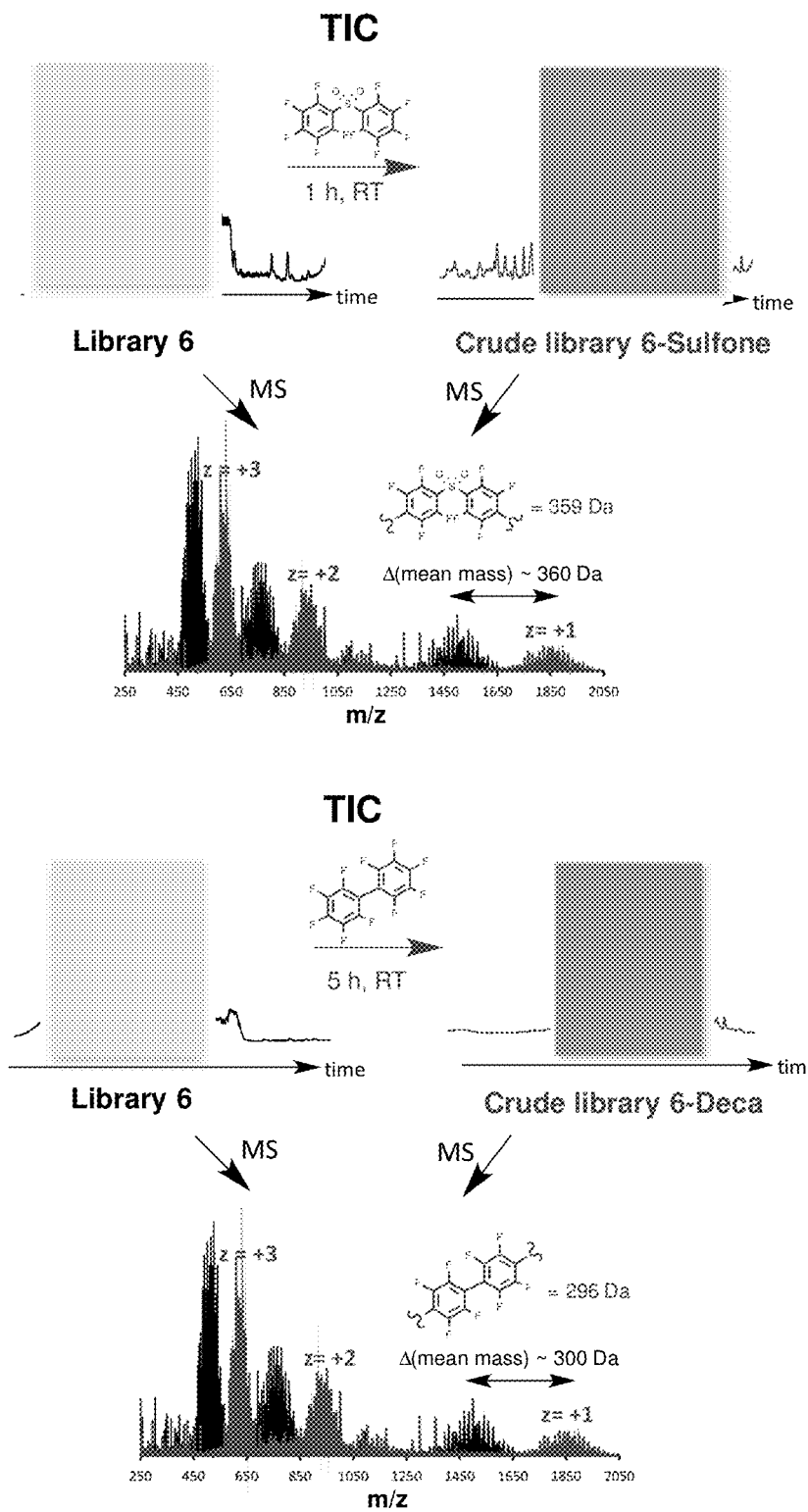

FIG. 116: Facile preparation of macrocyclic pDI libraries. Library 6-Sulfone and Library 6-Deca were efficiently synthesized in solution. Crude reaction mixtures were analyzed by LC-MS (method B) and obtained total ion chromatograms (TIC) were compared to Library 6 TIC to monitor macrocyclization. Overlaid MS spectra supported obtention of desired libraries without double arylation or crosslink side products.

Figure 117:
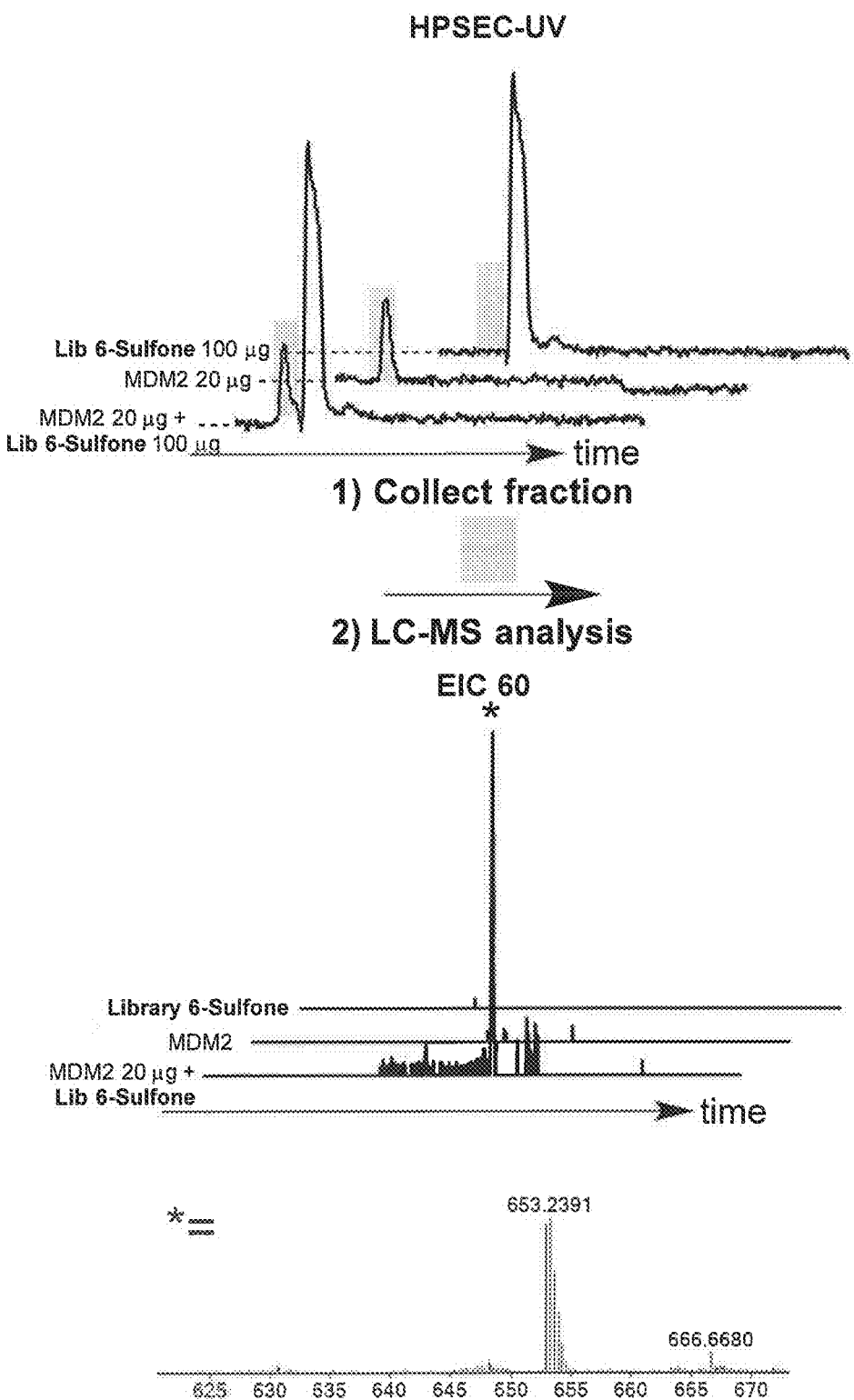

FIG. 117; pDI-Sulfone (60) was affinity selected from Library 6-Sulfone. Crude Library 6-Sulfone (100 µg, ~500 µM) was added to MDM2 (50 µg, 20 µM) in 100 µL final volume of mobile phase supplemented with L-arginine pH 7.5. The solution was mixed by pipetting and left to stand for 1 hour at room temperature before HPSEC using shorter BIO-SEC-3 7.8*50 mm. Top, protein fraction retention times were collected and subsequently analyzed using LC-MS method A. Peptide 60, marked with a (*), was only detected in the protein fraction for MDM2+Library 3-Sulfone condition. 60 identity was further confirmed using perfluorosulfone macrocycle excision conditions (FIG. 18) followed by MS/MS sequencing.

FIG. 118; Affinity selection results for Library 6-Sulfone and Library 6-Deca. Affinity selection from Library 6-Sulfone and Library 6-Deca only afforded perfluorosulfone macrocyclized 60. Decafluorobiphenyl macrocyclized 62a showed absence of binding, while sulfone macrocyclized 61a (based on affinity selected nanomolar sequence 5 from Library 2) showed substantially weaker binding compared to 60a. These controls confirmed the results of the affinity selection experiments where only one sequence was selected (60) and suggested that perfluorosulfone macrocyclization may not tolerate well the mutation of hotspots, and that decafluorobiphenyl abrogated binding to MDM2.

Figure 119:
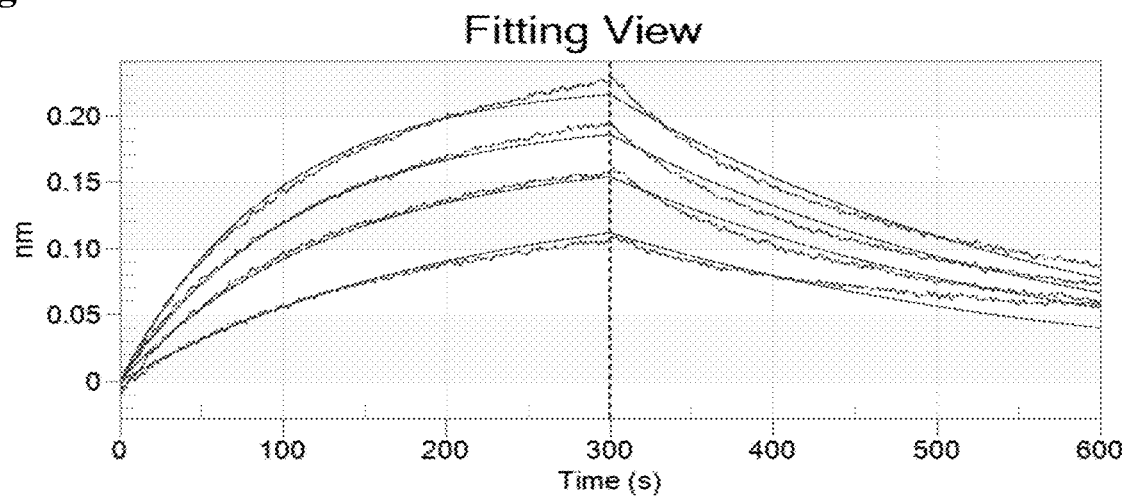

FIG. 119: Global fitting of association and dissociation curves of various concentrations of SUMO-[25-109] MDM2 (50 nM, 40 nM, 30 nM and 20 nM) with biotin labeled peptide 60a immobilized to streptavidin sensors. The $K_D$ was found to be 24 nM±0.3 nM. Coefficient of determination $R^2$=0.99.

Figure 120:
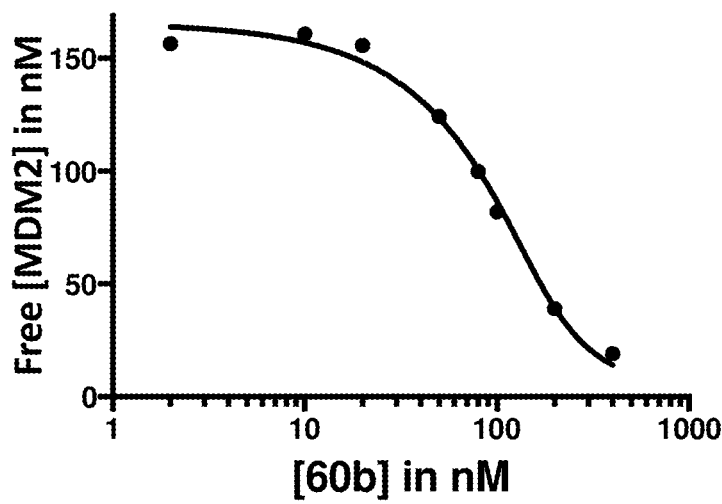

FIG. 120: SUMO-[25-109] MDM2 and peptide 60b (400 nM, 200 nM, 100 nM, 80 nM, 50 nM, 40 nM, 20 nM and 2 nM) were mixed together following the protocol for in solution competition assay. [MDM2] was determined using calibration curve and the obtained titration curve was fitted. The $K_D$ was found to be 23 nM±4.8 nM. Coefficient of determination $R^2$=0.99.

Figure 121:
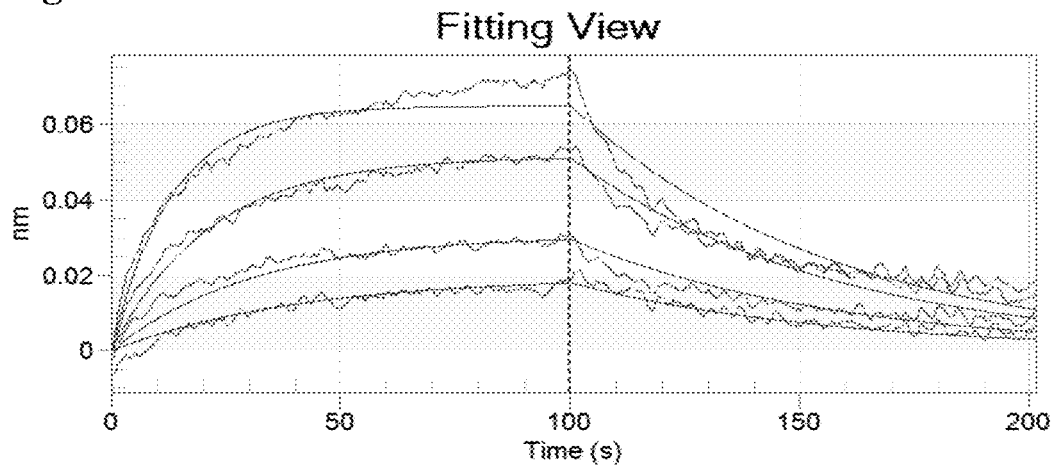

FIG. 121: Global fitting of association and dissociation curves of various concentrations of SUMO-[25-109] MDM2 (400 nM, 200 nM, 100 nM and 50 nM) with biotin labeled peptide 61a immobilized to streptavidin sensors. The $K_D$ was found to be 310 nM±5 nM. Coefficient of determination R2=0.97.

Figure 122:
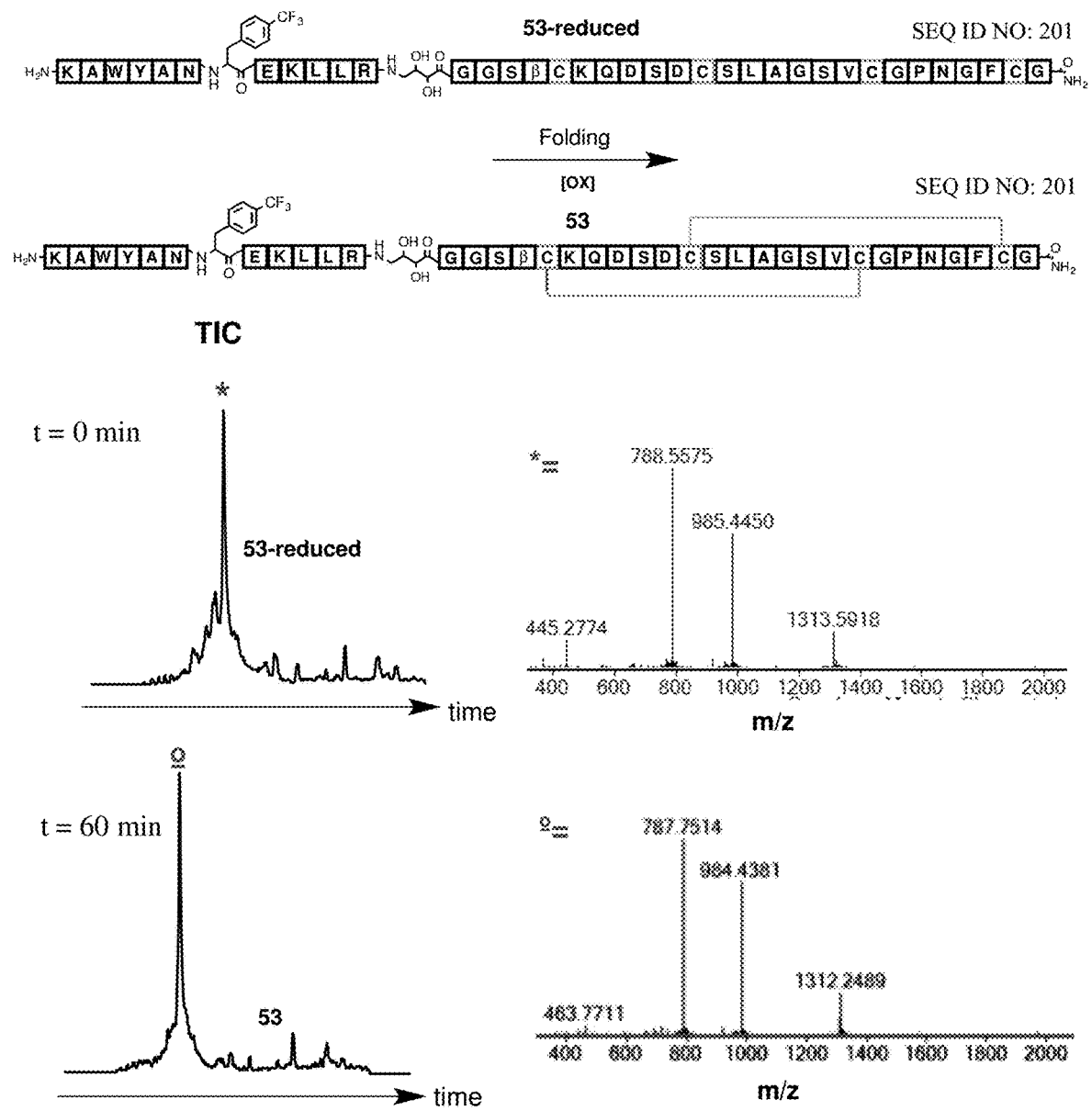

FIG. 122: D-configured mini-proteins based on knottin scaffold are efficiently folded under oxidative conditions. Oxidative folding of the cystine stabilized beta-sheet (CSB) motif of D-configured (squares) and diol amino acid containing 53-reduced. Top, scheme describing the formation of 2 disulfide bridges (in orange) upon oxidation. Bottom, total ion chromatogram (TIC) and corresponding MS spectra demonstrating the obtention of one single folded product 53 with loss of 4 Da.

Figure 19:
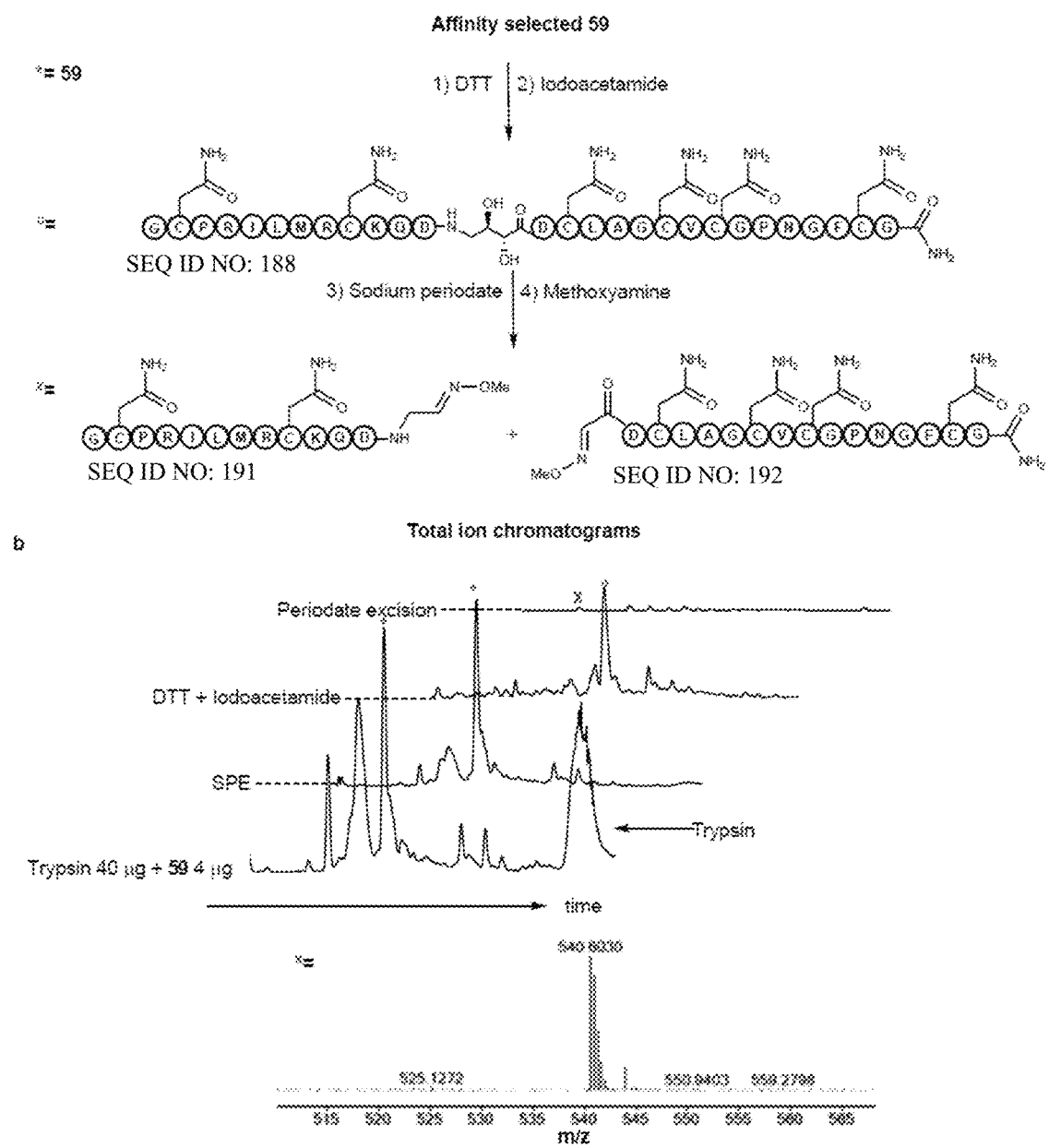
FIG. 19: Affinity selection followed by efficient in situ backbone cleavage of 59 by sodium periodate to yield linear trypsin binding loop. Top, chemical transformations describing reduction and alkylation (°) then cleavage of 59 (*) to afford linear trypsin binding loop (X). Middle, total ion chromatogram (TIC, LC-MS method A) illustrating, after solid phase extraction (SPE), the successful conversion of affinity selected 59 (*) into (X). Briefly, 59 (4 μg, 13 μM) was mixed with trypsin (40 μg, 17 μM) in 100 μL of mobile phase and after 1 hour at room temperature, the binding mixture was subjected to size exclusion chromatography. Protein fraction was collected and solid phase extracted using Pierce C-18 spin columns (Thermo Fisher Scientific, CA) to remove trypsin. 59 was selectively eluted by 50 μL 70/30 water/acetonitrile (with 0.2% TFA). The eluate was then diluted to 100 μL with 100 mM Tris buffer at pH 8.5 and 36 mg of solid urea were added (~6 M final concentration). Then a freshly prepared solution of DTT (0.5 M in 50 mM Tris, pH 8.5) was added to a final concentration of 5 mM for 15 min at room temperature followed by addition of freshly prepared ioadoacetamide solution (0.28 M in 50 mM Tris, pH 8.5) to a final concentration of 15 mM and the mixture was kept in the dark for 30 min at room temperature. Reduced and alkylated 59 was then desalted using solid phase extraction and eluted in 50 μL of 70/30 water/acetonitrile (with 0.2% TFA). 50 μL of 2 mM NaIO$_4$ in 200 mM sodium acetate was then added and pH was set to 5.5. The resulting cleavage mixture was incubated at room temperature for 45 minutes and finally quenched with 2 μL of 50% glycerol solution and 2 μL of freshly prepared 0.5 M methoxyamine in 100 mM Tris buffer. Bottom, MS spectra confirming the identity of (X). X's sequence is provided in FIG. 19.
Figure 21:
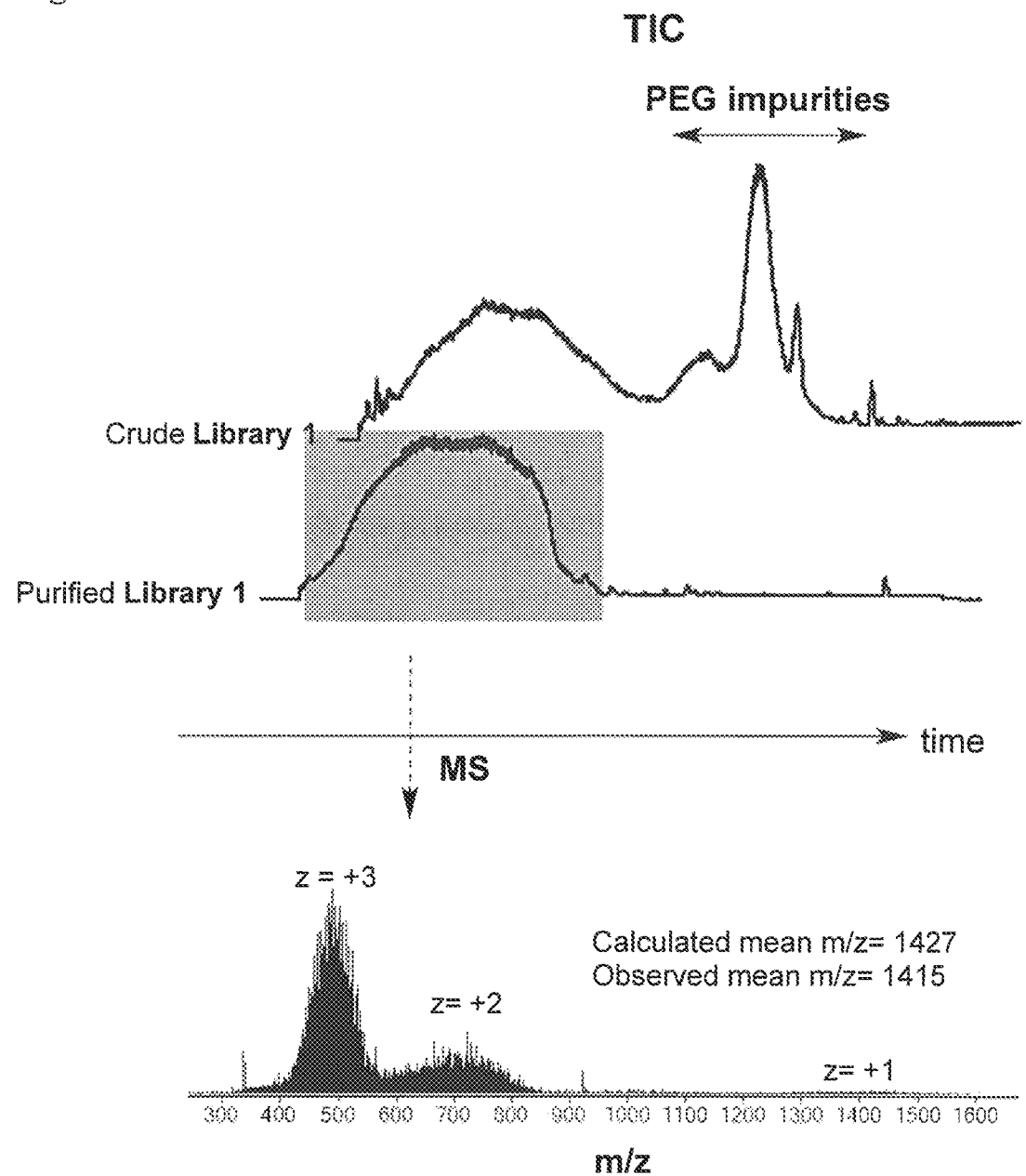
FIG. 21: Facile purification and in solution characterization of million membered Library 1. Top, total ion chromatogram (TIC, LC-MS method B) of crude and purified Library 1. Library 1 was purified using RP-HPLC to remove PEG impurities released during resin cleavage in strongly acidic conditions (TFA). Bottom, Mass and charge distribution confirming correct synthesis of Library 1.
Figure 22:
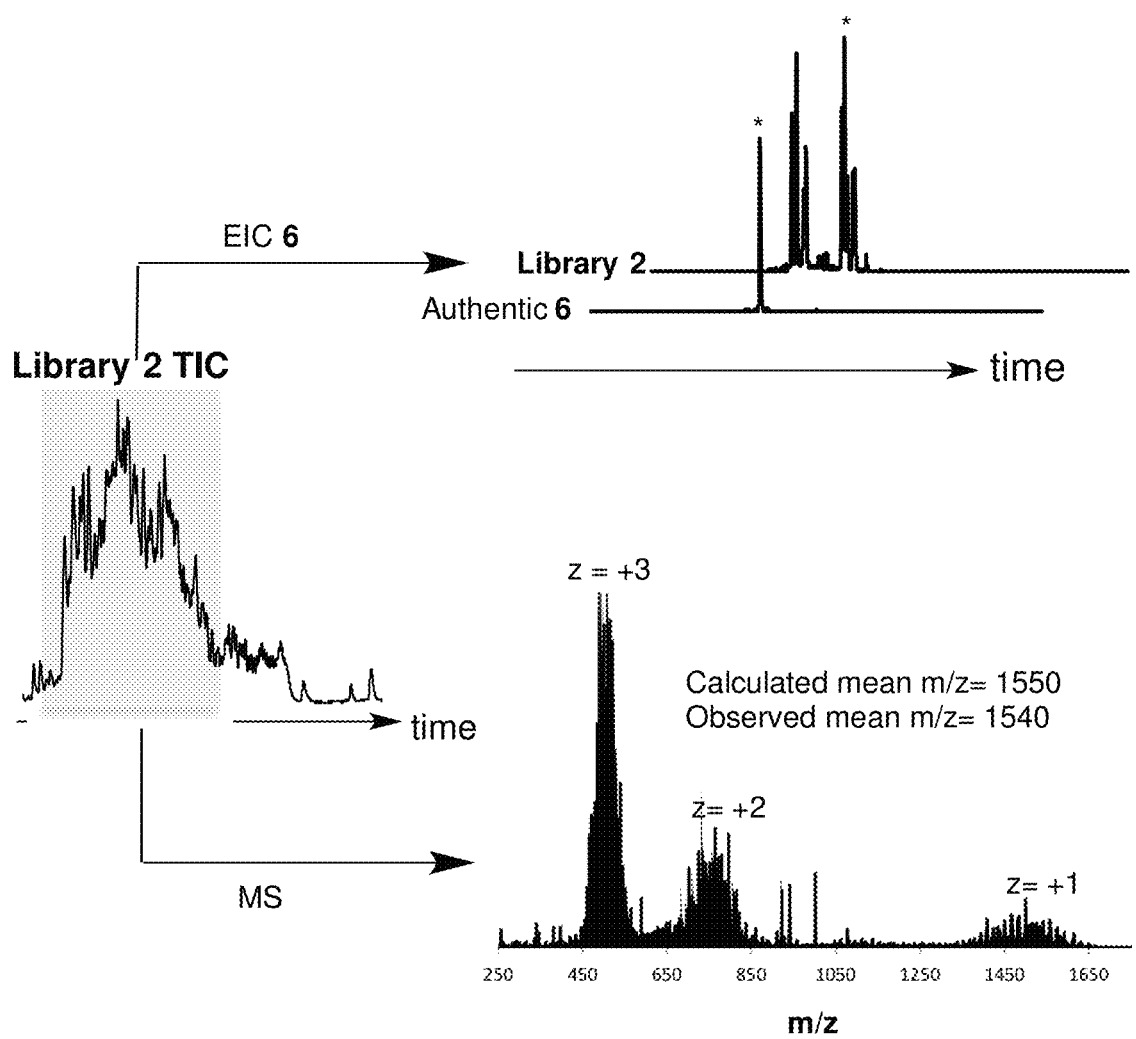
FIG. 22: Facile purification and in solution characterization of thousand membered Library 2. LC-MS characterization of purified Library 2 (method B). Top, extract ion chromatogram (EIC, LC-MS method A) of peptide 6 within Library 2. 6 was detected at the expected retention time and exact mass. Bottom, mean mass and library charge distribution together confirm correct synthesis of Library 2.
Figure 23:
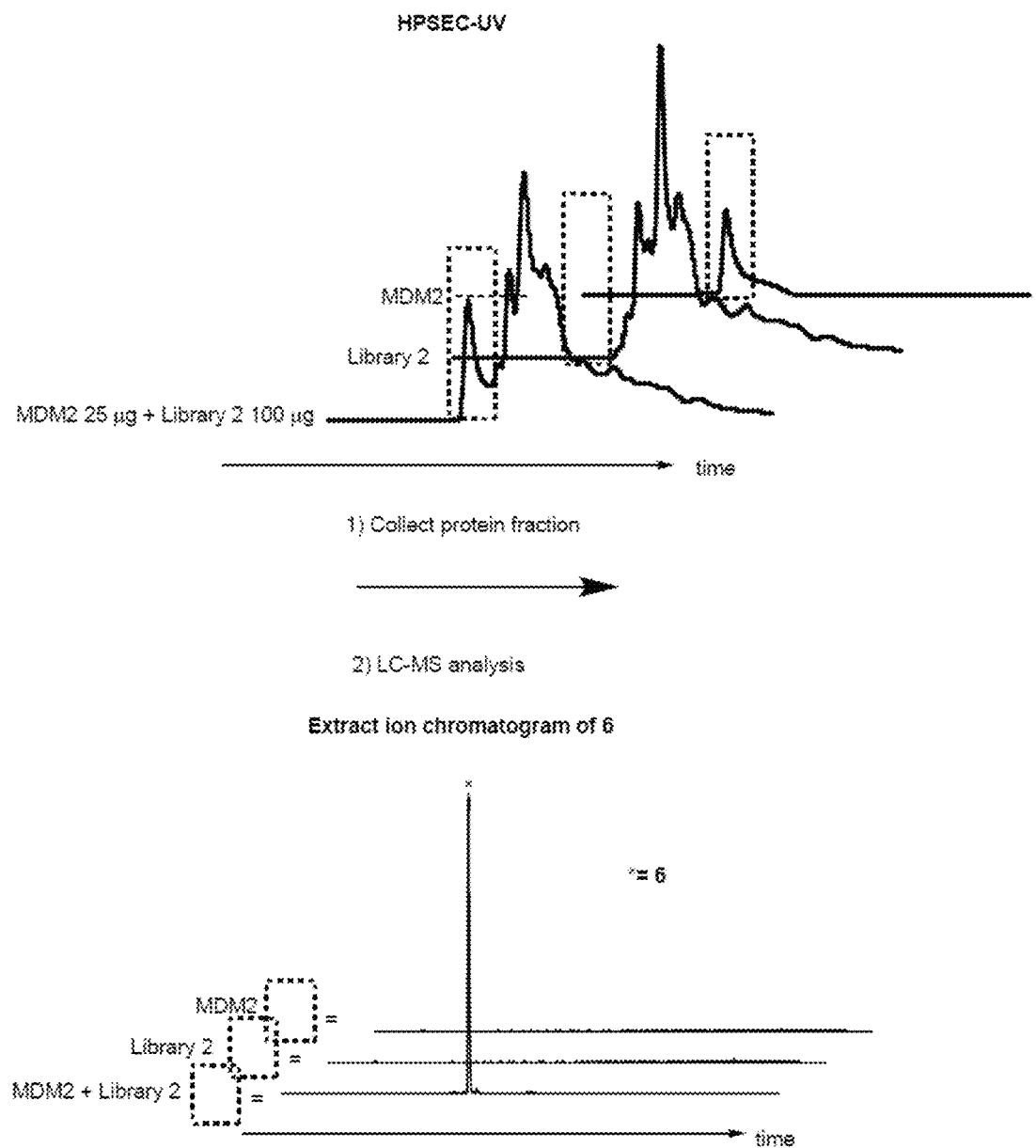
FIG. 23: Efficient affinity selection of 6 in the library context. Library 2 (100 µg, ~~600 µM) was added to MDM2 (20 µg, 17 µM) in 100 µL final volume of mobile phase supplemented with L-arginine pH 7.5. The solution was mixed by pipetting and left to stand for 1 hour at room temperature before size exclusion chromatography. Top, HPSEC traces show that MDM2 (25 µg, 10.6 µM in the binding mixture) was resolved from Library 2 (100 µg, ~600 µM in the binding mixture). Fractions corresponding to protein retention times (dashed boxes) were collected and subsequently analyzed (bottom) using LC-MS analysis. Selections were performed in these conditions two times, varying the amounts of Library 2 (10 ug or 100 ug). LC-MS analyses were performed one time each (representative outcome shown). The selection yield of 6 marked by (*) was estimated to be roughly equivalent in these conditions to the single binder selection case (FIG. 8).
Figure 123:
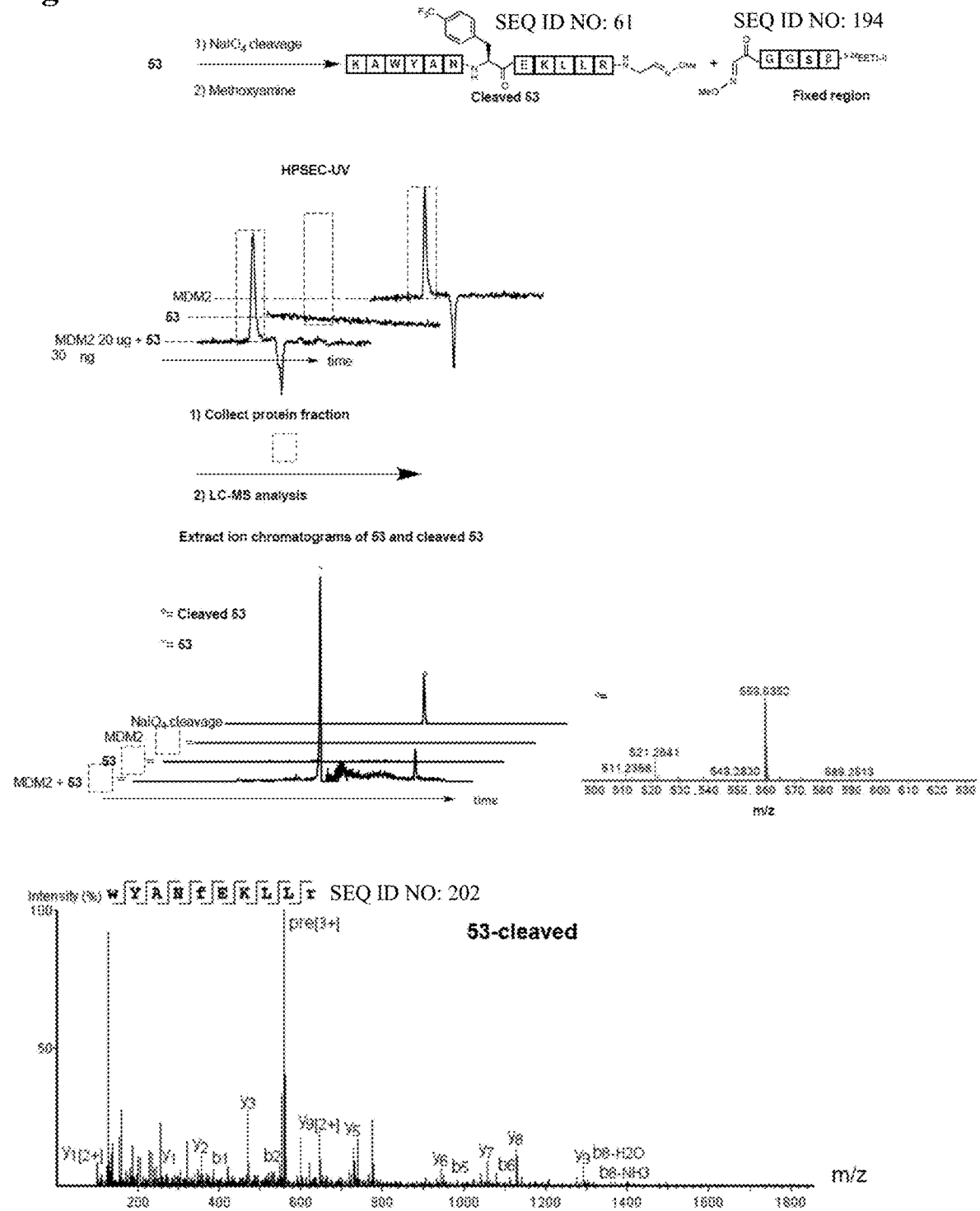

FIG. 123: Efficient in situ backbone cleavage of affinity selected mini-protein 53 and robust MS/MS decoding of MDM2 binding loop (53-cleaved). 53 (30 ng, 76 nM) was added to MDM2 (20 µg, 8.6 µM) in 100 µL final volume of mobile phase supplemented with L-arginine pH 7.5. The solution was mixed by pipetting and left to stand for 1 hour at room temperature before size exclusion chromatography. Top, reaction scheme for the oxidative cleavage of 53 inspired by decoding of 59 (FIG. 19). After size exclusion chromatography, protein fraction retention times were collected and subsequently analyzed using LC-MS method A. Peptide 53 is marked with a (*) and was detected only in the protein fraction for the MDM2+53 condition. Addition of solid sodium periodate to the protein fraction to a final concentration of 30 mM and incubation for 45 min at 37° C. followed by quenching with glycerol and addition of methoxyamine hydrochloride (final concentration of 30 mM) cleanly afforded MDM2 binding loop, 53-cleaved (°). This linear short peptide was efficiently de novo sequenced (97% ALC) using PEAKS software. $^1$Lys-$^2$Ala was set as a fixed PTM to allow for higher sequence coverage, and the expected PTM corresponding to diol cleavage was found on $^{12}$Arg. Peptide Fixed region-cleaved was also detected by LC-MS after periodate treatment (data not shown).

Figure 124:
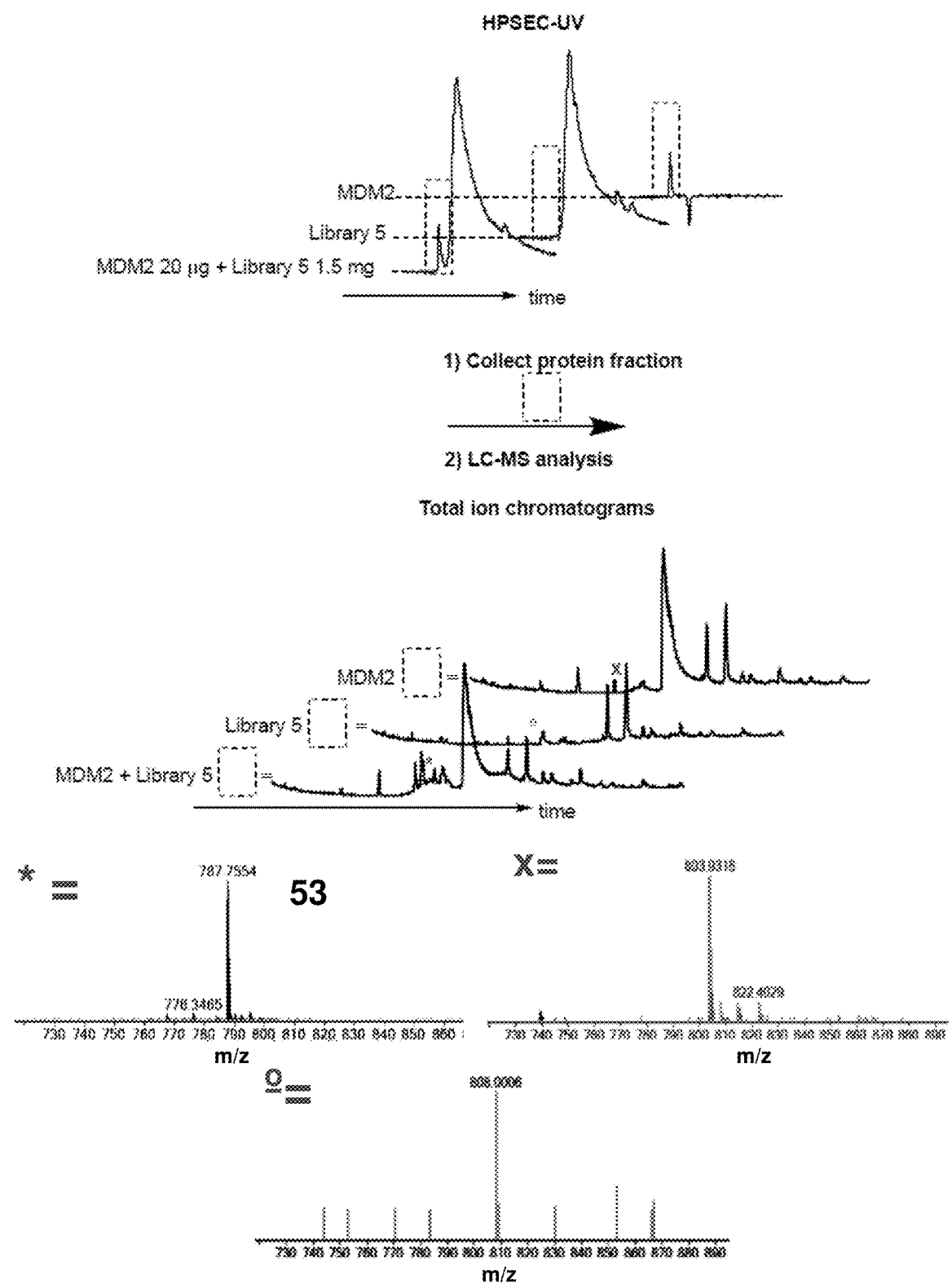

FIG. 124: Affinity selection of multiple mini-protein binders from Library 5. Crude folded Library 5 (1.5 µg, ~3.75 µM) was added to MDM2 (20 µg, 8.5 µM) in 100 µL final volume of mobile phase supplemented with L-arginine pH 7.5, pH 7.5. The solution was mixed by pipetting and left to stand for 1 hour at room temperature before size exclusion chromatography. Top, protein fraction retention times were collected and subsequently analyzed using LC-MS method B. Inspection of total ion chromatogram (TIC) LC-MS traces and direct comparison of MS spectra at the same retention times across different selection conditions (*), ($), (†) shows specific mini-proteins selection in the MDM2+ Library 5 condition including positive control 53 (*). Addition of solid sodium periodate to the protein fraction to a final concentration of 30 mM and incubation for 45 min at 37° C. followed by quenching with glycerol and addition of methoxyamine hydrochloride at a final concentration of 30 mM cleanly afforded the binding loops of selected mini-proteins.

FIG. 125. Affinity selected mini-protein binders were efficiently sequenced using sodium periodate mediated diol cleavage (vide supra, FIG. 123). In bold italic are represented randomized residues, and shown are the residues modified compared to reference 53. Comparing exact masses for each affinity selected binders before and after periodate cleavage, the mass difference was found to be invariably 2255.8 Da. This difference corresponded to the exact mass of Fixed region peptide (vide supra, FIG. 123) proving correct folding for all affinity selected mini-proteins.

FIG. 126: Resynthesized mini-protein sequences were nanomolar to low nanomolar affinity MDM2 binders. Full list of resynthesized mini-protein binders that were affinity selected from Library 5 and controls 55 and 56. 54b corresponds to the D-PMI-p based MDM2 binding loop of 53. Binding affinities to MDM2 were estimated by in solution competition assay using BLI.

Figure 127:
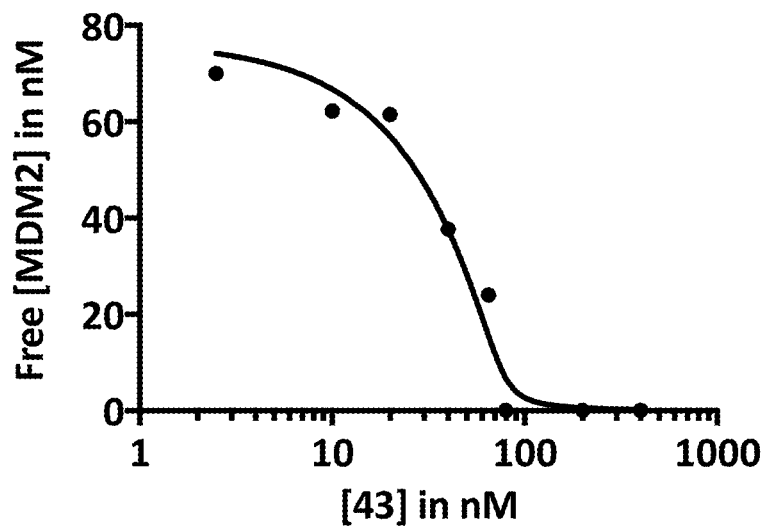

FIG. 127: SUMO-$^{25-109}$ MDM2 and peptide 43 (400 nM, 200 nM, 80 nM, 65 nM, 40 nM, 20 nM, 10 nM and 2.5 nM) were mixed together following the protocol for in solution competition assay. [MDM2] was determined using calibration curve and the obtained titration curve was fitted. The $K_D$ was found to be 1 nM±1.2 nM. Coefficient of determination $R^2$=0.97.

Figure 128:
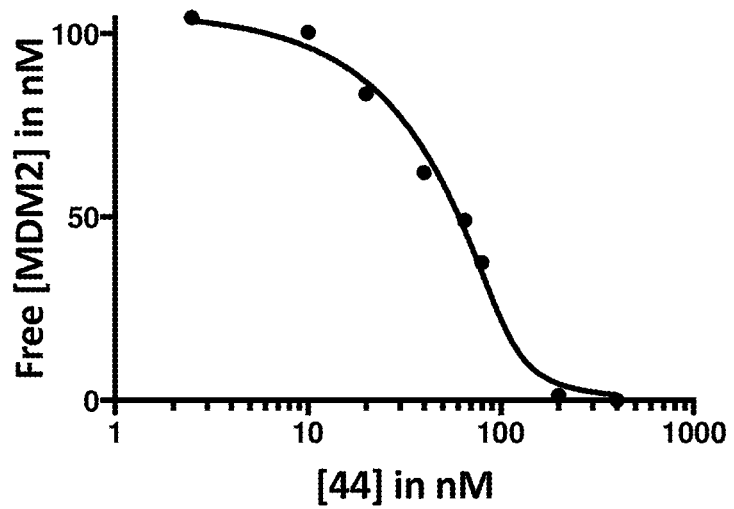

FIG. 128: SUMO-$^{25-109}$ MDM2 and peptide 44 (200 nM, 80 nM, 65 nM, 40 nM, 20 nM, 10 nM and 2.5 nM) were mixed together following the protocol for in solution competition assay. [MDM2] was estimated using calibration curve and the obtained titration curve was fitted. Calculated $K_D$ was 4.5 nM±1.7 nM.

Figure 129:
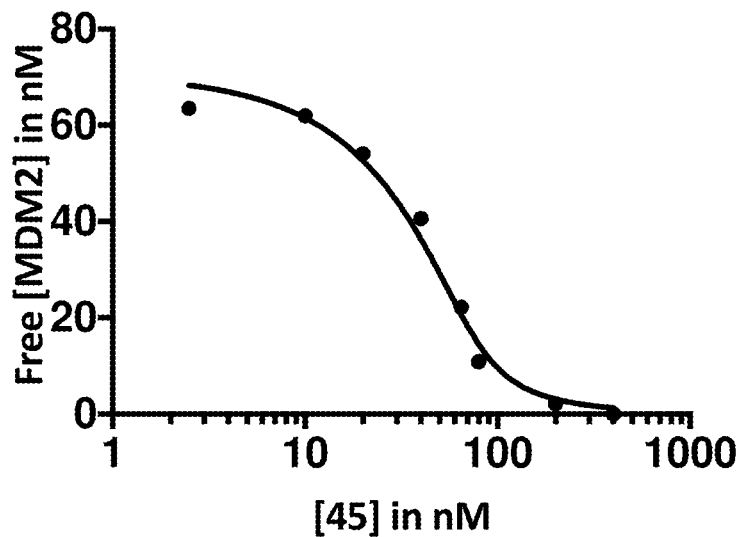

FIG. 129: SUMO-$^{25-109}$ MDM2 and peptide 45 (400 nM, 200 nM, 80 nM, 65 nM, 40 nM, 20 nM, 10 nM and 2.5 nM) were mixed together following the protocol for in solution competition assay. [MDM2] was determined using calibration curve and the obtained titration curve was fitted. The $K_D$ was found to be 6.1 nM±2.0 nM. Coefficient of determination $R^2$=0.988.

Figure 130:
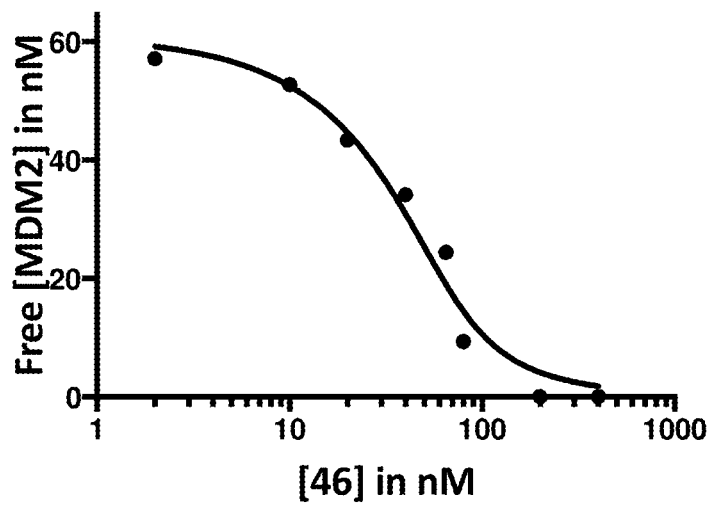

FIG. 130: SUMO-$^{25-109}$ MDM2 and peptide 46 (400 nM, 200 nM, 80 nM, 65 nM, 40 nM, 20 nM, 10 nM and 2.5 nM) were mixed together following the protocol for in solution competition assay. [MDM2] was determined using calibration curve and the obtained titration curve was fitted. The $K_D$ was found to be 10 nM±4.0 nM. Coefficient of determination $R^2$=0.98.

Figure 131:
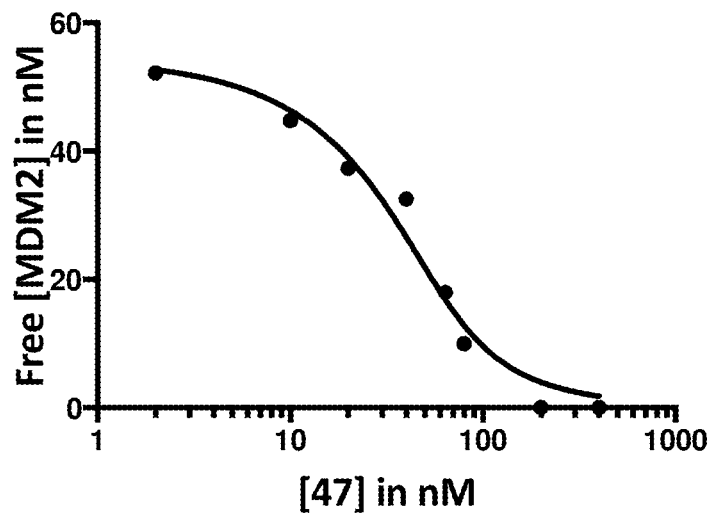

FIG. 131: SUMO-$^{25-109}$ MDM2 and peptide 47 (200 nM, 80 nM, 65 nM, 40 nM, 20 nM, 10 nM and 2.5 nM) were mixed together following the protocol for in solution competition assay. [MDM2] was estimated using calibration curve and the obtained titration curve was fitted. Calculated $K_D$ was 13 nM±3.3 nM.

Figure 132:
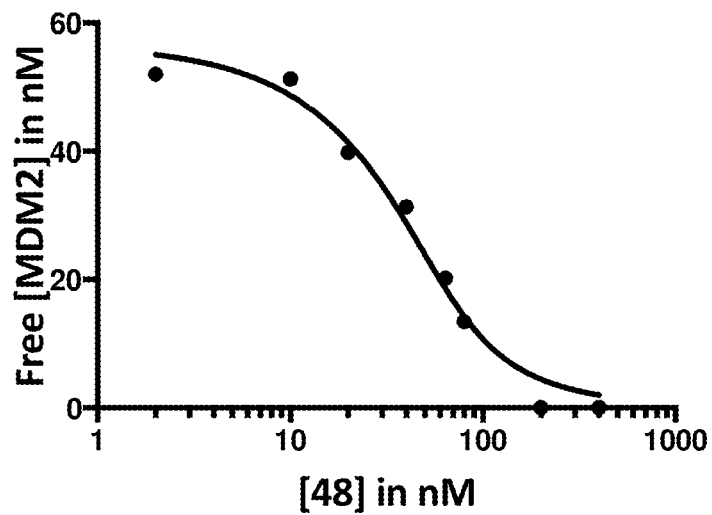

FIG. 132: SUMO-$^{25-109}$ MDM2 and peptide 48 (200 nM, 80 nM, 65 nM, 40 nM, 20 nM, 10 nM and 2.5 nM) were mixed together following the protocol for in solution competition assay. [MDM2] was estimated using calibration curve and the obtained titration curve was fitted. Calculated $K_D$ was 13 nM±4.4 nM.

Figure 133:
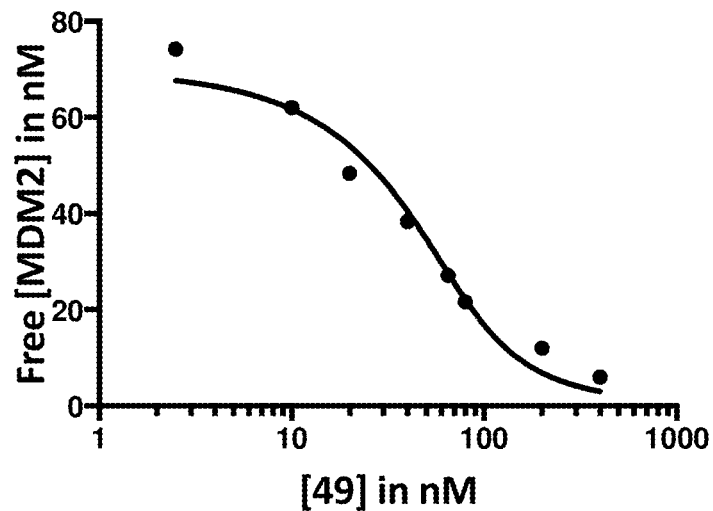

FIG. 133: SUMO-$^{25-109}$ MDM2 and peptide 49 (200 nM, 80 nM, 65 nM, 40 nM, 20 nM, 10 nM and 2.5 nM) were mixed together following the protocol for in solution competition assay. [MDM2] was estimated using calibration curve and the obtained titration curve was fitted. Calculated $K_D$ was 16 nM±3.0 nM.

Figure 134:
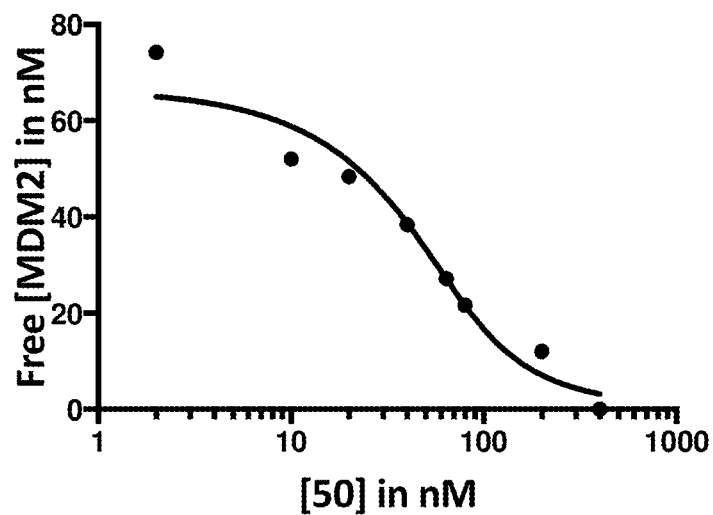

FIG. 134: SUMO-$^{25-109}$ MDM2 and peptide 50 (400 nM, 200 nM, 80 nM, 65 nM, 40 nM, 20 nM, 10 nM and 2.5 nM) were mixed together following the protocol for in solution competition assay. [MDM2] was determined using calibration curve and the obtained titration curve was fitted. The $K_D$ was found to be 17 nM±7.0 nM. Coefficient of determination $R^2$=0.96.

Figure 135:
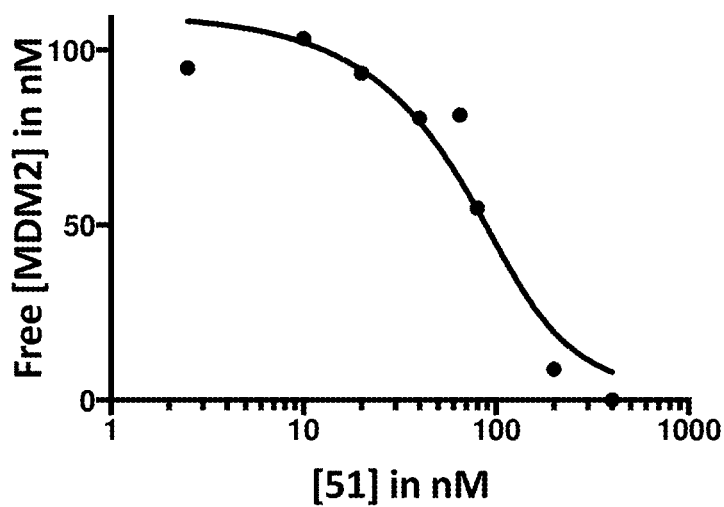

FIG. 135: SUMO-$^{25-109}$ MDM2 and peptide 51 (400 nM, 200 nM, 80 nM, 65 nM, 40 nM, 20 nM, 10 nM and 2.5 nM) were mixed together following the protocol for in solution competition assay. [MDM2] was determined using calibration curve and the obtained titration curve was fitted. The $K_D$ was found to be 23 nM±13 nM. Coefficient of determination $R^2$=0.95.

Figure 136:
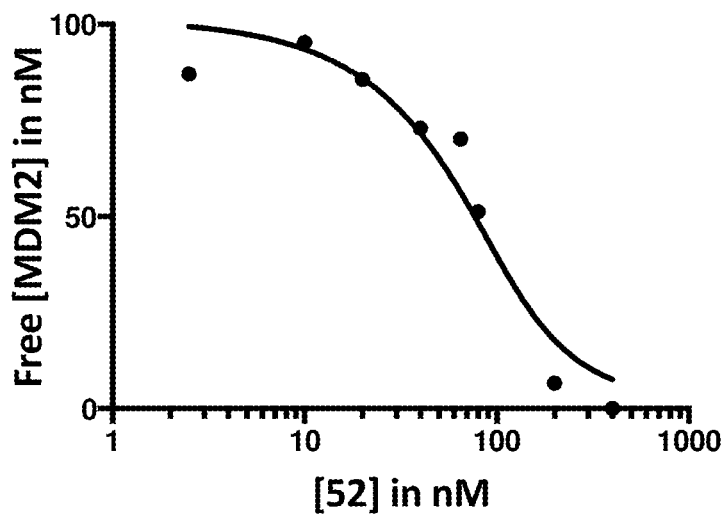

FIG. 136: SUMO-$^{25-109}$ MDM2 and peptide 52 (400 nM, 200 nM, 80 nM, 65 nM, 40 nM, 20 nM, 10 nM and 2.5 nM) were mixed together following the protocol for in solution competition assay. [MDM2] was determined using calibration curve and the obtained titration curve was fitted. The $K_D$ was found to be 25 nM±13 nM. Coefficient of determination $R^2$=0.95.

Figure 137:
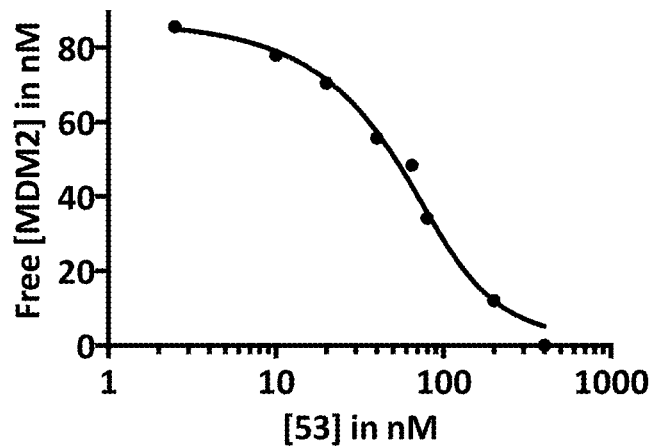

FIG. 137: SU SUMO-$^{25-109}$ MDM2 and peptide 53 (400 nM, 200 nM, 80 nM, 65 nM, 40 nM, 20 nM, 10 nM and 2.5 nM) were mixed together following the protocol for in solution competition assay. [MDM2] was estimated using calibration curve and the obtained titration curve was fitted. Calculated $K_D$ was 26 nM±6.7 nM.

Figure 138:
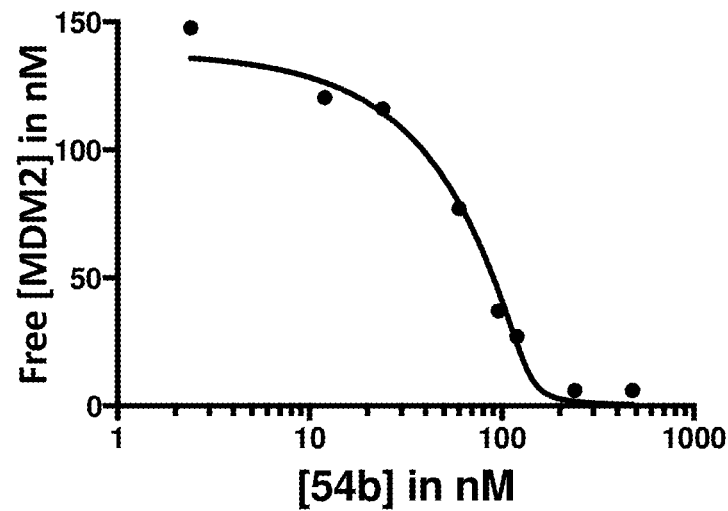

FIG. 138: SUMO-$^{25-109}$ MDM2 and peptide 54b (500 nM, 250 nM, 120 nM, 100 nM, 60 nM, 25 nM, and 2.5 nM) were mixed together following the protocol for in solution competition assay. [MDM2] was estimated using calibration curve and the obtained titration curve was fitted. Calculated $K_D$ was 1.3 nM±4.9 nM.

Figure 139:
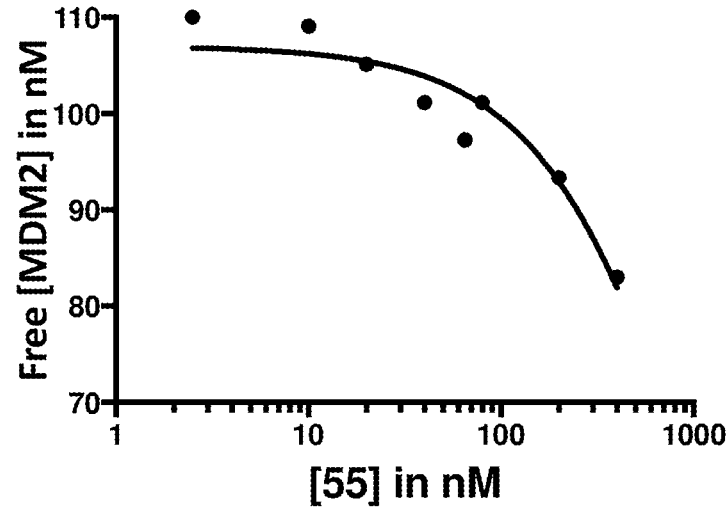

FIG. 139: SUMO-$^{25-109}$ MDM2 and peptide 55 (1000 nM, 200 nM, 80 nM, 65 nM, 40 nM, 20 nM, 10 nM) were mixed together following the protocol for in solution competition assay. [MDM2] was estimated using calibration curve and the obtained titration curve was fitted. Calculated $K_D$ was 1183 f 270 nM.

Figure 140:
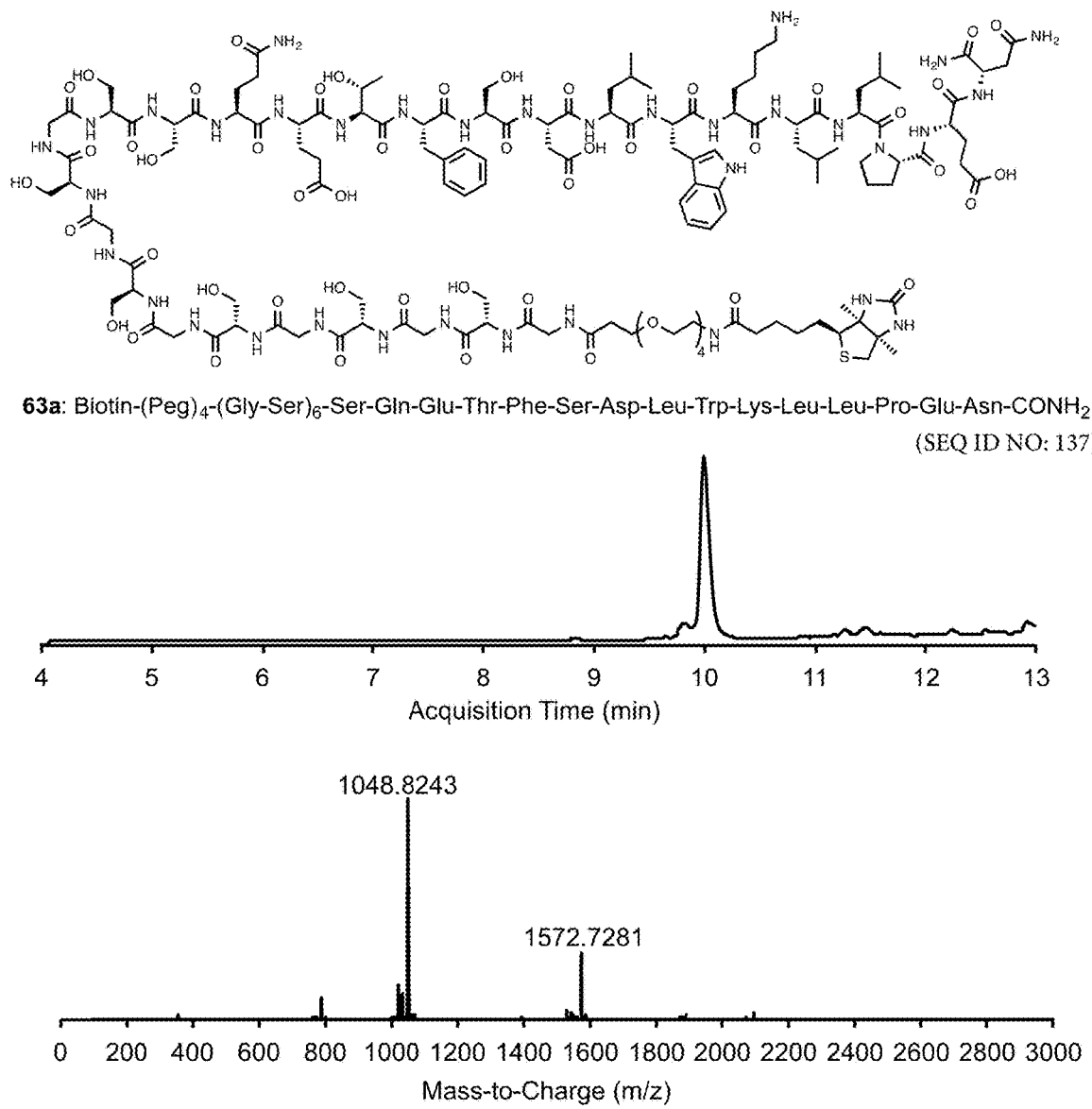

FIG. 140: LC-MS analytical data of fast flow synthesized and biotin labeled peptide 63a for BLI competition assay validations. Peptide 63a: LC-MS analysis Method D. TIC trace and Mass spectrum of peptide 63a prepared according to the representative protocol for fast flow synthesis and biotin labeling. m/z calcd. $[M+2H]^{2+}$: 1048.48 found 1048.49.

Figure 141:
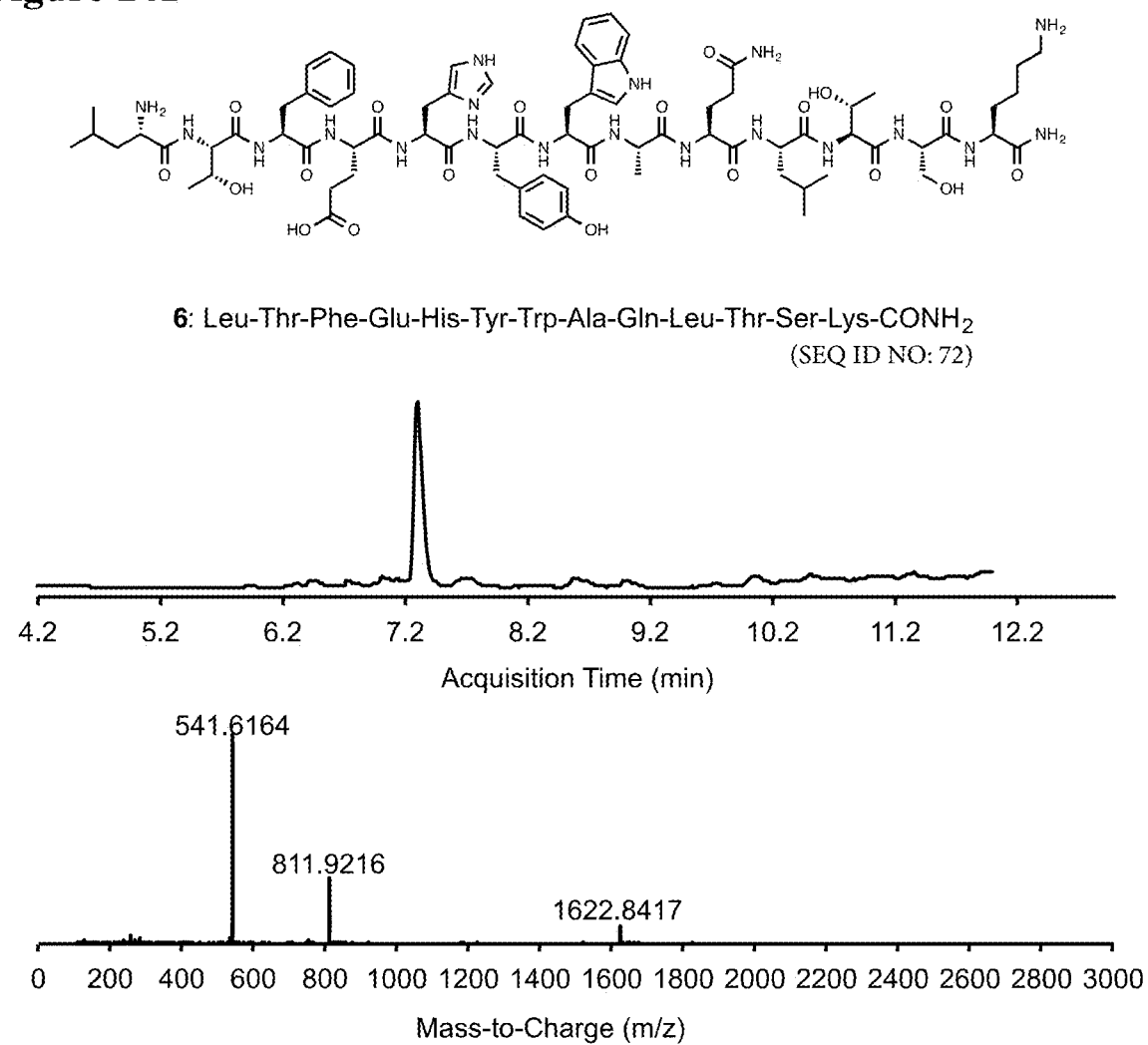

FIG. 141: LC-MS analytical data of fast flow synthesized model peptide 6-Peptide 37 was similarly synthesized and purified. Peptide 6: LC-MS analysis Method C. TIC trace and Mass spectrum of peptide 6 prepared according to the representative protocol for fast flow synthesis. m/z calcd. $[M+3H]^{3+}$: 541.60 found 541.61.

FIG. 142: LC-MS analytical data of SPPS and fast flow synthesized model peptide 59-Peptide 58 was similarly synthesized, folded and purified. Peptide 59: LC-MS analysis Method C. TIC trace and Mass spectrum of peptide 59 prepared according to the representative protocol for folding, fast flow synthesis and SPPS. Cysteines marked with a (*) are oxidized and involved in disulfide bridges, diol amino acid is shown. m/z calcd. $[M+4H]^{4+}$: 732.31 found 732.31.

Figure 143:
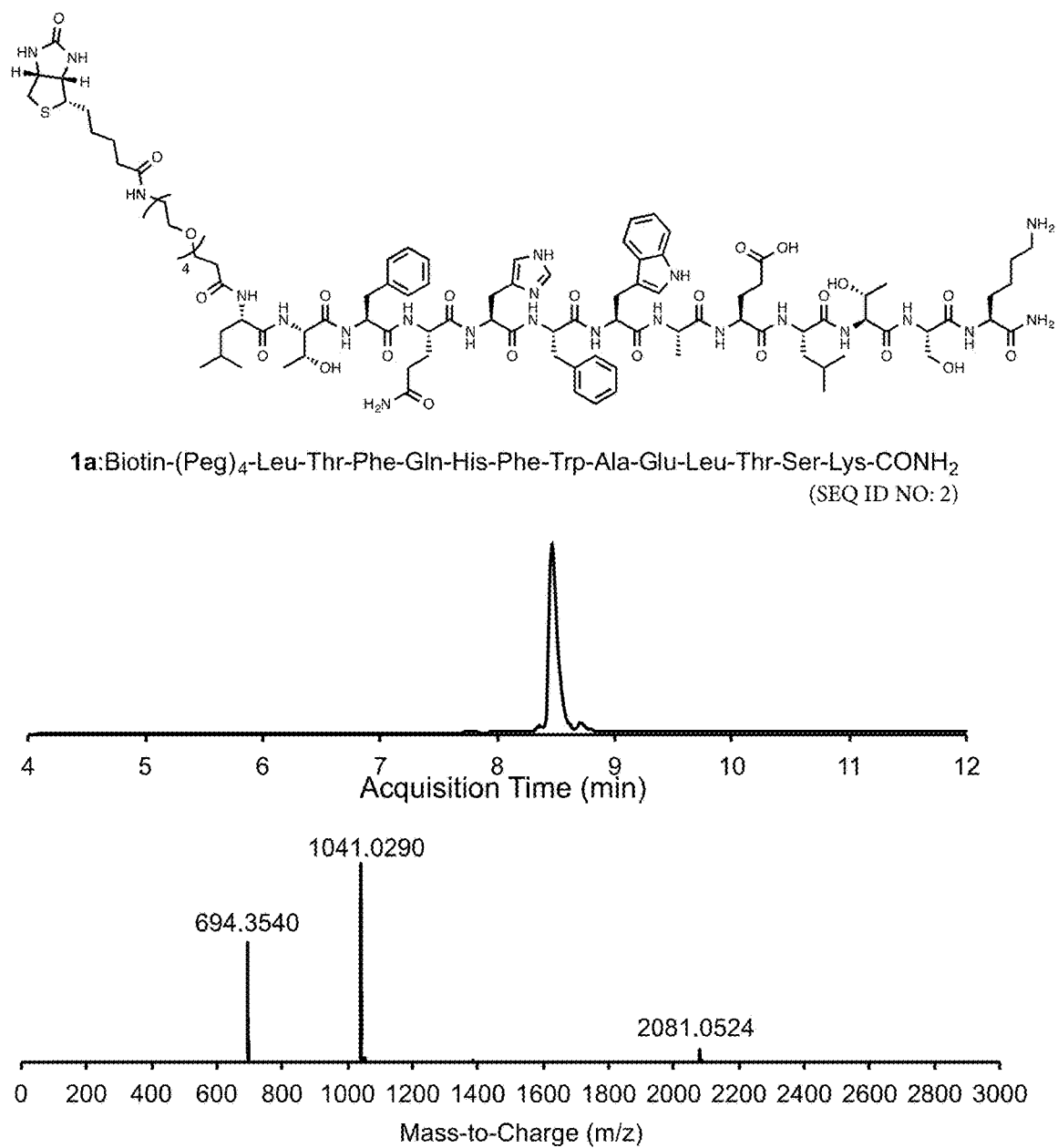

FIG. 143: LC-MS analytical data of fast flow synthesized and biotin labeled binder 1a from Library 1-Peptides 2a to 4a were similarly synthesized and purified. Peptide 1a: LC-MS analysis Method C. TIC trace and Mass spectrum of peptide 1a prepared according to the representative protocol for fast flow synthesis and biotin labeling. m/z calcd. $[M+2H]^{2+}$: 1040.52 found 1040.52.

Figure 144:
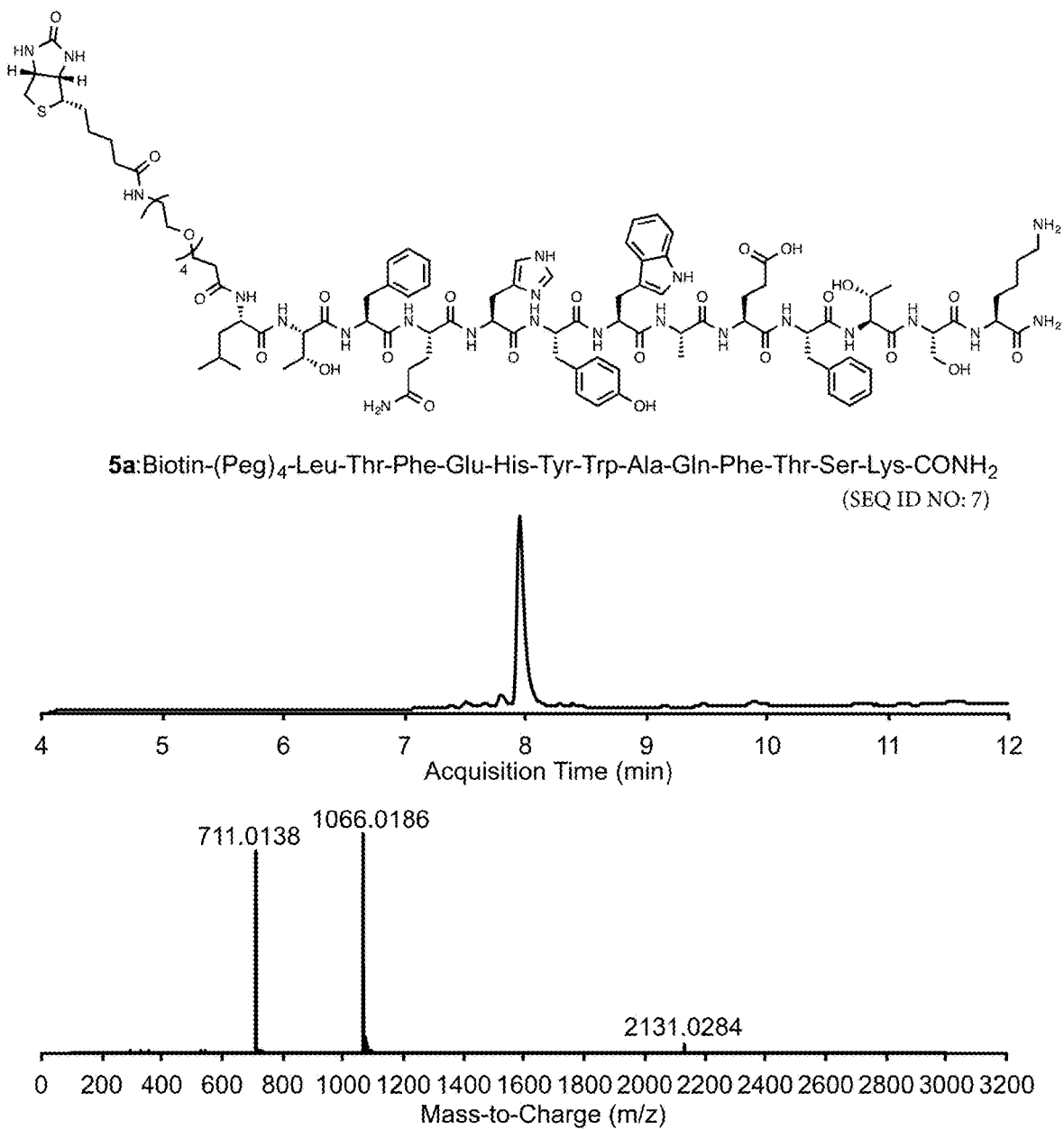

FIG. 144: LC-MS analytical data of fast flow synthesized and biotin labeled binder 5a from Library 2-peptides 6a to 9a were similarly synthesized and purified. Peptide 5a: LC-MS analysis Method D. TIC trace and Mass spectrum of peptide 5a prepared according to the representative protocol for fast flow synthesis and biotin labeling. m/z calcd. $[M+2H]^{2+}$: 1065.51 found 1065.52.

Figure 145:
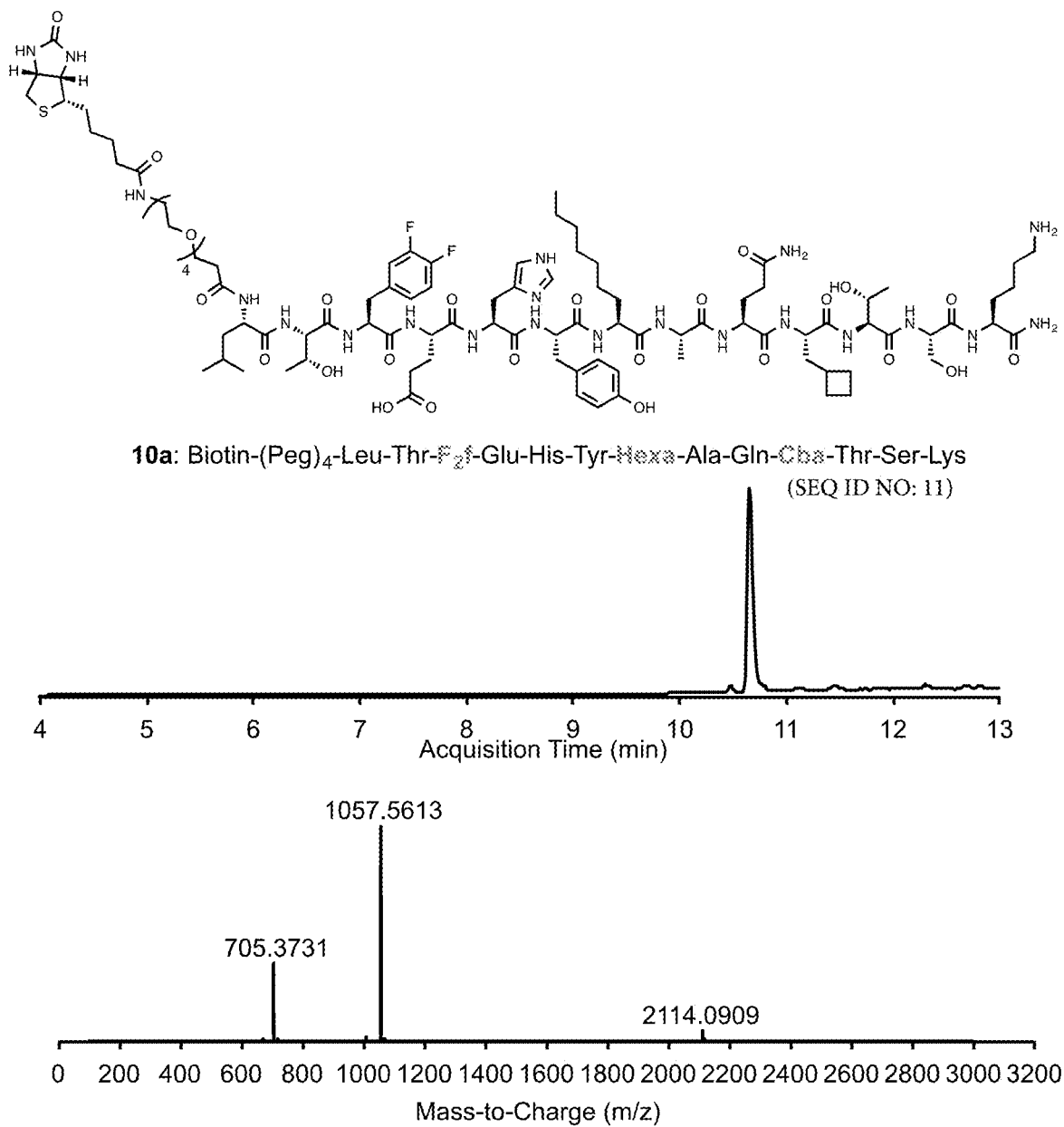

FIG. 145: LC-MS analytical data of SPPS synthesized and biotin labeled non-canonical binder 10a from Library 3-Peptides 57a and 11a to 29a were similarly synthesized and purified. Peptide 10a: LC-MS analysis Method D. TIC trace and Mass spectrum of peptide 10a prepared according to the representative protocol for SPPS synthesis and biotin labeling. Represented are non-canonical residues. m/z calcd. $[M+2H]^{2+}$: 1057.05 found 1057.06.

Figure 146:
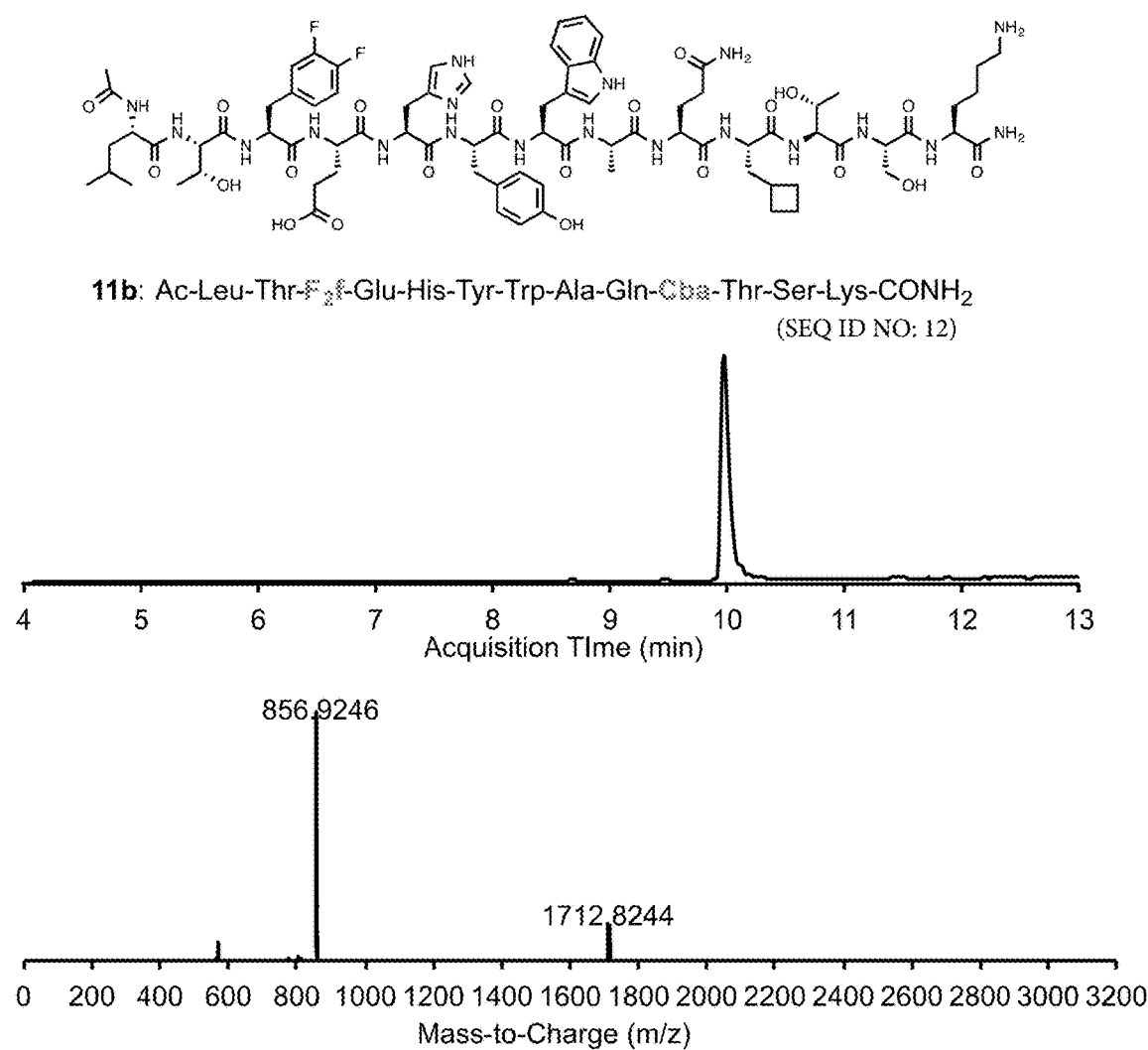

FIG. 146: LC-MS analytical data of SPPS synthesized non-canonical binder 11b from Library 3-Peptides 10b, 54b, 10c and 11c-unstaple were similarly synthesized and purified. Peptide 11b: LC-MS analysis Method D. TIC trace and Mass spectrum of peptide 11b prepared according to the representative protocol for SPPS synthesis. Represented are non-canonical residues m/z calcd. $[M+2H]^{2+}$: 1712.80 found 1712.82.

Figure 47:
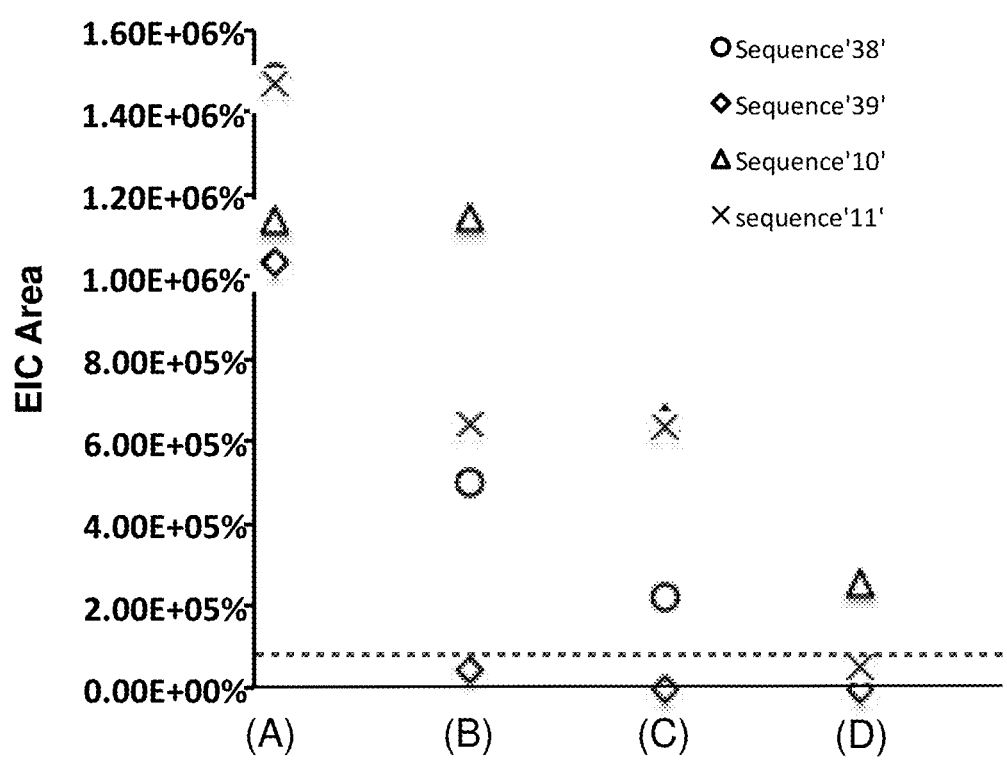
FIG. 47: Adding a soluble competitor and decreasing MDM2 concentration were used for the discrimination of binding sequences based on their affinity. Indicative extract ion chromatogram (EIC) peak areas after affinity selection of nanomolar 38, 39 and low nanomolar 10 and 11 sequences under increasing stringency conditions. Condition (A) corresponds to usual stringency, condition (B) to addition of 100 µM of 6. Condition (C) and (D) correspond to adding 100 µM of 6 concurrently with lowering MDM2 concentration from 20 µM to respectively 7.5 (C) and 1.5 µM (D). Affinity selection and LC-MS analysis conditions were such as in condition (A) the EIC peak area for most selected sequences was largely superior (>10 fold) to the EIC peak area to reach MS/MS threshold (dashed). EIC peak areas for sequences 38 and 39 diminished more rapidly than for 10 and 11 (the two highest affinity binding sequences, vide infra S21) across conditions (A) to (D). In condition (D) 38 and 39 were completely undetectable (below both our defined MS/MS threshold and MS instrument detection limit), while 10 and 11 were detected but only 10 was above MS/MS threshold. Sequence 10 EIC peak area varied only by 4.5 fold from (A) to (D) by stark contrast to other sequences (11 varied by 30 fold). These observations suggest that the stringency conditions led to the selection of high affinity binders.
Figure 49:
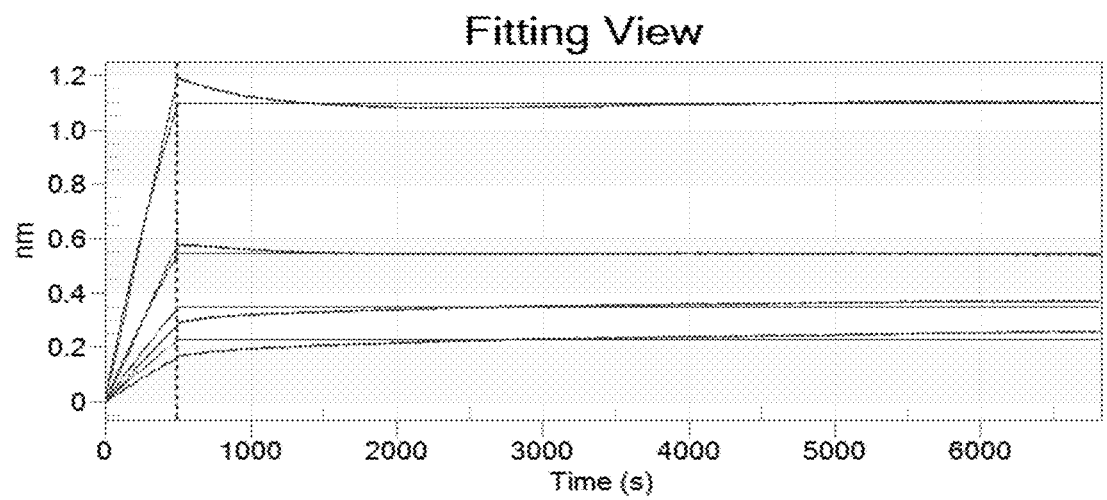
FIG. 49: Global fitting of association and dissociation curves of various concentrations of SUMO-$^{25\text{-}109}$ MDM2 (10 nM, 5 nM, 2.5 nM and 1.25 nM) with biotin labeled peptide 10a immobilized to streptavidin sensors. The $K_D$ was found to be 0.5 nM±0.2 nM. Coefficient of determination $R^2$=0.9968.
Figure 50:
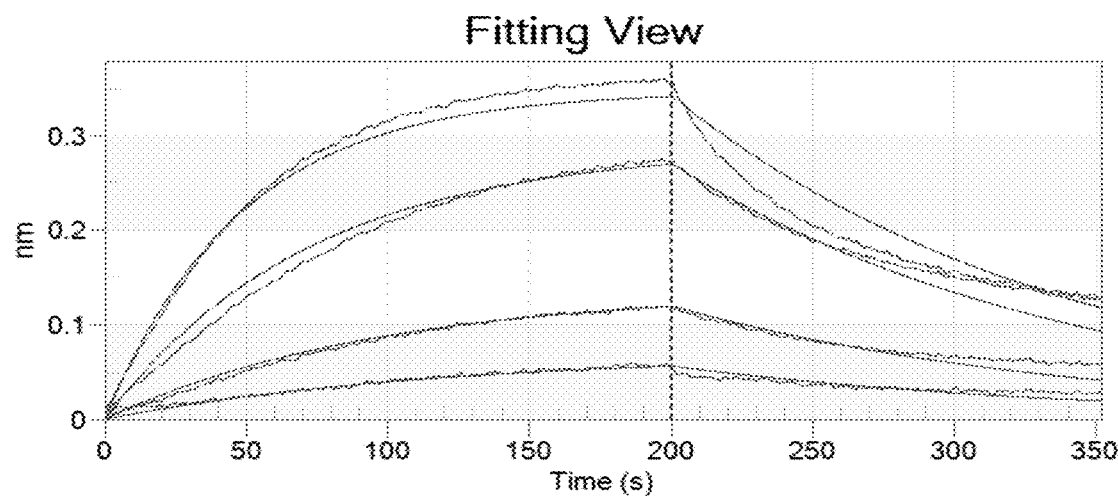
FIG. 50: Global fitting of association and dissociation curves of various concentrations of $^{1\text{-}137}$MDMX (50 nM, 25 nM, 12.5 nM and 6.3 nM) with biotin labeled peptide 10a immobilized to streptavidin sensors. The $K_D$ was found to be 26 nM±0.6 nM. Coefficient of determination $R^2$=0.9868.
Figure 51:
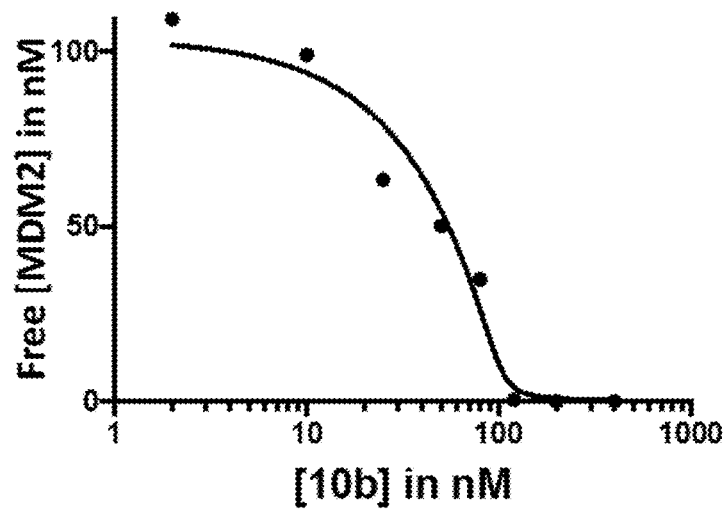
FIG. 51: SUMO-$^{25\text{-}109}$ MDM2 and peptide 10b (400 nM, 200 nM, 120 nM, 80 nM, 50 nM, 25 nM, 10 nM and 2 nM) were mixed together following the protocol for in solution competition assay. [MDM2] was estimated using calibration curve and the obtained titration curve was fitted. Calculated $K_D$ was 0.8 nM±1.9 nM.
Figure 52:
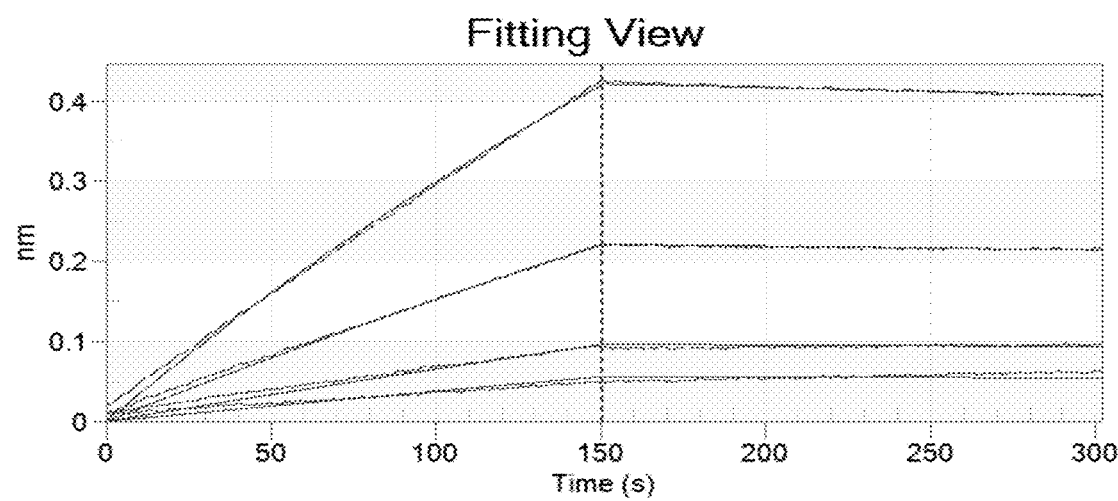
FIG. 52: Global fitting of association and dissociation curves of various concentrations of SUMO-25-109 MDM2 (10 nM, 5 nM, 2.5 nM and 1.25 nM) with biotin labeled peptide 11a immobilized to streptavidin sensors. The $K_D$ was found to be 2.0 nM±0.2 nM. Coefficient of determination R2=0.9989.
Figure 53:
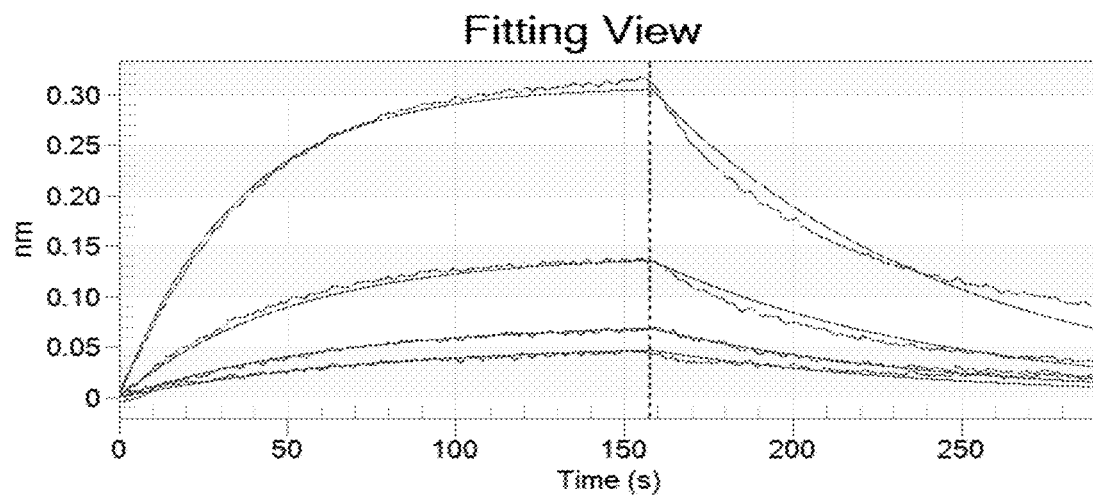
FIG. 53: Global fitting of association and dissociation curves of various concentrations of $^{1\text{-}137}$MDMX (50 nM, 25 nM, 12.5 nM and 6.3 nM) with biotin labeled peptide 11a immobilized to streptavidin sensors. The $K_D$ was found to be 33 nM±0.7 nM. Coefficient of determination $R^2$=0.9942.
Figure 54:
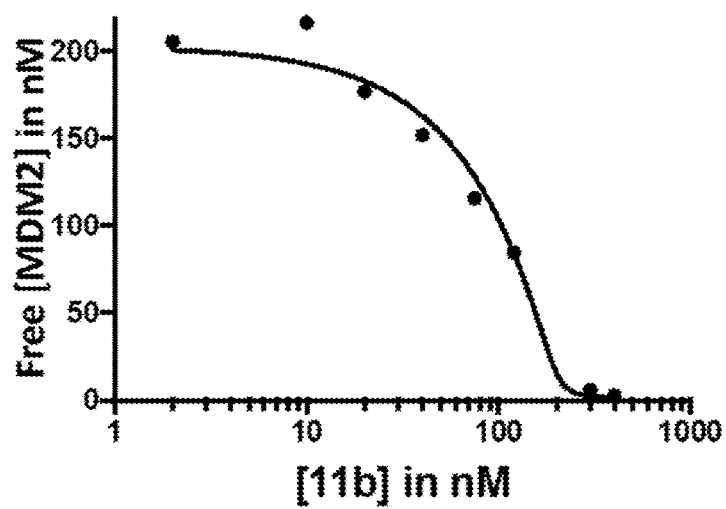
FIG. 54: SUMO-$^{25\text{-}109}$ MDM2 and peptide 11b (400 nM, 300 nM, 120 nM, 80 nM, 40 nM, 20 nM, 10 nM and 2 nM) were mixed together following the protocol for in solution competition assay. [MDM2] was estimated using calibration curve and the obtained titration curve was fitted. Calculated $K_D$ was 1.2 nM±4.7 nM.
Figure 55:
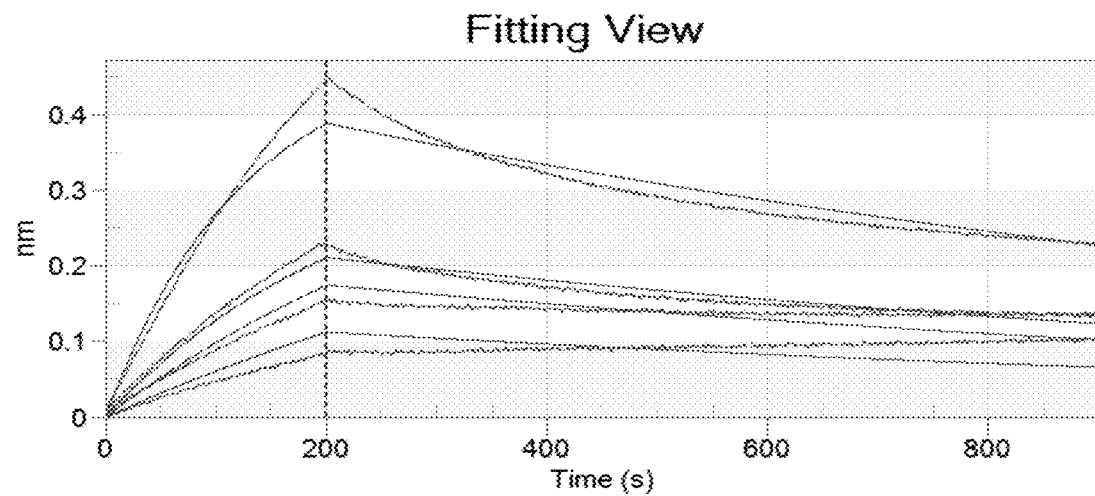
FIG. 55: Global fitting of association and dissociation curves of various concentrations of SUMO-$^{25\text{-}109}$ MDM2 (20 nM, 10 nM, 5 nM and 2.5 nM) with biotin labeled peptide 12a immobilized to streptavidin sensors. The $K_D$ was found to be 2.1 nM±0.6 nM. Coefficient of determination $R^2$=0.97.
Figure 56:
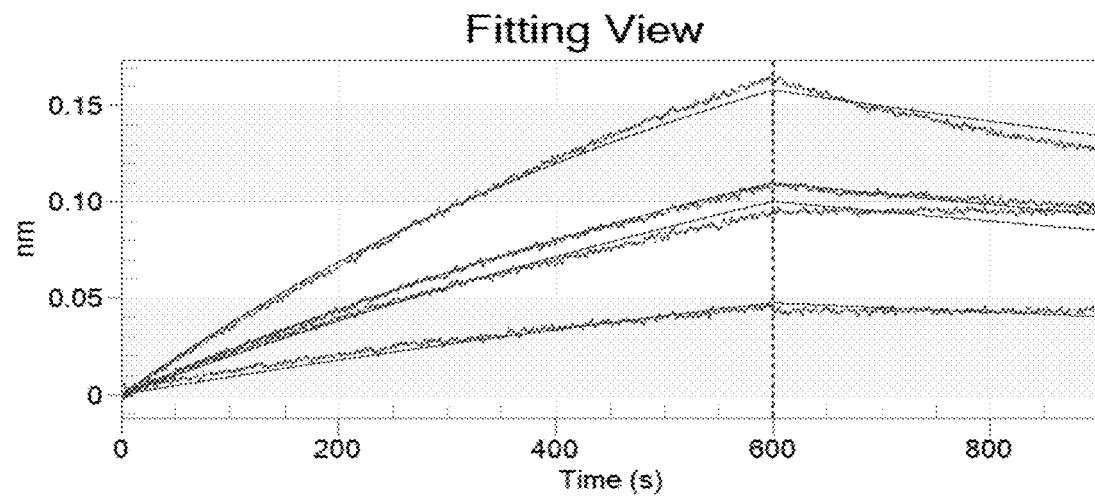
FIG. 56: Global fitting of association and dissociation curves of various concentrations of SUMO-$^{25\text{-}109}$ MDM2 (5 nM, 2.5 nM, 1.25 nM and 0.5 nM) with biotin labeled peptide 13a immobilized to super streptavidin sensors. The $K_D$ was found to be 2.9 nM±0.1 nM. Coefficient of determination $R^2$=0.9949.
Figure 57:
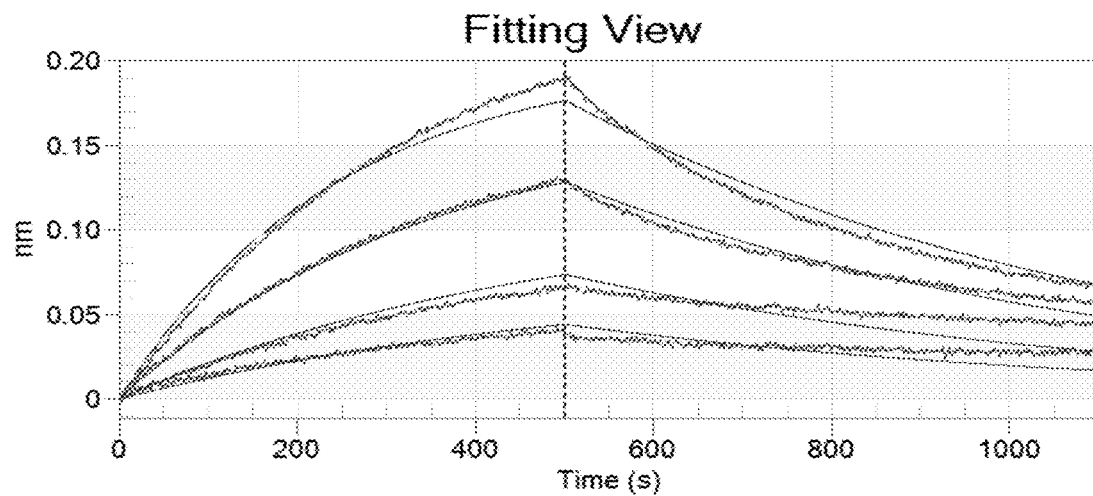
FIG. 57: Global fitting of association and dissociation curves of various concentrations of SUMO-$^{25\text{-}109}$ MDM2 (5 nM, 2.5 nM, 1.25 nM and 0.5 nM) with biotin labeled peptide 14a immobilized to streptavidin sensors. The $K_D$ was found to be 3.2 nM±0.6 nM. Coefficient of determination $R^2$=0.98.
Figure 58:
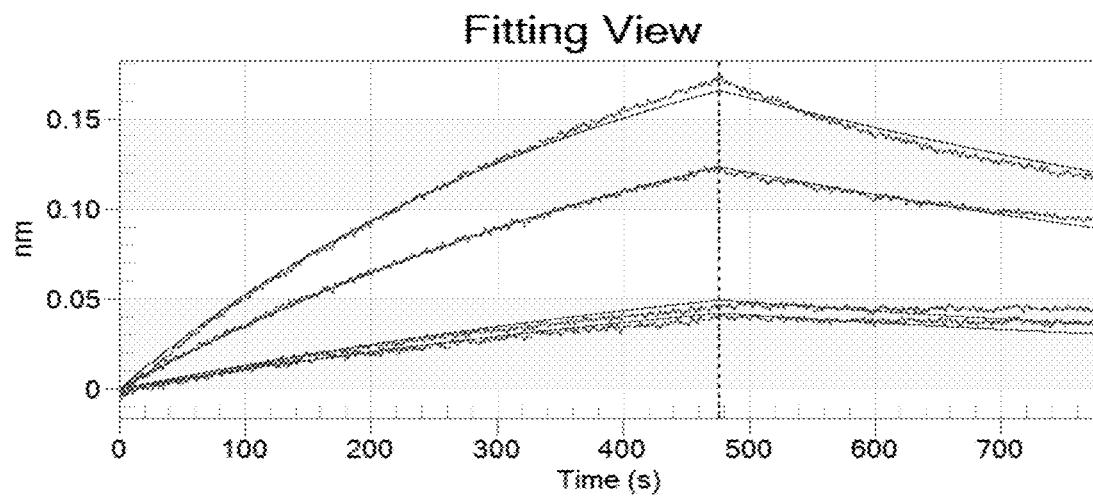
FIG. 58: Global fitting of association and dissociation curves of various concentrations of SUMO-$^{25\text{-}109}$ MDM2 (5 nM, 2.5 nM, 1.25 nM and 0.5 nM) with biotin labeled peptide 15a immobilized to streptavidin sensors. The $K_D$ was found to be 3.8 nM±0.8 nM. Coefficient of determination $R^2$=0.9954.
Figure 59:
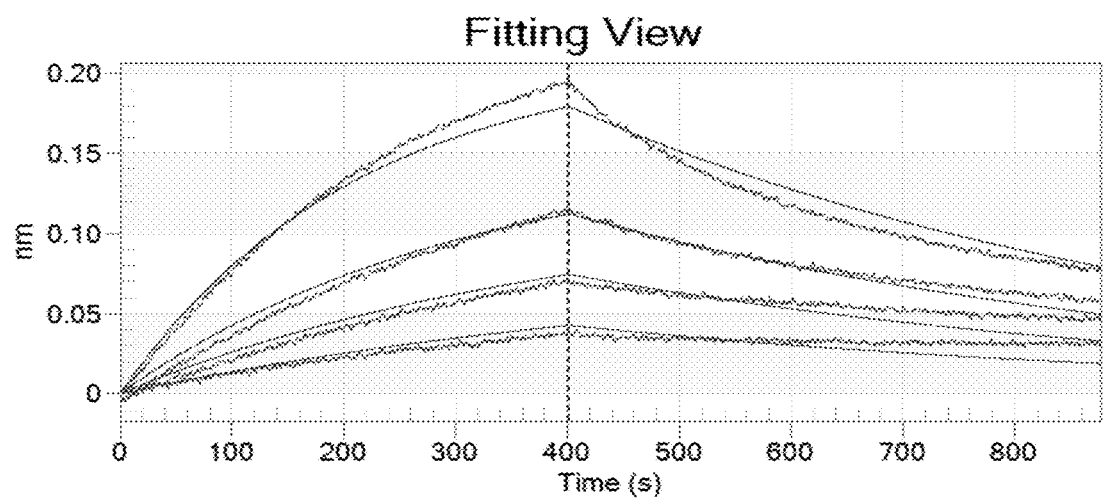
FIG. 59: Global fitting of association and dissociation curves of various concentrations of SUMO-$^{25\text{-}109}$ MDM2 (10 nM, 5 nM, 2.5 nM and 1.25 nM) with biotin labeled peptide 16a immobilized to streptavidin sensors. The $K_D$ was found to be 5.6 nM±0.2 nM. Coefficient of determination $R^2$=0.98.
Figure 60:
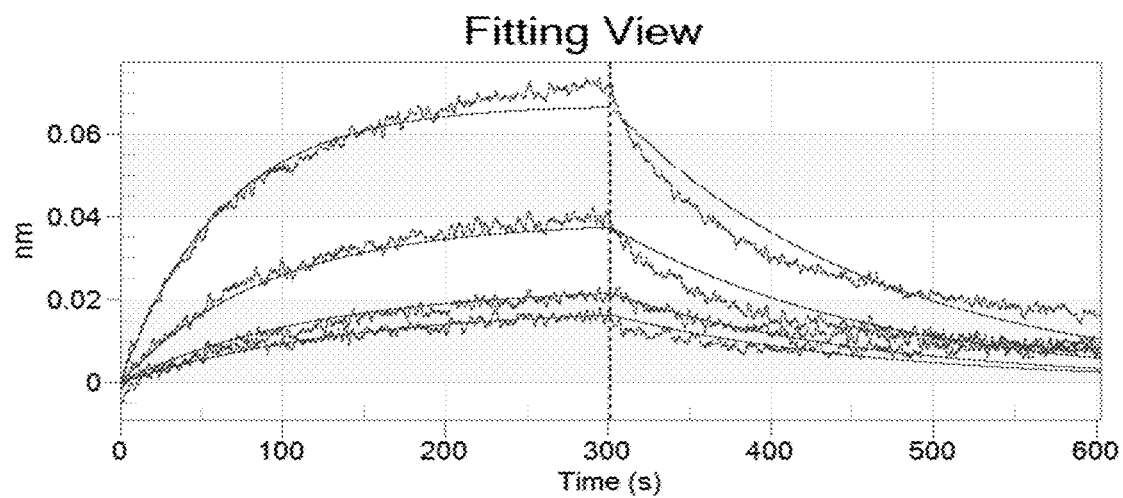
FIG. 60: Global fitting of association and dissociation curves of various concentrations of SUMO-$^{25\text{-}109}$ MDM2 (10 nM, 5 nM, 2.5 nM and 1.25 nM) with biotin labeled peptide 17a immobilized to streptavidin sensors. The $K_D$ was found to be 6.3 nM±0.2 nM. Coefficient of determination $R^2$=0.97.
Figure 61:
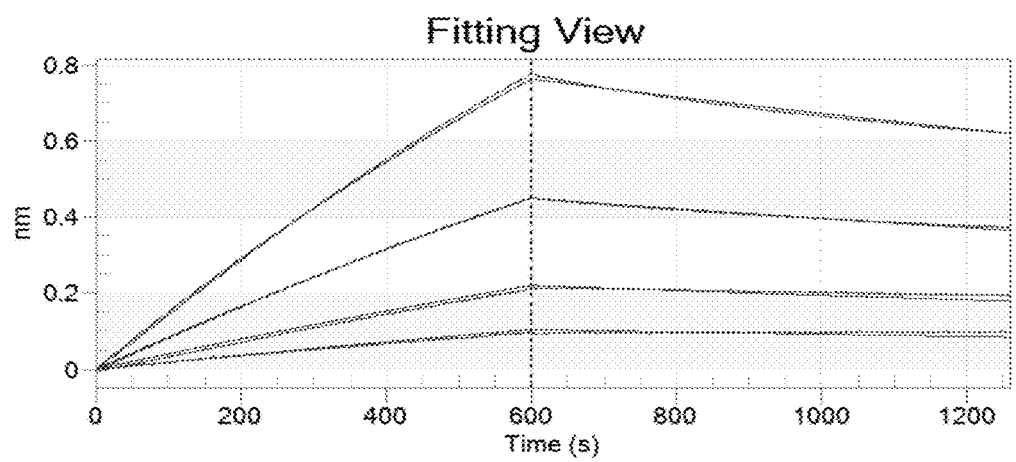
FIG. 61: Global fitting of association and dissociation curves of various concentrations of SUMO-$^{25\text{-}109}$ MDM2 (10 nM, 5 nM, 2.5 nM and 1.25 nM) with biotin labeled peptide 18a immobilized to streptavidin sensors. The $K_D$ was found to be 7.6 nM±0.2 nM. Coefficient of determination $R^2$=0.9993.
Figure 62:
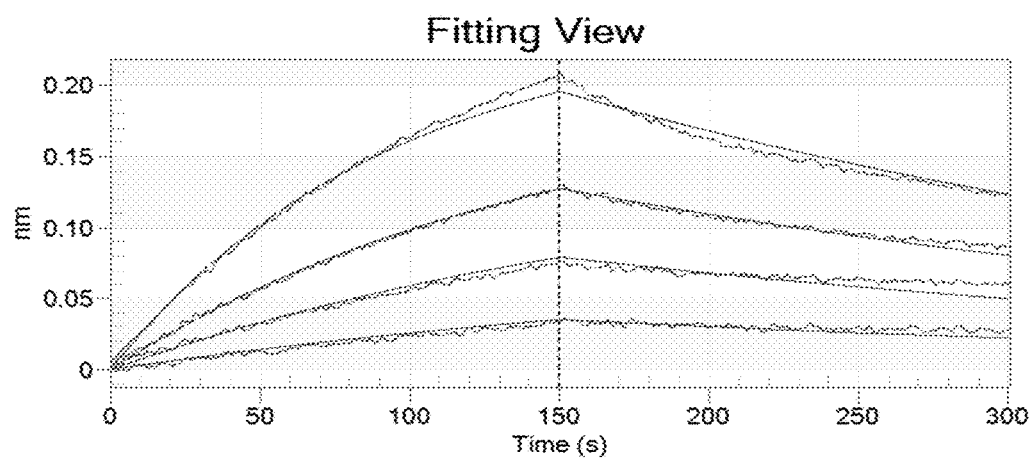
FIG. 62: Global fitting of association and dissociation curves of various concentrations of SUMO-$^{25\text{-}109}$ MDM2 (20 nM, 10 nM, 5 nM and 2.5 nM) with biotin labeled peptide 19a immobilized to streptavidin sensors. The $K_D$ was found to be 8.0 nM±0.2 nM. Coefficient of determination $R^2$=0.9952.
Figure 63:
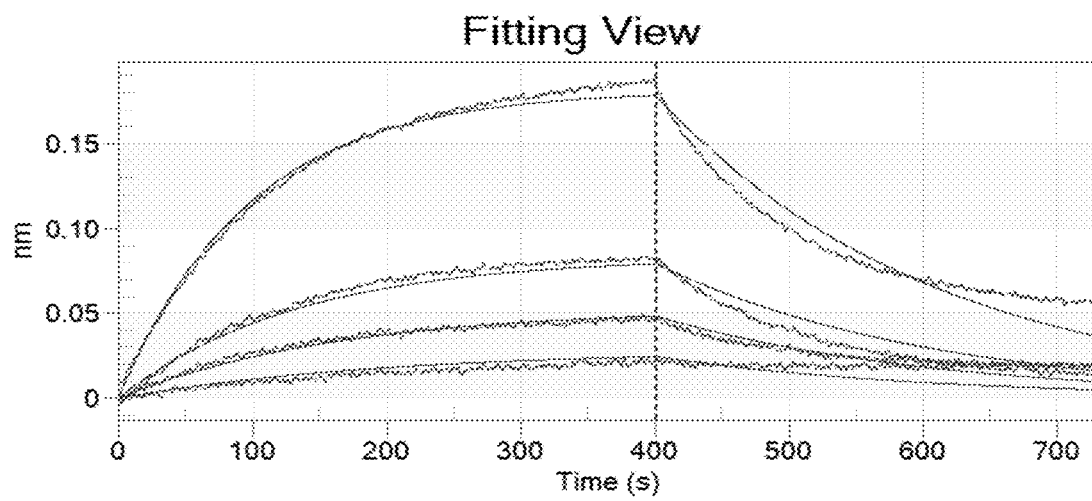
FIG. 63: Global fitting of association and dissociation curves of various concentrations of SUMO-$^{25\text{-}109}$ MDM2 (10 nM, 5 nM, 2.5 nM and 1.25 nM) with biotin labeled peptide 20a immobilized to streptavidin sensors. The $K_D$ was found to be 8.9 nM±0.2 nM. Coefficient of determination $R^2$=0.985.
Figure 64:
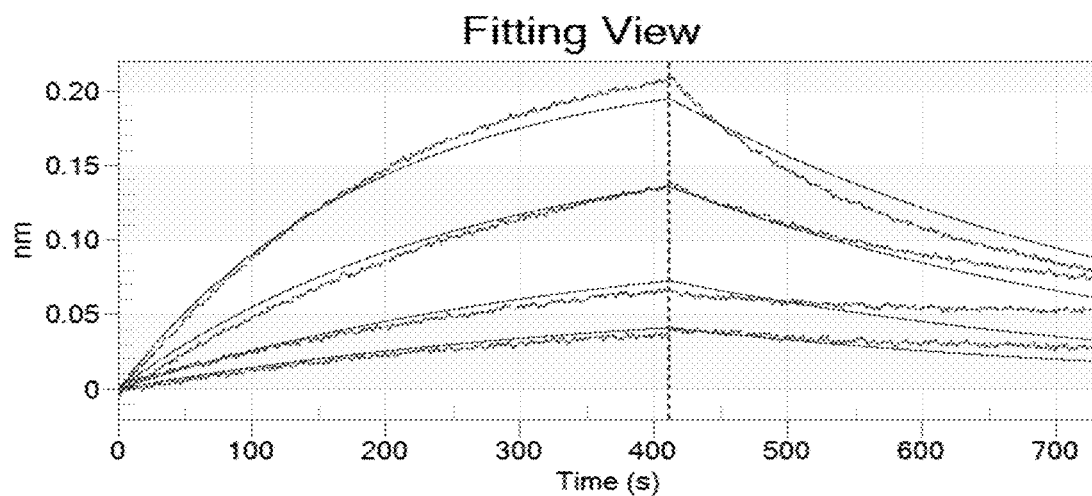
FIG. 64: Global fitting of association and dissociation curves of various concentrations of SUMO-$^{25\text{-}109}$ MDM2 (10 nM, 5 nM, 2.5 nM and 1.25 nM) with biotin labeled peptide 21a immobilized to streptavidin sensors. The $K_D$ was found to be 8.9 nM±0.2 nM. Coefficient of determination $R^2$=0.985.
Figure 65:
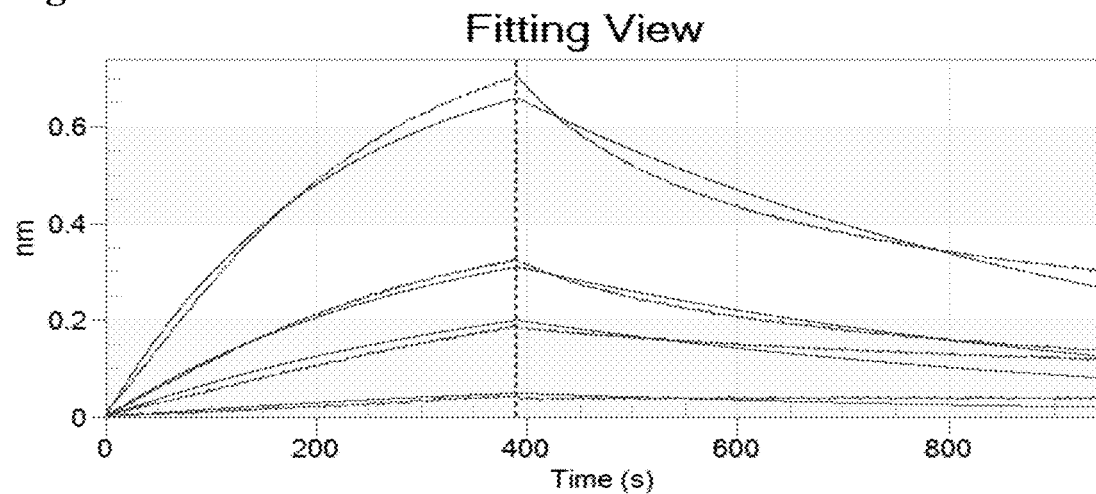
FIG. 65: Global fitting of association and dissociation curves of various concentrations of SUMO-$^{25\text{-}109}$ MDM2 (20 nM, 10 nM, 5 nM and 1.25 nM) with biotin labeled peptide 22a immobilized to streptavidin sensors. The $K_D$ was found to be 10 nM±0.2 nM. Coefficient of determination $R^2$=0.9902.
Figure 66:
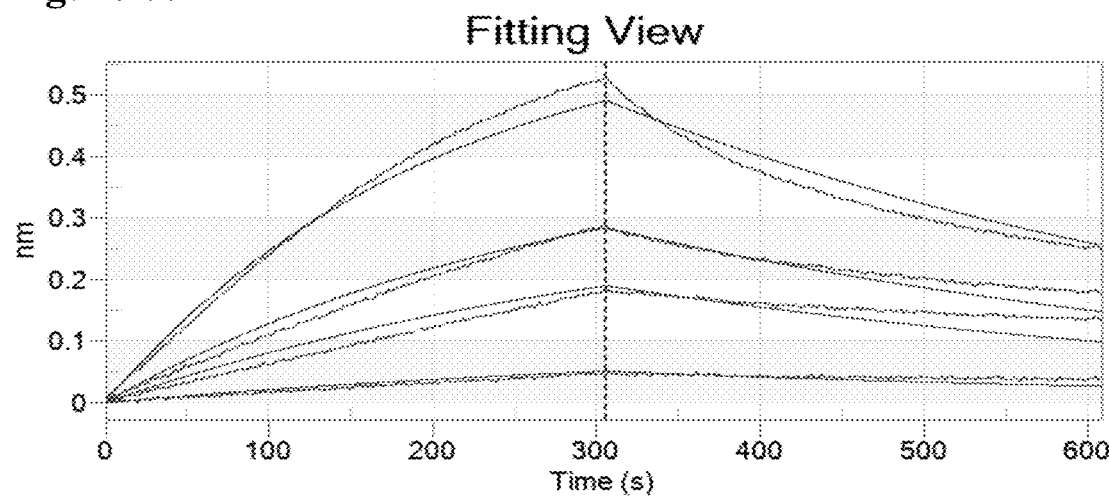
FIG. 66: Global fitting of association and dissociation curves of various concentrations of SUMO-$^{25\text{-}109}$ MDM2 (20 nM, 10 nM, 5 nM and 2.5 nM) with biotin labeled peptide 23a immobilized to streptavidin sensors. The $K_D$ was found to be 15 nM±0.5 nM. Coefficient of determination $R^2$=0.986.
Figure 67:
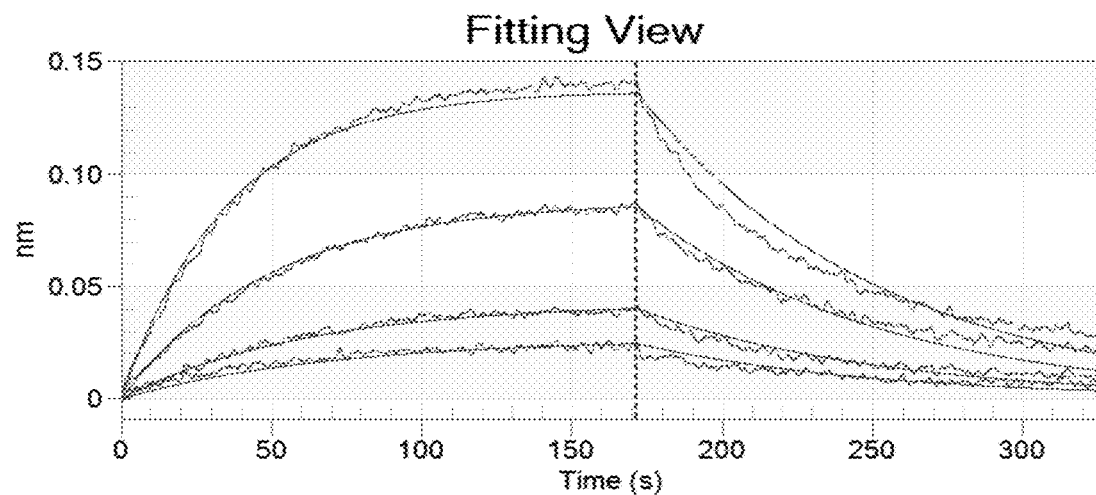
FIG. 67: Global fitting of association and dissociation curves of various concentrations of SUMO-$^{25\text{-}109}$ MDM2 (20 nM, 10 nM, 5 nM and 2.5 nM) with biotin labeled peptide 24a immobilized to streptavidin sensors. The $K_D$ was found to be 16 nM±0.5 nM. Coefficient of determination $R^2$=0.9904.
Figure 68:
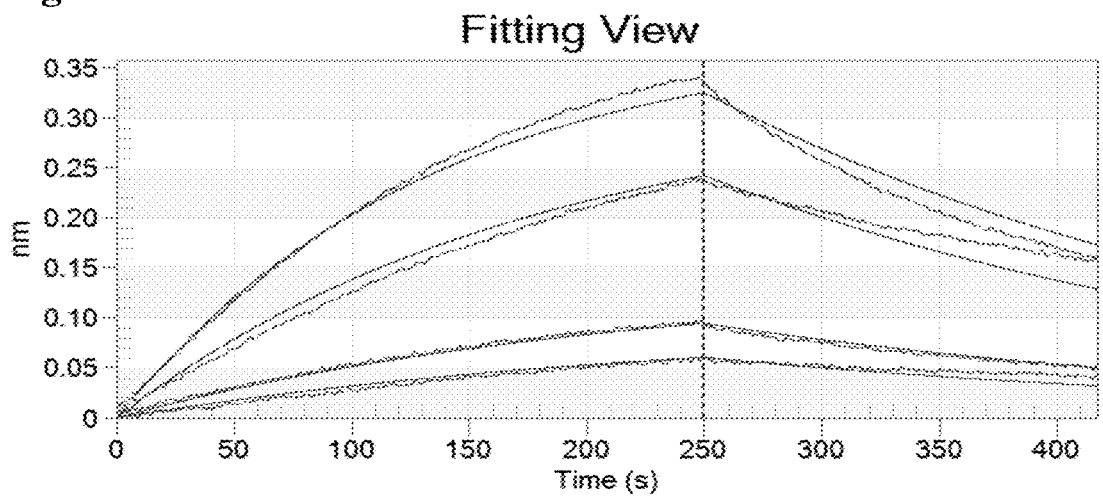
FIG. 68: Global fitting of association and dissociation curves of various concentrations of SUMO-$^{25\text{-}109}$ MDM2 (20 nM, 10 nM, 5 nM and 2.5 nM) with biotin labeled peptide 25a immobilized to streptavidin sensors. The $K_D$ was found to be 20 nM±0.7 nM. Coefficient of determination $R^2$=0.9904.
Figure 69:
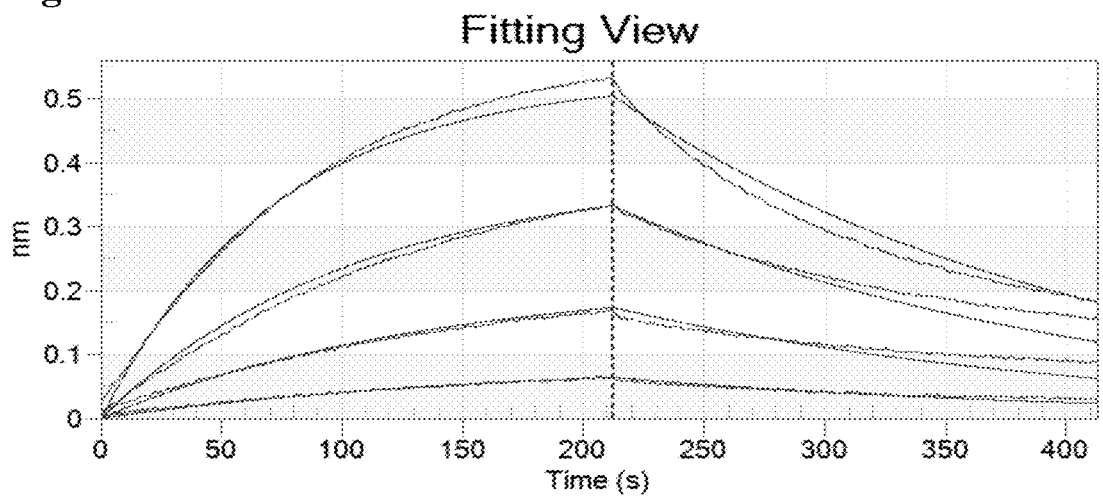
FIG. 69: Global fitting of association and dissociation curves of various concentrations of SUMO-$^{25\text{-}109}$ MDM2 (40 nM, 20 nM, 10 nM and 5 nM) with biotin labeled peptide 26a immobilized to streptavidin sensors. The $K_D$ was found to be 23 nM±0.5 nM. Coefficient of determination $R^2$=0.9916.
Figure 70:
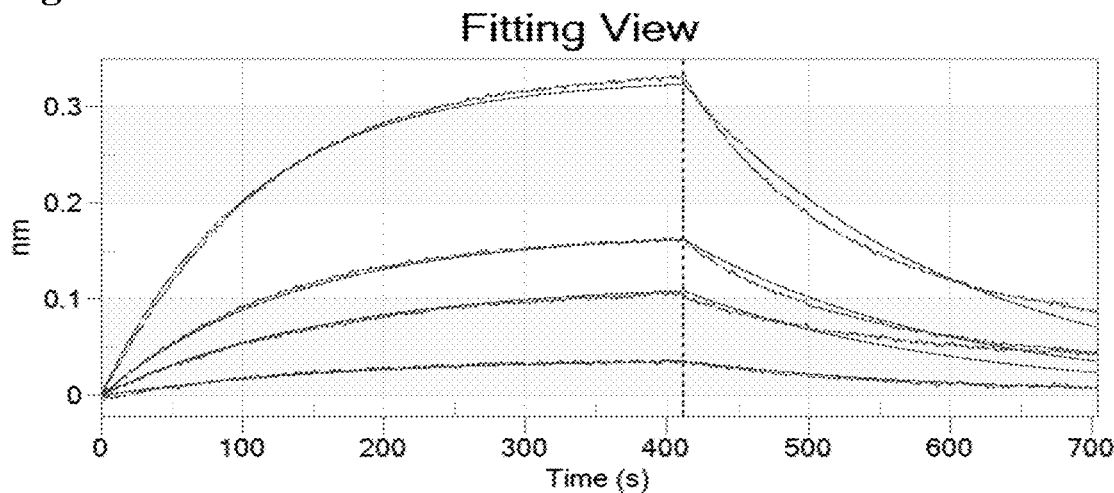
FIG. 70: Global fitting of association and dissociation curves of various concentrations of SUMO-$^{25\text{-}109}$ MDM2 (40 nM, 20 nM, 10 nM and 5 nM) with biotin labeled peptide 27a immobilized to streptavidin sensors. The $K_D$ was found to be 23 nM±0.5 nM. Coefficient of determination $R^2$=0.9955.
Figure 74:
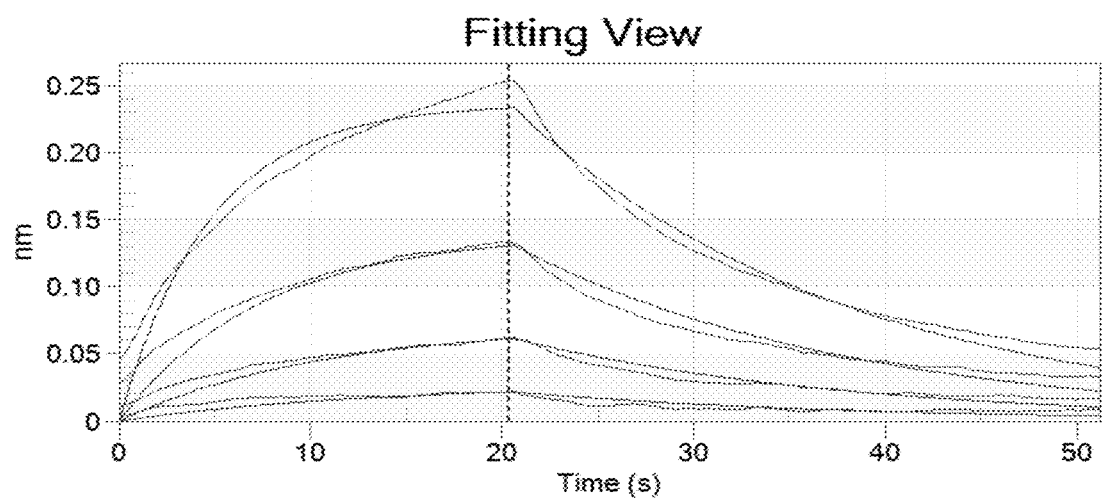
FIG. 74: Global fitting of association and dissociation curves of various concentrations of SUMO-C-CA (300 nM, 150 nM, 75 nM and 37.5 nM) with biotin labeled peptide 31a immobilized to streptavidin sensors. The $K_D$ was found to be 120 nM±7 nM. Coefficient of determination R2=0.9855.
Figure 75:
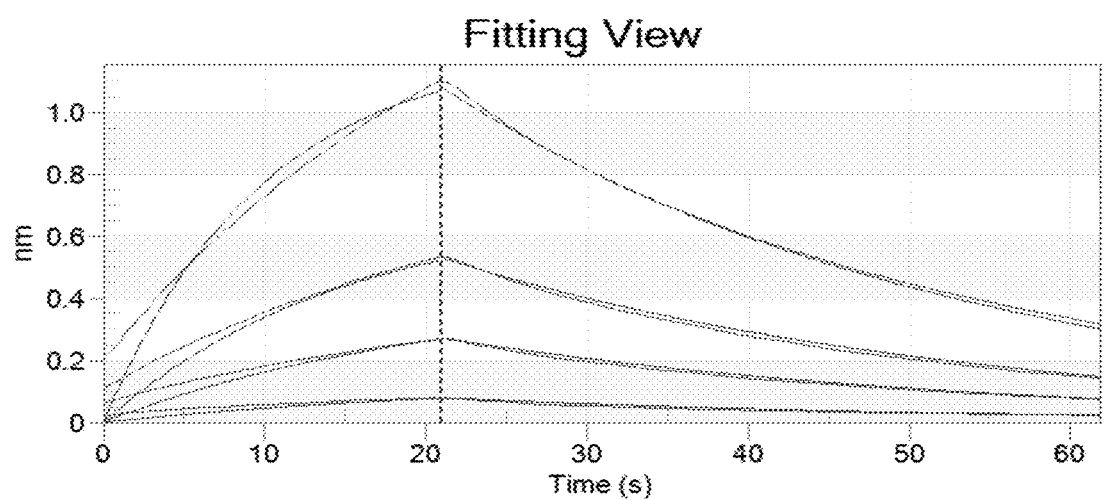
FIG. 75: Global fitting of association and dissociation curves of various concentrations of SUMO-C-CA (300 nM, 150 nM, 75 nM and 37.5 nM) with biotin labeled peptide 32a immobilized to streptavidin sensors. The $K_D$ was found to be 140 nM±8 nM. Coefficient of determination $R^2$=0.9916.
Figure 76:
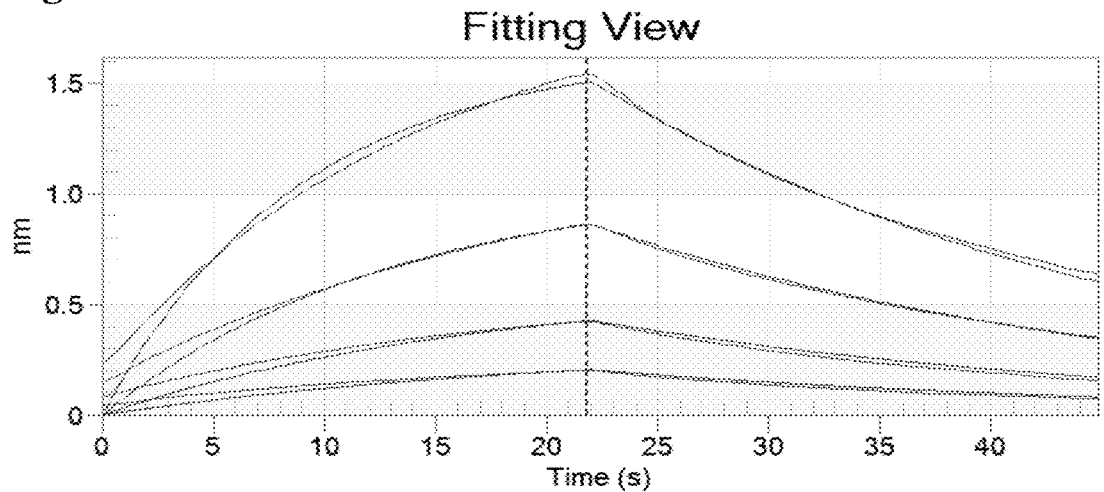
FIG. 76: Global fitting of association and dissociation curves of various concentrations of SUMO-C-CA (300 nM, 150 nM, 75 nM and 37.5 nM) with biotin labeled peptide 33a immobilized to streptavidin sensors. The $K_D$ was found to be 320 nM±17 nM. Coefficient of determination $R^2$=0.9929.
Figure 77:
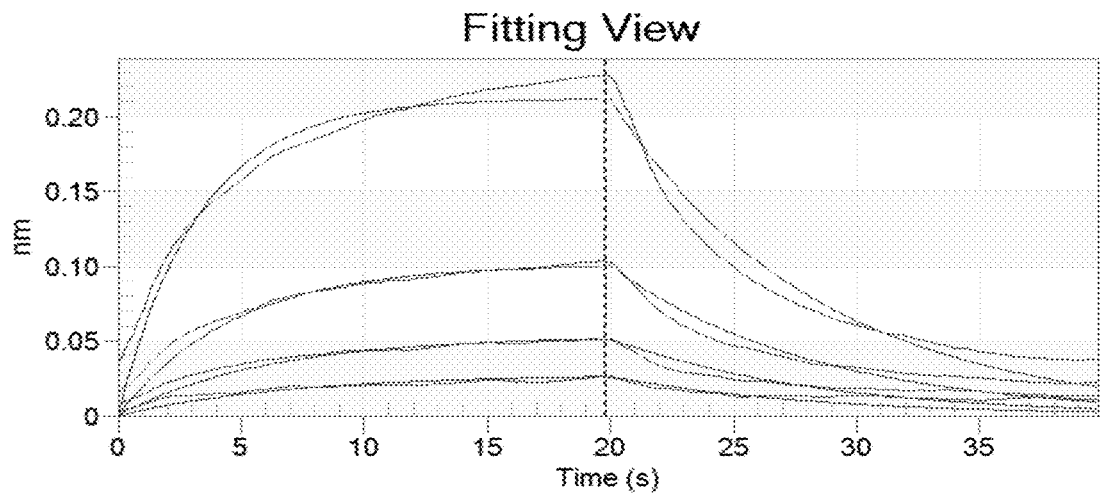
FIG. 77: Global fitting of association and dissociation curves of various concentrations of SUMO-C-CA (300 nM, 150 nM, 75 nM and 37.5 nM) with biotin labeled peptide 34a immobilized to streptavidin sensors. The $K_D$ was found to be 400 nM±35 nM. Coefficient of determination $R^2$=0.9853.
Figure 78:
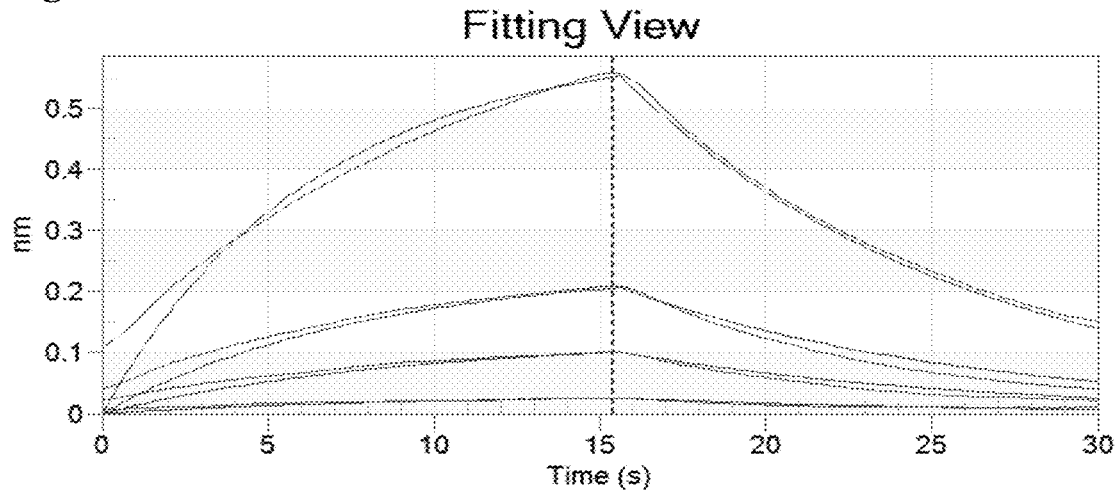
FIG. 78: Global fitting of association and dissociation curves of various concentrations of SUMO-C-CA (300 nM, 150 nM, 75 nM and 37.5 nM) with biotin labeled peptide 35a immobilized to streptavidin sensors. The $K_D$ was found to be 480 nM±70 nM. Coefficient of determination $R^2$=0.991.
Figure 79:
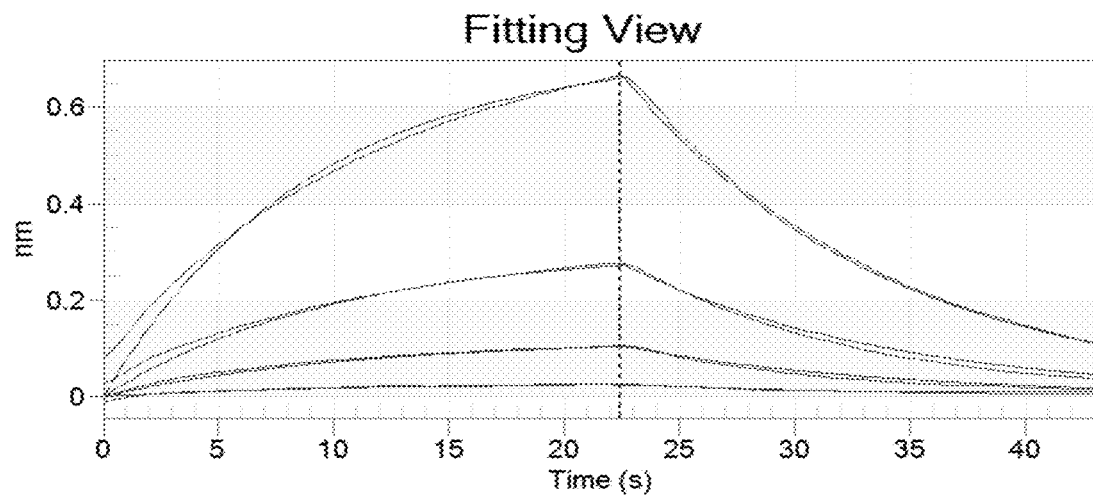
FIG. 79: Global fitting of association and dissociation curves of various concentrations of SUMO-C-CA (1250 nM, 613 nM, 306 nM and 153 nM) with biotin labeled peptide 36a immobilized to streptavidin sensors. The $K_D$ was found to be 1.2 μM±0.2 μM. Coefficient of determination $R^2$=0.991.
Figure 80:
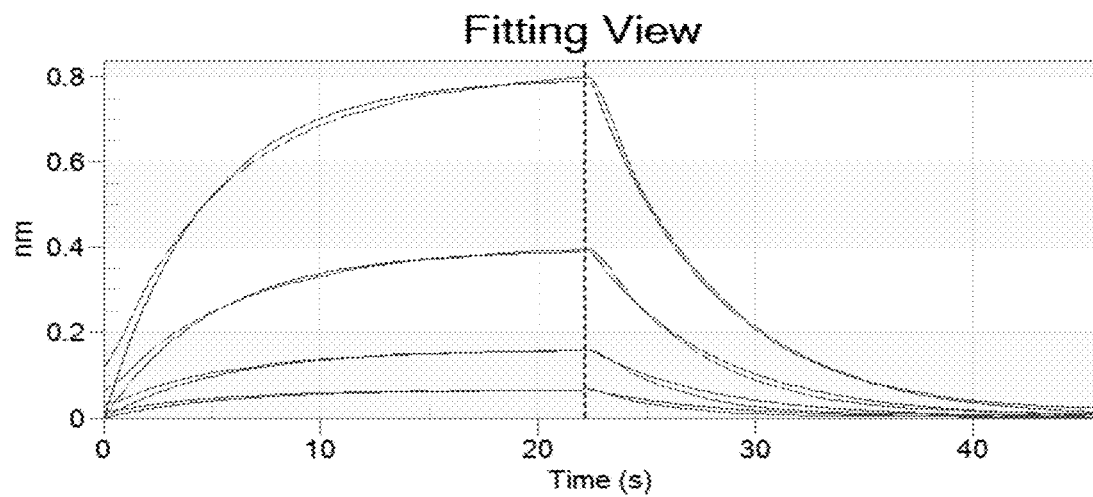
FIG. 80: Global fitting of association and dissociation curves of various concentrations of SUMO-C-CA (2500 nM, 1250 nM, 613 nM and 306 nM) with biotin labeled peptide 37a immobilized to streptavidin sensors. The Ku was found to be 2.2 μM±0.5 μM. Coefficient of determination $R^2$=0.9971.

FIG. 47: LC-MS analytical data of SPPS synthesized and biotin labeled non-canonical binder 30a from Library 4-Peptides 31a to 37a were similarly synthesized and purified. Peptide 30a: LC-MS analysis Method C. TIC trace and Mass spectrum of peptide 30a prepared according to the representative protocol for SPPS synthesis and biotin labeling. Represented are non-canonical residues m/z calcd. $[M+3H]^{3+}$: 860.37 found 860.38.

FIG. 148: LC-MS analytical data of SPPS synthesized and RCM macrocylized 10b-M-Peptides 10a-M, 10b-M unclosed, 10b-M scramble, 11b-M, 22b-M, 27b-M and ATSP-7041 were similarly synthesized and purified starting from the biotinylated or acetylated sequence. Peptide 10b-M: LC-MS analysis using Method D. TIC trace and Mass spectrum of peptide 10b-M prepared according to the representative protocol for SPPS and ring closing metathesis macrocyclization. Represented are non-canonical residues. Shown are residues modified in 10 to allow for macrocycle formation. m/z calcd. $[M+2H]^{2+}$: 875.48 found 875.49.

FIG. 149: LC-MS analytical data of SPPS synthesized and perfluorosulfone macrocylized 11b-S1-Peptides 10b-S1, 10b-S4, 11a-S1, 11b-S4, 11b-S1 scramble, 22b-S1, 22b-S4, 27b-S1, 27b-S4 were similarly synthesized and purified starting from the biotinylated or acetylated sequence. Peptide 11b-S1: LC-MS and LC-UV analysis using Method D. TIC, UVC traces and Mass spectrum of peptide 11b-S1 prepared according to the representative protocol for SPPS and perfluorosulfone electrophile macrocyclization. Represented are non-canonical residues. Shown are residues modified to allow for macrocycle formation. m/z calcd. $[M+H]^{+}$: 2018.74 found 2018.74.

Figure 150:
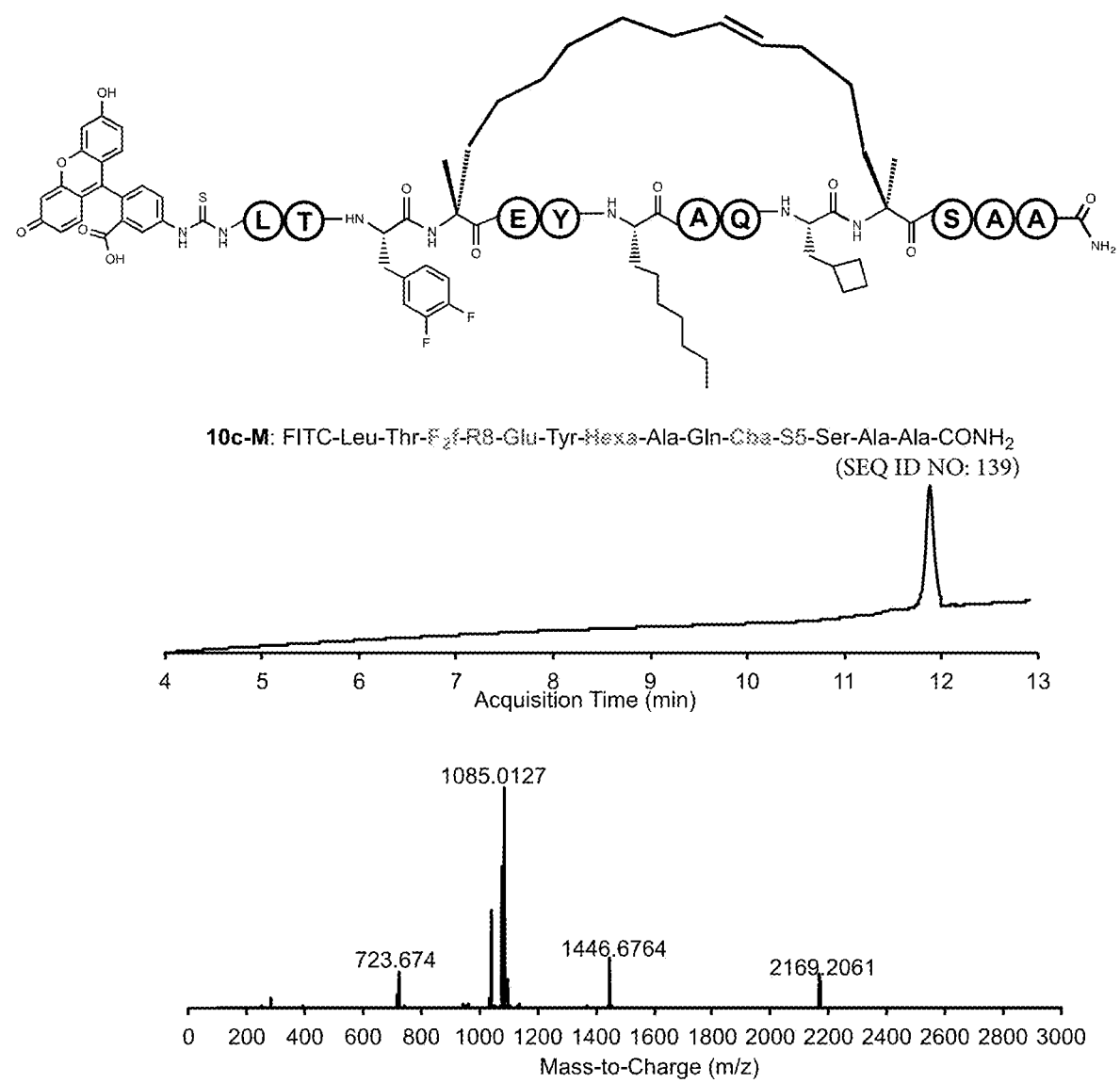

FIG. 150: LC-MS analytical data of SPPS synthesized, FITC labeled and RCM macrocylized 10c-M-Peptides 10c-M unclosed and 10c-M scramble. Peptide 10c-M: LC-UV and MS analysis using Method D. UVC trace and Mass spectrum of peptide 11c-S1 prepared according to the representative protocol for SPPS, FITC labeling and perfluorosulfone electrophile macrocyclization. Represented are non-canonical residues. Shown are residues modified to allow for macrocycle formation. m/z calcd. $[M+H]^{+}$: 2018.74 found 2018.74.

Figure 151:
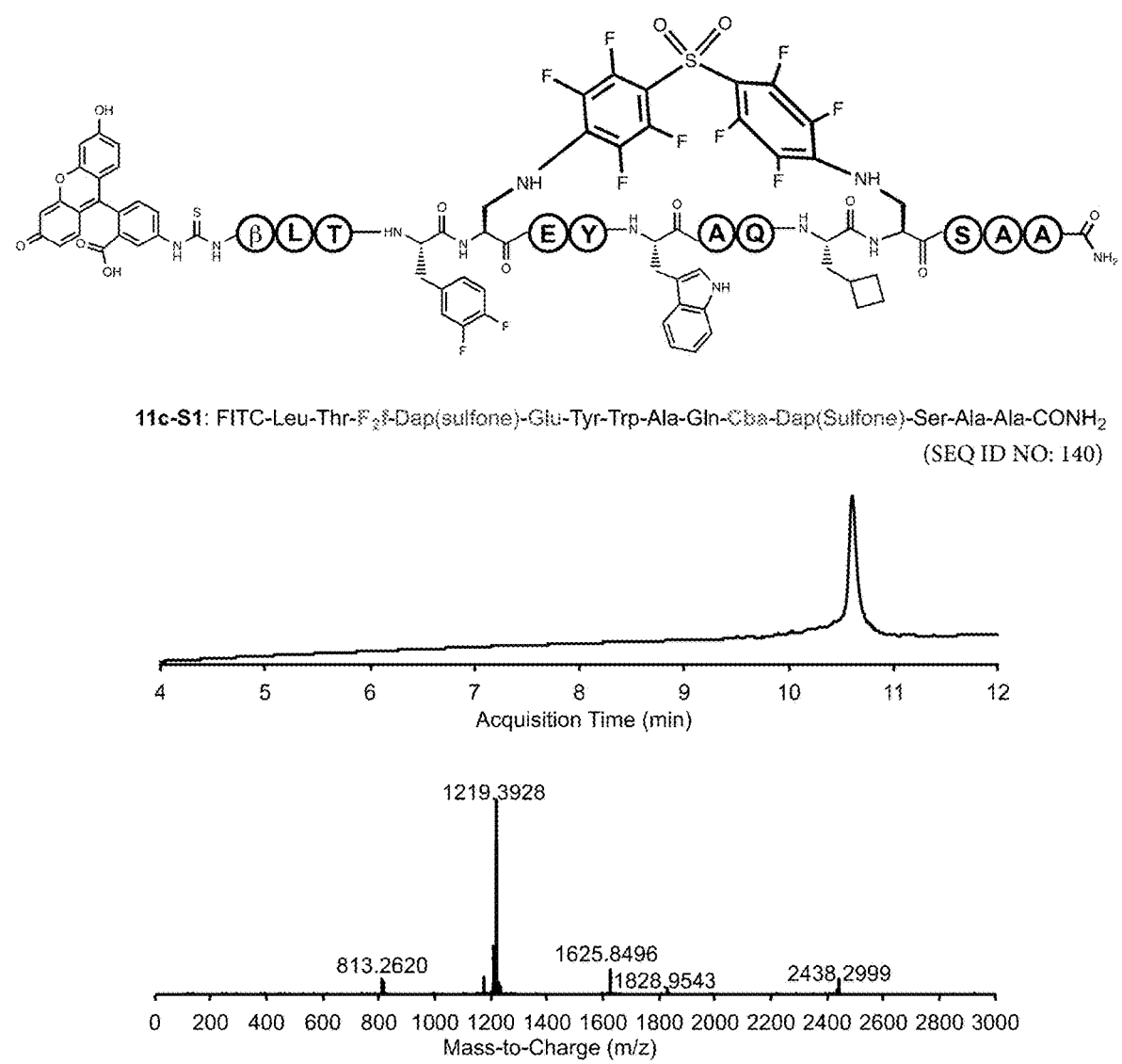

FIG. 151: LC-MS analytical data of SPPS synthesized, FITC labeled and perfluorosulfone macrocyclized 11c-S1-Peptide 11c-scramble was similarly synthesized and purified. Peptide 11c-S1: LC-UV and MS analysis using Method D. UVC trace and Mass spectrum of peptide 11c-S1 prepared according to the representative protocol for SPPS, FITC labeling and perfluorosulfone electrophile macrocyclization. Represented are non-canonical residues. Shown are residues modified to allow for macrocycle formation. m/z calcd. $[M+H]^{+}$: 2018.74 found 2018.74.

FIG. 152: LC-MS analytical data of SPPS synthesized and macrocyclized 60-Peptides 60a, 60b, 61a and 62a were similarly synthesized and purified starting from the biotinylated or acetylated sequence. Peptide 60: LC-MS analysis using Method D. TIC trace and Mass spectrum of peptide 60 prepared according to the representative protocol for SPPS and perfluorosulfone electrophile macrocyclization. m/z calcd. $[M+2H]^{2+}$: 1232.45 found 1232.45.

Figure 153:
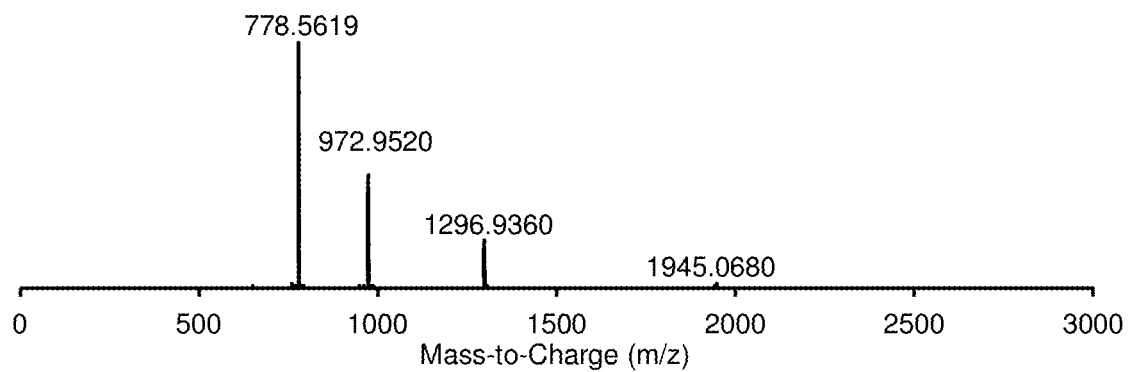

FIG. 153: LC-MS analytical data of fast flow and SPPS synthesized folded D-configured mini-protein 43-Peptides 44 to 53, 55 and 56 were similarly synthesized, folded and purified. Peptide 43: LC-MS analysis using Method C. TIC trace and Mass spectrum of mini-protein 43 prepared according to the representative protocol for fast flow, SPPS synthesis and folding. Represented are non-canonical residues. Cysteines marked with a (*) were oxidized and involved in disulfide bridges, non-canonical residues and diol amino acid are shown. m/z calcd. $[M+5H]^{5+}$: 778.16 found 778.16.

DETAILED DESCRIPTION OF CERTAIN EMBODIMENTS OF THE INVENTION

The present invention provides novel peptides (e.g., peptides, macrocyclic peptides, mini-proteins) that modulate protein-protein interactions or salts thereof. In some embodiments, the peptides are high affinity inhibitors (e.g., $K_D$ of at most 100 nM, at most 10 nM, at most 1 nM) of a protein-protein interaction. In certain embodiments, these peptides interfere with p53-MDM2 binding interactions (e.g., by binding to MDM2 (GenBank® Gene ID: 4193)). In some embodiments, the peptides interfere with the dimerization of the C-terminal domain of the human immunodeficiency virus (HIV) capsid protein (C-CA), comprising residues 146-231 of the HIV capsid protein (e.g., by binding to the C-terminal domain of the HIV capsid protein (C-CA), thereby inhibiting the dimeric interface of HIV capsid protein, thereby inhibiting viral assembly).

In some embodiments, the peptide has a high affinity for a target protein (e.g., MDM2, HIV capsid protein). A high affinity in some embodiments refers to a dissociation constant ($K_D$) of at most 1000 nM, at most 900 nM, at most 800 nM, at most 700 nM, at most 600 nM, at most 500 nM, at most 400 nM, at most 300 nM, at most 200 nM, at most 100 nM, at most 90 nM, at most 80 nM, at most 70 nM, at most 60 nM, at most 50 nM, at most 40 nM, at most 30 nM, at most 20 nM, at most 10 nM, at most 9 nM, at most 8 nM, at most 7 nM, at most 6 nM, at most 5 nM, at most 4 nM, at most 3 nM, at most 2 nM, at most 1 nM, at most 0.9 nM, at most 0.8 nM, at most 0.7 nM, at most 0.6 nM, at most 0.5 nM, at most 0.4 nM, at most 0.3 nM, at most 0.2 nM, at most 0.1 nM, or at most 0.01 nM.

In some embodiments, the peptides comprise canonical amino acids. In some embodiments, the peptides comprise at least one non-canonical amino acid (e.g., at least 2, at least 3, at least 4, at least 5, at least 6, at least 7, at least 8, at least 9, at least 10, or more non-canonical amino acids in the sequence). In some embodiments, the peptide is derived from a known inhibitor of a protein-protein interaction (e.g., knottin, a known MDM2 inhibitor). In some embodiments, the peptide comprises L-configured amino acids. In some embodiments, the peptide comprises D-configured amino acids.

In some embodiments, the peptide comprises a linear peptide.

In some embodiments, the peptide comprises a precursor to a macrocyclic peptide. In such embodiments, the peptide may comprise at least two amino acids that each comprise at least one terminally unsaturated amino acid side chain. In some embodiments, the at least 2 amino acids that comprise at least one terminally unsaturated amino acid side chain are non-adjacent in the amino acid sequence (e.g., 2 amino acids apart, 3 amino acids apart, 4 amino acids apart, 5 amino acids apart, 6 amino acids apart, 7 amino acids apart or a greater number of amino acids apart). In some embodiments, the peptide may comprise at least two amino acid side chains that each comprise one or more thiols (e.g., cysteine). Such peptides may be reacted under suitable conditions to form novel macrocyclic peptides or salts thereof.

In some embodiments, the peptide comprises a macrocyclic peptide. The term macrocyclic peptide as referred to herein refers to a peptide that has been chemically reacted with a suitably reactive reagent (e.g., a Grubbs catalyst, a reagent comprising aromatic groups and/or one or more halogens (e.g. fluorine)) in order to form a staple and/or a cross-link between a first amino acid side chain in the peptide and a second amino acid side chain in the peptide.

In some embodiments, the peptide comprises a mini-protein (e.g., a folded mini-protein). The term "mini-protein" herein may refer to a peptide or polypeptide having a length of less than or equal to 50 amino acid residues that exhibits one or more secondary structures (e.g., one or more alpha helices, one or more beta sheets, one or more mini-protein domains) and a tertiary structure. Without wishing to be bound by theory, mini-proteins may serve as model systems to study protein folding and stability. In some embodiments, the mini-protein comprises one or more D-configured amino acid residues. In some embodiments, the mini-protein is all D-configured, wherein each amino acid residue is D-configured.

The present invention also provides pharmaceutical compositions comprising an inventive peptide, macrocyclic peptide, mini-protein, or salt thereof. Furthermore, the present invention provides methods of making and using the inventive peptides, macrocyclic peptides, mini-proteins, and salts thereof.

These inventive peptides were rapidly generated and identified using novel methods described herein comprising combinatorial peptide synthesis and/or solution affinity selection.

Inventive peptides, macrocyclic peptides, mini-proteins, and salts thereof as described herein, may be useful wherever such compositions are advantageous, for example, as a therapeutic agent, as a biological probe, or as a drug delivery agent. The inventive peptides, macrocyclic peptides, mini-proteins, and salts thereof may function as modulators of protein-protein binding interactions or protein-ligand binding interactions. In certain embodiments, these inventive peptides, macrocyclic peptides, mini-proteins, and salts thereof are useful in the treatment of proliferative, neurological, immunological, endocrinologic, cardiovascular, hematologic, autoimmune, infectious, and/or inflammatory diseases, disorders, and/or conditions, and conditions characterized by premature or unwanted cell death.

In some embodiments, these peptides have strong therapeutic properties. For example, some of the peptides have significant intracellular loading and are potent killers of cancer cells (e.g., peptides having nanomolar binding affinity to MDM2), and some of the peptides demonstrate effectiveness at preventing the proliferation of HIV (e.g., peptides having nanomolar binding affinity to C-CA). In addition, the novel methods by which these novel peptides were synthesized and affinity selected present a platform for the discovery of other therapeutics that interfere with protein-protein interactions or protein-ligand interactions by binding to a target protein.

Peptides, Macrocyclic Peptides, and Mini-Proteins

In one aspect, the present invention provides a peptide, or a salt thereof, comprising a sequence of the formula (I):

(SEQ ID NO: 1)
LTFX$_1$HX$_2$WAX$_3$LTSK (I), wherein:
X$_1$ is Gln, Pro, or Glu;
X$_2$ is Phe, Tyr, or Glu; and
X$_3$ is Glu, Gln, Ala, or Leu.

In some embodiments, X$_1$ is Gln, X$_2$ is Phe, X$_3$ is Glu. In some embodiments, X$_1$ is Gin, X$_2$ is Tyr, X$_3$ is Glu. In some embodiments, X$_1$ is Pro, X$_2$ is Tyr, X$_3$ is Glu. In some embodiments, X$_1$ is Pro, X$_2$ is Phe, X$_3$ is Glu. In some embodiments, the peptide comprises a sequence of the formula (I) having any one of the sequences in Table 4 with side chains in the sequence specified.

In some embodiments, where the peptide comprises a sequence of formula (I), the sequence is homologous to known peptide pDI (6) (see FIG. 6). In some embodiments, the peptide comprising a sequence of formula (I) interferes with the p53-MDM2 binding interaction by binding MDM2. In some embodiments, the peptide comprising a sequence of formula (I) may be used for the treatment of proliferative diseases (e.g., cancer).

In some embodiments, the peptide comprising a sequence of formula (t) comprises a peptide sequence of a peptide from Library 1 (see, e.g., FIGS. 2A-2B, FIGS. 35-36; e.g., sequences 1a, 2a, 3a, 4a). In some embodiments, the peptide comprises a biotinylated N-terminus. In embodiments, the peptide comprises an amidated C-terminus. In some embodiments, the peptide is a linear peptide having a biotinylated N-terminus and an amidated C-terminus. In some embodiments, the peptide is 13 amino acids long. In some embodiments, the sequence may have a mutation at the third amino acid position (e.g., F in formula (I)), the $4^{th}$ amino acid position, the $6^{th}$ amino acid position, the $7^{th}$ amino acid position, the $9^{th}$ amino acid position, and/or the $10^{th}$ amino acid position. In some embodiments, the peptide has a $K_D$ with respect to MDM2 of at most 120 nM, at most 100 nM, at most 80 nM, at most 70 nM, at most 62 nM, at most 60 nM, at most 50 nM, or at most 45 nM.

In another aspect, the present invention provides a peptide, or a salt thereof, comprising a sequence of the formula (II):

LTFEHYWAQX$_1$TSK (II), (SEQ ID NO: 6)

wherein.

X$_1$ is Phe or Leu.

In some embodiments, X$_1$ is a hydrophobic residue. In some embodiments, X$_1$ is Phe. In some embodiments, X$_1$ is Leu. In some embodiments, the peptide comprises a sequence of the formula (II) having any one of the sequences in Table 4 with side chains in the sequence specified.

In some embodiments, where the peptide comprises a sequence of formula (II), the sequence is homologous to known peptide pDI (6) (see FIG. 6). In some embodiments, the peptide comprising a sequence of formula (II) interferes with the p53-MDM2 binding interaction by binding MDM2. In some embodiments, the peptide comprising a sequence of formula (II) may be used for the treatment of proliferative diseases (e.g., cancer).

Figure 27:
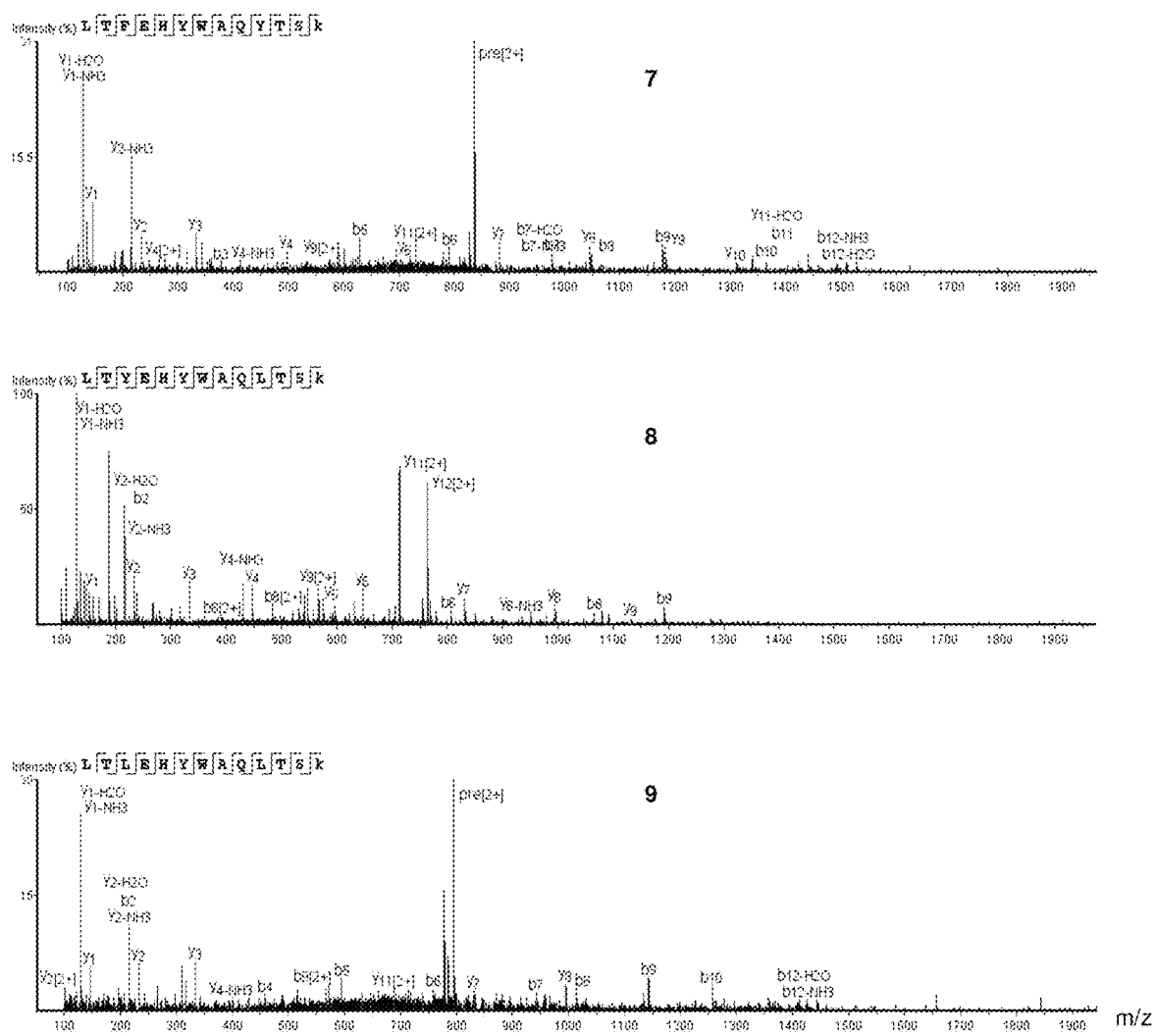
FIG. 27: Affinity selection from Library 2 was used for the identification of new binding sequences with mutated hotspots. Top, affinity selected and decoded sequences from Library 2 with their respective m/z, retention time (LC-MS method B) and ALC scores. In bold italic are represented randomized residues, and shown are the residues modified compared to reference 6. Bottom, MS/MS spectra proving efficient sequencing and identity of these binders.
Figure 28:
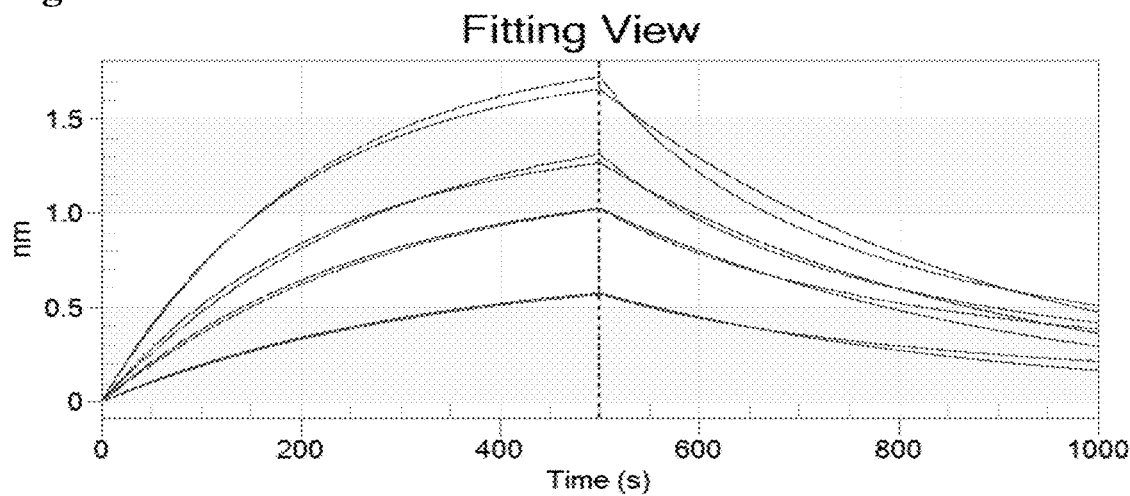
FIG. 28: Global fitting of association and dissociation curves of various concentrations of SUMO-$^{25-109}$-MDM2 (40 nM, 30 nM, 20 nM and 10 nM) with biotin labeled peptide 5a immobilized to streptavidin sensors. The $K_D$ was found to be 39±0.5 nM. Coefficient of determination $R^2$=0.9928.
Figure 29:
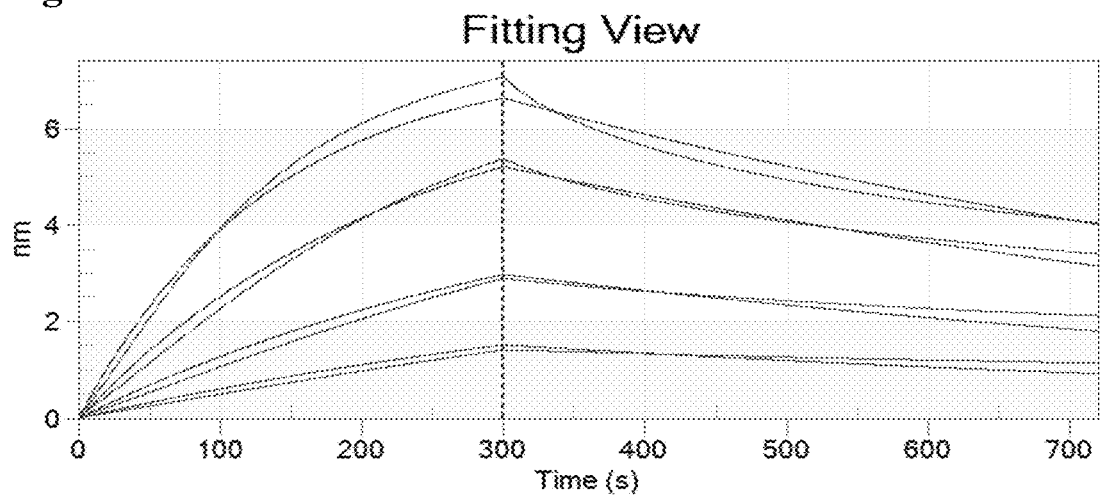
FIG. 29: Global fitting of association and dissociation curves of various concentrations of SUMO-$^{25-109}$MDM2 (50 nM, 30 nM, 20 nM and 10 nM) with biotin labeled peptide 6a (pDI) immobilized to streptavidin sensors. The $K_D$ was found to be 47±2 nM. Coefficient of determination $R^2$=0.999.
Figure 30:
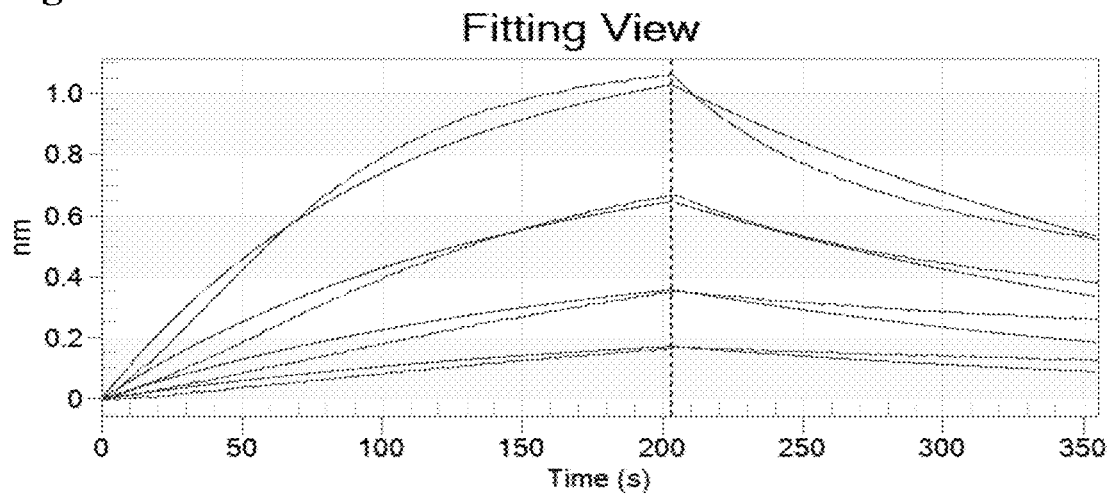
FIG. 30: Global fitting of association and dissociation curves of various concentrations of $^{1-137}$MDMX (100 nM, 50 nM, 25 nM and 12.5 nM) with biotin labeled peptide 6a (pDI) immobilized to super streptavidin sensors. The $K_D$ was found to be 83±4 nM. Coefficient of determination $R^2$=0.98.
Figure 31:
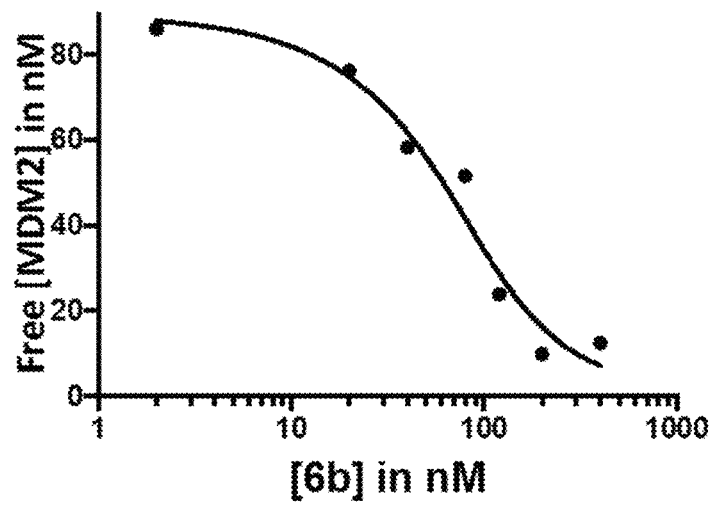
FIG. 31: SUMO-$^{25-109}$MDM2 and peptide pDI/6b (400 nM, 200 nM, 120 nM, 80 nM, 40 nM, 20 nM, and 2 nM) were mixed together following the protocol for in solution competition assay. [MDM2] was estimated using calibration curve and the obtained titration curve was fitted. Calculated $K_D$ was 36 nM±4.5 nM.
Figure 32:
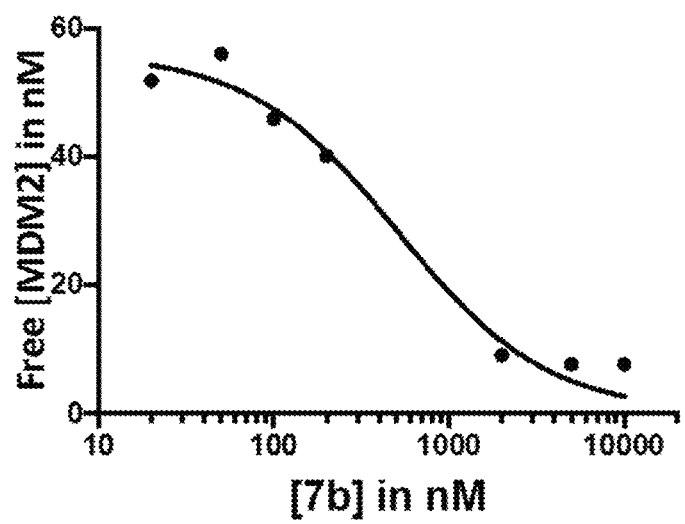
FIG. 32: SUMO-$^{25-109}$ MDM2 and peptide 7b (10000 nM, 5000 nM, 2000 nM, 200 nM, 100 nM, 50 nM and 20 nM) were mixed together following the protocol for in solution competition assay. [MDM2] was estimated using calibration curve and the obtained titration curve was fitted. Calculated $K_D$ was 490 nM±150 nM.
Figure 33:
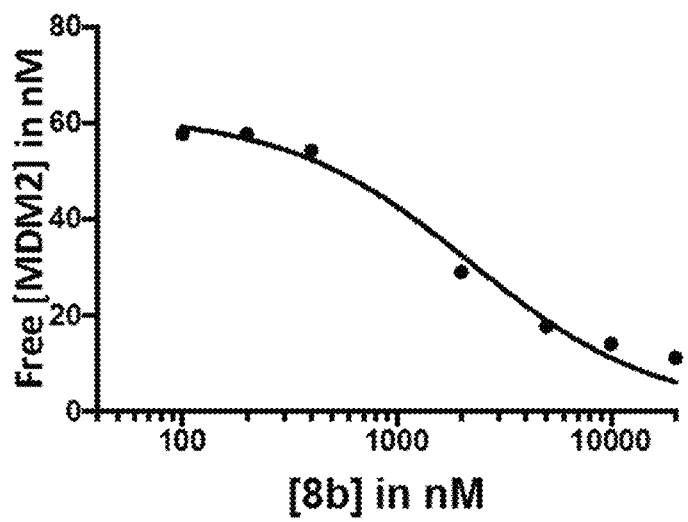
FIG. 33: SUMO-$^{25-109}$ MDM2 and peptide 8b (20000 nM, 10000 nM, 5000 nM, 2000 nM, 400 nM, 200 nM and 100 nM) were mixed together following the protocol for in solution competition assay. [MDM2] was estimated using calibration curve and the obtained titration curve was fitted. Calculated $K_D$ was 2500 nM±390 nM.
Figure 34:
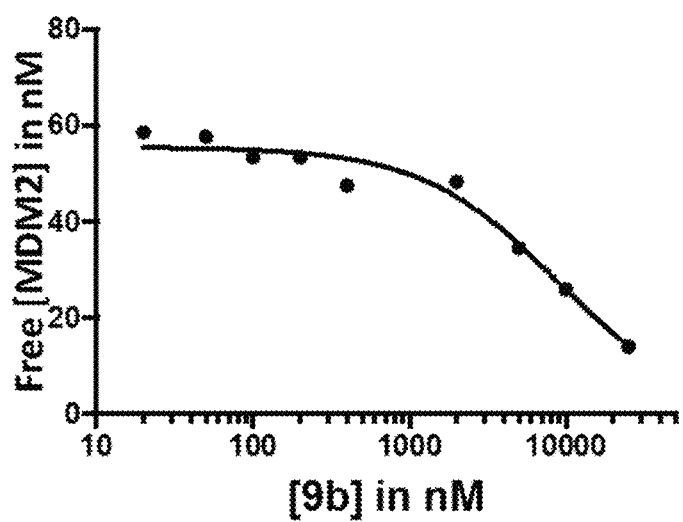
FIG. 34: SUMO-$^{25-109}$ MDM2 and peptide 9b (25000 nM, 10000 nM, 5000 nM, 2000 nM, 400 nM, 200 nM, 100 nM, 50 nM and 20 nM) were mixed together following the protocol for in solution competition assay. [MDM2] was estimated using calibration curve and the obtained titration curve was fitted. Calculated $K_D$ was 8700 nM±1200 nM.

In some embodiments, the peptide comprising a sequence of formula (II) comprises a peptide sequence of a peptide from Library 2 (see, e.g., FIGS. 2A-2B, FIG. 27; e.g., 5a, 6a). In some embodiments, the peptide comprises a biotinylated N-terminus. In embodiments, the peptide comprises an acetylated N-terminus. In embodiments, the peptide comprises an amidated C-terminus. In some embodiments, the peptide is a linear peptide having a biotinylated N-terminus and an amidated C-terminus. In some embodiments, the peptide is 13 amino acids long. In some embodiments, the sequence may have a mutation at the third amino acid position (e.g., F in formula (II)), the $7^{th}$ amino acid position, and/or the $10^{th}$ amino acid position. In some embodiments, the peptide has a $K_D$ with respect to MDM2 of at most 100 nM, at most 80 nM, at most 60 nM, at most 50 nM, at most 47 nM, or at most 36 nM.

In another aspect, the present invention provides a peptide, or a salt thereof, comprising a sequence of the formula (III):

LTX$_1$EHYX$_2$AQX$_3$TSK (III), (SEQ ID NO: 9)

wherein:

X$_1$ is Ff, F$_2$f, F$_3$f, or Phe;

X$_2$ is Hexa, Trp, Napha, or Anta; and

X$_3$ is Cba, Cha, Ff, F$_2$f, F$_3$f, F$_5$f, Hexa, Homof, or Leu.

In some embodiments, X$_1$ is F$_2$f, X$_2$ is Hexa, and X$_3$ is Cba. In some embodiments, X$_1$ is F$_2$f, X$_2$ is Trp, and X$_3$ is Cba. In some embodiments, the peptide comprises a sequence of the formula (III) having any one of the sequences in Table 4 with side chains in the sequence specified.

Figure 2C:
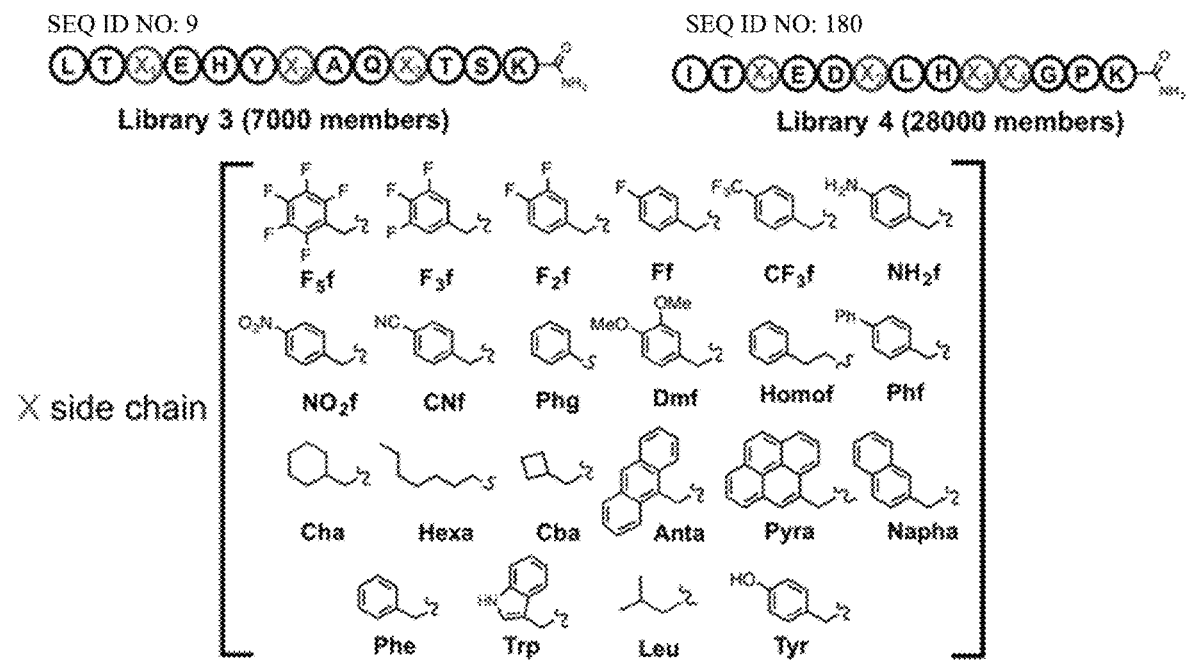

In some embodiments, where the peptide comprises a sequence of formula (III), the sequence is homologous to known peptide pDI (6) (see FIG. 6). In some embodiments, the peptide comprising a sequence of formula (III) interferes with the p53-MDM2 binding interaction by binding MDM2. In some embodiments, the peptide comprising a sequence of formula (III) may be used for the treatment of proliferative diseases (e.g., cancer). In some embodiments, at least one amino acid side chain in the sequence is a non-canonical amino acid side chain (e.g., a side chain as depicted in FIG. 2C). In some embodiments, at least 2 amino acid side chains in the sequence are non-canonical amino acid side chains (e.g., 2 amino acid side chains, 3 amino acid side chains, or more).

In some embodiments, the peptide comprising a sequence of formula (III) comprises a peptide sequence of a peptide from Library 3 (see, e.g., FIG. 2C, FIG. 41, FIG. 48; e.g., 38a, 10a, 10b, 11a, 11b, 12a, 13a, 14a, 15a, 16a, 17a, 18a, 19a, 20a, 21a, 22a, 23a, 24a, 25a, 26a, 27a, 28a). In some embodiments, the peptide comprises a biotinylated N-terminus. In some embodiments, the peptide comprises an acetylated N-terminus. In embodiments, the peptide comprises an amidated C-terminus. In some embodiments, the peptide is a linear peptide having a biotinylated N-terminus and an amidated C-terminus. In some embodiments, the peptide is a linear peptide having an acetylated N-terminus and an amidated C-terminus. In some embodiments, the peptide is 13 amino acids long. In some embodiments, the sequence may have a mutation at the third amino acid position (e.g., X$_1$ in formula (I1)), the $7^{th}$ amino acid position, and/or the $10^{th}$ amino acid position. In some embodiments, the peptide has a $K_D$ with respect to MDM2 of at most 100 nM, at most 80 nM, at most 60 nM, at most 40 nM, at most 30 nM, at most 24 nM, at most 20 nM, at most 16 nM, at most 15 nM, at most 10 nM, at most 9 nM, at most 8 nM, at most 7 nM, at most 6 nM, at most 5 nM, at most 4 nM, at most 3 nM, at most 2 nM, at most 1 nM, at most 0.9 nM, at most 0.8 nM, at most 0.7 nM, at most 0.6 nM, at most 0.5 nM, at most 0.4 nM, at most 0.3 nM, at most 0.2 nM, or at most 0.1 nM. In some embodiments, without wishing to be bound by theory, a peptide comprising one or more non-canonical amino acid side chains has a significantly lower $K_D$ with respect to MDM2 than a homologous peptide having fewer or no non-canonical amino acid side chains. In some embodiments, without wishing to be bound by theory, a peptide comprising X$_2$ as Hexa, Napha, or Anta has a significantly lower $K_D$ with respect to MDM2 than a homologous peptide having X$_2$ as Trp. In some embodiments, without wishing to be bound by theory, a peptide comprising X$_1$ as Ff, F$_2$f, or F$_3$f has a significantly lower $K_D$ with respect to MDM2 than a homologous peptide having X$_1$ as Phe. In some embodiments, without wishing to be bound by theory, a peptide comprising X$_3$ as Cba, Cha, Ff, F$_2$f, F$_3$f, F$_5$f, Hexa, or Homof has a significantly lower $K_D$ with respect to MDM2 than a homologous peptide having X$_3$ as Leu.

In some embodiments, peptides disclosed herein (e.g., comprising a sequence of formula (III)) bind both MDM2 and MDMX with a $K_D$ of e.g. less than 100 nM or less than 50 nM, and may be referred to as dual MDM2/MDMX inhibitors. Some embodiments, without wishing to be bound by theory, peptides that are dual MDM2/MDMX inhibitors interfere with both the p53-MDM2 binding interaction and the p53-MDMX binding interaction.

In another aspect, the present invention provides a peptide, or a salt thereof, comprising a sequence of the formula (IV):

IT(F$_2$f)ED(Cba)LHX$_1$X$_2$GP (IV),   (SEQ ID NO: 30)

wherein:
X$_1$ is Tyr or Dmf; and
X$_2$ is Tyr or F$_2$f.

In some embodiments, X$_1$ is Tyr and X$_2$ is Tyr. In some embodiments, X$_1$ is Dmf and X$_2$ is Tyr. In some embodiments, X$_1$ is Dmf and X$_2$ is F$_2$f. In some embodiments, the peptide comprises a sequence of the formula (IV) having any one of the sequences in Table 4 with side chains in the sequence specified.

In some embodiments, the C-terminal end of the sequence of formula (IV) is covalently bound to a portion of the peptide having (GS)$_n$K (SEQ ID NO: 178) on its N-terminal end, and where n is an integer from 0 to 12 (e.g., 0, 1, 2, 3, 4, 5, 6, 7, 8, 9, 10, 11, 12; e.g., (GS)$_6$K). In some such embodiments, the C-terminus (e.g., K) is biotinylated, either directly or through a linker. In some embodiments, the C-terminus is amidated. In some embodiments, the peptide is a linear peptide having a biotinylated C-terminus. In some embodiments, the peptide is a linear peptide having an amidated C-terminus.

In some embodiments, where the peptide comprises a sequence of formula (IV), the sequence is homologous to known peptide CAI (37) (see FIG. 6). In some embodiments, the peptide comprising a sequence of formula (IV) interferes with the dimeric interface of HIV capsid protein by binding allosterically to C-CA. In some embodiments, the peptide comprising a sequence of formula (IV) may be used for the treatment of immunological diseases and autoimmune diseases (e.g., HIV, AIDS). In some embodiments, at least one amino acid side chain in the sequence is a non-canonical amino acid side chain (e.g., a side chain as depicted in FIG. 2C). In some embodiments, at least 2 amino acid side chains in the sequence are non-canonical amino acid side chains (e.g., 2 amino acid side chains, 3 amino acid side chains, 4 amino acid side chains, or more).

In some embodiments, the peptide comprising a sequence of formula (IV) comprises a peptide sequence of a peptide from Library 4 (see, e.g., FIG. 2C, FIG. 2E, FIG. 72; e.g., 30a, 31a, 32a). In some embodiments, the peptide is from 12 to 25 amino acids long. In some embodiments, the sequence may have a mutation at the third amino acid position (e.g., F$_2$f in formula (IV), e.g., to Phe), the 6$^{th}$ amino acid position (e.g., Cba to Leu), the 9$^{th}$ amino acid position, and/or the 10$^{th}$ amino acid position. In some embodiments, the peptide has a dissociation constant K$_D$ with respect to C-CA of at most 500 nM, at most 200 nM, at most 160 nM, at most 140 nM, at most 120 nM, at most 100 nM, at most 90 nM, at most 88 nM, or at most 80 nM. In some embodiments, without wishing to be bound by theory, a peptide comprising X$_1$ as Tyr has a significantly lower K$_D$ with respect to C-CA than a homologous peptide having X$_1$ as Dmf. In some embodiments, without wishing to be bound by theory, a peptide comprising X$_2$ as Tyr has a significantly lower K$_D$ with respect to C-CA than a homologous peptide having X$_2$ as F$_2$f.

In another aspect, the present invention provides a peptide or a macrocyclic peptide, or a salt thereof, comprising a sequence of the formula (X):

LTX$_1$X$_2$EX$_3$X$_4$AX$_5$(Cba)X$_6$SX$_7$ (X),   (SEQ ID NO: 62)

wherein:
X$_1$ is F$_2$f or Phe;
X$_2$ is a non-canonical alpha-amino acid (e.g., R8 or Dap) or a portion of a cross-link or staple;
X$_3$ is Tyr or Phe:
X$_4$ is Hexa, Napha, or Trp;
X$_5$ is Gln or Glu;
X$_6$ is a non-canonical alpha-amino acid (e.g., S5 or Dap) or a portion of a cross-link or staple; and
X$_7$ is (Ala)$_m$ where m is an integer from 0 to 2 (e.g., 0, 1, 2).

In some embodiments, the non-canonical alpha-amino acid has a structure like that of R8 or S5 but with a side chain of length from 3 to 12 carbons, or any suitable unsaturated amino acid side chain amenable to cross-linking. In some embodiments, the peptide comprises a sequence of the formula (X), formula (IX), or formula (V) having any one of the sequences in Table 4 with side chains in the sequence specified.

In some embodiments, the present invention provides a peptide or a macrocyclic peptide, or a salt thereof, comprising a sequence of the formula (IX):

LTX$_1$X$_2$EX$_3$X$_4$AX$_5$(Cba)X$_6$SX$_7$ (IX),   (SEQ ID NO: 63)

wherein:
X$_1$ is F$_2$f or Phe;
X$_2$ is R8 or Dap or a portion of a cross-link or staple;
X$_3$ is Tyr or Phe;
X$_4$ is Hexa, Napha, or Trp;
X$_5$ is Gln or Glu;
X$_6$ is S5 or Dap or a portion of a cross-link or staple; and
X$_7$ is (Ala)$_m$ where m is an integer from 0 to 2 (e.g., 0, 1, 2).

In some embodiments, the side chain of X$_2$ and the side chain of X$_6$ are joined together by a linker to form a cross-link or staple. In some such embodiments, the peptide comprises a macrocyclic peptide. In some embodiments, the side chain of X$_2$ and the side chain of X$_6$ are not joined together. In some such embodiments, the peptide comprises a precursor to a macrocyclic peptide. In some embodiments, the peptide comprises a sequence of the formula (X), formula (IX), or formula (V) having any one of the sequences in Table 4 with side chains in the sequence specified.

In some embodiments, the present invention provides a peptide or a macrocyclic peptide, or a salt thereof, comprising a sequence of the formula (V):

LTX$_1$X$_2$EX$_3$X$_4$AX$_5$(Cba)X$_6$SAA (V),   (SEQ ID NO: 34)

wherein:
X$_1$ is F$_2$f or Phe;
X$_2$ is R8 or Dap or a portion of a cross-link or staple;
X$_3$ is Tyr or Phe;
X$_4$ is Hexa, Napha, or Trp;
X$_5$ is Gln or Glu; and
X$_6$ is S5 or Dap or a portion of a cross-link or staple.

In some embodiments, a portion of a cross-link or staple may be a precursor (e.g., a side chain amenable to cross-linking or stapling) to a cross-link or staple. In some embodiments, X$_1$ is F$_2$f, X$_2$ is R8, X$_3$ is Tyr, X$_4$ is Hexa, X$_5$ is Gln, and X$_6$ is S5. In some embodiments, X$_1$ is F$_2$f, X$_2$ is a portion of a cross-link or staple from R8 or Dap or another side chain amenable to cross-linking, X$_3$ is Tyr, X$_4$ is Hexa, X$_5$ is Gln, and X$_6$ is a portion of a cross-link or staple from S5 or Dap or another side chain amenable to cross-linking (e.g., cross-linked or stapled to $X_2$). In some embodiments, $X_1$ is $F_2f$, $X_2$ is Dap, $X_3$ is Tyr, X is Hexa, $X_5$ is Gln, and $X_6$ is Dap. In some embodiments, $X_1$ is $F_2f$, $X_2$ is R8, $X_3$ is Tyr, $X_4$ is Napa (also herein Napha), $X_5$ is Glu, and $X_6$ is SS. In some embodiments, $X_1$ is $F_2f$, $X_2$ is Dap, $X_3$ is Phe, $X_4$ is Trp, $X_5$ is Gln, and $X_6$ is Dap. In some embodiments, the peptide comprises a sequence of the formula (X), formula (IX), or formula (V) having any one of the sequences in Table 4 with side chains in the sequence specified.

In some embodiments, the side chain of $X_2$ and the side chain of $X_6$ are joined together by a linker to form a crosslink or staple. In some such embodiments, the peptide comprises a macrocyclic peptide. In some embodiments, the side chain of $X_2$ and the side chain of $X_6$ are not joined together. In some such embodiments, the peptide comprises a precursor to a macrocyclic peptide.

In some embodiments, joining together by a linker to form a staple or crosslink may comprise as non-limiting examples perfluorosulfone stapling or cyclization (e.g., using the perfluorosulphone reagent shown in FIG. 115) and perfluoroayl cyclization.

In some embodiments, the C-terminal end of the sequence of formula (V) or formula (IX) or formula (X) is amidated. In some embodiments, the N-terminus (e.g., K) is biotinylated, either directly or through a linker (e.g., comprising a polyethylene glycol of length from 0 to 20 repeat units). In some embodiments, the N-terminus is acetylated. In some embodiments, the peptide is a linear peptide having a biotinylated or acetylated N-terminus. In some embodiments, the peptide is a linear peptide having an amidated C-terminus.

In some embodiments, where the peptide (e.g., macrocyclic peptide) comprises a sequence of formula (V) or formula (IX) or formula (X), the sequence is homologous to known peptide pDI (6) (see FIG. 6). In some embodiments, the peptide comprising a sequence of formula (V) or formula (IX) or formula (X) interferes with the p53-MDM2 binding interaction by binding MDM2. In some embodiments, the peptide comprising a sequence of formula (V) or formula (IX) or formula (X) may be used for the treatment of proliferative diseases (e.g., cancer). In some embodiments, at least one amino acid side chain in the sequence is a non-canonical amino acid side chain (e.g., a side chain as depicted in FIG. 2C). In some embodiments, at least 2 amino acid side chains in the sequence are non-canonical amino acid side chains (e.g., 2 amino acid side chains, 3 amino acid side chains, 4 amino acid side chains, 5 amino acid side chains, or more).

Figure 81:
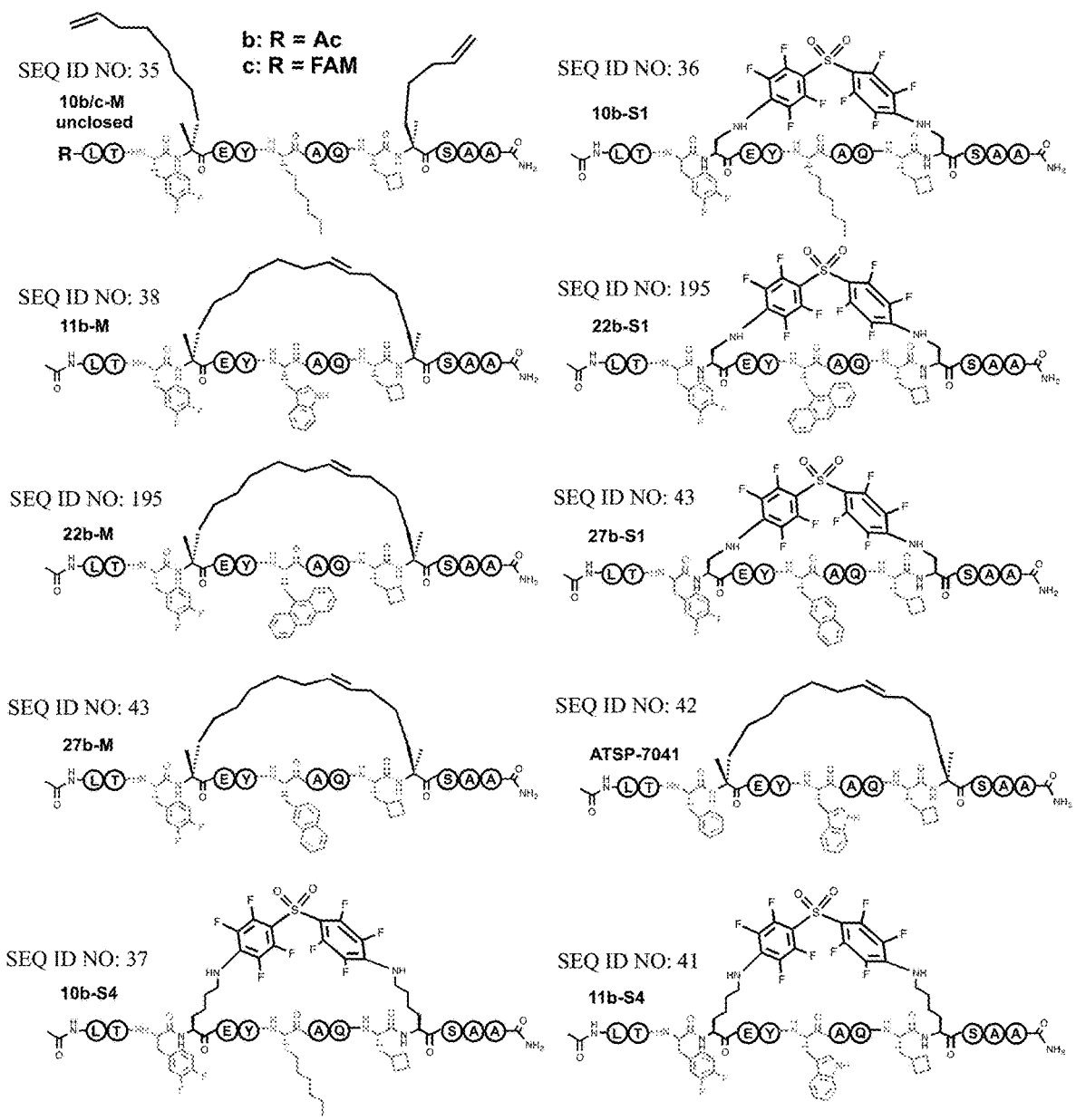
FIG. 81: Macrocyclic constructs and controls tested for binding and/or biological assays.
Figure 83:
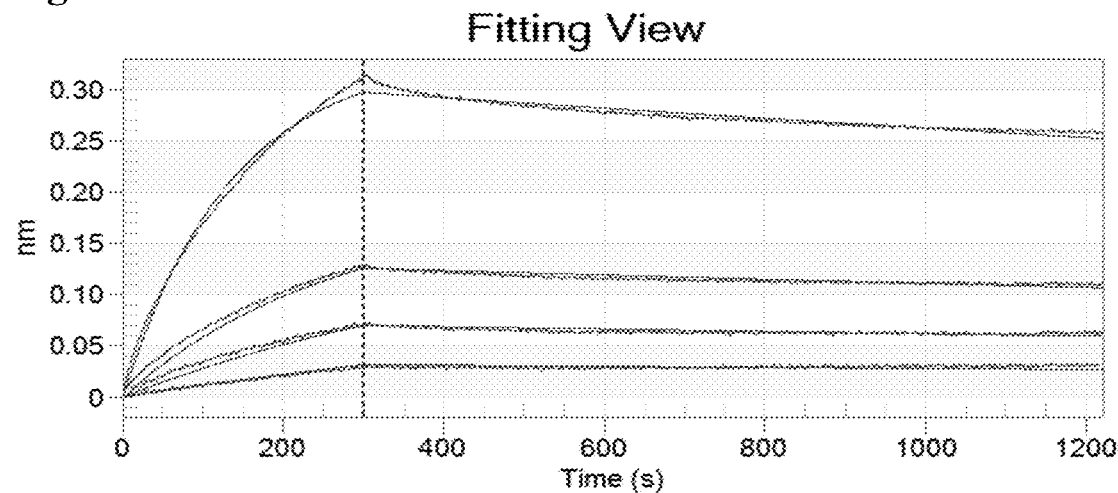
FIG. 83: Global fitting of association and dissociation curves of various concentrations of SUMO-$^{25-109}$ MDM2 (200 nM, 100 nM, 50 nM and 25 nM) with biotin labeled peptide 10a-M immobilized to streptavidin sensors. The $K_D$ was found to be 5 nM±0.4 nM. Coefficient of determination $R^2$=0.9985.
Figure 84:
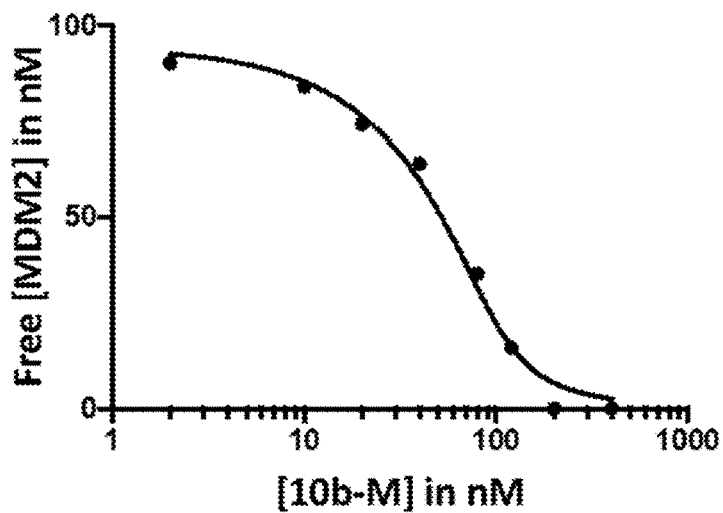
FIG. 84: SUMO-$^{25-109}$ MDM2 and peptide 10b-M (400 nM, 200 nM, 120 nM, 80 nM, 40 nM, 20 nM, 10 nM and 2 nM) were mixed together following the protocol for in solution competition assay. [MDM2] was determined using calibration curve and the obtained titration curve was fitted. The $K_D$ was found to be 8.7 nM±2.6 nM. Coefficient of determination $R^2$=0.99.
Figure 85:
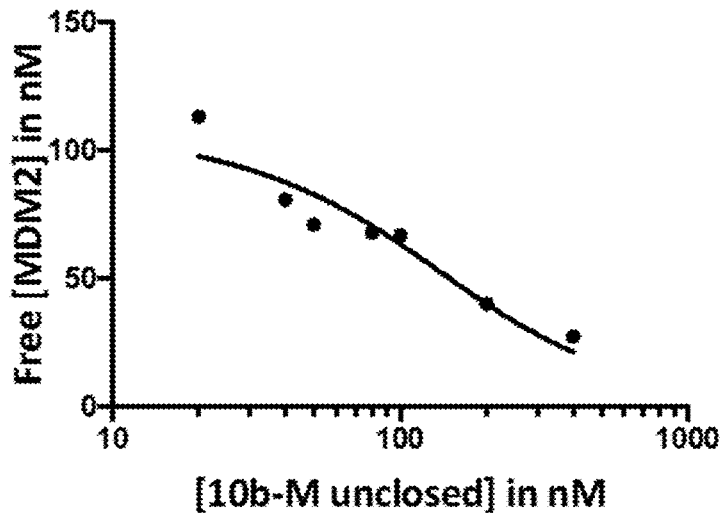
FIG. 85: SUMO-$^{25-109}$ MDM2 and peptide 10b-M unclosed (400 nM, 200 nM, 100 nM, 80 nM, 50 nM, 40 nM, 20 nM and 2 nM) were mixed together following the protocol for in solution competition assay. [MDM2] was determined using calibration curve and the obtained titration curve was fitted. The $K_D$ was found to be 75 nM±12 nM. Coefficient of determination $R^2$=0.98.
Figure 86:
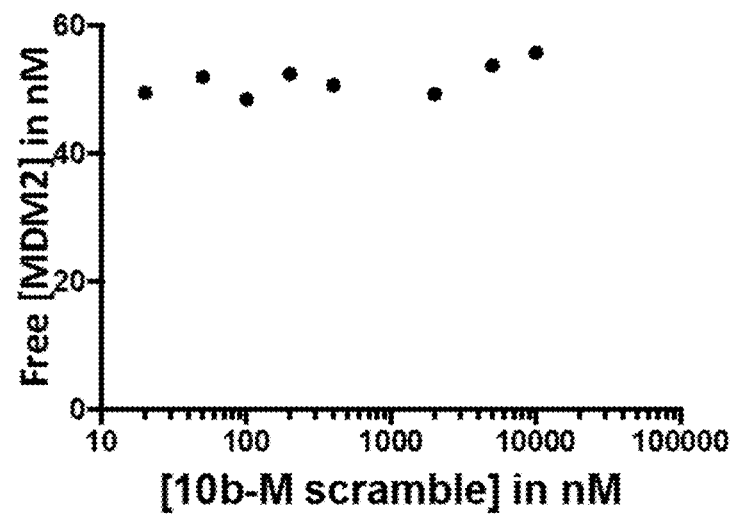
FIG. 86: SUMO-$^{25-109}$ MDM2 and peptide 10b-M scramble (10000 nM, 5000 nM, 2000 nM, 400 nM, 200 nM, 100 nM, 50 nM and 20 nM) were mixed together following the protocol for in solution competition assay. [MDM2] was determined using calibration curve and the $K_D$ was found to be >10000 nM.
Figure 87:
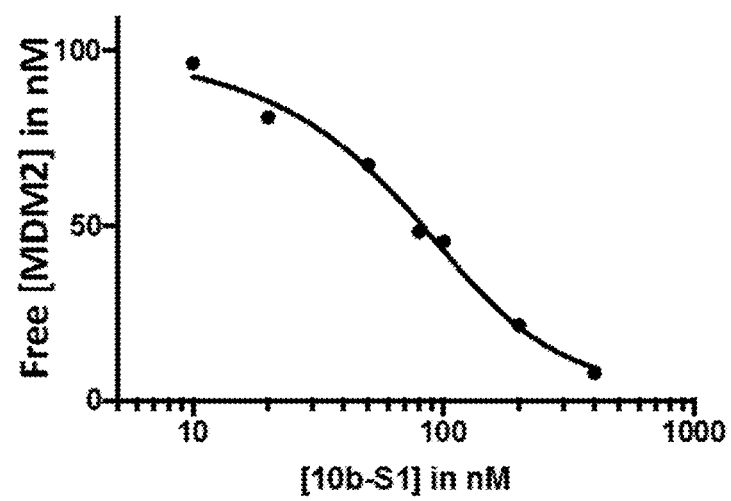
FIG. 87: SUMO-$^{25-109}$ MDM2 and peptide 10b-S1 (400 nM, 200 nM, 100 nM, 80 nM, 50 nM, 20 nM, 10 nM and 2 nM) were mixed together following the protocol for in solution competition assay. [MDM2] was determined using calibration curve and the obtained titration curve was fitted. The $K_D$ was found to be 30 nM±7 nM. Coefficient of determination $R^2$=0.98.
Figure 88:
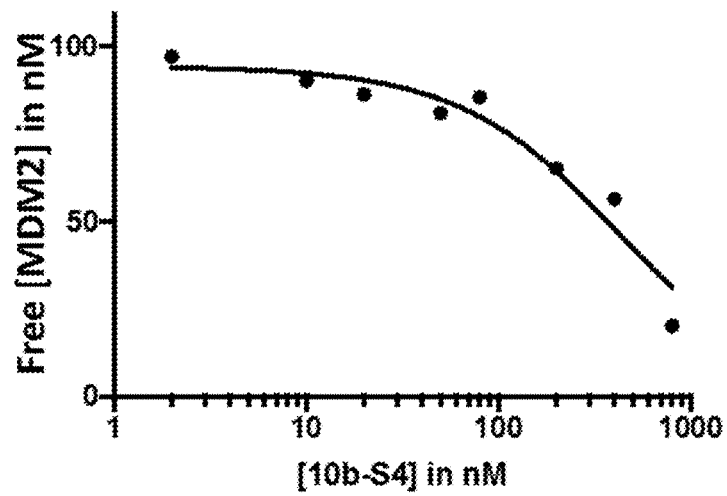
FIG. 88: SUMO-$^{25-109}$ MDM2 and peptide 10b-S4 (800 nM, 400 nM, 200 nM, 100 nM, 50 nM, 20 nM, 10 nM and 2 nM) were mixed together following the protocol for in solution competition assay. [MDM2] was determined using calibration curve and the obtained titration curve was fitted. The $K_D$ was found to be 298 nM±49 nM. Coefficient of determination $R^2$=0.97.
Figure 89:
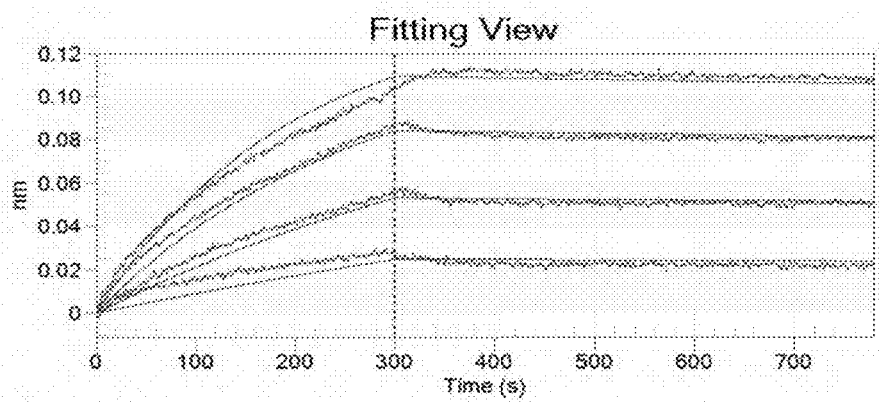
FIG. 89: Global fitting of association and dissociation curves of various concentrations of SUMO-$^{25-109}$ MDM2 (200 nM, 150 nM, 75 nM and 37.5 nM) with biotin labeled peptide 11a-S1 immobilized to streptavidin sensors. The $K_D$ was found to be 2.5 nM±0.2 nM. Coefficient of determination $R^2$=0.9891.
Figure 90:
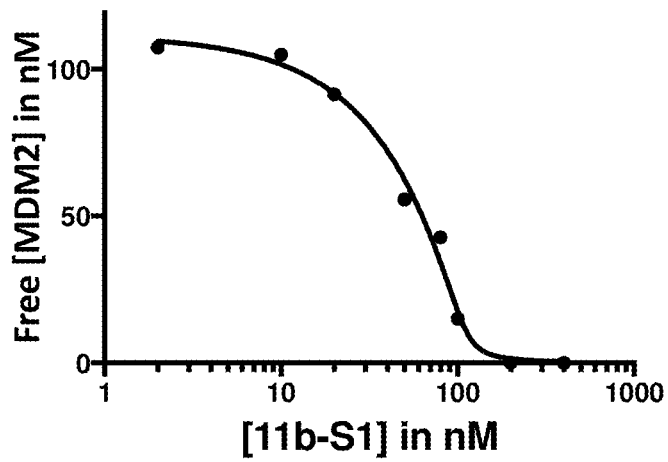
FIG. 90: SUMO-$^{25-109}$ MDM2 and peptide 11b-S1 (400 nM, 200 nM, 100 nM, 80 nM, 50 nM, 20 nM, 10 nM and 2 nM) were mixed together following the protocol for in solution competition assay. [MDM2] was estimated using calibration curve and the obtained titration curve was fitted. Calculated $K_D$ was 1.9 nM±1.5 nM.
Figure 91:
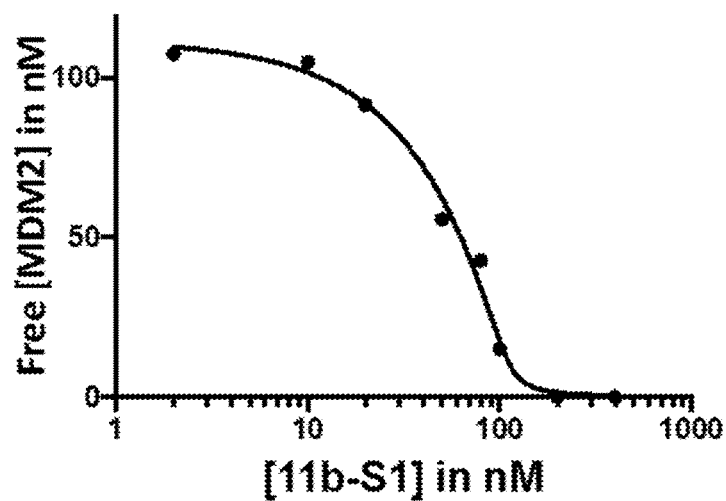
FIG. 91: SUMO-$^{25-109}$ MDM2 and peptide 11b-M (400 nM, 200 nM, 100 nM, 80 nM, 50 nM, 40 nM, 20 nM and 2 nM) were mixed together following the protocol for in solution competition assay. [MDM2] was determined using calibration curve and the obtained titration curve was fitted. The $K_D$ was found to be 4.1 nM±2.3 nM. Coefficient of determination $R^2$=0.99.
Figure 92:
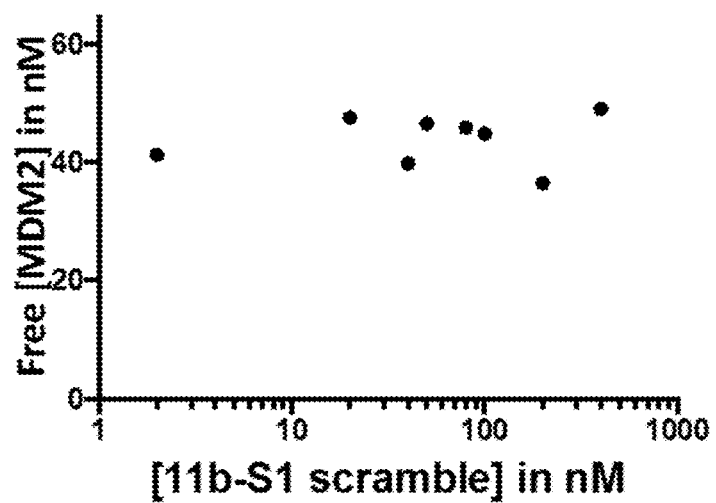
FIG. 92: SUMO-$^{25-109}$ MDM2 and peptide 11b-S1 scramble (400 nM, 200 nM, 100 nM, 80 nM, 50 nM, 20 nM, 10 nM and 2 nM) were mixed together following the protocol for in solution competition assay. [MDM2] was estimated using calibration curve. No binding was observed in this range of concentrations.
Figure 93:
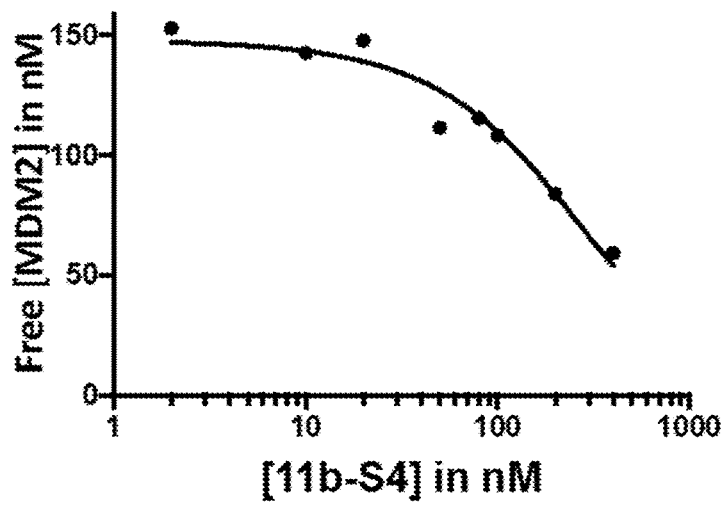
FIG. 93: SUMO-$^{25-109}$ MDM2 and peptide 11b-S4 (400 nM, 200 nM, 100 nM, 80 nM, 50 nM, 20 nM, 10 nM and 2 nM) were mixed together following the protocol for in solution competition assay. [MDM2] was estimated using calibration curve and the obtained titration curve was fitted. Calculated $K_D$ was 180 nM±37 nM.
Figure 94:
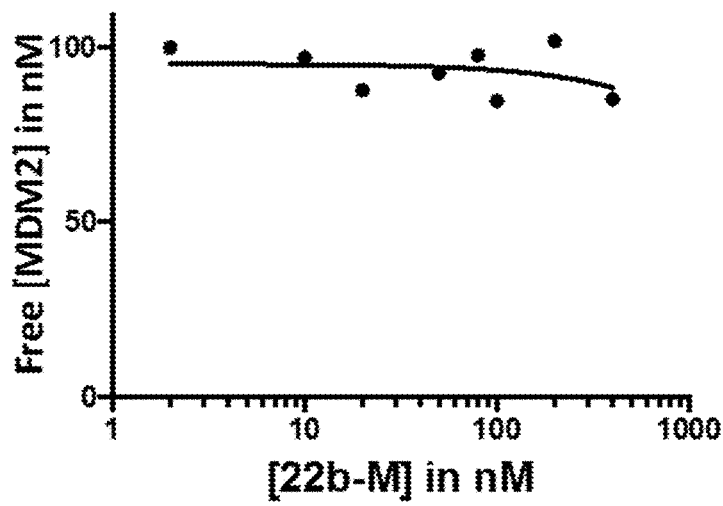
FIG. 94: SUMO-$^{25-109}$ MDM2 and peptide 22b-M (400 nM, 200 nM, 100 nM, 80 nM, 50 nM, 20 nM, 10 nM and 2 nM) were mixed together following protocol. [MDM2] was estimated using calibration curve and measured $K_D$ was >1000 nM.
Figure 95:
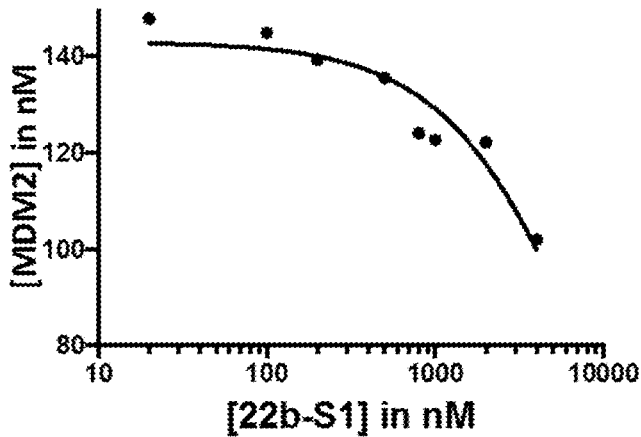
FIG. 95: SUMO-$^{25-109}$ MDM2 and peptide 22b-S1 (4000 nM, 2000 nM, 1000 nM, 800 nM, 500 nM, 200 nM, 100 nM and 20 nM) were mixed together following the protocol for in solution competition assay. [MDM2] was estimated using calibration curve and the obtained titration curve was fitted. Measured $K_D$ was >1000 nM.
Figure 96:
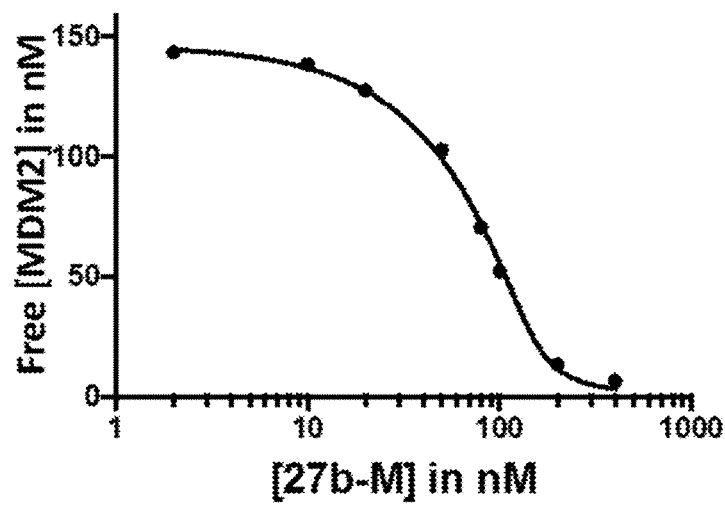
FIG. 96: SUMO-$^{25-109}$ MDM2 and peptide 27b-M (400 nM, 200 nM, 100 nM, 80 nM, 50 nM, 20 nM, 10 nM and 2 nM) were mixed together following the protocol for in solution competition assay. [MDM2] was estimated using calibration curve and the obtained titration curve was fitted. Calculated $K_D$ was 5.6 nM±1.4 nM.
Figure 97:
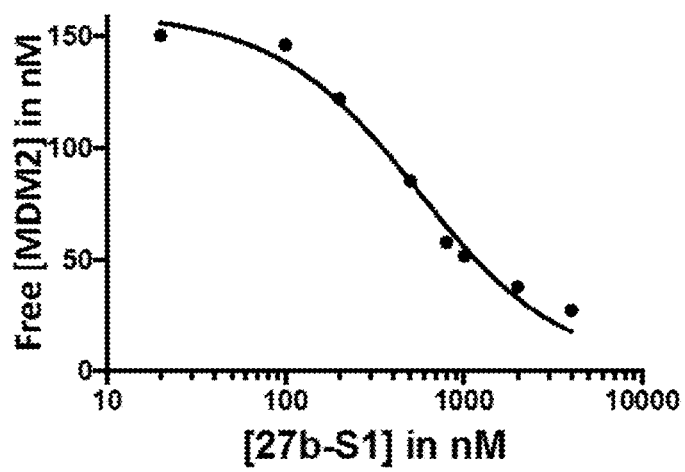
FIG. 97: SUMO-$^{25-109}$ MDM2 and peptide 27b-S1 (400 nM, 200 nM, 100 nM, 80 nM, 50 nM, 20 nM, 10 nM and 2 nM) were mixed together following the protocol for in solution competition assay. [MDM2] was estimated using calibration curve and the obtained titration curve was fitted. Calculated $K_D$ was 540 nM±69 nM.
Figure 98:
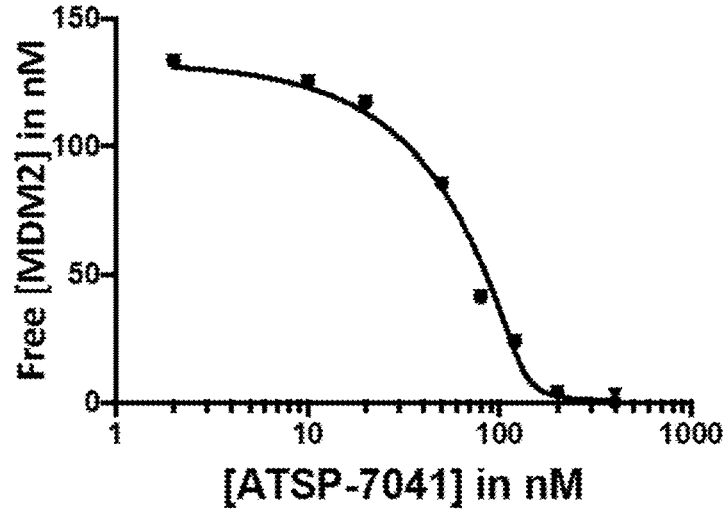
FIG. 98: SUMO-$^{25-109}$ MDM2 and peptide ATSP-7040 (400 nM, 200 nM, 100 nM, 80 nM, 50 nM, 20 nM, 10 nM and 2 nM) were mixed together following the protocol for in solution competition assay. [MDM2] was estimated using calibration curve and the obtained titration curve was fitted. Calculated $K_D$ was 1.3 nM±1.6 nM.

In some embodiments, the peptide comprising a sequence of formula (V) or formula (IX) or formula (X) has a sequence of a peptide (e.g., macrocyclic peptide) based on Library 3 (see, e.g., FIG. 81, FIG. 82; e.g., 10a-M, 10b-M, 10b-S1, 11a-S1, 11 b-S1, ATSP-7041; 27b-M).

In some embodiments, the peptide is 14 amino acids long.

In some embodiments, the sequence may have a mutation at the third amino acid position (e.g., $X_1$ in formulas (V), (IX), (X); e.g., to Phe), the $4^{th}$ amino acid position, the $5^{th}$ amino acid position, the $6^{th}$ amino acid position, the $7^{th}$ amino acid position, the $10^{th}$ amino acid position, and/or the $11^{th}$ amino acid position. In some embodiments, the peptide has a dissociation constant $K_D$ with respect to MDM2 of at most 500 nM, at most 300 nM, at most 200 nM, at most 100 nM, at most 75 nM, at most 50 nM, at most 30 nM, at most 20 nM, at most 10 nM, at most 5 nM, at most 2 nM, or at most 1 nM.

In another aspect, the present invention provides a peptide or a macrocyclic peptide, or a salt thereof, comprising a sequence of the formula (VI):

$$\text{IT}(F_2f)X_1DX_2LX_3X_4X_5GP \text{ (VI)}, \quad \text{(SEQ ID NO: 44)}$$

wherein:
$X_1$ is Cys or S5 or a portion of a cross-link or staple;
$X_2$ is Cba or Leu;
$X_3$ is Cys or S5 or a portion of a cross-link or staple;
$X_4$ is Tyr or Dmf; and
$X_5$ is Tyr or $F_2f$.

In some embodiments, $X_1$ is Cys, $X_2$ is Cba, $X_3$ is Cys, $X_4$ is Tyr, and X; is Tyr. In some embodiments, $X_1$ is S5, $X_2$ is Cba, $X_3$ is S5, $X_4$ is Tyr, and $X_5$ is Tyr. In some embodiments, $X_1$ is a portion of a cross-link or staple from S5 or another side chain amenable to cross-linking, $X_2$ is Cba, $X_3$ is a portion of a cross-link or staple from S5 or another side chain amenable to cross-linking (e.g., cross-linked or stapled to $X_1$), $X_4$ is Tyr, and $X_5$ is Tyr. In some embodiments, the peptide comprises a sequence of the formula (VI) having any one of the sequences in Table 4 with side chains in the sequence specified.

In some embodiments, the C-terminal end of the sequence of formula (VI) is covalently bound to a portion of the peptide having $(GS)_nK$ (SEQ ID NO: 178) on its N-terminal end, and where n is an integer from 0 to 12 (e.g., 0, 1, 2, 3, 4, 5, 6, 7, 8, 9, 10, 11, 12; e.g., $(GS)_6K$). In some such embodiments, the C-terminus (e.g., K) is biotinylated, either directly or through a linker. In some embodiments, the C-terminus is amidated. In some embodiments, the peptide comprises a linear peptide having a biotinylated C-terminus. In some embodiments, the peptide comprises a linear peptide having an amidated C-terminus.

In some embodiments, the side chain of $X_1$ and the side chain of $X_3$ are joined together by a linker to form a crosslink or staple. In some such embodiments, the peptide comprises a macrocyclic peptide. In some embodiments, the side chain of $X_1$ and the side chain of $X_3$ are not joined together. In some such embodiments, the peptide comprises a precursor to a macrocyclic peptide.

In some embodiments, joining together by a linker to form a staple or crosslink may comprise as non-limiting examples perfluorosulfone stapling or cyclization and perfluoroayl cyclization (e.g., using the perfluoroaryl reagent in FIG. 109); joining by a linker to form a staple or crosslink may comprise reacting the first amino acid side chain (e.g., a side chain comprising an unsaturated group, e.g. an alkylene) with the second amino acid side chain (e.g., a side chain comprising an unsaturated group, e.g. an alkylene) using a Grubbs catalyst (e.g., a second generation Grubbs catalyst) for a ring closing metathesis reaction.

In some embodiments, where the peptide (e.g., macrocyclic peptide) comprises a sequence of formula (VI), the sequence is homologous to known peptide CAI (37) (see FIG. 6). In some embodiments, the peptide comprising a sequence of formula (VI) interferes with the dimeric interface of HIV capsid protein by binding allosterically to C-CA. In some embodiments, the peptide comprising a sequence of formula (VI) may be used for the treatment of immunological diseases and autoimmune diseases (e.g., HIV, AIDS). In some embodiments, at least one amino acid side chain in the sequence is a non-canonical amino acid side chain (e.g., a side chain as depicted in FIG. 2C). In some embodiments, at least 2 amino acid side chains in the sequence are non-canonical amino acid side chains (e.g., 2 amino acid side chains, 3 amino acid side chains, 4 amino acid side chains, or more).

Figure 109:
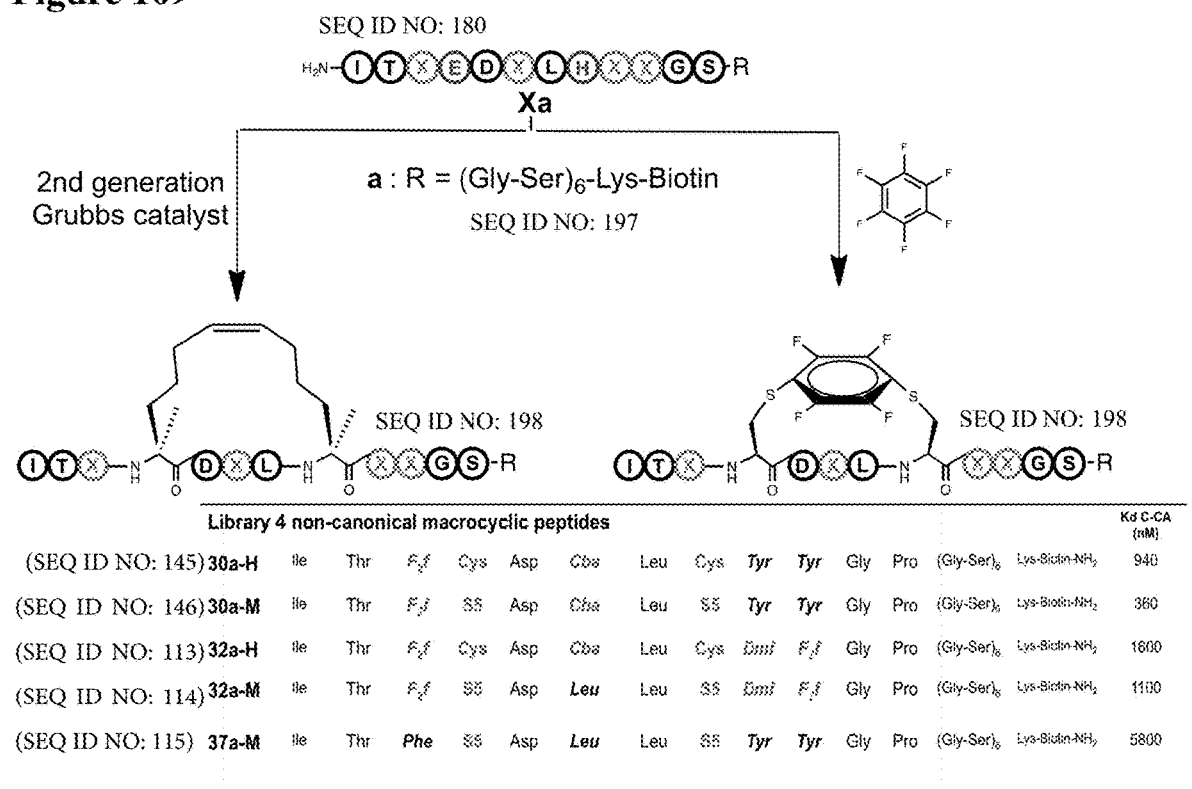
FIG. 109: Modification and macrocylization of non-canonical sequences from library 4 yielded potent macrocyclic inhibitors of C-CA. Macrocyclization of non-canonical sequences from Library 4 using RCM and cysteine perfluoroarylation by hexafluorobenzene[10]. Macrocyclization schemes of select Library 4 non-canonical sequences Xa using established i and i+4 macrocyclization chemistries (where X is the sequence number and Xa designate respectively C-terminal biotinylation). Peptide sequences were modified to allow for macrocyclization, using ring closing metathesis (yielding Xa-M) or hexafluoro arylation of cysteines (yielding Xa-H).
Figure 110:
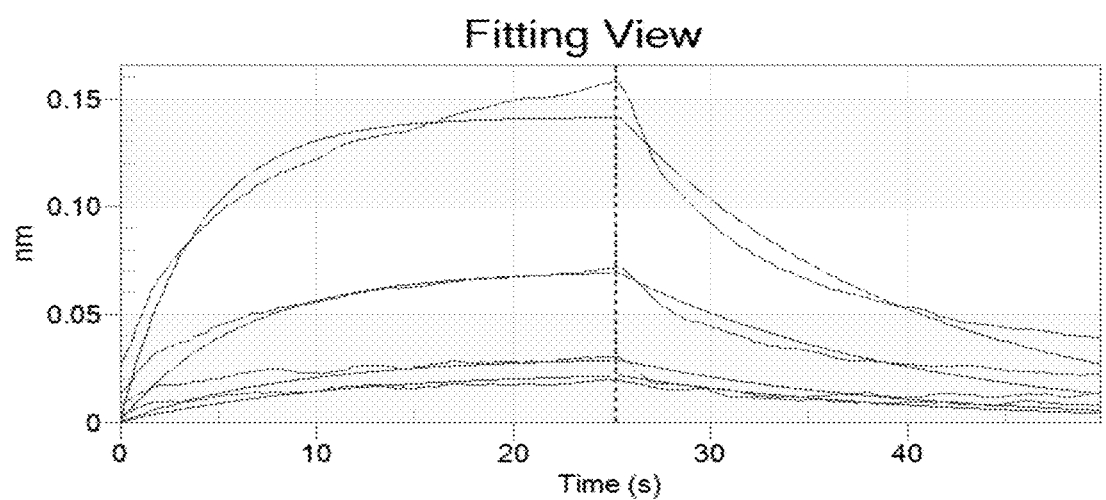
FIG. 110. Global fitting of association and dissociation curves of various concentrations of SUMO-C-CA (1000 nM, 500 nM, 250 nM and 125 nM) with biotin labeled peptide 30a-M immobilized to streptavidin sensors. The $K_D$ was found to be 360 nM±27 nM. Coefficient of determination $R^2$=0.98.
Figure 111:
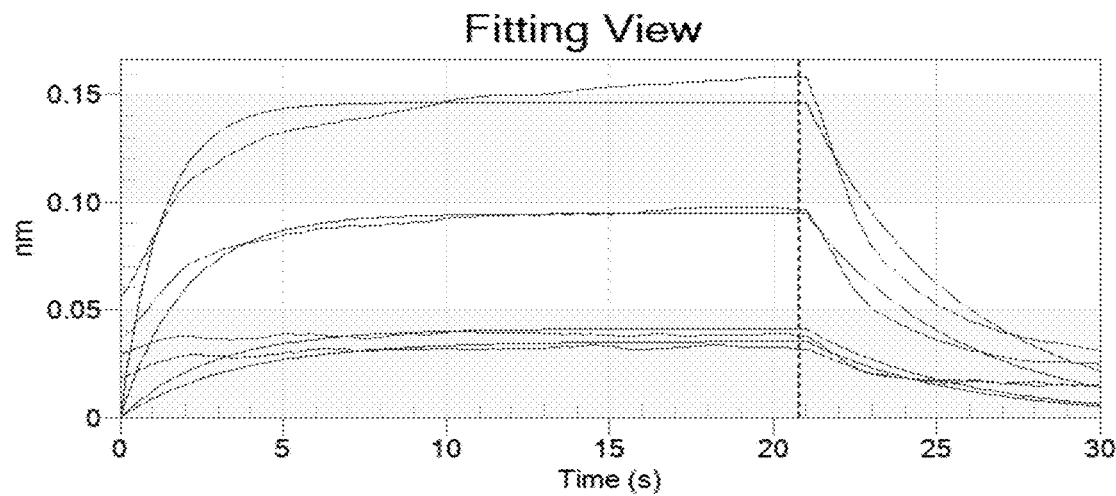
FIG. 111: Global fitting of association and dissociation curves of various concentrations of SUMO-C-CA (2500 nM, 1250 nM, 613 nM and 307 nM) with biotin labeled peptide 30a-H immobilized to streptavidin sensors. The $K_D$ was found to be 940 nM±130 nM. Coefficient of determination $R^2$=0.97.
Figure 112:
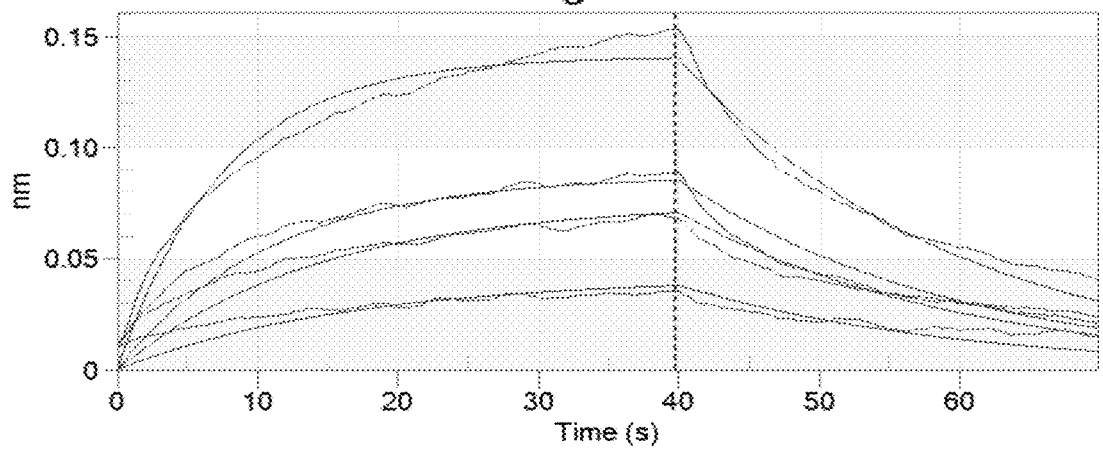
FIG. 112: Global fitting of association and dissociation curves of various concentrations of SUMO-C-CA (2500 nM, 1250 nM, 613 nM and 307 nM) with biotin labeled peptide 32a-H immobilized to streptavidin sensors. The $K_D$ was found to be 1.6 µM±0.2 µM. Coefficient of determination $R^2$=0.97.

In some embodiments, the peptide of formula (VI) has a sequence of a peptide (e.g., macrocyclic peptide) based on Library 4 (see, e.g., FIG. 109; e.g., 30a-M, 30a-H). In some embodiments, the peptide is from 12 to 25 amino acids long. In some embodiments, the sequence may have a mutation at the third amino acid position (e.g., $F_2f$ in formula (VI), e.g., to Phe), the $4^{th}$ amino acid position, the $6^{th}$ amino acid position (e.g., Cba to Leu), the $8^{th}$ amino acid position, the $9^{th}$ amino acid position, and/or the $10^{th}$ amino acid position. In some embodiments, the peptide (e.g., macrocyclic peptide) has a dissociation constant $K_D$ with respect to C-CA of at most 6000 nM, at most 5800 nM, at most 1200 nM, at most 1000 nM, at most 950 nM, at most 800 nM, at most 600 nM, at most 400 nM, at most 360 nM, at most 300 nM, at most 200 nM, at most 100 nM, or at most 50 nM.

In another aspect, the present invention provides a peptide or a macrocyclic peptide, or a salt thereof, comprising a sequence of the formula (VH):

$$LTFX_1HYWAQLX_2SK \text{ (VII)}, \quad \text{(SEQ ID NO: 47)}$$

wherein:
$X_1$ is Cys or Cys(ar) or a portion of a cross-link or staple; and
$X_2$ is Cys or Cys(ar) or a portion of a cross-link or staple.

In some embodiments, $X_1$ is Cys and $X_2$ is Cys. In some embodiments, $X_1$ is Cys(ar) and $X_2$ is Cys(ar). In some embodiments, $X_1$ is a portion of a cross-link or staple and $X_2$ is a portion of a cross-link or staple attached to $X_1$. In some embodiments, the peptide comprises a sequence of the formula (VII) having any one of the sequences in Table 4 with side chains in the sequence specified.

In some embodiments, the side chain of the first Cys(ar) and the side chain of the second Cys(ar) are joined together by a linker. In some embodiments, described herein, the linker for the macrocyclic peptide comprises a bond (e.g., a single bond, a double bond, a triple bond), optionally substituted alkylene, alkenylene, alkynylene, optionally substituted carbocyclylene, heterocyclylene, arylene, or heteroarylene, or a combination thereof. In some embodiments, Cys(ar) has an amino acid side chain:

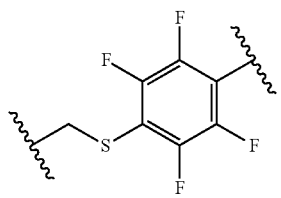 [SMILES: *CSc1c(F)c(F)c(*)c(F)c1F]

In some embodiments, the left-hand side of Cys(ar) side chain as depicted above is bound to the carbon along the backbone of the peptide and/or the right-hand side may be directly bonded to another side chain (e.g., Cys(ar)) or may be bonded through:

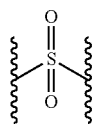

an example of a linker). In some embodiments, Cys(ar) is a portion of a cross-link or staple (e.g., FIG. 115).

In some embodiments, the C-terminal end of the sequence of formula (VII) is amidated. In some embodiments, the N-terminus is biotinylated, either directly or through a linker (e.g., a polyethylene glycol linker of length e.g. 4). In some embodiments, the N-terminus is acetylated. In some embodiments, the peptide comprises a linear peptide having an amidated C-terminus.

In some embodiments, the side chain of $X_1$ and the side chain of $X_2$ are joined together by a linker to form a crosslink or staple. In some such embodiments, the peptide comprises a macrocyclic peptide. In some embodiments, the side chain of $X_1$ and the side chain of $X_2$ are not joined together (e.g., when both are Cys). In some such embodiments, the peptide comprises a precursor to a macrocyclic peptide.

In some embodiments, a portion of the cross-link or staple comprises sulfur. In some embodiments, joining together by a linker to form a staple or crosslink may comprise as non-limiting examples perfluorosulfone stapling or cyclization (e.g., using a reagent in FIG. 115) and decafluorobiphenyl macrocyclization (e.g., using a reagent in FIG. 115).

In some embodiments, where the peptide comprises a sequence of formula (VII), the sequence is homologous to known peptide pDI (6) (see FIG. 6). In some embodiments, the peptide comprising a sequence of formula (VII) interferes with the p53-MDM2 binding interaction by binding MDM2. In some embodiments, the peptide comprising a sequence of formula (VII) may be used for the treatment of proliferative diseases (e.g., cancer).

In some embodiments, the peptide is 13 amino acids long.
In some embodiments, the sequence may have a mutation at the third amino acid position, the $4^{th}$ amino acid position, the $7^{th}$ amino acid position, the $8^{th}$ amino acid position, the $10^{th}$ amino acid position, and/or the $11^{th}$ amino acid position.

In some embodiments, the peptide (e.g., macrocyclic peptide) has a dissociation constant $K_D$ with respect to MDM2 of at most 500 nM, at most 400 nM, at most 310 nM, at most 300 nM, at most 200 nM, at most 100 nM, at most 50 nM, at most 30 nM, at most 24 nM, at most 22 nM, at most 20 nM, at most 10 nM, or at most 5 nM.

In some embodiments, where a mutation occurs in any sequence described herein, the change is to an amino acid side chain (e.g., a canonical or a non-nanonical amino acid side chain) that is of similar hydrophobicity, hydrophilicity, size, and/or charge to that of the original amino acid side chain in the sequence.

In some embodiments, formula (VII) has a sequence of a peptide (e.g., macrocyclic peptide) based on Library 6 (see, e.g., FIG. 115. FIG. 118; e.g., 60, 60a, 60b, 61a, 62a).

In another aspect, the present invention provides a macrocyclic peptide, or a salt thereof, comprising a sequence of the formula $(X_1)$:

$$LTFX_1HYWAQFX_2SK \text{ (XI)}, \quad \text{(SEQ ID NO: 64)}$$

wherein:
$X_1$ is Cys or Cys(ar) or a portion of a cross-link or staple; and
$X_2$ is Cys or Cys(ar) or a portion of a cross-link or staple.

In some embodiments, the side chain of the first Cys(ar) and the side chain of the second Cys(ar) are joined together by a linker. In some embodiments, the peptide comprises a sequence of the formula (X₁) having any one of the sequences in Table 4 with side chains in the sequence specified.

In another aspect, the present invention provides a peptide or a mini-protein, or a salt thereof, comprising a sequence of the formula (VIII):

KAWYANX₁EKLX₂R, (VIII), (SEQ ID NO: 50)

wherein:
$X_1$ is Hexa, Hepa, Cha, or $CF_3f$; and
$X_2$ is Homol, Cha, Cba, Leu, Hexa, or Trp.

In some embodiments, all amino acids in the peptide (e.g., mini-protein) are of the D-configuration. In some embodiments, all amino acids in the peptide (e.g., mini-protein) are of the L-configuration. In some embodiments, $X_1$ is Hexa and $X_2$ is Homol. In some embodiments, $X_1$ is Hexa and $X_2$ is Cha. In some embodiments, $X_1$ is Cha and $X_2$ is Leu. In some embodiments, $X_1$ is Hexa and $X_2$ is Hexa. In some embodiments, $X_1$ is Hexa and $X_2$ is Trp. In some embodiments, $X_1$ is $CF_3f$ and $X_2$ is Leu. In some embodiments, $X_1$ is Hepa and $X_2$ is Cba. In some embodiments, $X_1$ is Hepa and $X_2$ is Homol. In some embodiments, $X_1$ is Hepa and $X_2$ is Hexa. In some embodiments, $X_1$ is Hexa and $X_2$ is Cba. In some embodiments, $X_1$ is Hepa and $X_2$ is Cba. In some embodiments, $X_1$ is Hepa and $X_2$ is Cha. In some embodiments, $X_2$ is $CF_3f$ and $X_1$ is Leu. In some embodiments, the peptide comprises a sequence of the formula (VIII) having any one of the sequences in Table 4 with side chains in the sequence specified.

In some embodiments, the C-terminus of formula (VIII) in the peptide is bound to a portion that comprises an amino acid (e.g., a beta amino acid) comprising a vicinal diol along the backbone of the peptide. In some embodiments, the C-terminus of formula (VIII) in the peptide is bound to a portion that comprises the sequence GGS(beta-Ala) (SEQ ID NO: 194). In some embodiments, the C-terminus of formula (VIII) in the peptide is bound to a portion that comprises $^{9\text{-}28}$EETI-II (e.g., see FIG. 4B). In some embodiments, the C-terminus of the peptide (e.g., mini-protein) comprising formula (VIII) is amidated. In some embodiments, the N-terminus of the peptide (e.g., mini-protein) comprising formula (VIII) is acetylated.

Figure 4A:
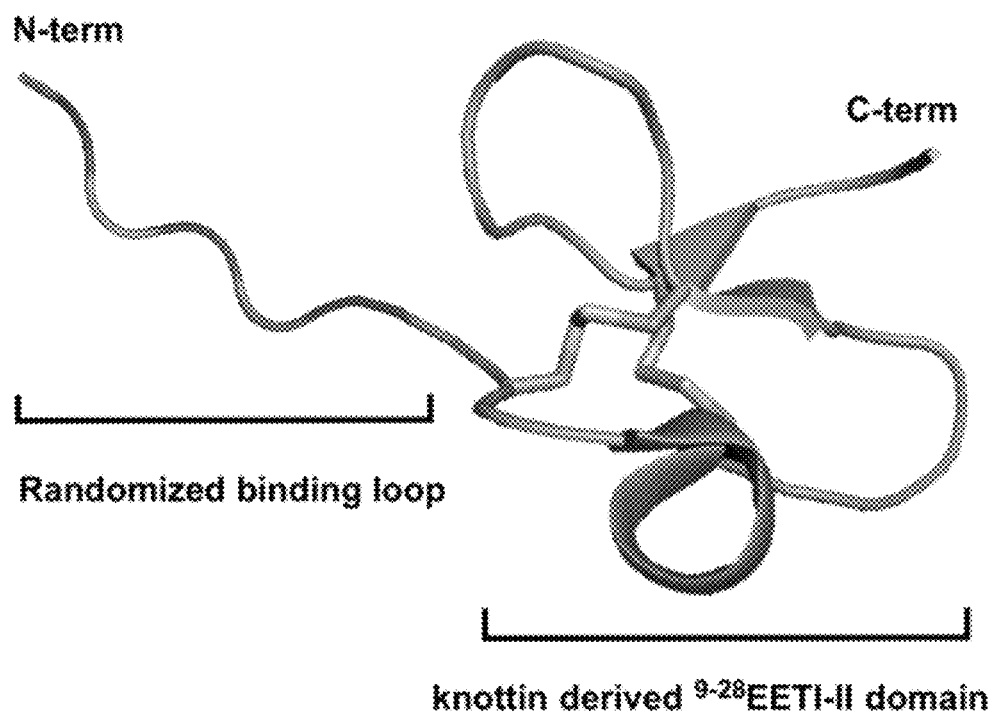
Figure 4B:
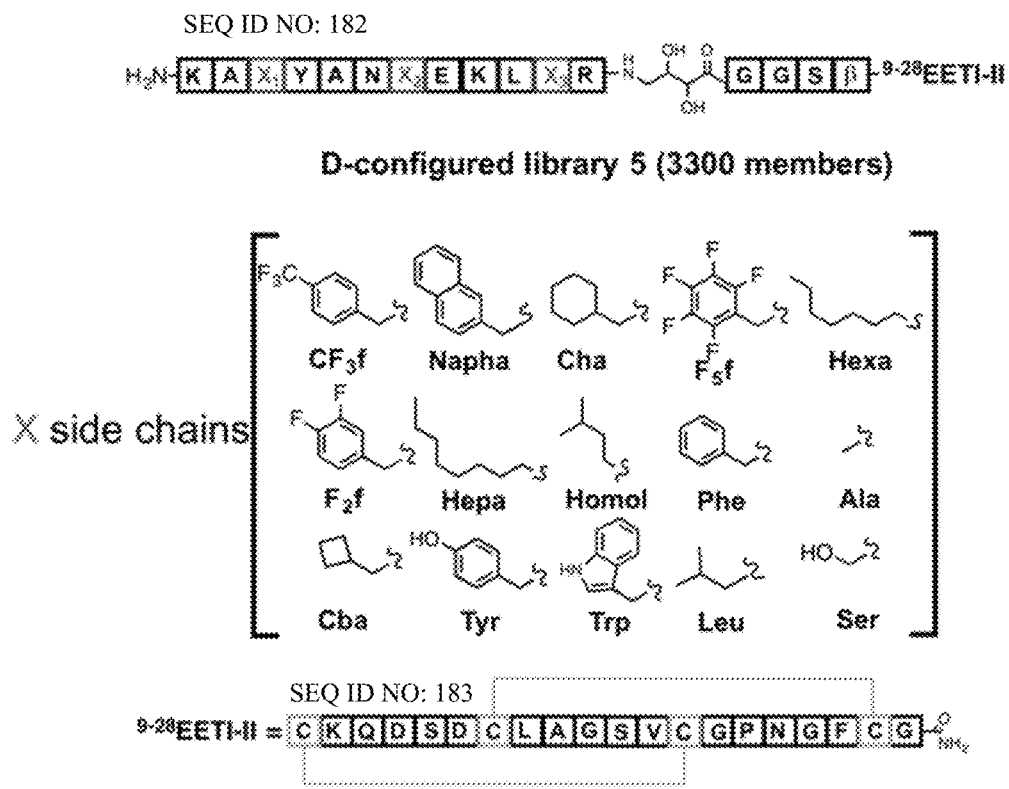
Figure 7:
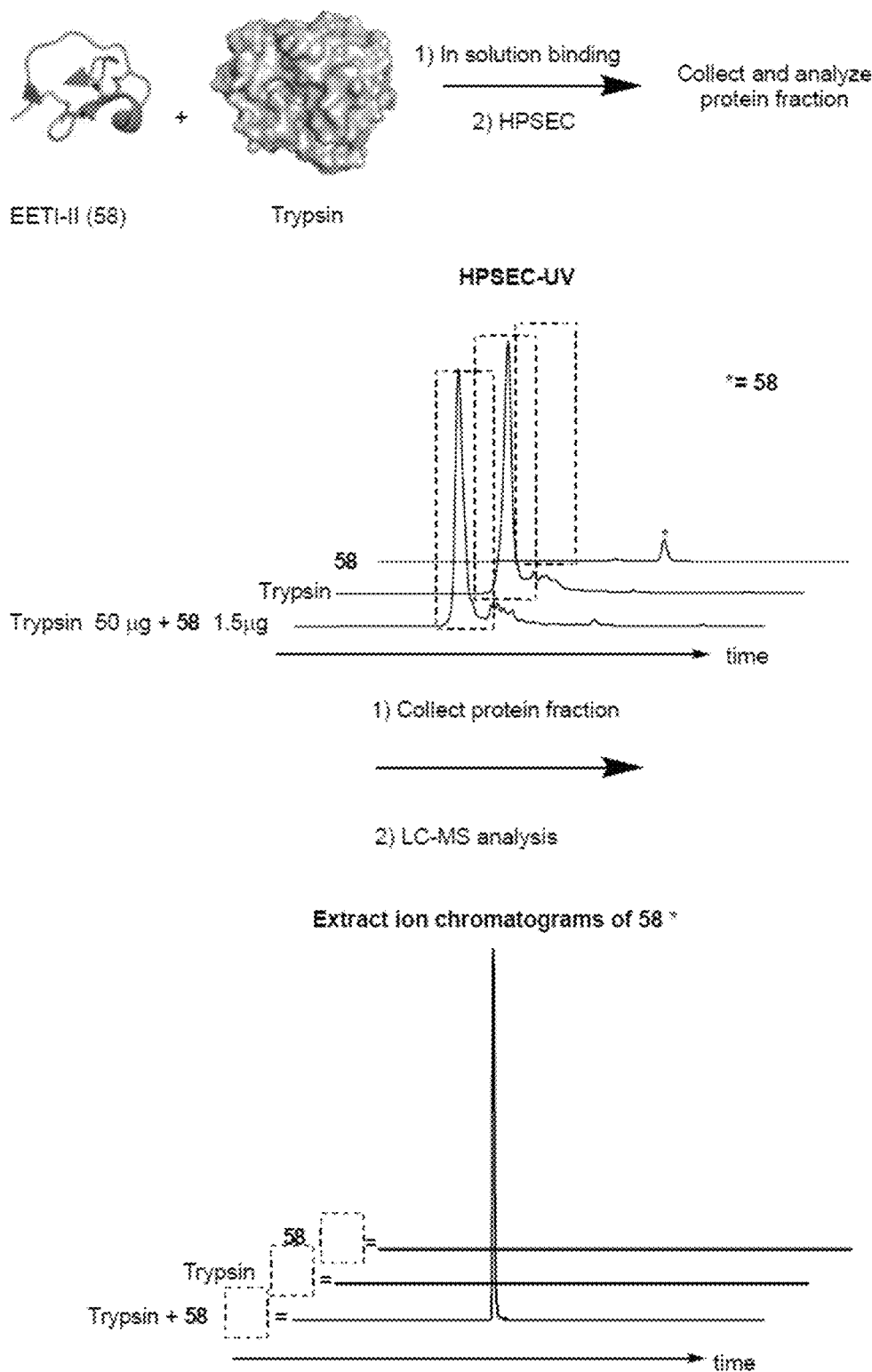
FIG. 7: HPSEC was used for the specific selection of EETI-II (58, ~3 kDa) in trypsin fraction (~23 kDa). EETI-II (1 μg, 3.3 μM) was added to trypsin (7 μg, 3.3 μM) in 100 μL final volume of mobile phase. The solution was thoroughly mixed and left to stand for 1 hour before size exclusion chromatography. Top, schematic selection of 58 by trypsin. 58 (*) was resolved from trypsin during HPSEC and protein fraction retention times (dashed boxes) were collected and analyzed by LC-MS (method A). Extract ion chromatogram (EIC) analysis demonstrated specific selection of 58 in the trypsin+EETI-II condition (bottom). When a different protein was used, 58 was undetectable in the protein fraction (data not shown). Selections performed four times, varying the amounts of 58 (1.5 μg, 100 ng, 10 ng or 1 ng). LC-MS analyses were performed one time each (representative outcome shown).
Figures 8A, 8B:
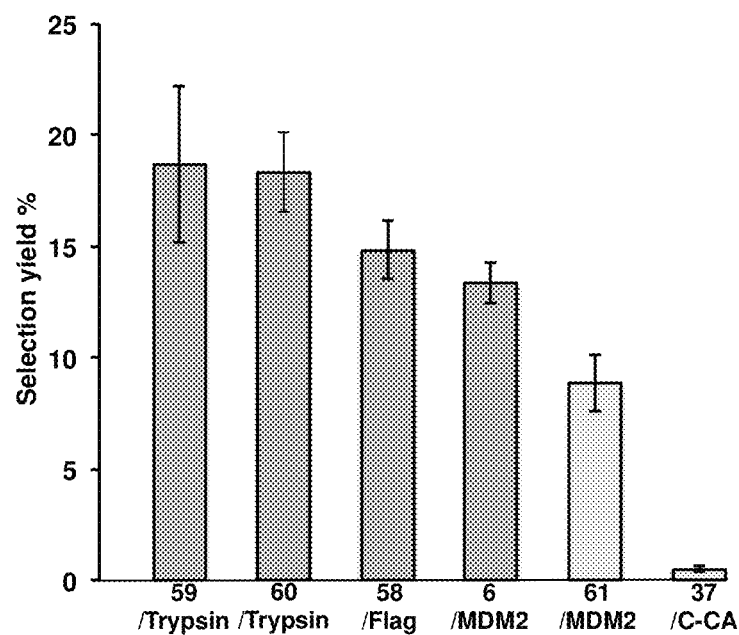
FIG. 8A: HPSEC was used for the specific selection of model binders with yields allowing for detection in library relevant context. Selection yields (in triplicate) are presented for several binder/protein duos with quantities relevant to library context (large protein excess and nanomolar concentrations of binders). Peptide binders (typically 1 to 10 ng, e.g., 30 to 65 nM) were added to an excess of protein target (typically 20 to 100 μg, e.g 5 to 20 μM) in 100 μL final volume of mobile phase (supplemented with arginine except for 37). The solution was mixed by pipetting and left to stand for 1 hour at room temperature before size exclusion chromatography. At the exception of micromolar 37 all peptides had nanomolar affinities but different hydrophobicities as evidenced by their LC-MS retention times (FIG. 6). Selection yields as determined using a 150*7.8 mm BIO-SEC-3 column. In light orange, Selection yields using a shorter 50*7.8 mm column. Selection yields were null if protein or binder were omitted or if the binder was affinity selected with a different protein than the natural partner.
FIG. 8B: HPSEC enables selection of model binders with yields compatible with their detection in library relevant conditions. Typical yields are presented for several binder/protein duos with quantities relevant to library screening conditions (protein excess and nanomolar concentrations of binders). Peptide binders (typically 1 to 10 μg, e.g. 30 to 65 nM) were added to an excess of protein target (typically 20 to 100 μg, e.g 5 to 20 μM) in 100 μL final volume of mobile phase (supplemented with arginine except for 37). The solution was mixed by pipetting and left to stand for 1 hour at room temperature before size exclusion chromatography. Peptide binder amounts were quantified in the collected protein fraction using a calibration curve to determine their selection yield. At the exception of micromolar 37 all peptides have nanomolar affinities.
Figure 9A:
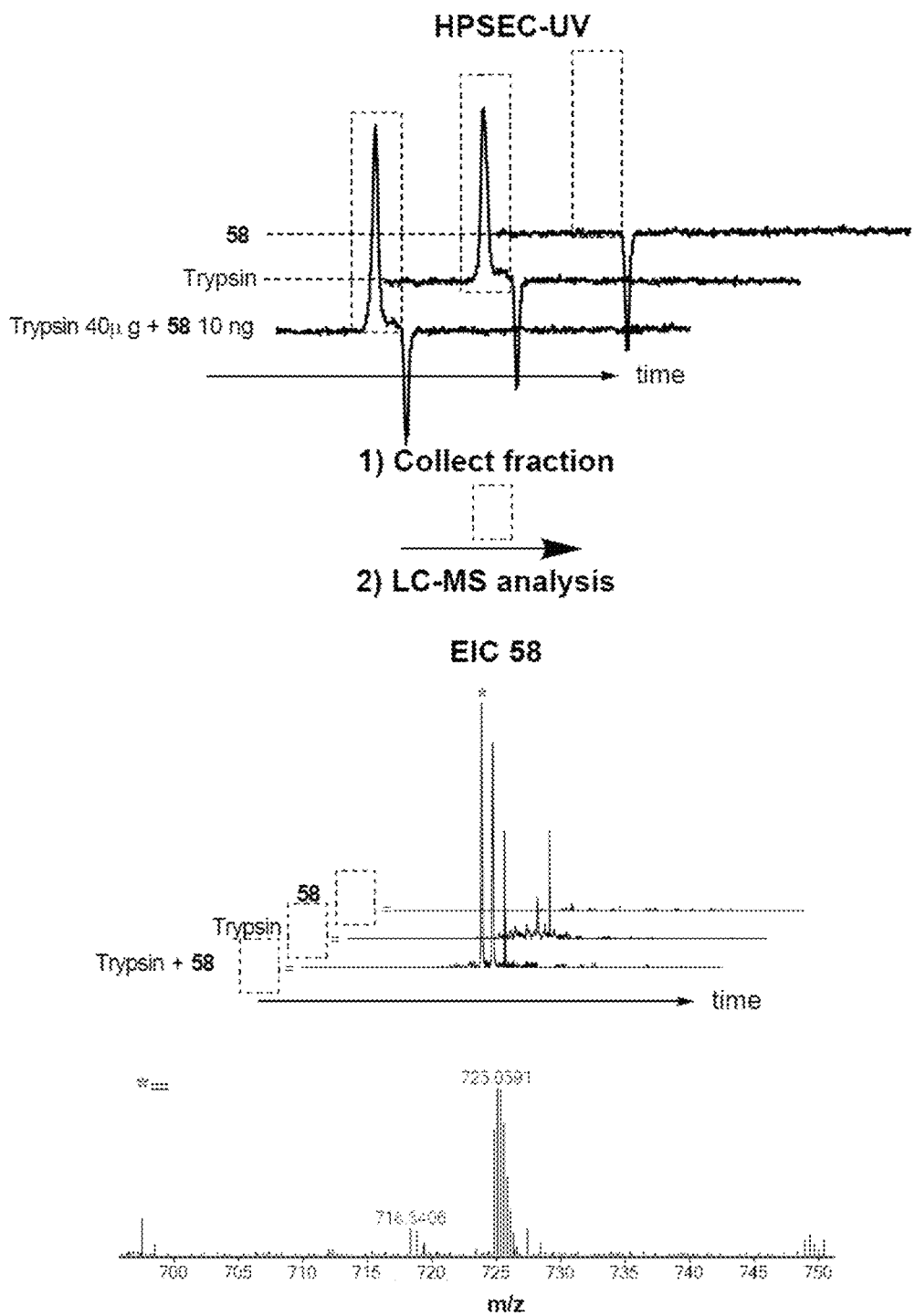
FIG. 9A: Protein fraction retention times (dashed boxes) were collected and subsequently analyzed using LC-MS method A. EETI-II (58) is marked with a (*) and was only detected in the protein fraction for the Trypsin+58 condition. Bottom, MS spectrum confirming 58 identity (asterisk).
Figure 11A:
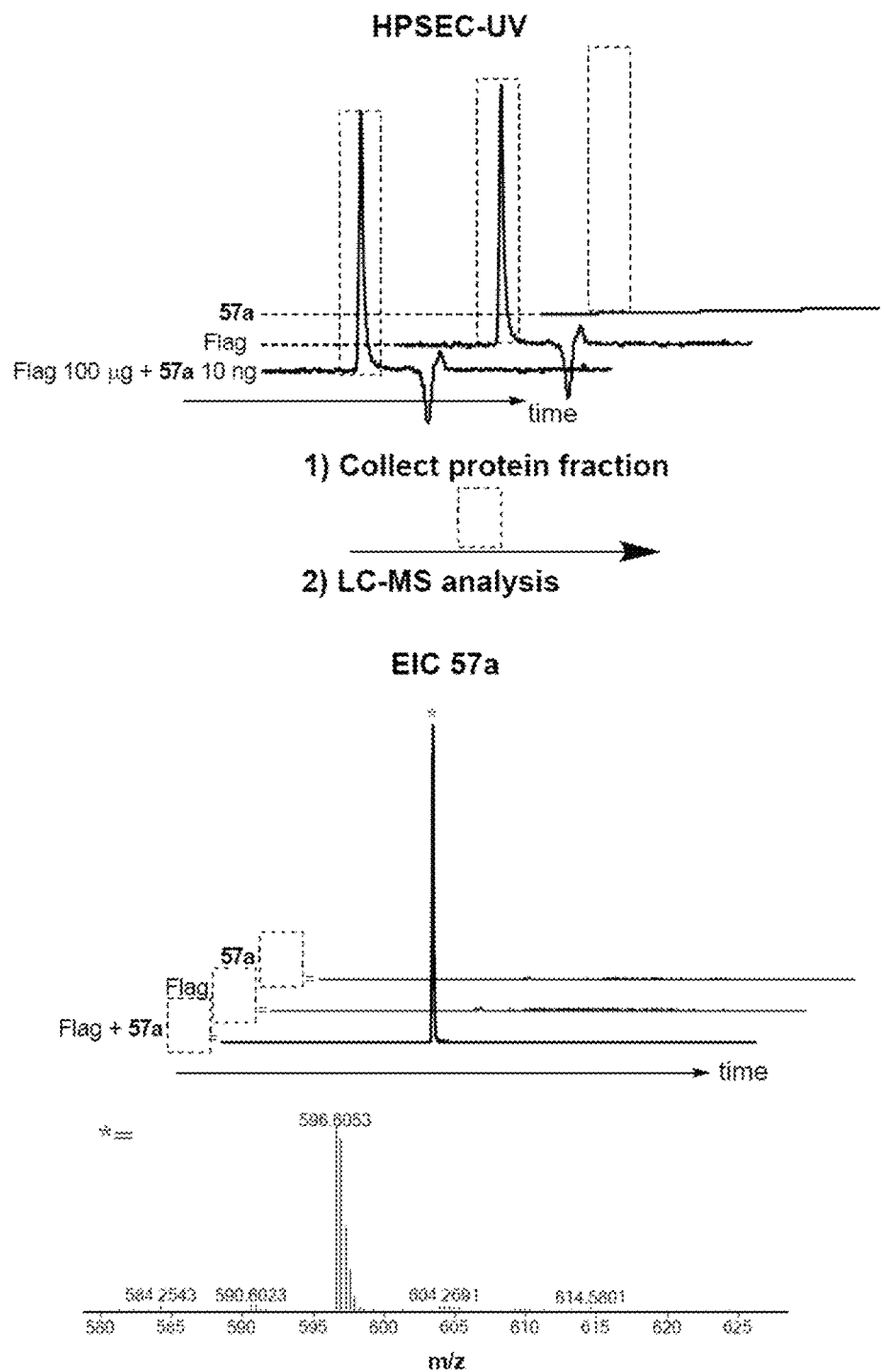
FIG. 11A: Protein fraction retention times (dashed boxes) were collected and subsequently analyzed using LC-MS method A. Flag peptide (57a) is marked with a (*) and was only detected in the protein fraction for the Flag antibody+ 57a condition. Bottom, MS spectrum confirming 57a identity (asterisk).
Figure 12A:
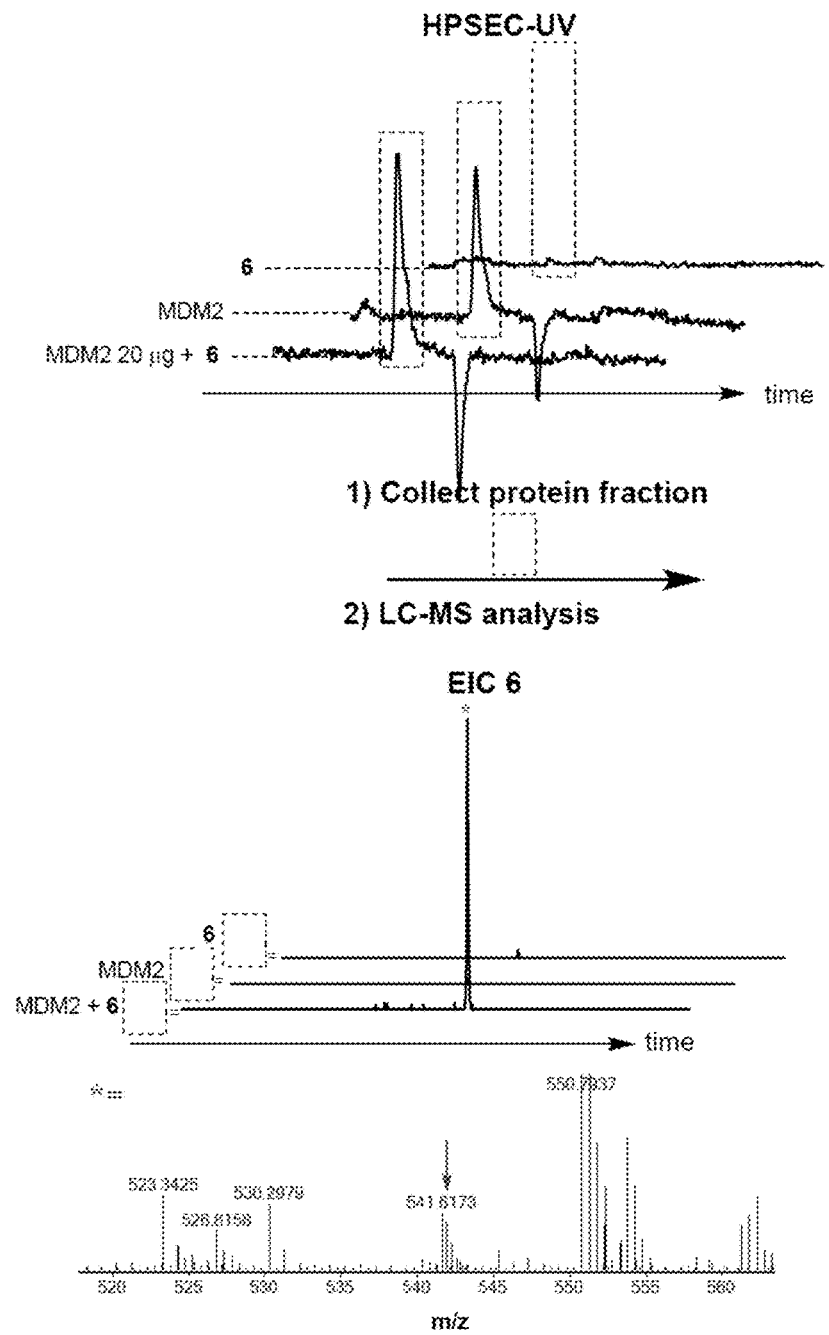
FIG. 12A: Protein fraction retention times (dashed boxes) were collected and subsequently analyzed using LC-MS method A. pDI (6) is marked with a (*) and was only detected in the protein fraction for the MDM2+6 condition. Bottom, MS spectrum confirming 6 identity (arrow).
Figure 13A:
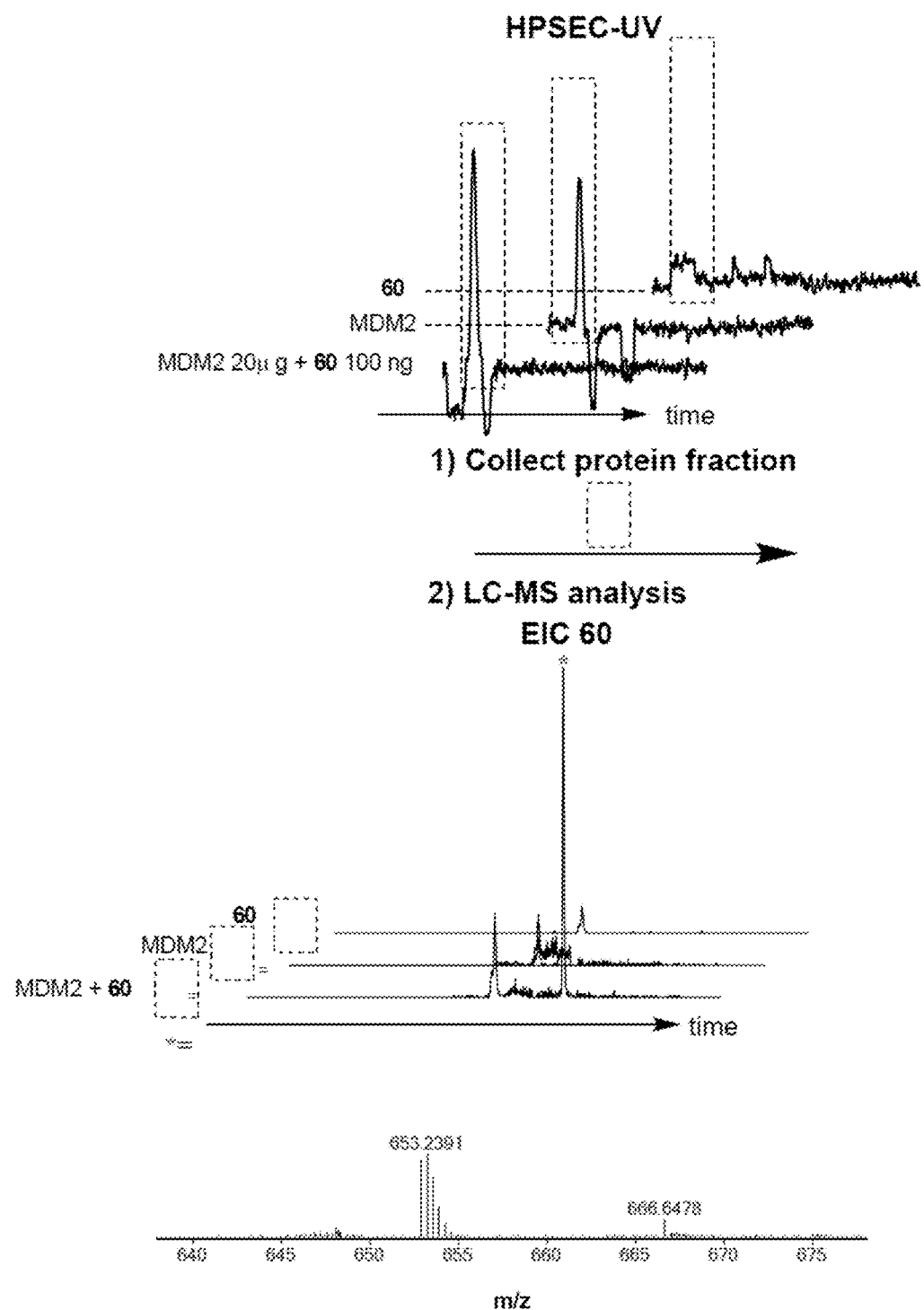
FIG. 13A: Protein fraction (dashed boxes) was collected and subsequently analyzed using method A (LC-MS). PDI-Sulfone peptide is marked with a (*) and only detected in the protein fraction for the MDM2+60 condition. Bottom, MS spectrum confirming 60 identity.
Figure 13B:
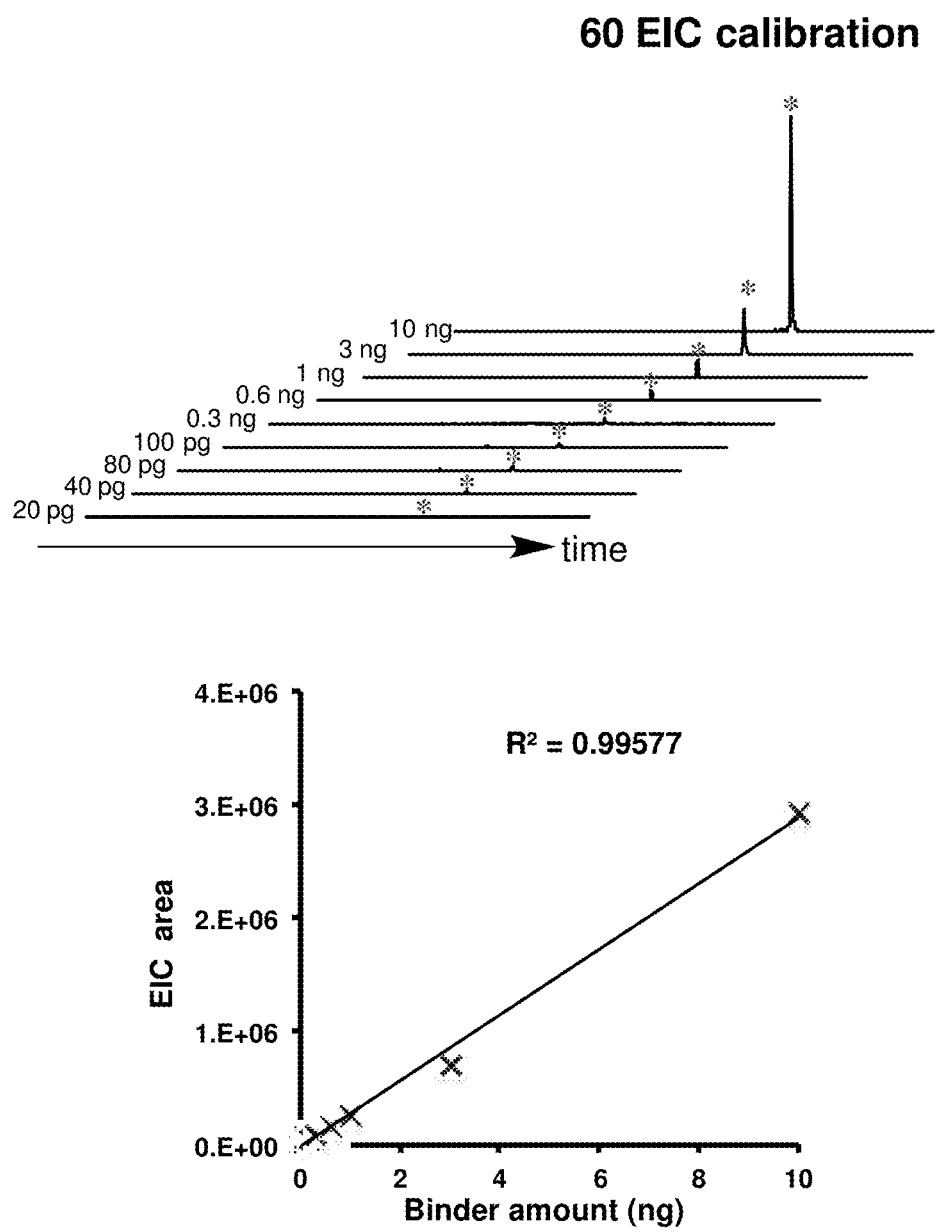
FIG. 13B: Using LC-MS method A serial dilutions of pure 60 (*) were analyzed and EIC peak area=f (60 amounts) was plotted to determine linear range. The obtained calibration curve was used to determine selection yield in the collected protein fraction.
Figure 14A:
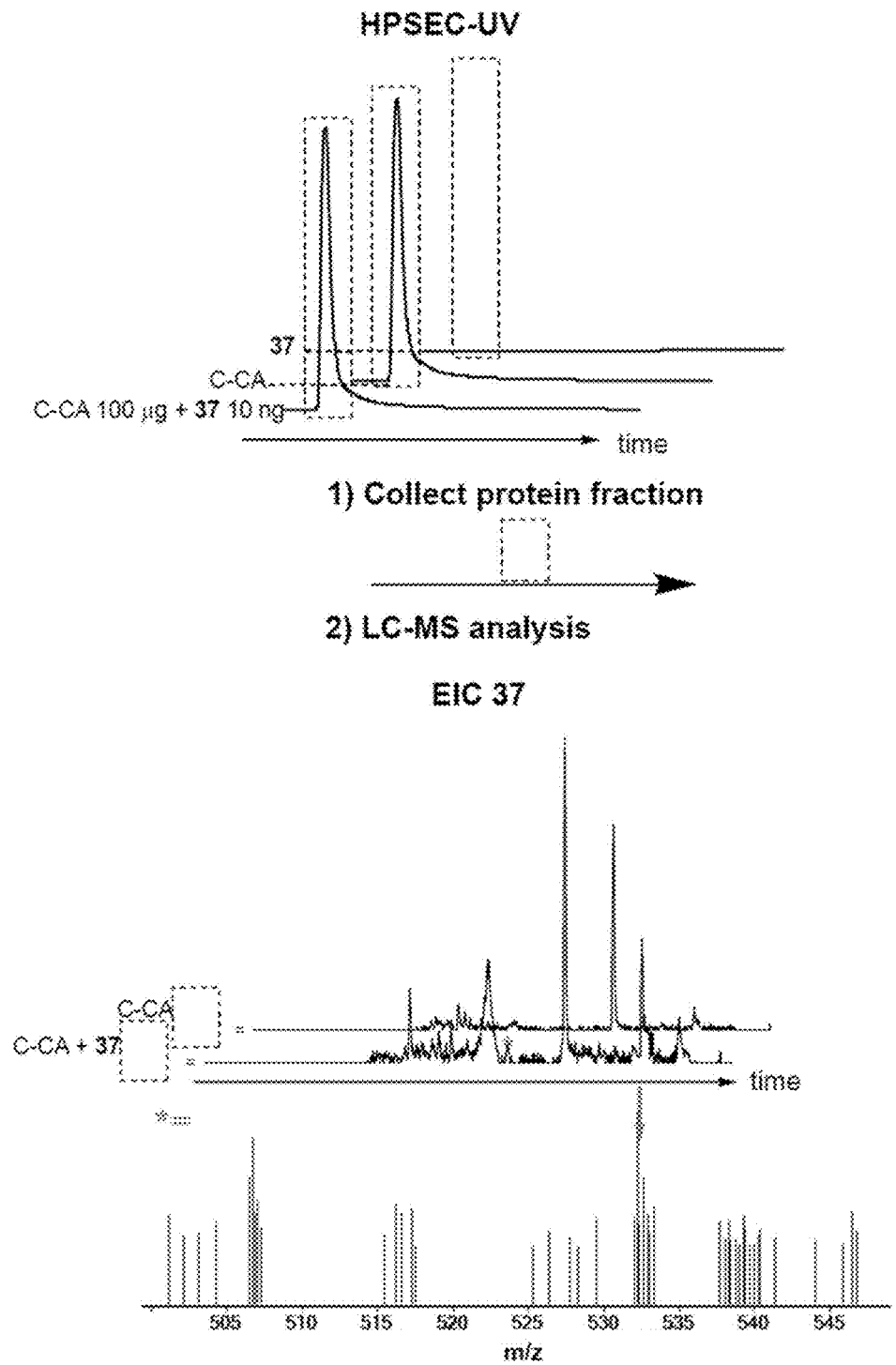
FIG. 14A: Protein fraction (dashed boxes) was collected and subsequently analyzed using method A (LC-MS). CAI peptide is marked with a (*) and only detected in the protein fraction for the C-CA+CAI condition. Bottom, MS spectrum confirming 37 identity (arrow).
Figure 14B:
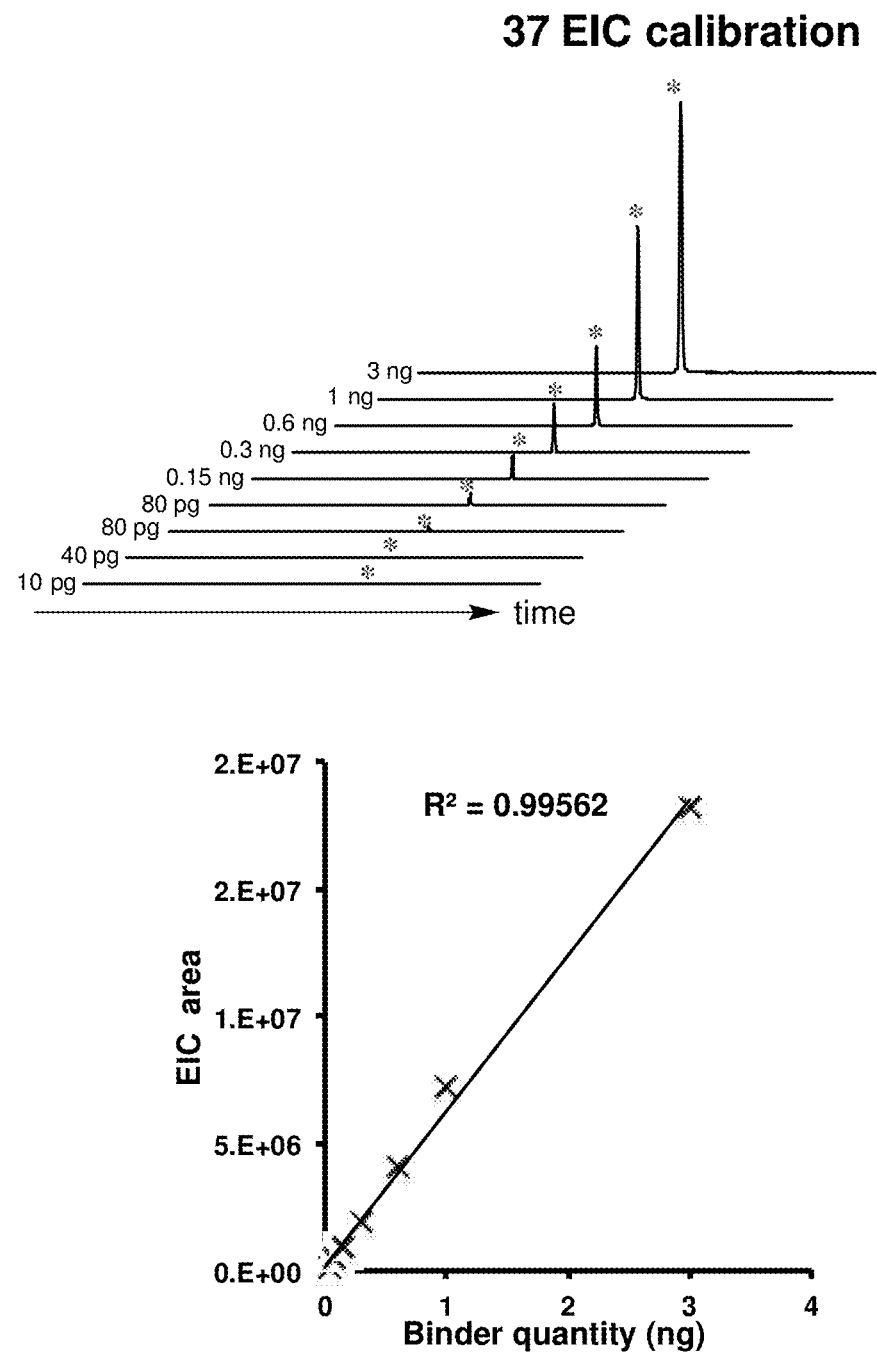
FIG. 14B: Using LC-MS method A serial dilutions of pure 37 (*) were analyzed and EIC peak area=f (37 amounts) was plotted to determine the linear range. The obtained calibration curve was used to determine selection yield in the collected protein fraction.
Figure 15:
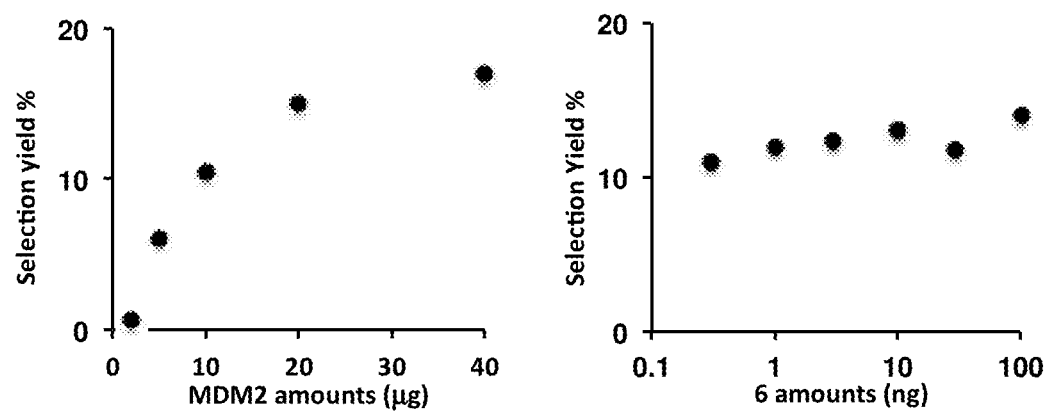
FIG. 15: Protein concentration in binding mixtures influences affinity selection yields in the case of pDI. Yield dependence was determined by either varying MDM2 amounts (2.5, 5, 10, 20, 40 μg corresponding respectively to ca 1, 2.1, 4.3, 8.5, 17 μM) for a fixed amount of 6 (10 ng, e.g. 61 nM); or by varying 6 amounts (0.3, 1, 3, 10, 30, and 100 ng corresponding respectively to 1.9, 6.1, 19, 61, 190, 610 nM) for a fixed amount of MDM2 (20 μg, e.g 8.5 μM). Optimal amounts of protein have to be used to allow for efficient recovery of 6.
Figure 16A:
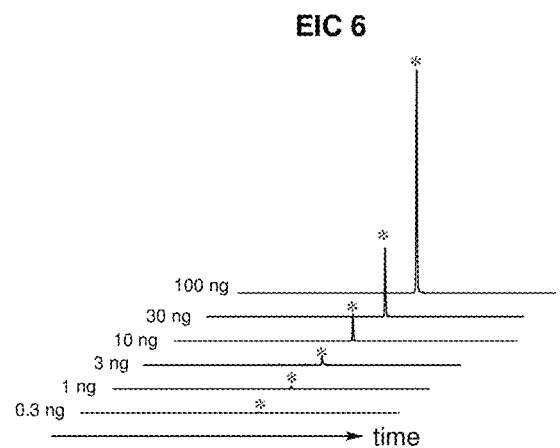
FIG. 16A: LC-MS/MS analysis was used for efficient sequencing of +3 charged model binders. Exemplary sequencing of linear 6 and determination of optimal MS/MS threshold. Presence of a C-terminal Lysine in 6's sequence and (+3) charge state for MS/MS precursor ion selection were found to significantly improve sequence coverage (ALC score). Extract ion chromatogram (EIC, LC-MS method A) analysis for different amounts of 6 in the binding mixture and after affinity selection using MDM2. Bottom, in the analysis conditions 6 was found to be efficiently sequenced for EIC peak areas >50 000 corresponding to an absolute MS/MS threshold >10^4 ion counts. These conditions were used for efficient sequencing down to 1 ng of affinity selected 6.
Figure 16B:
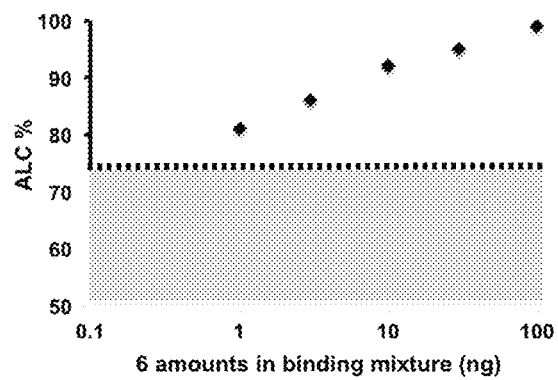
FIG. 16B: LC-MS/MS allows for efficient sequencing of affinity-selected pDI. Sequencing of linear binders was illustrated in the MDM2 system using pDI (6). Presence of a C-terminal Lysine in 6's sequence was found to significantly improve sequence coverage (ALC score). a) Extract ion chromatogram analysis after affinity selection with MDM2 protein of different amounts of 6 (0.3, 1, 3, 10 and 100 ng) in the binding mixture. b) Sequencing outcome for different amounts of 6. 6 can be efficiently sequenced (ALC>75%, above dashed line) after affinity selection for amounts as low as 1 ng (e.g 6 nM) in the binding mixture. In these conditions EIC peak areas are typically >50 000 corresponding to an absolute MS/MS threshold >10$^4$ ion counts for the precursor ion.
Figure 17:
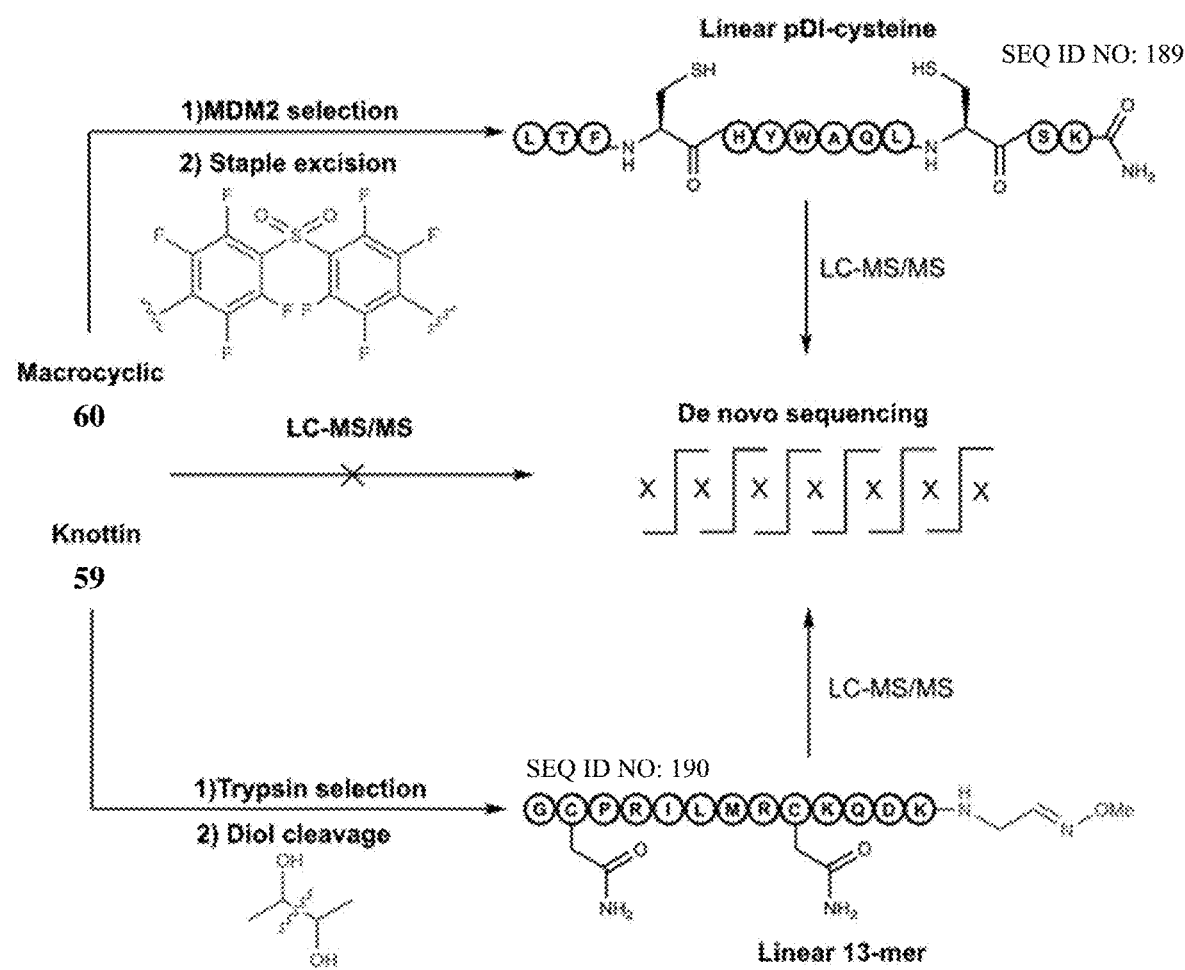
FIG. 17: Exemplary chemical strategies for the linearization of complex binders. Chemical strategies for the sequencing of perfluorosulfone macrocyclized peptide and >30-mer folded mini-protein binding loops. Top, decoding strategy exploiting the chemical lability of S—C(Ar) bonds in perfluorosulfone stapled peptides[3] (see, e.g., Example 2). Staple displacement by nucleophiles yields linear pDI-cysteine. Bottom, chemical strategy for backbone cleavage using a diol amino acid for knottin (59) derived from EETI-II (58). Upon reduction of disulfide bridges and oxidative cleavage, trypsin binding 59 yielded EETI-II (58) binding loop as a linear 13-mer.
Figure 26:
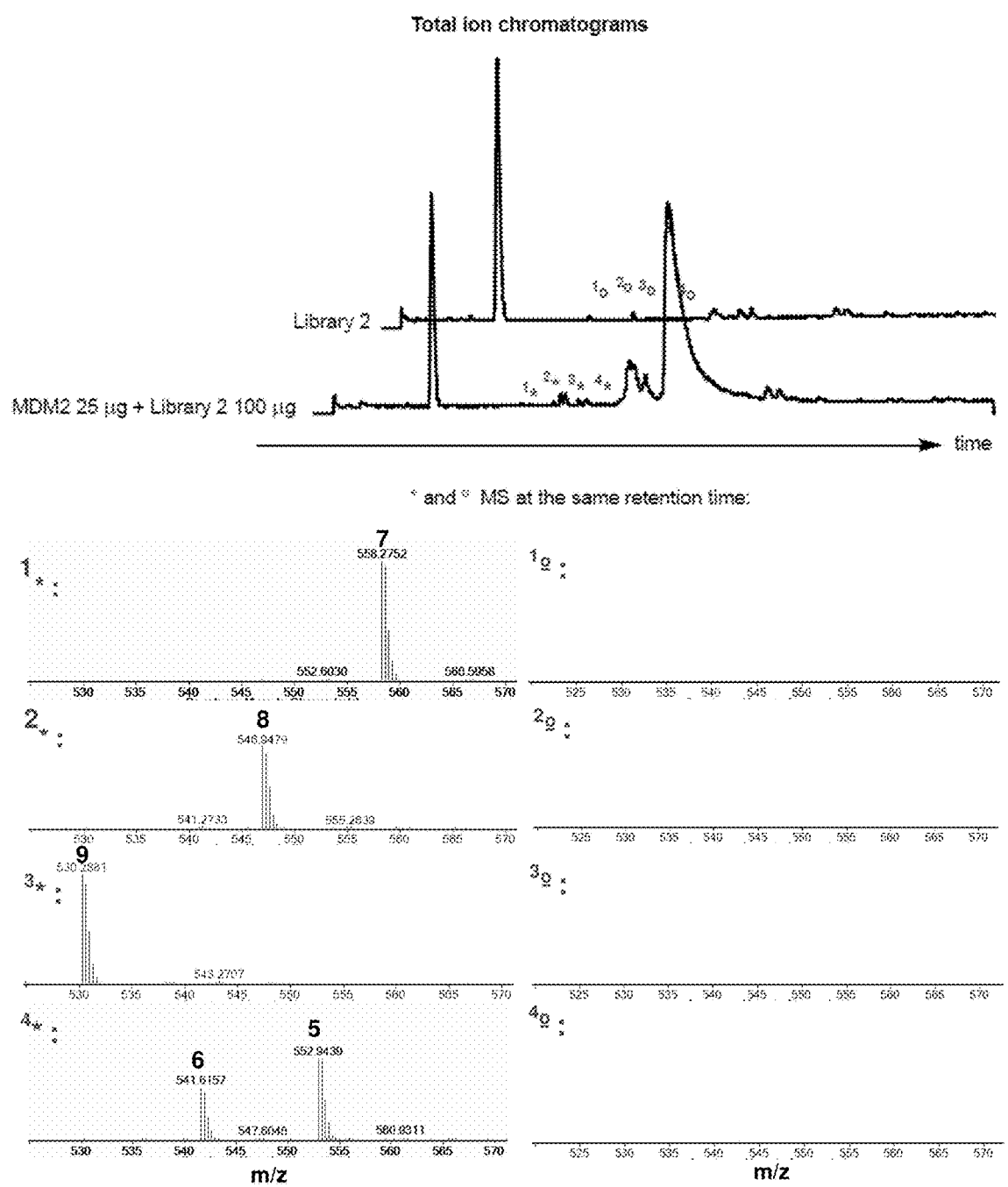
FIG. 26: Affinity selection from Library 2 in low stringency conditions yielded new binding sequences. Library 2 (100 µg, ~60 µM) was added to MDM2 (25 µg, 10.6 µM in the binding mixture) in 100 µL final volume of mobile phase. The solution was mixed by pipetting and left to stand for 1 hour at room temperature before size exclusion chromatography. Library 2 (100 µg) was injected twice into the SEC column and after short equilibration, Library 2+MDM2 was injected too. This measure was found to allow for the recovery of low affinity binders along with higher affinity ones. Top, total ion chromatograms for the analysis of protein fraction after affinity selection from Library 2 (100 µg, ~600 µM in the binding mixture) by MDM2 (25 µg, 10.6 µM in the binding mixture). Chromatogram inspection and direct comparison of MS spectra at the same retention times respectively ($1^*$) and ($1°$), ($2^*$) and ($2°$), ($3^*$) and ($3°$), ($4^*$) and ($4°$) demonstrates specific affinity selection of Library 2 members 4 to 9.

In some embodiments, formula (VIII) has a sequence of a mini-protein in Library 5 (see, e.g., FIG. 4B, FIG. 26; e.g., 43, 44, 45, 46, 47, 48-53, 54b).

In some embodiments, the peptide (e.g., mini-protein) is from 12 amino acids long to 50 amino acids long (e.g., from 12 amino acids long to 37 amino acids long).

In some embodiments, the peptide (e.g., mini-protein) comprising a sequence of formula (VIII) interferes with the p53-MDM2 binding interaction by binding MDM2. In some embodiments, the peptide comprising a sequence of formula (VIII) may be used for the treatment of proliferative diseases (e.g., cancer). In some embodiments, at least one amino acid side chain in the sequence is a non-canonical amino acid side chain (e.g., a side chain as depicted in FIG. 4B). In some embodiments, at least 2 amino acid side chains in the sequence are non-canonical amino acid side chains (e.g., 2 amino acid side chains, 3 amino acid side chains, or more).

In some embodiments, the peptide (e.g., mini-protein) has a dissociation constant $K_D$ with respect to MDM2 of at most 50 nM, at most 30 nM, at most 20 nM, at most 12 nM, at most 11 nM, at most 10 nM, at most 8 nM, at most 6 nM, at most 5 nM, at most 4 nM, at most 2 nM, or at most 1 nM.

TABLE 4

Formulas and Embodiments Thereof

| Formula | Sequence | SEQ ID NO: | Example Binders |
|---|---|---|---|
| (I) | LTFX₁HX₂WAX₃LTSK<br>wherein:<br>X₁ is Gln, Pro, or Glu;<br>X₂ is Phe, Tyr, or Glu; and<br>X₃ is Glu, Gln, Ala, or Leu | SEQ ID NO: 1 | |
| | LTFQHFWAELTSK | SEQ ID NO: 2 | 1a |
| | LTFQHYWAELTSK | SEQ ID NO: 3 | 2a |
| | LTFPHYWAELTSK | SEQ ID NO: 4 | 3a |
| | LTFPHFWAELTSK | SEQ ID NO: 5 | 4a |
| (II) | LTFEHYWAQX₁TSK<br>wherein:<br>X₁ is Phe or Leu | SEQ ID NO: 6 | |
| | LTFEHYWAQFTSK | SEQ ID NO: 7 | 5a |
| | LTFEHYWAQLTSK | SEQ ID NO: 8 | 6a |
| (III) | LTX₁EHYX₂AQX₃TSK<br>wherein:<br>X₁ is Ff, F₂f, F₃f, or Phe;<br>X₂ is Hexa, Trp, Napha, or Anta; and<br>X₃ is Cba, Cha, Ff, F₂f, F₃f, F₅f, Hexa, Homof, or Leu | SEQ ID NO: 9 | |
| | LT(Ff)EHY(Hexa)AQLTSK | SEQ ID NO: 10 | 38a |
| | LT(F₂f)EHY(Hexa)AQ(Cba)TSK | SEQ ID NO: 11 | 10a, 10b |
| | LT(F₂f)EHYWAQ(Cba)TSK | SEQ ID NO: 12 | 11a, 11b |
| | LT(Ff)EHY(Hexa)AQ(Cha)TSK | SEQ ID NO: 13 | 12a |
| | LT(Ff)EHY(Hexa)AQ(Cba)TSK | SEQ ID NO: 14 | 13a |
| | LT(F₃f)EHY(Hexa)AQ(Ff)TSK | SEQ ID NO: 15 | 14a |
| | LT(F₂f)EHY(Hexa)AQ(Ff)TSK | SEQ ID NO: 16 | 15a |
| | LT(F₃f)EHY(Hexa)AQ(Cha)TSK | SEQ ID NO: 17 | 16a |
| | LT(F₃f)EHY(Hexa)AQ(Hexa)TSK | SEQ ID NO: 18 | 17a |
| | LT(F₂f)EHY(Hexa)AQ(F₃f)TSK | SEQ ID NO: 19 | 18a |
| | LT(F₂f)EHYWAQ(Hexa)TSK | SEQ ID NO: 20 | 19a |
| | LT(F₃f)EHYWAQ(Cha)TSK | SEQ ID NO: 21 | 20a |

TABLE 4-continued

Formulas and Embodiments Thereof

| Formula | Sequence | SEQ ID NO: | Example Binders |
|---|---|---|---|
| | LT($F_2$f)EHY(Hexa)AQ(Homof)TSK | SEQ ID NO: 22 | 21a |
| | LT($F_3$f)EHY(Anta)AQ(Cba)TSK | SEQ ID NO: 23 | 22a |
| | LT($F_3$f)EHY(Hexa)AQ($F_3$f)TSK | SEQ ID NO: 24 | 23a |
| | LT($F_3$f)EHY(Hexa)AQ($F_5$f)TSK | SEQ ID NO: 25 | 24a |
| | LT($F_2$f)EHYWAQ($F_2$f)TSK | SEQ ID NO: 26 | 25a |
| | LT($F_2$f)EHYWAQ($F_3$f)TSK | SEQ ID NO: 27 | 26a |
| | LT($F_2$f)EHY(Napa)AQ(Cba)TSK | SEQ ID NO: 28 | 27a |
| | LT($F_2$f)EHY(Napa)AQ(Ff)TSK | SEQ ID NO: 29 | 28a |
| (IV) | IT($F_2$f)ED(Cba)LHX$_1$X$_2$GP<br>wherein:<br>X$_1$ is Tyr or Dmf; and<br>X$_2$ is Tyr or $F_2$f | SEQ ID NO: 30 | |
| | IT($F_2$f)ED(Cba)LHYYGP | SEQ ID NO: 31 | 30a |
| | IT($F_2$f)ED(Cba)LH(Dmf)YGP | SEQ ID NO: 32 | 31a |
| | IT($F_2$f)ED(Cba)LH(Dmf)($F_2$f)GP | SEQ ID NO: 33 | 32a |
| (X) | LTX$_1$X$_2$EX$_3$X$_4$AX$_5$(Cba)X$_6$SX$_7$<br>wherein:<br>X$_1$ is $F_2$f or Phe;<br>X$_2$ is a non-canonical alpha-amino acid<br>(e.g., R8 or Dap) or a portion of a cross-link or staple;<br>X$_3$ is Tyr or Phe;<br>X$_4$ is Hexa, Napha, or Trp;<br>X$_5$ is Gln or Glu;<br>X$_6$ is a non-canonical alpha-amino acid<br>(e.g., S5 or Dap) or TABLE 4-continued Formulas and Embodiments Thereof

| Formula | Sequence | SEQ ID NO: | Example Binders |
|---------|----------|------------|-----------------|
|  | IT(F₂f)CD(Cba)LCYYGP | SEQ ID NO: 45 | 30a-H |
|  | IT(F₂f)(S5)D(Cba)L(S5)YYGP | SEQ ID NO: 46 | 30a-M |
| (VII) | LTFX₁HYWAQLX₂SK<br>wherein:<br>X₁ is Cys or Cys(ar) or a portion of a cross-link or staple; and<br>X₂ is Cys or Cys(ar) or a portion of a cross-link or staple | SEQ ID NO: 47 |  |
|  | LTFCHYWAQLCSK | SEQ ID NO: 48 | 60 |
|  | LTFCys(ar)HYWAQLCys(ar)SK | SEQ ID NO: 49 | 60a, 60b |
| (XI) | LTFX₁HYWAQFX₂SK<br>wherein:<br>X₁ is Cys or Cys(ar) or a portion of a cross-link or staple; and<br>X₂ is Cys or Cys(ar) or a portion of a cross-link or staple | SEQ ID NO: 64 |  |
|  | LTFCys(ar)HYWAQFCys(ar)SK | SEQ ID NO: 65 | 61a |
| (VIII) | KAWYANX₁EKLX₂R<br>wherein:<br>X₁ is Hexa, Hepa, Cha, or CF₃f; and<br>X₂ is Homol, Cha, Cba, Leu, Hexa, or Trp | SEQ ID NO: 50 |  |
|  | KAWYAN(Hexa)EKL(Homol)R | SEQ ID NO: 51 | 43 |
|  | KAWYAN(Hexa)EKL(Cha)R | SEQ ID NO: 52 | 44 |
|  | KAWYAN(Cha)EKLLR | SEQ ID NO: 53 | 45 |
|  | KAWYAN(Hexa)EKL(Hexa)R | SEQ ID NO: 54 | 46 |
|  | KAWYAN(Hexa)EKLWR | SEQ ID NO: 55 | 47 |
|  | KAWYAN(Hepa)EKL(Cba)R | SEQ ID NO: 56 | 48 |
|  | KAWYAN(Hepa)EKL(Homol)R | SEQ ID NO: 57 | 49 |
|  | KAWYAN(Hepa)EKL(Hexa)R | SEQ ID NO: 58 | 50 |
|  | KAWYAN(Hexa)EKL(Cba)R | SEQ ID NO: 59 | 51 |
|  | KAWYAN(Hepa)EKL(Cha)R | SEQ ID NO: 60 | 52 |
|  | KAWYAN(CF₃f)EKLLR | SEQ ID NO: 61 | 53, 54b |

In some embodiments, the mini-protein or macrocyclic peptide may be synthesized with one or more modifications during the process of producing a library of such mini-proteins or macrocyclic peptides and affinity selecting using the library. In some embodiments, for one or more modifications, the mini-protein or macrocyclic peptide comprises one or more diols along the backbone of the mini-protein or macrocyclic peptide, incorporated during peptide synthesis. In some embodiments, the mini-protein or macrocyclic peptide comprises one or more diols (e.g., vicinal diols, 1,2-diols) along the backbone, such that the mini-protein or macrocyclic peptide can be cleaved along the backbone (e.g., using sodium periodate). In some embodiments, the mini-protein or macrocyclic peptide is cleaved along the backbone to sequence the mini-protein or macrocyclic peptide (e.g., using liquid chromatography-tandem mass spectrometry). Without wishing to be bound by a particular theory, introducing one or more diols along the backbone of the mini-protein or macrocyclic peptide may result in facilitated linearization of the mini-protein or macrocyclic peptide for sequencing.

Suitable amino acid side chains include, but are not limited to, both natural and non-canonical amino acid side chains as provided in Tables 1 to 3, and as described herein.

In some embodiments, the peptide, the macrocyclic peptide, the mini-protein, or the salt thereof may have any suitable number of amino acids. For example, the peptide, macrocyclic peptide, mini-protein, or salt thereof, may have up to 20 amino acids, from 20 to 30 amino acids, from 30 to 40 amino acids, from 40 to 50 amino acids, or from 50 to 100 amino acids.

In some embodiments, the sequence of the peptide, the macrocyclic peptide, the mini-protein, or the salt thereof, may be modified by at least one amino acid relative to a provided or known sequence. For example, the sequence may be modified by one amino acid, two amino acids, 3 amino acids, 4 amino acids, five amino acids, six amino acids, or more relative to its respective provided or known sequence.

As is understood by one skilled in the art, in all embodiments and aspects herein, the left-hand side of the sequence (also referred to herein as the peptide chain) corresponds to the N-terminal end and the right-hand side of the sequence corresponds to the C-terminal end of the peptide chain. The N-terminal end and/or the C-terminal end of the peptide chain may be modified, for example by biotinylation, acetylation, acylation, or amidation. In some embodiments, the N-terminal end and/or the C-terminal end of the peptide chain may comprise a peptide or a protein. In some embodiments, the peptide may be a portion of for example a macrocyclic peptide, a mini-protein, or a protein, or a salt thereof.

In some embodiments, the C-terminal end of the peptide chain is amidated, biotinylated, or attached to another peptide or polypeptide or protein domain; or is hydrogen, cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a suitable hydroxyl, amino, or thiol protecting group; or a substituted or unsubstituted 5- to 6-membered heterocyclic or heteroaromatic ring.

In some embodiments, the N-terminal end of the peptide chain is hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a suitable amino protecting group; a label optionally joined by a linker, wherein the linker is selected from cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene.

In certain embodiments, the N-terminal end of the peptide chain is hydrogen. In certain embodiments, the N-terminal end of the peptide chain is $C_{1-6}$ alkyl. In certain embodiments, the N-terminal end of the peptide chain is —$CH_3$. In certain embodiments, the N-terminal end of the peptide chain is a suitable amino protecting group. In certain embodiments, the N-terminal end of the peptide chain is -Boc. In certain embodiments, the N-terminal end of the peptide chain is -Fmoc. In certain embodiments, the N-terminal end of the peptide chain is acyl. In certain embodiments, the N-terminal end of the peptide chain is —(C=O)$CH_3$.

In certain embodiments, the N-terminal end of the peptide chain is a label optionally joined to the peptide by a linker, wherein the linker is cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene, or a combination thereof.

Exemplary labels include, but are not limited to FITC and biotin:

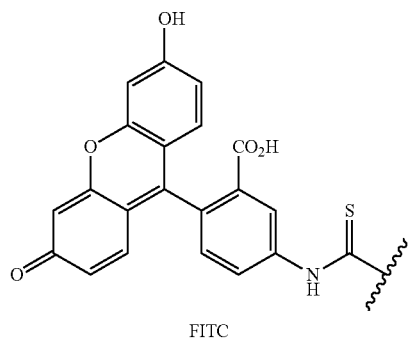

FITC

-continued

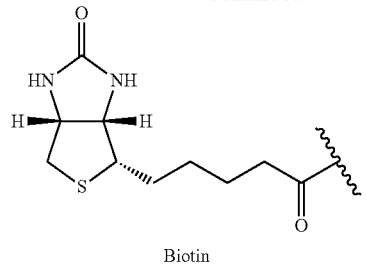

Biotin

In certain embodiments, the label is directly joined to the inventive peptide, macrocyclic peptide, mini-protein, or salt thereof (e.g., through a bond).

In certain embodiments, the label is indirectly joined to the inventive peptide, macrocyclic peptide, mini-protein, or salt thereof (e.g., through a linker).

In certain embodiments, the linker is a cyclic or acyclic, branched or unbranched, substituted or unsubstituted alkylene. In certain embodiments, the linker is a cyclic or acyclic, branched or unbranched, substituted or unsubstituted alkenylene. In certain embodiments, the linker is a cyclic or acyclic, branched or unbranched, substituted or unsubstituted alkynylene. In certain embodiments, the linker is a cyclic or acyclic, branched or unbranched, substituted or unsubstituted heteroalkylene. In certain embodiments, the linker is a cyclic or acyclic, branched or unbranched, substituted or unsubstituted heteroalkenylene. In certain embodiments, the linker is a cyclic or acyclic, branched or unbranched, substituted or unsubstituted heteroalkynylene. In certain embodiments, the linker is a substituted or unsubstituted arylene. In certain embodiments, the linker is a substituted or unsubstituted heteroarylene. In certain embodiments, the linker is a substituted or unsubstituted acylene.

Methods of Synthesis

The present invention is also directed to methods of synthesizing inventive peptides, macrocyclic peptides, mini-proteins, and salts thereof. Peptides can be synthesized using methods known in the art, e.g., solid phase peptide synthesis, solution phase peptide synthesis; see generally, Bodanszky and Bodanszky, *The Practice of Peptide Synthesis*, Springer-Verlag, Berlin, 1984; Atherton and Sheppard, *Solid Phase Peptide Synthesis: A Practical Approach*, IRL Press at Oxford University Press Oxford, England, 1989, and Stewart and Young, *Solid phase Peptide Synthesis*, 2nd edition, Pierce Chemical Company, Rockford, 1984, the entire contents of each of which are incorporated herein by reference. In both solution phase and solid phase techniques, the choice of the protecting groups must be considered, as well as the specific coupling techniques to be utilized. For a detailed discussion of peptide synthesis techniques for solution phase and solid phase reactions, see, *Bioorganic chemistry: Peptides and Proteins*, Hecht, Oxford University Press, New York: 1998, the entire contents of which are incorporated herein by reference.

In certain embodiments, the method comprises a solution phase synthesis of an inventive peptide, macrocyclic peptide, mini-protein, or salt thereof. Solution phase synthesis, as mentioned above, is a well-known technique for the construction of polypeptides. An exemplary solution phase synthesis comprises the steps of: (1) providing an amino acid protected at the N-terminus with a suitable amino protecting group; (2) providing an amino acid protected at the C-terminus with a suitable carboxylic acid protecting group; (3) coupling the N-protected amino acid to the C-protected amino acid; (4) deprotecting the product of the coupling reaction; and (5) repeating steps (3) to (4) until a desired polypeptide is obtained, wherein at least two of the amino acids coupled at any of the above steps each comprise at least one terminally unsaturated amino acid sidechain. During the course of the above synthesis, various parameters can be varied, including, but not limited to placement of amino acids with terminally unsaturated side chains, stereochemistry of amino acids, terminally unsaturated side chain length and functionality, and amino acid residues utilized.

In certain embodiments, the method comprises a solid phase synthesis of an inventive peptide, macrocyclic peptide, mini-protein, or salt thereof. Solid phase synthesis, as mentioned above, is a well-known technique for the construction of polypeptides. An exemplary solid phase synthesis comprises the steps of: (1) providing a resin-bound amino acid; (2) deprotecting the resin bound amino acid; (3) coupling an amino acid to the deprotected resin-bound amino acid; (4) repeating steps (3) until a desired peptide is obtained, wherein in some embodiments at least two of the amino acids coupled at any of the above steps each comprise at least one terminally unsaturated amino acid sidechain. During the course of the above synthesis, various parameters can be varied, including, but not limited to placement of amino acids with terminally unsaturated side chains, stereochemistry of amino acids, terminally unsaturated side chain length and functionality, and amino acid residues utilized.

After a desired peptide or salt thereof is synthesized using an appropriate technique, the peptide or salt thereof may be contacted with a specific catalyst and/or reacted with a cross-linking agent to promote "stapling" of the polypeptide to form a macrocyclic peptide. For example, the resin-bound polypeptide may be contacted with a catalyst to promote "stapling," or may first be cleaved from the resin, and then contacted with a catalyst and/or reacted with a cross-linking agent to promote "stapling."

Additional Modifications

The peptides can be modified in any suitable manner, at the C-terminus, at the N-terminus, and/or at a side chain. In certain embodiments, such modifications include reduction, oxidation, and nucleophilic or electrophilic additions to a functional group (e.g., a double bond provided from a metathesis reaction) of the cross-link to provide a synthetically modified peptide. Other modifications may include conjugation of a peptide, or a synthetically modified peptide, with a biologically active agent, label or diagnostic agent anywhere on the peptide scaffold, e.g., such as at the N-terminus of the peptide, the C-terminus of the peptide, on an amino acid side chain of the peptide, or at one or more modified or unmodified sites (e.g., to a staple). Such modification may be useful in delivery of the peptide (e.g., peptide, macrocyclic peptide, mini-protein, or salt thereof) to a cell, tissue, or organ. Such modifications may allow for targeting to a particular type of cell or tissue.

Thus, in certain embodiments, the above synthetic method further comprises treating the peptide with a suitably reactive agent under suitable conditions to provide a synthetically modified stapled peptide, also referred to herein as a macrocyclic peptide.

One of ordinary skill in the art will appreciate that a wide variety of reactions, conditions, and "suitably reactive agent(s)" may be employed to promote such a transformation, therefore, a wide variety of reactions, conditions, and reactive agents are envisioned; see generally, *March's Advanced Organic Chemistry: Reactions, Mechanisms, and Structure*, M. B. Smith and J. March, 5$^{th}$ Edition, John Wiley & Sons, 2001; *Advance Organic Chemistry, Part B: Reactions and Synthesis*, Carey and Sundberg, 3$^{rd}$ Edition, Plenum Press, New York, 1993; and *Comprehensive Organic Transformations*, R. C. Larock, 2$^{nd}$ Edition, John Wiley & Sons, 1999, the entirety of each of which is hereby incorporated herein by reference. Exemplary "suitably reactive agents" may be any agent reactive with a multiple bond (e.g., a double or triple bond). In certain embodiments, suitably reactive agents are able to react with a double bond or triple bond, for example, via a hydrogenation, osmylation, hydroxylation (mono- or di-), amination, halogenation, cycloaddition (e.g., cyclopropanation, aziridination, epoxidation), oxy-mercuration, and/or a hydroboronation reaction, to provide a functionalized single bond or double bond. As one of ordinary skill in the art will clearly recognize, these above-described transformations will introduce functionalities compatible with the particular stabilized structures and the desired biological interactions; such functionalities include, but are not limited to, hydrogen, cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted amino; substituted or unsubstituted thiol, halo; cyano; nitro; azido; imino; oxo; and thiooxo.

In another aspect, in certain embodiments, the above method further comprises treating the polypeptide with a suitably reactive agent to provide a synthetically modified peptide (e.g., stapled peptide), and treating the modified peptide with a biologically active agent to provide a modified peptide conjugated to a biologically-active agent.

Furthermore, in another aspect, in certain embodiments, the above method comprises treating a stapled peptide with a biologically active agent to provide a stapled peptide conjugated to a biologically-active agent.

In another aspect, in certain embodiments, the above method further comprises treating the peptide with a suitable reagent to provide a synthetically modified stapled peptide, and treating the modified stapled polypeptide with a diagnostic agent to provide a modified stapled polypeptide conjugated to a diagnostic agent.

Furthermore, in another aspect, in certain embodiments, the above method comprises treating a stapled peptide of step (vi) with a diagnostic agent to provide a stapled peptide conjugated to a diagnostic agent.

Conjugation of an agent (e.g., a label, a diagnostic agent, a biologically active agent) to the inventive peptide (e.g., peptide, macrocyclic peptide, mini-protein, or salt thereof) may be achieved in a variety of different ways. The agent may be covalently conjugated, directly or indirectly, to the polypeptide at the site of stapling, or to the N-terminus or the C-terminus of the polypeptide chain. Alternatively, the agent may be noncovalently conjugated, directly or indirectly, to the polypeptide at the site of stapling, or to the N-terminus or the C-terminus of the polypeptide chain. Indirect covalent conjugation is by means of one or more covalent bonds. Indirect noncovalent conjugation is by means of one or more noncovalent bonds. Conjugation may also be via a combination of non-covalent and covalent forces/bonds. The agent may also be conjugated through a covalent or non-covalent linking group.

Any suitable bond may be used in the conjugation of a biologically active agent and/or diagnostic agent to the inventive polypeptide present invention. Such bonds include amide linkages, ester linkages, disulfide linkages, carbon-carbon bonds, carbamate, carbonate, urea, hydrazide, and the like. In some embodiments, the bond is cleavable under physiological conditions (e.g., enzymatically cleavable, cleavable with a high or low pH, with heat, light, ultrasound, x-ray, etc). However, in some embodiments, the bond is not cleavable.

Combinatorial Synthesis of Peptides

It will also be appreciated by one of ordinary skill in the art that the synthetic method as described above can also be applied to combinatorial synthesis of inventive peptides. Although combinatorial synthesis techniques can be applied in solution, it is more typical that combinatorial techniques are performed on the solid phase using split-and-pool techniques. During the course of the combinatorial synthesis, various parameters can be varied, including, but not limited to placement of amino acids with terminally unsaturated side chains, stereochemistry of amino acids, terminally unsaturated side chain length and functionality, and amino acid residues utilized.

The present invention, in one aspect, provides methods for the synthesis of libraries of novel inventive polypeptides, as described above, comprising (1) providing a collection of resin-bound amino acids; (2) deprotecting each of said resin bound amino acids; (3) separating said collection of deprotected resin bound amino acids into n equal portions, wherein n represents the number of different types of amino acids to be coupled; (4) coupling of each of n types of amino acids to the deprotected amino acid; (5) combining each of the n portions together; and (6) repeating steps (2)-15) until a desired polypeptide is obtained, wherein in some embodiments at least two of the amino acids coupled at any of the above steps each comprise at least one terminally unsaturated amino acid sidechain. After a desired polypeptide is synthesized, the resin-bound polypeptide may be contacted with a catalyst to promote "stapling," or may first be cleaved from the resin, and then contacted with a catalyst to promote "stapling."

It will be appreciated by one of ordinary skill in the art that the libraries of peptides having stabilized secondary structures can be further diversified at specific functional moieties after the desired stabilized structures are formed. For example, free or latent amino acid functionalities may be diversified, or alternatively or additionally, free or latent functionality present on the cross-linkers may be diversified. In particularly preferred embodiments, in but one example, the hydrophilicity of stabilized structures may be increased by the introduction of hydroxyl moieties. As one of ordinary skill in the art will realize, the diversification reactions will be selected to introduce functionalities compatible with the particular stabilized structures and the desired biological interactions, and these functionalities include, but are not limited to hydrogen, cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted amino; substituted or unsubstituted thiol, halo; cyano; nitro; azido; imino; oxo; and thiooxo.

Methods of Identification, Screening, and Selection

The present invention is also directed to methods of identifying one or more modulators (e.g., peptides) of a protein-protein interaction. In some embodiments, methods of identifying one or more binders (e.g., peptide) for inhibiting a protein-protein interaction are provided.

The method may comprise incubating a library (e.g., a peptide library) with a protein target in solution under suitable conditions to form a mixture comprising one or more modulator-protein target complexes (e.g., one or more peptide-protein target complexes).

In some embodiments, the library (e.g., peptide library) comprises at least 100 members, at least 1000 members, or at least 1 million members. In some embodiments, members of the library (e.g., peptide library) are linear peptides, macrocyclic peptides, mini-proteins, or salts thereof. In some embodiments, members of the peptide library have their N-terminus modified with biotinylation or acetylation. In some embodiments, the peptide library is based on anyone of formulas (I)-(X) herein.

In some embodiments, the mixture comprises a buffer (e.g., Tris buffer). In some embodiments, the buffer comprises L-arginine. In some embodiments, one or more amino acids (e.g., arginine) is included in the mixture, and/or in the mobile phase for HPSEC. In some embodiments, each of the one or more amino acids is present in the mixture and/or the mobile phase at from 0 M to 0.75 M (e.g., from 0.1 M to 0.3 M, 0.2 M). In some embodiments, the buffer and/or the mobile phase comprises e.g. L-proline, glycine, or glutamate. In some embodiments, the buffer has a pH similar to physiological conditions (e.g., a pH of 7.0, 7.1, 7.2, 7.3, 7.4, 7.5, 7.7, 7.8, 7.9, 8.0). In some embodiments, the buffer has a pH of 7.4 or 7.5. In some embodiments, the mixture is incubated at from 15 minutes to 24 hours and at from 20° C. to 30° C. In some embodiments, the mixture is incubated at one hour at room temperature.

The method may comprise fractionating the mixture comprising the one or more modulator-protein target complexes (e.g., one or more peptide-protein target complexes) using high-pressure size exclusion chromatography (HPSEC) into a first plurality of fractions.

In some embodiments, fractionation comprises separating one or more non-binding members (e.g., peptides) in the library from one or more modulator-protein target complexes. In some embodiments, the first plurality of fractions comprises at least one protein fraction, which herein refers to a fraction comprising the protein target and/or one or more modulator-protein target complexes, and at least one unbound fraction, comprising one or more non-binding members (e.g., peptides) from the library.

In some embodiments, the difference in molecular weight between a non-binding member (e.g., peptide) and a modulator-protein target complex that is fractionated from the non-binding member is less than or equal to 100 kDa, less than or equal to 80 kDa, less than or equal to 50 kDa, or less than or equal to 30 kDa. In some embodiments, the difference in molecular weight between a non-binding member and a modulator-protein target complex that is fractionated from the non-binding member is less than or equal to 30 kDa.

In some embodiments, a mobile phase used for HPSEC comprises the same components as the buffer used in the mixture, in the same or different ratios. Without wishing to be bound by theory, the supplementation of the buffer and/or mobile phase with L-arginine dramatically increases the yield and efficiency of fractionation by HPSEC relative to that obtained using other buffers used for protein analysis by those of skill in the art. In some embodiments, without wishing to be bound by theory, the presence of L-arginine allows peptide-protein target complexes to be eluted from a column using HPSEC, whereas in the absence of L-arginine, the peptide-protein target complexes do not elute from the column.

The method may comprise fractionating a reference solution comprising the protein target using HPSEC, using substantially identical conditions to those used for the mixture comprising the one or more modulator-protein target complexes, into a second plurality of fractions comprising a protein fraction comprising the protein target.

The method may comprise selecting a protein fraction of the first plurality of fractions, wherein at least the protein target and/or one or more modulator-protein target complexes was eluted. In some embodiments, the protein fraction of the first plurality of fractions has a closer elution time to the protein fraction of the second plurality of fractions than does the unbound fraction.

The method may comprise analyzing the protein fraction of the first plurality of fractions directly (e.g, by liquid chromatography-tandem mass spectrometry (LC-MS/MS)) to obtain structural information (e.g., a peptide sequence) of the modulator (e.g., peptide). In some embodiments, the method comprises subjecting the protein fraction to chemical conditions to form a linearized fraction having a linearized modulator (e.g., peptide). In some embodiments, the method for linearizing a modulator (e.g., macrocyclic peptide) for analysis comprises exposing the modulator (e.g., polymer) to the appropriate chemical conditions (e.g., exposing to sodium periodate) to cleave the polymer along the backbone using one or more diols along the backbone of the modulator (e.g., peptide).

In some embodiments, the method for linearizing a modulator (e.g., macrocyclic peptide) for analysis can be carried out by first introducing one or more diols along the backbone of the modulator, e.g. polymer (e.g., peptide, macrocyclic peptide, mini-protein, protein), during synthesis. In some embodiments, synthesis of the modulator comprises macrocyclizing the modulator (e.g., peptide) using a chemical transformation.

In some embodiments, the method comprises analyzing the linearized fraction (e.g., by LC-MS/MS) to obtain structural information (e.g., a peptide sequence) of the modulator (e.g., peptide).

In some embodiments, the method comprises synthesizing a library (e.g., a peptide library). In some embodiments, the library (e.g., the peptide library) has at least 100 members, at least 500 members, at least 1000 members (e.g., at least 1000 members, at least 5000 members, at least 10,000 members, at least 50,000 members, at least 100,000 members, at least 500,000 members, at least 1 million members, at least 1.5 million members, at least 2 million members). In some embodiments, synthesizing the library (e.g., peptide library) comprises using a split and pool technique. In some embodiments, synthesizing the library (e.g., peptide library) comprises randomizing one or more residues (e.g., one residue, to residues, 3 residues, 4 residues, 5 residues, 6 residues, 7 residues, 8 residues, 9 residues, 10 residues, or more) in a peptide sequence.

In some embodiments, the method comprises re-synthesizing and/or modifying the modulator using the structural information (e.g., the peptide sequence). In some embodiments, the method comprises validating binding of the modulator (e.g., peptide) to the protein target using an assay (e.g., a binding assay, a functional assay).

Pharmaceutical Compositions

In another aspect, the present invention is directed to pharmaceutical compositions comprising a peptide, a macrocyclic peptide, a mini-protein, or a salt thereof described herein.

The present invention provides pharmaceutical compositions comprising an inventive peptide, macrocyclic peptide, mini-protein, or salt thereof described herein, or pharmaceutically acceptable form thereof, and a pharmaceutically acceptable carrier. Such pharmaceutical compositions may optionally comprise one or more additional biologically-active substances. In accordance with some embodiments, a method of administering a pharmaceutical composition comprising inventive compositions to a subject in need thereof is provided. In some embodiments, inventive compositions are administered to humans. For the purposes of the present invention, the phrase "active ingredient" generally refers to an inventive peptide, macrocyclic peptide, mini-protein, or salt thereof, as described herein.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions of the invention is contemplated include, but are not limited to, humans and/or other primates; mammals, including commercially relevant mammals such as cattle, pigs, horses, sheep, cats, and/or dogs; and/or birds, including commercially relevant birds such as chickens, ducks, geese, and/or turkeys.

The formulations of the pharmaceutical compositions described herein may be prepared by any method known or hereafter developed in the art of pharmacology. In general, such preparatory methods include the step of bringing the active ingredient into association with a carrier and/or one or more other accessory ingredients, and then, if necessary and/or desirable, shaping and/or packaging the product into a desired single- or multi-dose unit.

A pharmaceutical composition of the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable carrier, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutical formulations of the present invention may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy*, 21$^{st}$ Edition, A. R. Gennaro, (Lippincott, Williams & Wilkins, Baltimore, Md., 2006) discloses various carriers used in formulating pharmaceutical compositions and known techniques for the preparation thereof. Except insofar as any conventional carrier medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof A pharmaceutical composition of the invention may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more of the additional ingredients described herein. Other ophthalmically-administrable formulations which are useful include those which comprise the active ingredient in microcrystalline form and/or in a liposomal preparation. Ear drops and/or eye drops are contemplated as being within the scope of this invention.

General considerations in the formulation and/or manufacture of pharmaceutical agents may be found, for example, in *Remington: The Science and Practice of Pharmacy* $21^{st}$ ed., Lippincott Williams & Wilkins, 2005.

Methods of Use

The present invention provides a method of treating a disease, disorder, or condition comprising administering to a subject diagnosed with or having susceptibility to the disease, disorder, or condition, a therapeutically effective amount of a peptide, a macrocyclic peptide, a mini-protein, or a salt thereof described herein, or pharmaceutically acceptable form thereof. Exemplary diseases, disorders, or conditions which may be treated by administration of an inventive polypeptide include proliferative, neurological, immunological, endocrinologic, cardiovascular, hematologic, autoimmune, infectious, and inflammatory diseases, disorders, or conditions.

As used herein a proliferative disease, condition, or disorder includes, but is not limited to, cancer, hematopoietic neoplastic disorders, proliferative breast disease, proliferative disorders of the lung, proliferative disorders of the colon, proliferative disorders of the liver, and proliferative disorders of the ovary.

Examples of cancers treatable by the above method include carcinoma, sarcoma, or metastatic disorders, breast cancer, ovarian cancer, colon cancer, lung cancer, fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma, Examples of hematopoietic neoplastic disorders treatable by the above method includes diseases involving hyperplastic/neoplastic cells of hematopoietic origin, e.g., arising from myeloid, lymphoid or erythroid lineages, or precursor cells thereof. In certain embodiments, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Stemberg disease.

Examples of proliferative breast disease treatable by the above method includes epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of proliferative disorders of the lung treatable by the above method include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Examples of proliferative disorders of the colon treatable by the above method include, but are not limited to, non-neoplastic polyps, adenomas, familial syndromes, colorectal carcinogenesis, colorectal carcinoma, and carcinoid tumors.

Examples of proliferative disorders of the liver treatable by the above method include, but are not limited to, nodular hyperplasias, adenomas, and malignant tumors, including primary carcinoma of the liver and metastatic tumors.

Examples of proliferative disorders of the ovary treatable by the above method include, but are not limited to, ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecomafibromas, androblastomas, hill cell tumors, and gonadoblastoma; and metastatic tumors such as Krukenberg tumors.

The inventive peptides may serve to treat the above-described diseases, disorders, or conditions, by disrupting native protein-protein, protein-ligand, and/or protein-receptor interactions. For example, many biologically important protein/protein interactions, such as p53/MDM2 and Bcl-X1/Bak, are mediated by one protein donating a helix into a cleft of its helix-accepting partner. The interaction of p53 and MDM2 and mutations in the p53 gene have been identified in virtually half of all reported cancer cases (see, Shair *Chem. & Biol.* 1997, 4, 791, the entire contents of which are incorporated herein by reference). As stresses are imposed on a cell, p53 is believed to orchestrate a response that leads to either cell-cycle arrest and DNA repair, or programmed cell death. As well as mutations in the p53 gene that alter the function of the p53 protein directly, p53 can be altered by changes in MDM2. The MDM2 protein has been shown to bind to p53 and disrupt transcriptional activation by associating with the transactivation domain of p53. For example, an 11 amino-acid peptide derived from the transactivation domain of p53 forms an amphipathic alpha-helix of 2.5 turns that inserts into the MDM2 crevice.

In certain embodiments, an inventive peptide, macrocyclic peptide, mini-protein, or salt thereof described herein is capable of binding tightly to MDM2 and disrupting native protein/protein interactions. These structures may then be screened using methods of identifying a binder described herein to identify high performing peptides, macrocyclic peptides, mini-proteins, or salts thereof. The novel structures that disrupt the MDM2 interaction might be useful for many applications, including, but not limited to, control of soft tissue sarcomas (which overexpresses MDM2 in the presence of wild type p53). These cancers may be held in check with molecules that could intercept MDM2, thereby preventing suppression of p53. Additionally, molecule disrupters of MDM2-p53 interactions could be used as adjuvant therapy to help control and modulate the extent of the p53 dependent apoptosis response in conventional chemotherapy.

In certain embodiments, the inventive peptide, macrocyclic peptide, mini-protein, or salt thereof is homologous to a known peptide. In certain embodiments, the inventive peptide, macrocyclic peptide, mini-protein, or salt thereof is modified by at most 10 amino acids, at most 9 amino acids, at most 8 amino acids, at most 7 amino acids, at most 6 amino acids, at most 5 amino acids, at most 4 amino acids, at most 3 amino acids, at most 2 amino acids, or at most 1 amino acid relative to its respective known peptide.

In addition, the inventive polypeptides may be useful in the area of materials science. For example, molecules such as lipids and other polymeric molecules may be attached to the terminal peptide moieties and thus generate potentially important biomaterials.

In addition to the above-mentioned uses, the inventive polypeptides may be used for studies in bioinorganic chemistry or in catalysis, either as a ligand for a transition metal capable of mimicking an important biological environment, or by acting in concert with a particular transition metal catalyst to effect a desired chemical reaction.

Also provided herein are peptides, macrocyclic peptides, and mini-proteins, and salts thereof, and pharmaceutical compositions thereof, for any of the uses described herein (e.g., for use in treating and/or preventing a disease described herein).

Also provided herein are uses of peptides, macrocyclic peptides, and mini-proteins, and salts thereof, and pharmaceutical compositions thereof, in the preparation of medicaments for treating and/or preventing any of the diseases described herein.

Administration

In some embodiments, a therapeutically effective amount of an inventive pharmaceutical composition is delivered to a patient and/or organism prior to, simultaneously with, and/or after diagnosis with a disease, disorder, and/or condition. In some embodiments, a therapeutic amount of an inventive composition is delivered to a patient and/or organism prior to, simultaneously with, and/or after onset of symptoms of a disease, disorder, and/or condition. In some embodiments, the amount of inventive composition is sufficient to treat, alleviate, ameliorate, relieve, delay onset of, inhibit progression of, reduce severity of, and/or reduce incidence of one or more symptoms or features of the disease, disorder, and/or condition.

In one aspect, the present invention is directed to methods of treating cancer, and/or of treating or preventing HIV in a subject in need thereof comprising administering a peptide, a macrocyclic peptide, a mini-protein, or a salt thereof described herein. In some embodiments, the method comprises preventing an HIV capsid from forming using a peptide, a macrocyclic peptide, a mini-protein, or a salt thereof described herein.

In some embodiments, the present invention is directed to methods for disrupting a protein-protein interaction (e.g., a p53-MDM2 interaction) using a peptide, a macrocyclic peptide, a mini-protein, or a salt thereof described herein.

The compositions, according to the method of the present invention, may be administered using any amount and any route of administration effective for treatment. The exact amount required will vary from subject to subject, depending on the species, age, and general condition of the subject, the severity of the infection, the particular composition, its mode of administration, its mode of activity, and the like. The compositions of the invention are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disorder being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The pharmaceutical compositions of the present invention may be administered by any route. In some embodiments, the pharmaceutical compositions of the present invention are administered variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, enteral, sublingual; by intratracheal instillation, bronchial instillation, and/or inhalation; and/or as an oral spray, nasal spray, and/or aerosol. Specifically contemplated routes are systemic intravenous injection, regional administration via blood and/or lymph supply, and/or direct administration to an affected site. In general the most appropriate route of administration will depend upon a variety of factors including the nature of the agent (e.g., its stability in the environment of the gastrointestinal tract), the condition of the subject (e.g., whether the subject is able to tolerate oral administration), etc. At present the oral and/or nasal spray and/or aerosol route is most commonly used to deliver therapeutic agents directly to the lungs and/or respiratory system. However, the invention encompasses the delivery of the inventive pharmaceutical composition by any appropriate route taking into consideration likely advances in the sciences of drug delivery.

In certain embodiments, the compositions of the invention may be administered at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

In some embodiments, the present invention encompasses "therapeutic cocktails" comprising inventive peptides, macrocyclic peptides, mini-proteins, or salts thereof described herein. In some embodiments, the inventive peptides, macrocyclic peptides, mini-proteins, or salts thereof described herein comprises a single species which can bind to multiple targets. In some embodiments, different inventive peptides, macrocyclic peptides, mini-proteins, or salts thereof described herein comprise different targeting moiety species, and all of the different targeting moiety species can bind to the same target. In some embodiments, different inventive peptides, macrocyclic peptides, mini-proteins, or salts thereof described herein comprise different targeting moiety species, and all of the different targeting moiety species can bind to different targets. In some embodiments, such different targets may be associated with the same cell type. In some embodiments, such different targets may be associated with different cell types.

It will be appreciated that inventive peptides, macrocyclic peptides, mini-proteins, or salts thereof described herein and pharmaceutical compositions of the present invention can be employed in combination therapies. The particular combination of therapies (therapeutics or procedures) to employ in a combination regimen will take into account compatibility of the desired therapeutics and/or procedures and the desired therapeutic effect to be achieved. It will be appreciated that the therapies employed may achieve a desired effect for the same purpose (for example, an inventive conjugate useful for detecting tumors may be administered concurrently with another agent useful for detecting tumors), or they may achieve different effects (e.g., control of any adverse effects).

Pharmaceutical compositions of the present invention may be administered either alone or in combination with one or more other therapeutic agents. By "in combination with," it is not intended to imply that the agents must be administered at the same time and/or formulated for delivery together, although these methods of delivery are within the scope of the invention. The compositions can be administered concurrently with, prior to, or subsequent to, one or more other desired therapeutics or medical procedures. In general, each agent will be administered at a dose and/or on a time schedule determined for that agent. Additionally, the invention encompasses the delivery of the inventive pharmaceutical compositions in combination with agents that may improve their bioavailability, reduce and/or modify their metabolism, inhibit their excretion, and/or modify their distribution within the body.

The particular combination of therapies (therapeutics and/or procedures) to employ in a combination regimen will take into account compatibility of the desired therapeutics and/or procedures and/or the desired therapeutic effect to be achieved. It will be appreciated that the therapies employed may achieve a desired effect for the same disorder (for example, an inventive peptide, macrocyclic peptide, mini-protein, or salt thereof described herein may be administered concurrently with another biologically active agent used to treat the same disorder), and/or they may achieve different effects (e.g., control of any adverse effects). In some embodiments, peptides, macrocyclic peptides, mini-proteins, or salts thereof of the invention are administered with a second biologically active agent that is approved by the U.S. Food and Drug Administration.

In will further be appreciated that biologically active agents utilized in this combination may be administered together in a single composition or administered separately in different compositions.

In general, it is expected that biologically active agents utilized in combination be utilized at levels that do not exceed the levels at which they are utilized individually. In some embodiments, the levels utilized in combination will be lower than those utilized individually.

In some embodiments, inventive pharmaceutical compositions may be administered in combination with any biologically active agent or therapeutic regimen that is useful to treat, alleviate, ameliorate, relieve, delay onset of, inhibit progression of, reduce severity of, and/or reduce incidence of one or more symptoms or features of cancer. For example, inventive compositions may be administered in combination with traditional cancer therapies including, but not limited to, surgery, chemotherapy, radiation therapy, hormonal therapy, immunotherapy, complementary or alternative therapy, and any combination of these therapies.

In some embodiments, inventive compositions are administered in combination with surgery to remove a tumor. Because complete removal of a tumor with minimal or no damage to the rest of a patient's body is typically the goal of cancer treatment, surgery is often performed to physically remove part or all of a tumor. If surgery is unable to completely remove a tumor, additional therapies (e.g. chemotherapy, radiation therapy, hormonal therapy, immunotherapy, complementary or alternative therapy) may be employed.

In some embodiments, inventive compositions are administered in combination with radiation therapy. Radiation therapy (also known as radiotherapy, X-ray therapy, or irradiation) is the use of ionizing radiation to kill cancer cells and shrink tumors. Radiation therapy may be used to treat almost any type of solid tumor, including cancers of the brain, breast, cervix, larynx, lung, pancreas, prostate, skin, stomach, uterus, or soft tissue sarcomas. Radiation can be used to treat leukemia and lymphoma. Radiation therapy can be administered externally via external beam radiotherapy (EBRT) or internally via brachytherapy. Typically, the effects of radiation therapy are localized and confined to the region being treated. Radiation therapy injures or destroys tumor cells in an area being treated (e.g. a target organ, tissue, and/or cell) by damaging their genetic material, preventing tumor cells from growing and dividing. In general, radiation therapy attempts to damage as many tumor cells as possible while limiting harm to nearby healthy tissue. Hence, it is often administered in multiple doses, allowing healthy tissue to recover between fractions.

In some embodiments, inventive compositions are administered in combination with immunotherapy. Immunotherapy is the use of immune mechanisms against tumors which can be used in various forms of cancer, such as breast cancer (e.g. trastuzumab/Herceptin®), leukemia (e.g. gemtuzumab ozogamicin/Mylotarg®), and non-Hodgkin's lymphoma (e.g. rituximab/Rituxan®). In some embodiments, immunotherapy agents are monoclonal antibodies directed against proteins that are characteristic to the cells of the cancer in question. In some embodiments, immunotherapy agents are cytokines that modulate the immune system's response. In some embodiments, immunotherapy agents may be vaccines.

In some embodiments, vaccines can be administered to prevent and/or delay the onset of cancer. In some embodiments, cancer vaccines prevent and/or delay the onset of cancer by preventing infection by oncogenic infectious agents. In some embodiments, cancer vaccines prevent and/or delay the onset of cancer by mounting an immune response against cancer-specific epitopes. To give but one example of a cancer vaccine, an experimental vaccine for HPV types 16 and 18 was shown to be 100% successful at preventing infection with these types of HPV and, thus, are able to prevent the majority of cervical cancer cases (Harper et al., 2004, *Lancet*, 364:1757).

In some embodiments, inventive compositions are administered in combination with complementary and alternative medicine treatments. Some exemplary complementary measures include, but are not limited to, botanical medicine (e.g. use of mistletoe extract combined with traditional chemotherapy for the treatment of solid tumors); acupuncture for managing chemotherapy-associated nausea and vomiting and in controlling pain associated with surgery; prayer; psychological approaches (e.g. "imaging" or meditation) to aid in pain relief or improve mood. Some exemplary alternative measures include, but are not limited to, diet and other lifestyle changes (e.g. plant-based diet, the grape diet, and the cabbage diet).

In some embodiments, inventive compositions are administered in combination with any of the traditional cancer treatments described herein, which are often associated with unpleasant, uncomfortable, and/or dangerous side effects. For example, chronic pain often results from continued tissue damage due to the cancer itself or due to the treatment (i.e., surgery, radiation, chemotherapy). Alternatively or additionally, such therapies are often associated with hair loss, nausea, vomiting, diarrhea, constipation, anemia, malnutrition, depression of immune system, infection, sepsis, hemorrhage, secondary neoplasms, cardiotoxicity, hepatotoxicity, nephrotoxicity, ototoxicity, etc. Thus, inventive compositions which are administered in combination with any of the traditional cancer treatments described herein may be also be administered in combination with any therapeutic agent or therapeutic regimen that is useful to treat, alleviate, ameliorate, relieve, delay onset of, inhibit progression of, reduce severity of, and/or reduce incidence of one or more side effects of cancer treatment. To give but a few examples, pain can be treated with opioids and/or analgesics (e.g. morphine, oxycodone, antiemetics, etc.); nausea and vomiting can be treated with 5-$HT_3$ inhibitors (e.g. dolasetron/Anzemet®, granisetron/Kytril®, ondansetron/Zofran®, palonsetron/Aloxi®) and/or substance P inhibitors (e.g. aprepitant/Emend®); immunosuppression can be treated with a blood transfusion; infection and/or sepsis can be treated with antibiotics (e.g. penicillins, tetracyclines, cephalosporins, sulfonamides, aminoglycosides, etc.); and so forth.

In some embodiments, inventive compositions may be administered and/or inventive diagnostic methods may be performed in combination with any therapeutic agent or therapeutic regimen that is useful to diagnose one or more symptoms or features of cancer (e.g. detect the presence of and/or locate a tumor). In some embodiments, inventive peptides, macrocyclic peptides, mini-proteins, or salts thereof described herein may be used in combination with one or more diagnostic agents.

EXAMPLES

Example 1

A solution-phase combinatorial strategy for the facile discovery of functional peptidomimetics based on the use of non-canonical amino acids and scaffolds is presented herein. This approach allows for the robust screening of large combinatorial libraries ranging from thousands to millions of peptides in one single experiment with virtually no false positives. Novel and high affinity non-canonical inhibitors of well-studied PPIs were rapidly discovered and it was demonstrated that using established chemistry, these inhibitors can rapidly be turned into potent bioactive macrocyclic inhibitors. Proof of concept is also provided herein for the affinity selection of mini-protein-based structures to rapidly discover new functional scaffolds featuring non-canonical side chains. Such capabilities are illustrated by presenting original high affinity knottin-derived non-canonical MDM2 inhibitors with low nanomolar affinities.

Figure 1A:
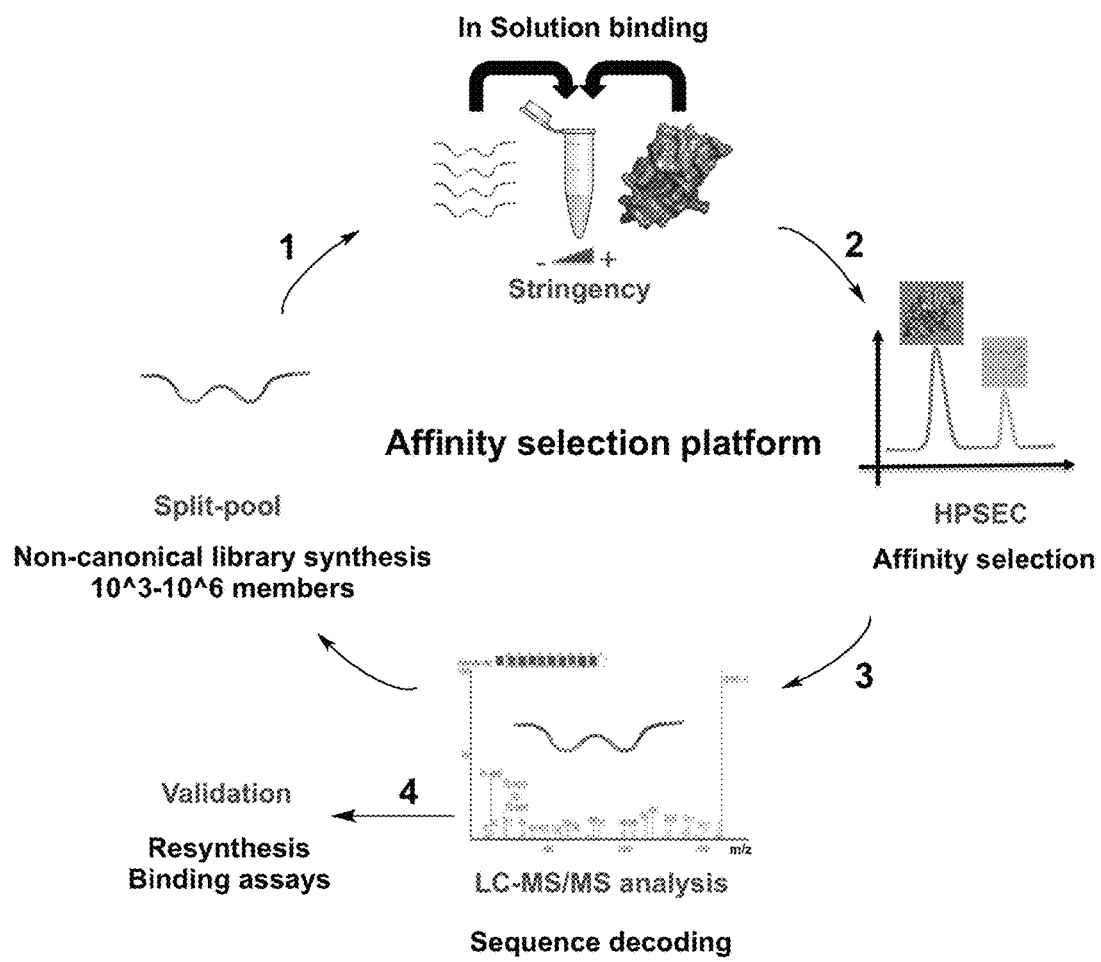
FIG. 1A-1B: Affinity selection platform for the rapid and robust discovery of high affinity non-canonical binders.
Figure 1B:
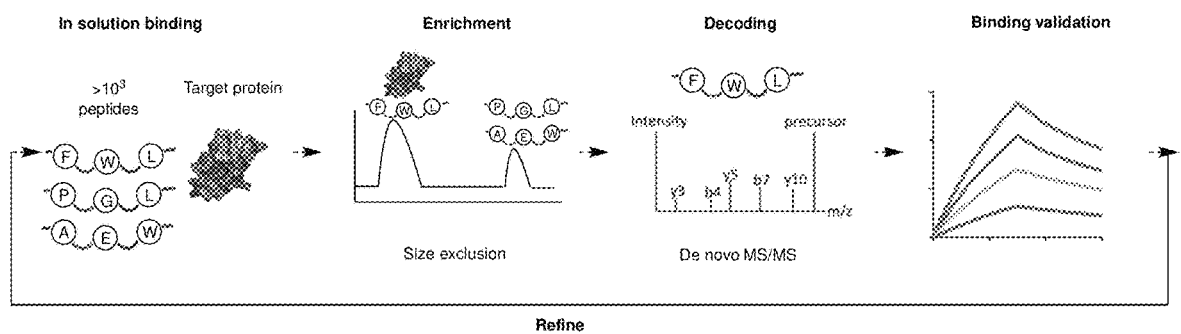

Presented herein is an affinity selection platform harnessing combinatorial chemistry to rapidly synthesize large peptide libraries, specifically enrich in solution and high throughput sequence peptide and peptidomimetic binders (FIG. 1) with the aim to facilitate the discovery of non-canonical inhibitors of important PPIs. Drawing from seminal work in the field of affinity selection using mass spectrometry [10],[11], this chemical platform was based on a stringent high-pressure size exclusion chromatography (HPSEC). Adapting the latter to peptide libraries allowed for the high-resolution separation of peptide-protein complexes from unbound library members even for large peptide structures (>30 mer) and small molecular weight target proteins (<30 Kda). The determinants and boundaries of this assay have been explored in model systems with single peptide-based binders of various structures, sizes, hydrophobicities and affinities (FIGS. 6-8 and 15), as well as in the library context (FIGS. 21-24) showing highly specific enrichment. Operating in solution, the platform is enabled with a chemical toolbox that allows for the sequencing of non-linear peptide binders. The practicality of such chemical strategies was demonstrated in the case of macrocyclic peptides and folded mini-proteins since de novo tandem mass spectrometry sequencing of such peptides is still challenging (FIGS. 16-20).

Figure 25:
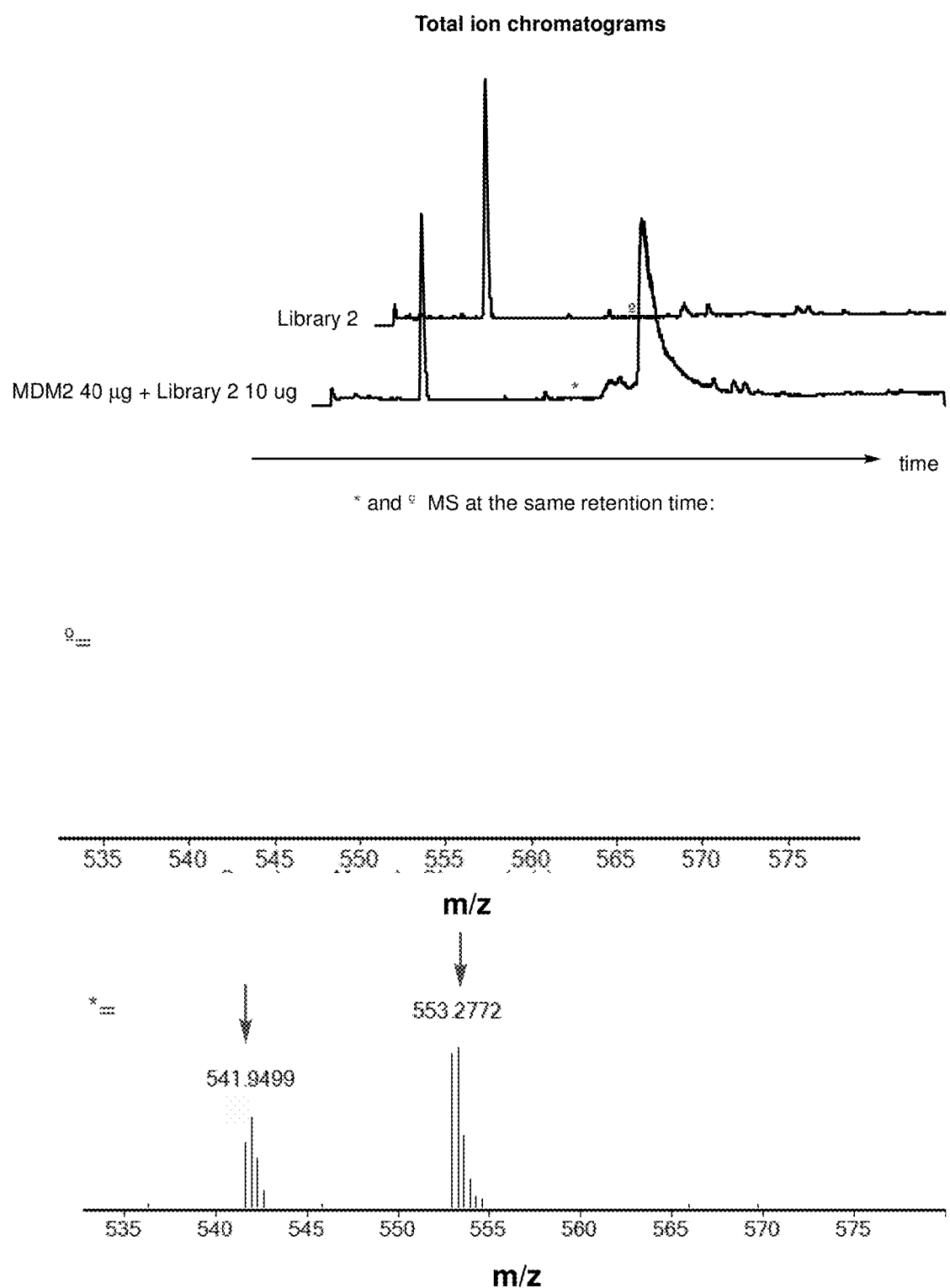
FIG. 25: Affinity selection from Library 2 in usual stringency conditions yielded sequence (5). Library 2 (10 µg, ~60 µM) was added to MDM2 (40 µg, 17 µM) in 100 µL final volume of mobile phase supplemented with L-arginine pH 7.5. The solution was mixed by pipetting and left to stand for 1 hour at room temperature before size exclusion chromatography. Top, total ion chromatogram (TIC, LC-MS method B) corresponding to the analysis of protein fraction after HPSEC. Chromatogram inspection and direct comparison of MS spectra at the same retention time (*) and (°) demonstrates selective selection of library members 5 and 6.
Figure 35:
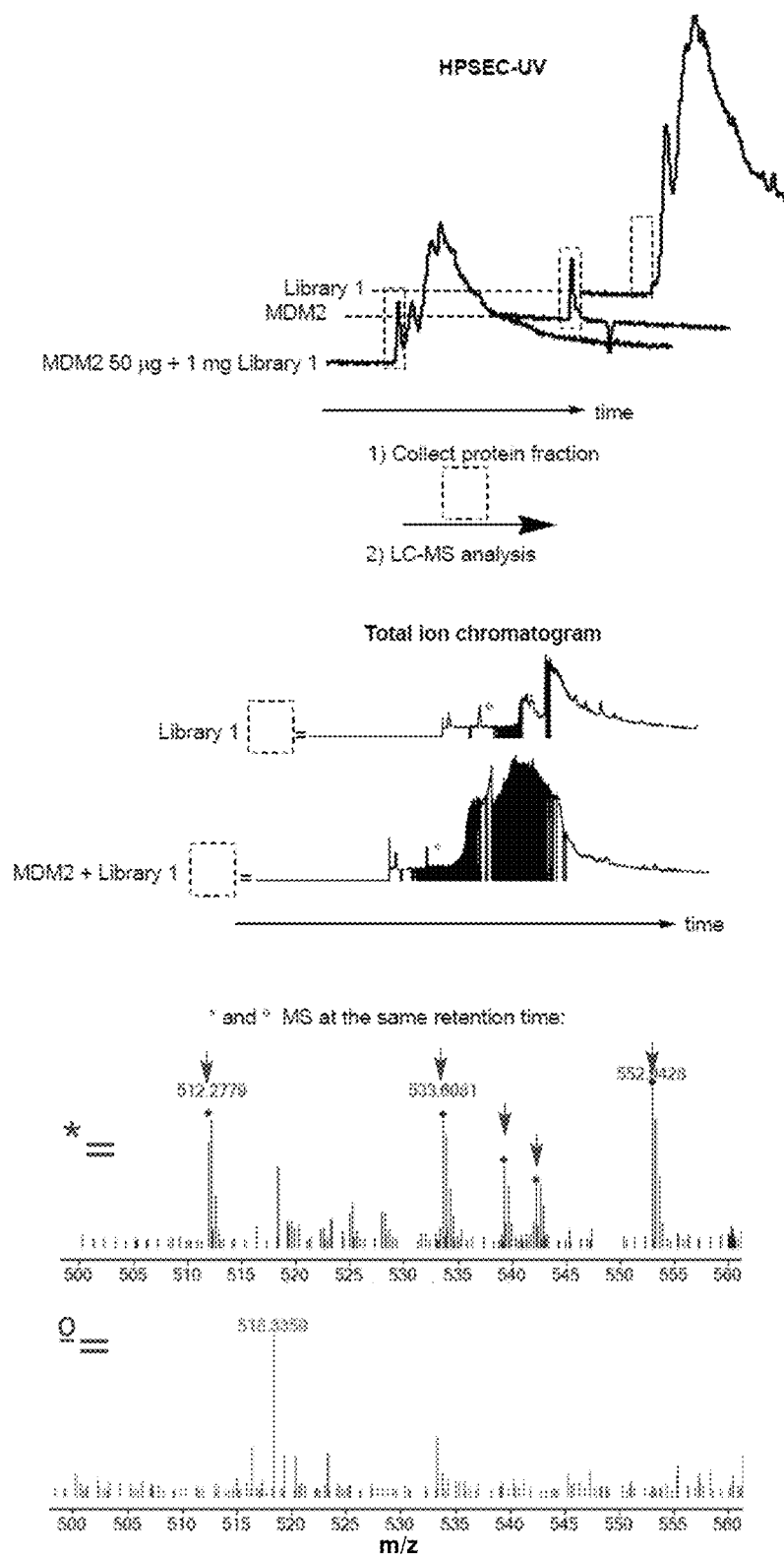
FIG. 35: Affinity selection using Library 1 yields 18 putative binders. Top, MDM2 (20 µg, 8.5 µM) was resolved from Library 1 (1 mg, ~6.50 mM) during HPSEC and protein fraction retention times (dashed boxes) were collected and analyzed using LC-MS. Bottom, total ion chromatogram inspection and direct comparison of mass spectra at the same retention times demonstrates specific selection of Library 1 members (arrows).
Figure 37:
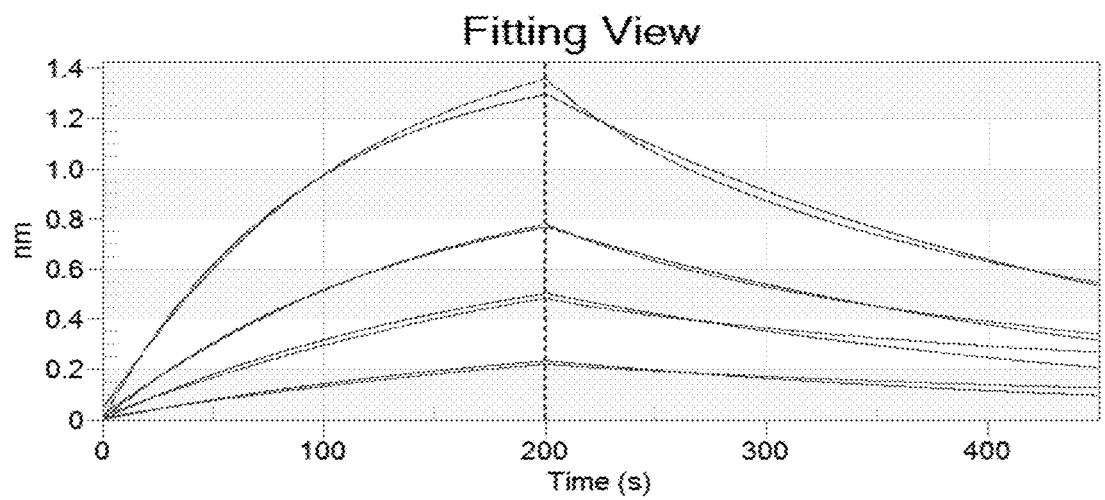
FIG. 37: Global fitting of association and dissociation curves of various concentrations of SUMO-$^{25-109}$ MDM2 (100 nM, 50 nM, 25 nM and 12.5 nM) with biotin labeled peptide 1a immobilized to streptavidin sensors. The $K_D$ was found to be 45 f 1 nM. Coefficient of determination $R^2$=0.9959.
Figure 38:
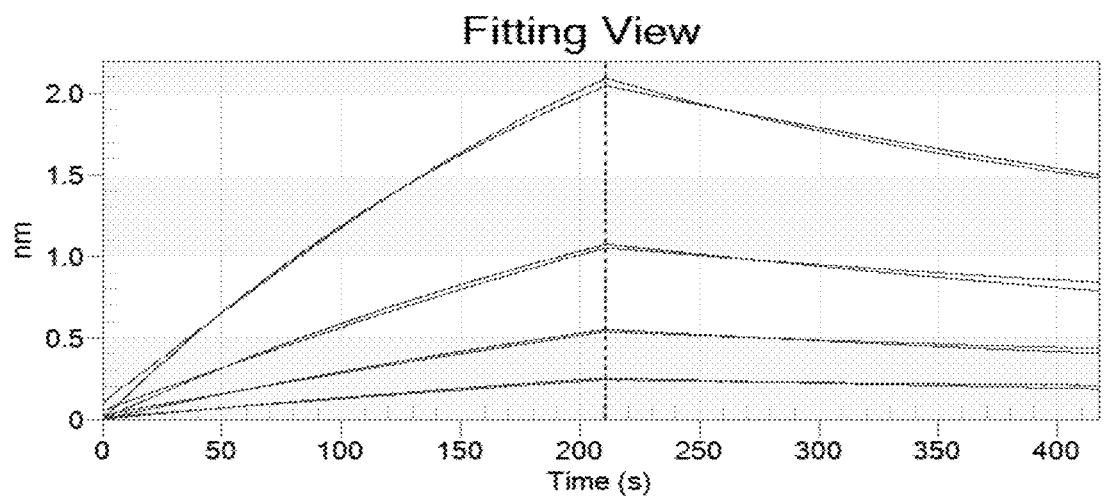
FIG. 38: Global fitting of association and dissociation curves of various concentrations of SUMO-$^{25-109}$ MDM2 (100 nM, 50 nM, 25 nM and 12.5 nM) with biotin labeled peptide 2a immobilized to streptavidin sensors. The $K_D$ was found to be 59±1 nM. Coefficient of determination $R^2$=0.9987.
Figure 39:
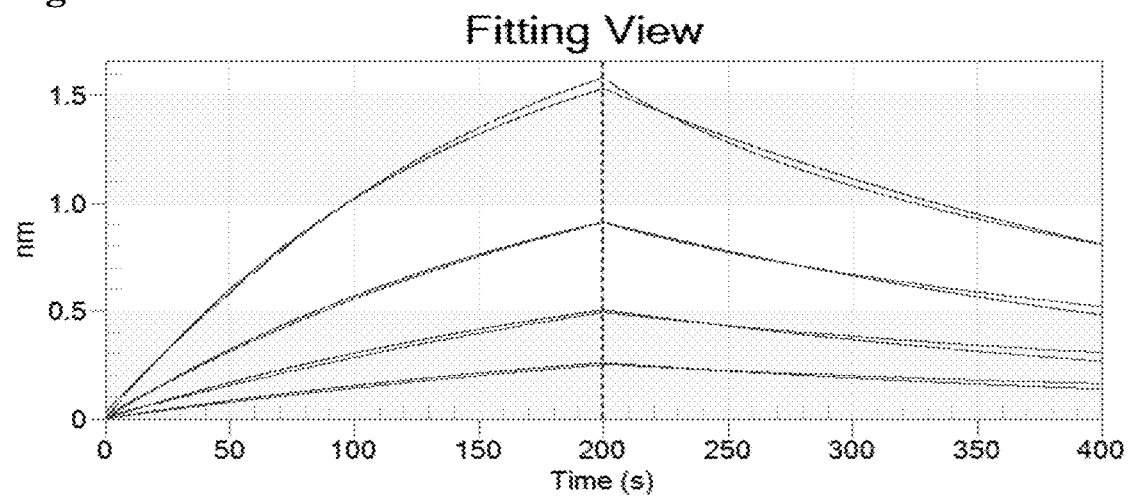
FIG. 39: Global fitting of association and dissociation curves of various concentrations of SUMO-$^{21-109}$ MDM2 (100 nM, 50 nM, 25 nM and 12.5 nM) with biotin labeled peptide 3a immobilized to streptavidin sensors. The $K_D$ was found to be 86±2 nM. Coefficient of determination $R^2$=0.998.
Figure 40:
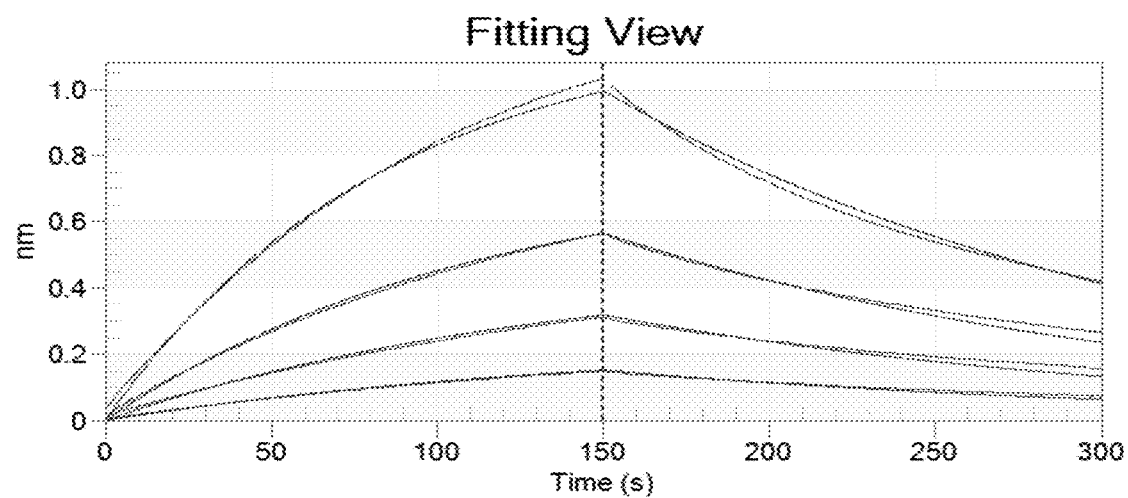
FIG. 40: Global fitting of association and dissociation curves of various concentrations of SUMO-25-109 MDM2 (100 nM, 50 nM, 25 nM and 12.5 nM) with biotin labeled peptide 4a immobilized to streptavidin sensors. The $K_D$ was found to be 96±2 nM. Coefficient of determination $R^2$=0.997.
Figure 42:
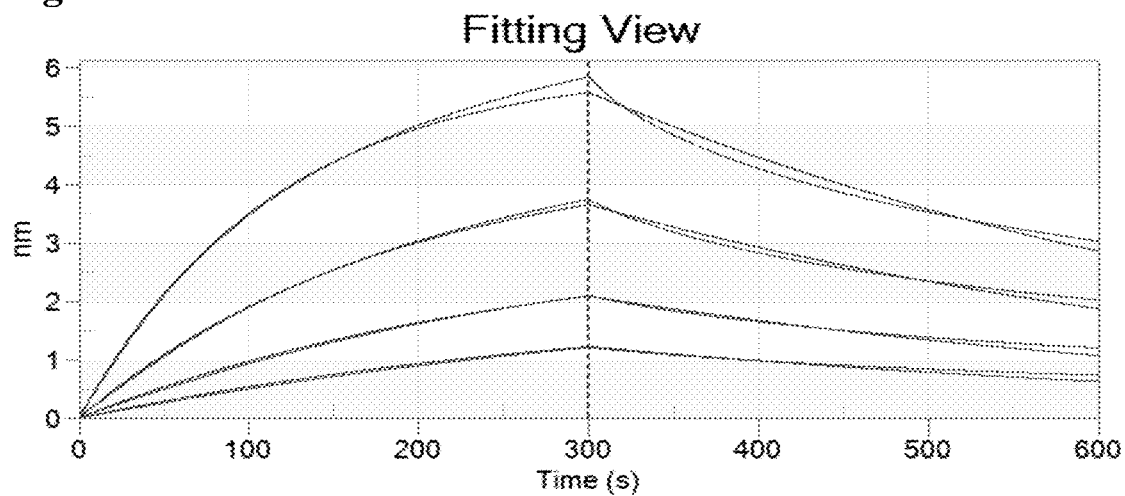
FIG. 42: Global fitting of association and dissociation curves of various concentrations of SUMO-$^{25-109}$ MDM2 (200 nM, 100 nM, 50 nM and 25 nM) with biotin labeled peptide 38a immobilized to streptavidin sensors. The $K_D$ was found to be 58 t 0.5 nM. Coefficient of determination $R^2$=0.9976.
Figure 43:
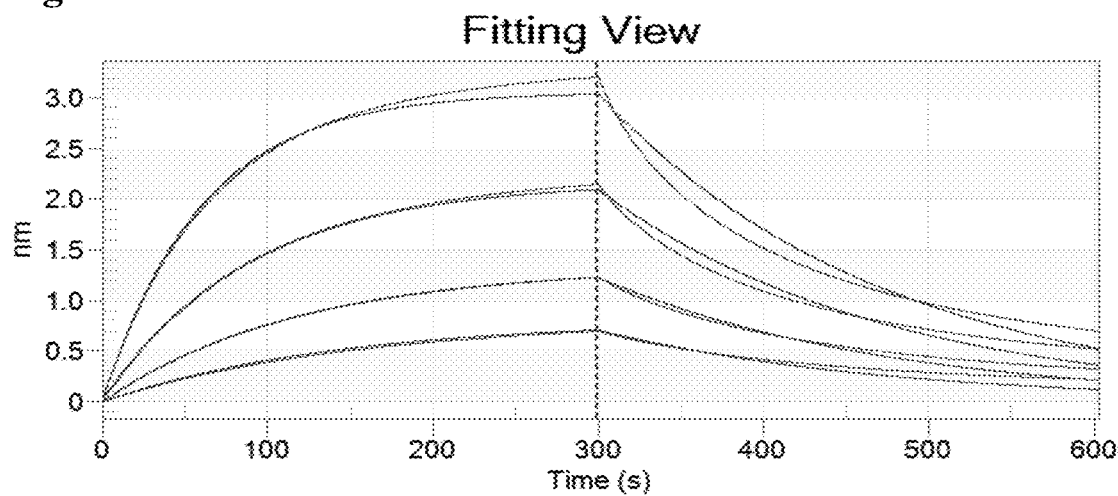
FIG. 43: Global fitting of association and dissociation curves of various concentrations of SUMO-$^{26-109}$ MDM2 (200 nM, 100 nM, 50 nM and 25 nM) with biotin labeled peptide 39a immobilized to streptavidin sensors. The $K_D$ was found to be 140±2 nM. Coefficient of determination $R^2$=0.9921.
Figure 44:
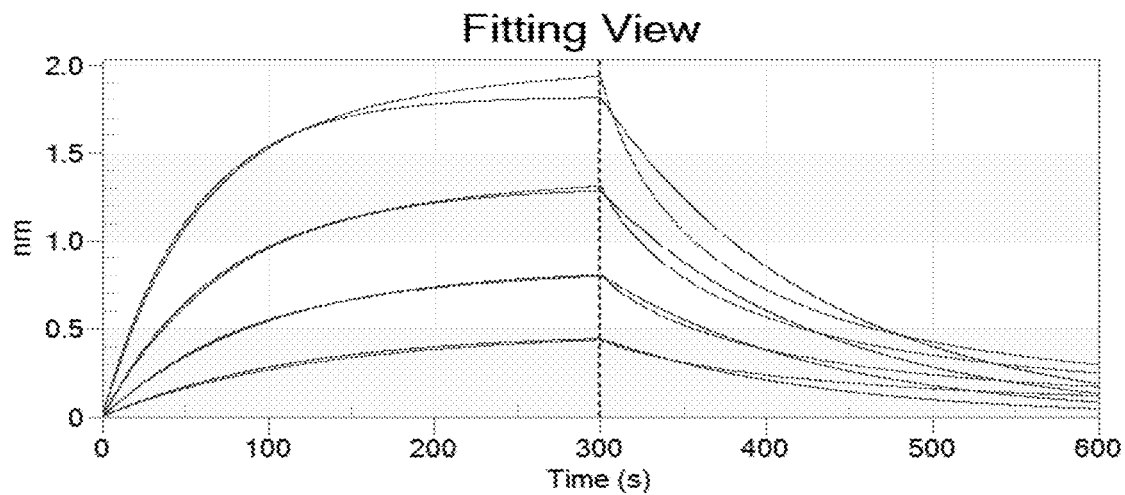
FIG. 44: Global fitting of association and dissociation curves of various concentrations of SUMO-$^{25-109}$ MDM2 (200 nM, 100 nM, 50 nM and 25 nM) with biotin labeled peptide 40a immobilized to streptavidin sensors. The $K_D$ was found to be 160±3 nM. Coefficient of determination $R^2$=0.987.
Figure 45:
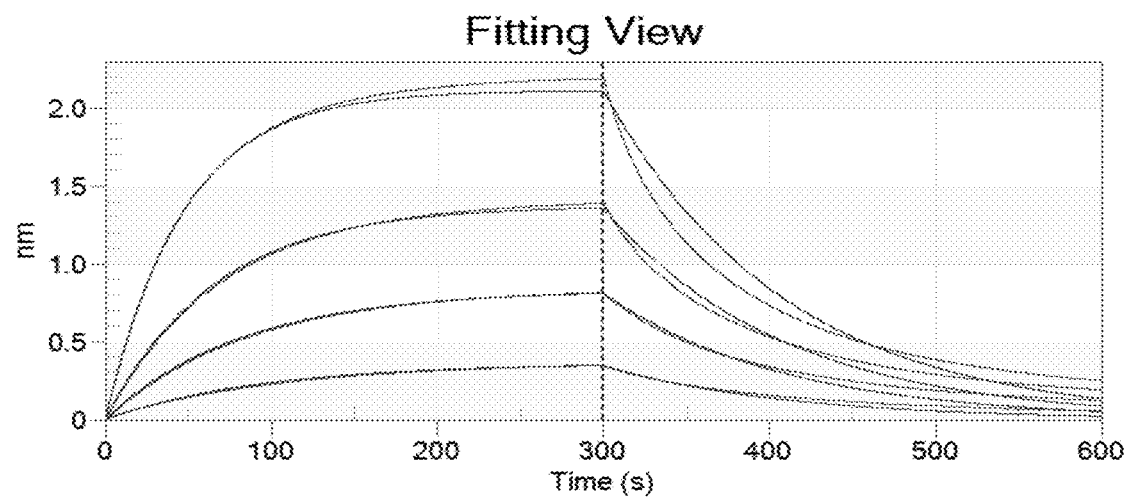
FIG. 45: Global fitting of association and dissociation curves of various concentrations of SUMO-$^{25-109}$ MDM2 (200 nM, 100 nM, 50 nM and 25 nM) with biotin labeled peptide 41a immobilized to super streptavidin sensors. The $K_D$ was found to be 220±3 nM. Coefficient of determination $R^2$=0.9926.
Figure 46:
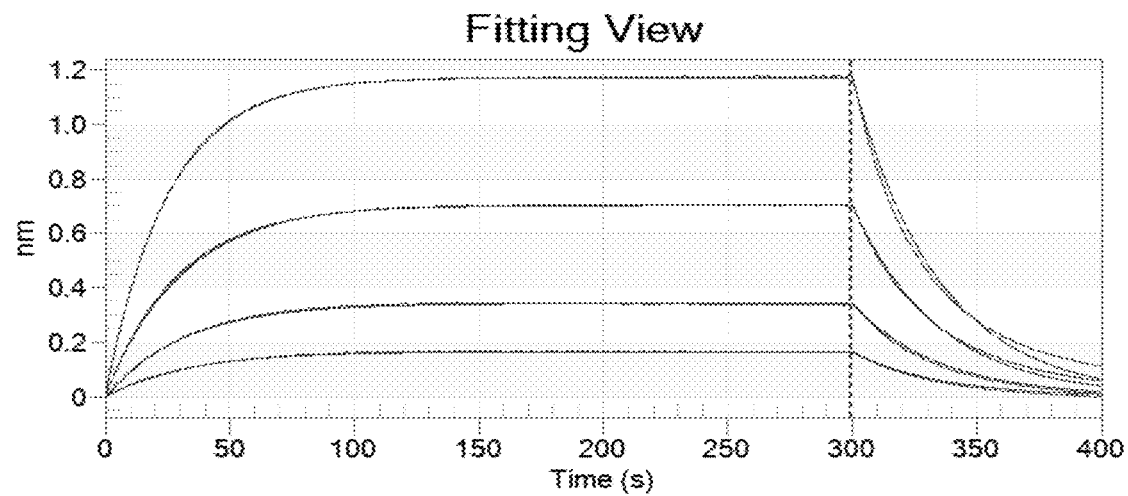
FIG. 46: Global fitting of association and dissociation curves of various concentrations of SUMO-$^{25-109}$ MDM2 (200 nM, 100 nM, 50 nM and 25 nM) with biotin labeled peptide 42a immobilized to streptavidin sensors. The $K_D$ was found to be 530±8 nM. Coefficient of determination $R^2$=0.9994.

To illustrate its efficacy, the thoroughly studied p53-MDM2 PPI was selected as a benchmark [12] and it was first aimed to re-extract critical information on how pDI (6), a p53-like peptide, binds MDM2 using usual L-configured amino acids. Classically, such insights are obtained through systematic mutational studies like Ala-scanning [13], though combinatorial approaches using phage display have also been reported [14]. Library 1 was designed and synthesized (FIGS. 2A and 21) by randomizing residues of peptide 6 and screened this library of one million peptides against MDM2 (FIGS. 2B and 35-36). More than 20 binder were affinity selected and MS/MS sequenced, (FIG. 36) four of which were randomly picked, and after resynthesis and N-terminal biotinylation (1a to 4a) were validated for binding using Bio-Layer Interferometry (BLI, FIG. 2B). It was determined that these sequences had nanomolar affinities to MDM2 and further analysis showed that all identified sequences have in a common the (F, W, L) triad (FIGS. 2B and 36) confirming the well documented result [13], [14] that these residues are required for high affinity binding to MDM2. To gain further insights on the mutational tolerance of these hotspots Library 2 was prepared, where these critical residues are randomized (FIG. 2A). Screening this library at different stringencies (FIGS. 25-26) yielded five sequences including reference 6 (5a to 9b) that were resynthesized (FIGS. 2B and 27) for validation. The commonality between these binders is the conservation of the $^7$Trp central hotspot, suggesting that it is imparting a high binding energy contribution, another well-known result for p53-derived binders [15]. On the other hand, mutation of $^{10}$Leu to Phe (5a) still yielded a nanomolar binder suggesting that MDM2 binding pocket for this residue can tolerate larger hydrophobic residues, while by contrast mutation to more polar Tyr (7a) significantly weakened binding. Likewise, mutating $^3$Phe to Leu or Tyr (8a and 9a) significantly weakened the binding to MDM2 indicating that $^3$Phe binds optimally to MDM2 pocket. Taken together these results demonstrate that with a few simple experiments the affinity selection approach provides a robust guide to rapidly gain molecular insights on the binding mode of 6 with MDM2.

Figure 2D:
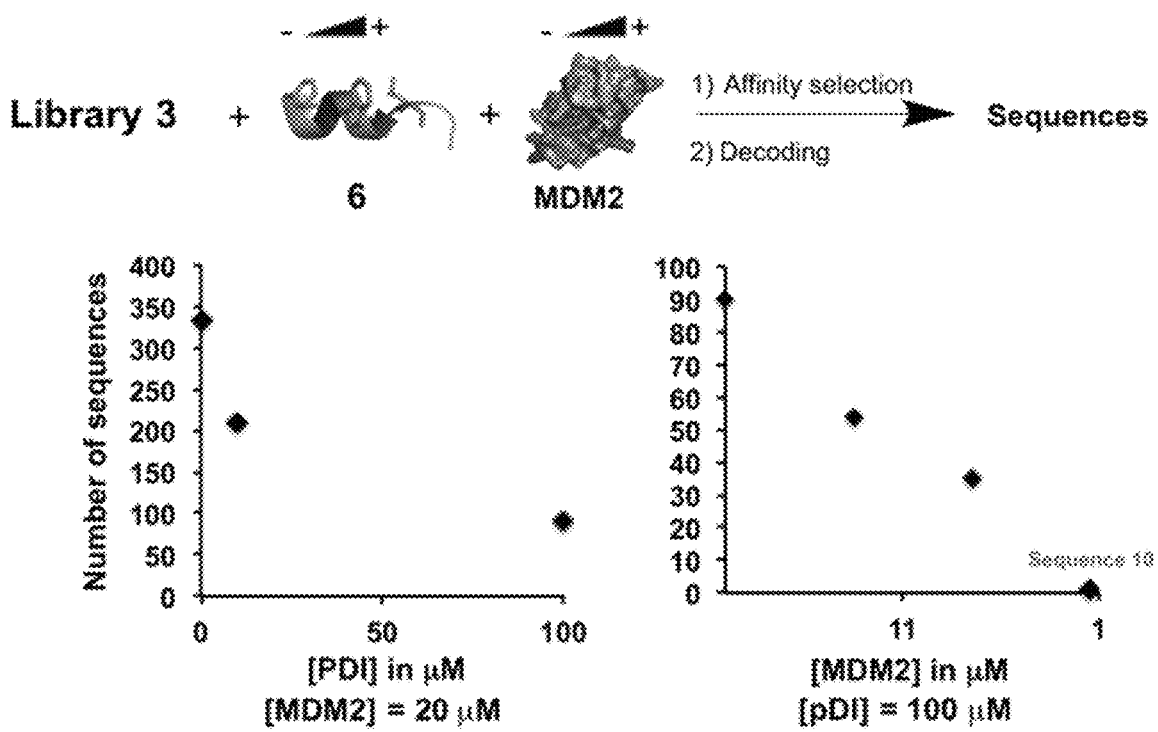

Then, to discover non-canonical binders to MDM2, the three hot spots of linear 6 were randomized by using non-canonical L-configured amino acids spanning different side chain hydrophobicity, rigidity and sterics (Library 3, FIG. 2C). By contrast to Library 2, the first screens allowed for the specific selection of hundreds of sequences suggesting that non-canonical side chains favor binding to MDM2 pocket. Resynthesis and validation of five random sequences with high de novo sequencing scores (Average Local Confidence, ALC, FIG. 41) showed that these binders have lower affinities than 6 for MDM2. In order to discover superior affinity inhibitors, the stringency of the selections was increased (FIGS. 2D and 47) by adding an excess of 6 as a soluble competitor. Increasing progressively 6 concentrations lowered the number of sequences able to reach MS/MS threshold indicating that ion counts for these sequences are dramatically diminishing (FIGS. 2D and 47). Moreover, since protein concentration plays an essential role both in the HPSEC assay (FIG. 15) and for in solution competition, lowering progressively the latter drastically diminished the number of sequences reaching MS/MS threshold to only one single sequence (FIGS. 2D and 47). Then, 20 non-canonical sequences that were both affinity selected and efficiently sequenced even when high concentrations of 6 were selected for resynthesis and validation (FIGS. 2E and 48). Notably, the sequence (FIGS. 47-48) that resisted best these stringent conditions was also found to be a high affinity binder (10a, FIG. 2F) and was further validated by an orthogonal label free in solution competition assay (peptide 10b, FIG. 48), confirming its low nanomolar affinity to MDM2 and the ability of the stringency conditions to distinguish sequences based on their affinity. Within this list of 20 sequences, in contrast to Library 2, 7Trp was advantageously replaced by the flexible and hydrophobic hexyl alanine, the bulky Anthryl alanine or the 2-naphthyl alanine residues to yield nanomolar binders to MDM2. These findings underline the remarkable plasticity of MDM2 binding pocket around this hotspot (FIG. 2E and FIG. 48) and suggest these residues have a different binding mode than $^7$Trp for which the indole nitrogen is reported to be involved in a critical hydrogen bond with MDM2 backbone [15]. Invariably, $^3$Phe was replaced for these high affinity binders only by more hydrophobic fluorinated phenylalanines while $^{10}$Leu was replaced by bulkier hydrophobic side chains including cyclobutyl alanine, cyclohexyl alanine or fluorinated phenylalanines (FIG. 48). Only one false positive was found among this list and corresponded to one of the sequences with the poorest ALC score. Importantly, as illustrated with 10a and 11a (FIG. 48), these non-canonical sequences also retained their potential for dual MDMX inhibition. Furthermore, replacing $^7$Trp which may be prone to degradation [16] by inert non-canonical side chains opens up the possibility of discovering bioactive peptides with superior metabolic stability, an important requirement for hit to lead maturation in the context of drug discovery. The results suggested that even for a thoroughly studied PPI like p53/MDM2 this affinity selection approach can rapidly shed new light on the molecular requirements of MDM2 binding and that such findings may inspire the design of novel peptidomimetic inhibitors to strike MDM2 based on these non-canonical side chains.

To confirm the generality and robustness of this approach, the use of non-canonical side chains was extended to CAI (37) a micromolar allosteric binder to C-terminal capsid domain (C-CA) that inhibits the dimeric interface of HIV capsid protein [17]. A similar approach was used, and reported [18] interaction hot spots of CAI were randomized using the same non-canonical amino acid set (Library 4, FIG. 2C. In this case, only a handful of sequences (including 37 itself) were detected and sequenced (FIG. 72) and most of these had in common the replacement of $^5$Leu by cyclobutyl alanine (FIG. 2E). C-terminal biotinylation of these sequences and their validation allowed for the discovery of 30a a nanomolar peptide binder to C-CA (FIGS. 2E, 2F and 72) an attractive finding since further development of CAI based inhibitors has not been considered due to their low affinity [19].

Figures 3A, 3B:
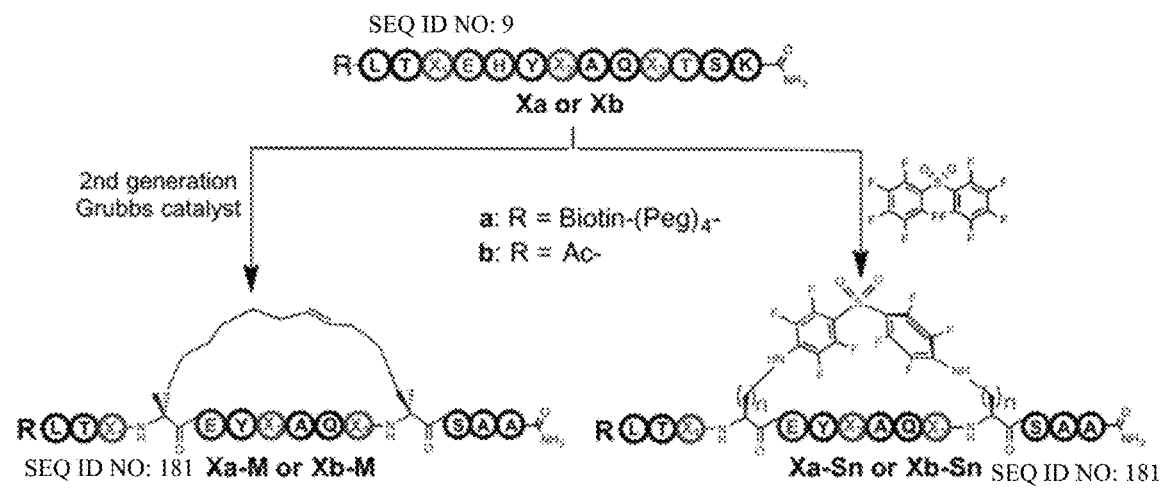
FIGS. 3A-3F: Affinity selected non-canonical sequences were macrocylized and used for the discovery of potent macrocyclic inhibitors.

To illustrate further the usefulness of the approach, the discovery platform was merged with peptide macrocyclization chemistry to illustrate the rapid discovery of bioactive non-canonical PPI inhibitors. Using well established chemical transformations of peptides [4], non-canonical sequences discovered by affinity selection from Library 3 (FIG. 3A) were macrocyclized and only 3 sequences and 4 marocyclic binders were found to have low nanomolar affinities to MDM2 (FIG. 3B, FIG. 82). Interestingly these sequences have all in common the presence of difluorinated phenylalanine and cyclobutyl alanine side chains while the central hotspot was a hexylalanine, Napthylalanine or Trp residue (FIG. 3B). Furthermore, 11 was the only non-canonical sequence to be compatible with perfluorosulfone stapling, underlining the more demanding structural requirements for perfluoroaryl stapling, a trend also observed with the exemplary marocyclization and affinity selection of Library 6 (FIGS. 115-118). Notably, peptide 11b-S1 is the first reported low nanomolar perfluoroaryl cyclized MDM2 binder. Similarly, using i and i+4 macrocyclization scheme [4] [20], non-canonical C-CA binding sequences were stapled and 30a-M a tight macrocyclic C-CA binder was obtained with higher affinity than the reference bioactive NYAD peptide (37a-M) (FIG. 109).

Figure 3C:
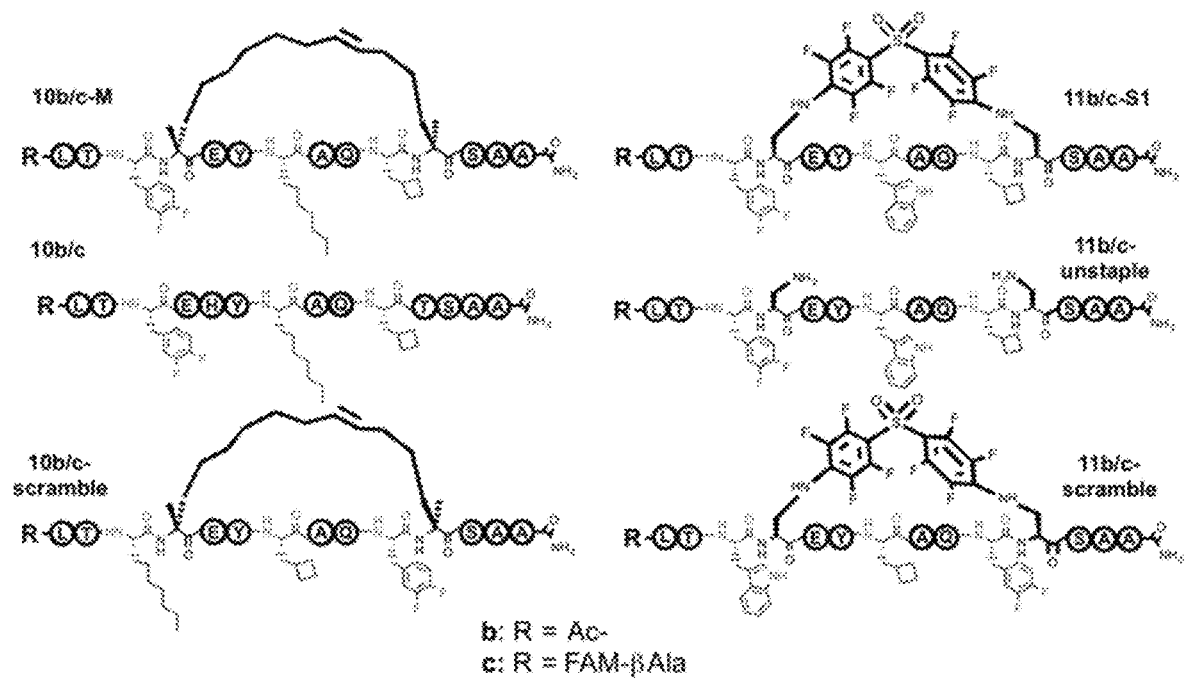
Figure 3D:
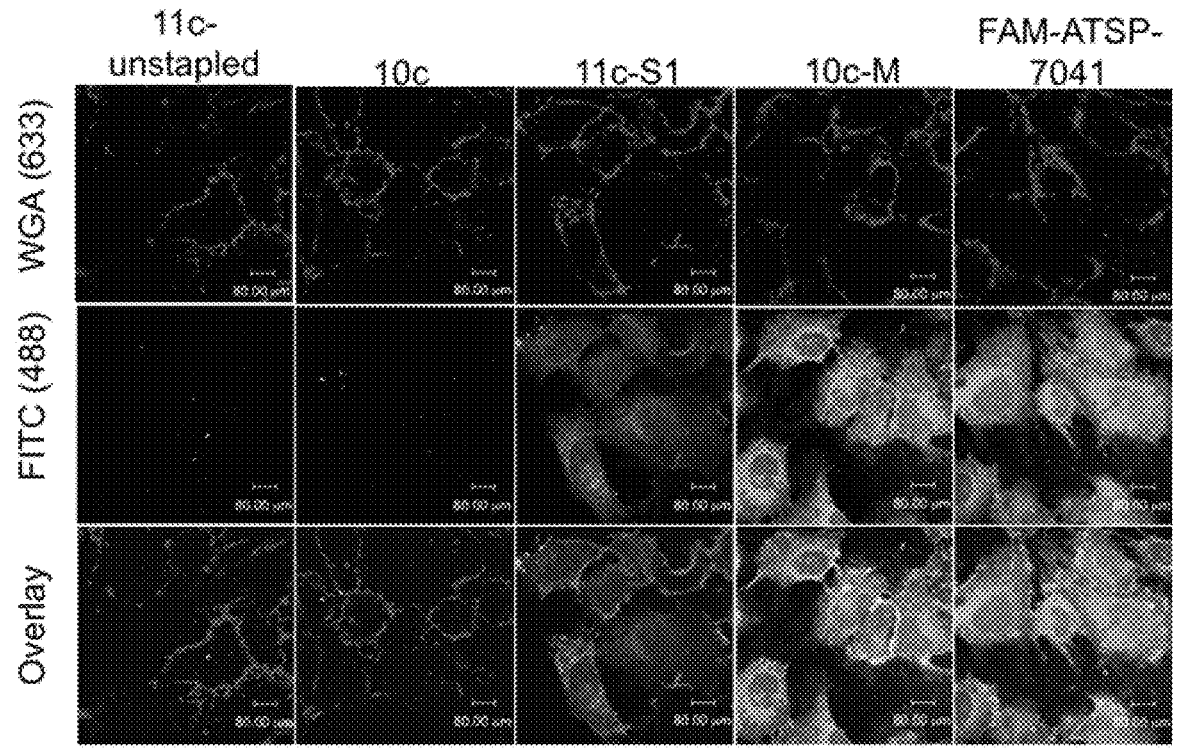
Figure 3E:
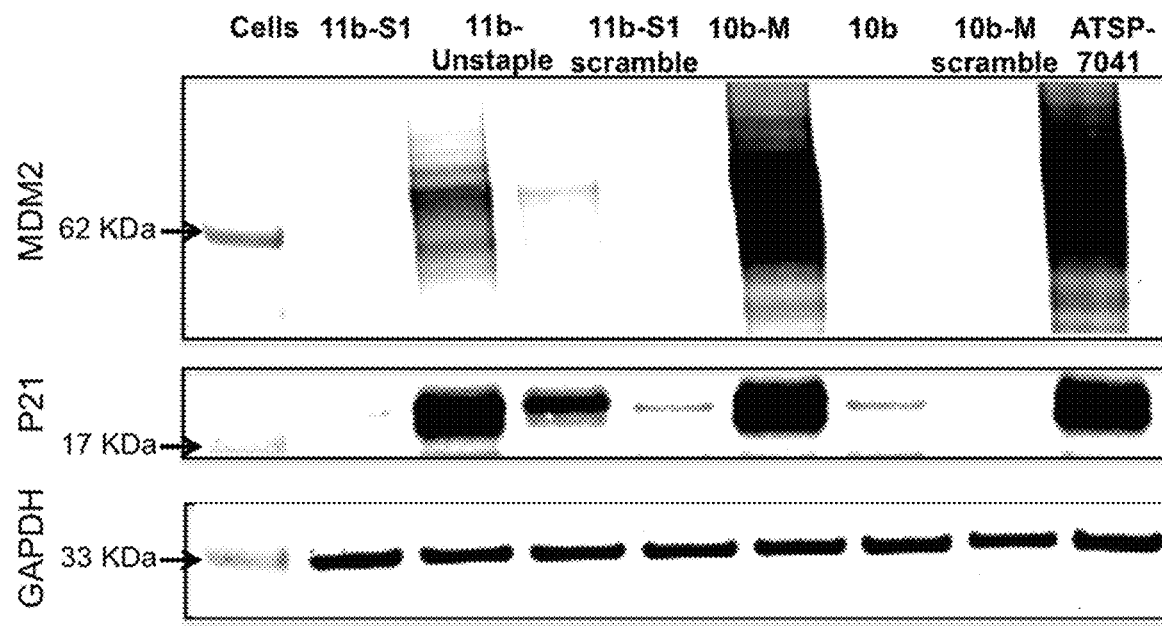
Figure 3F:
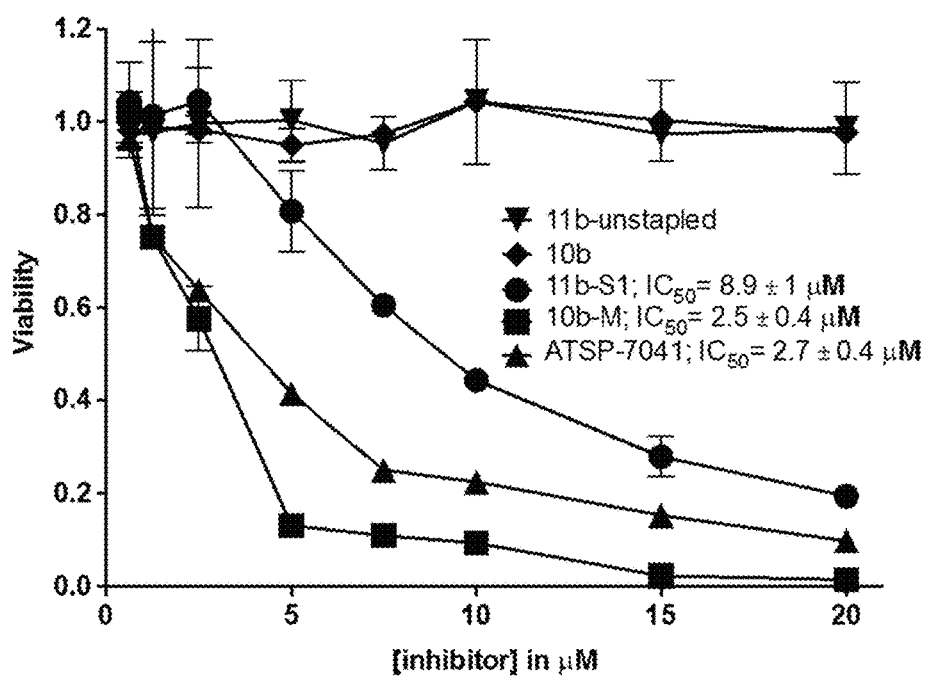
Figure 99:
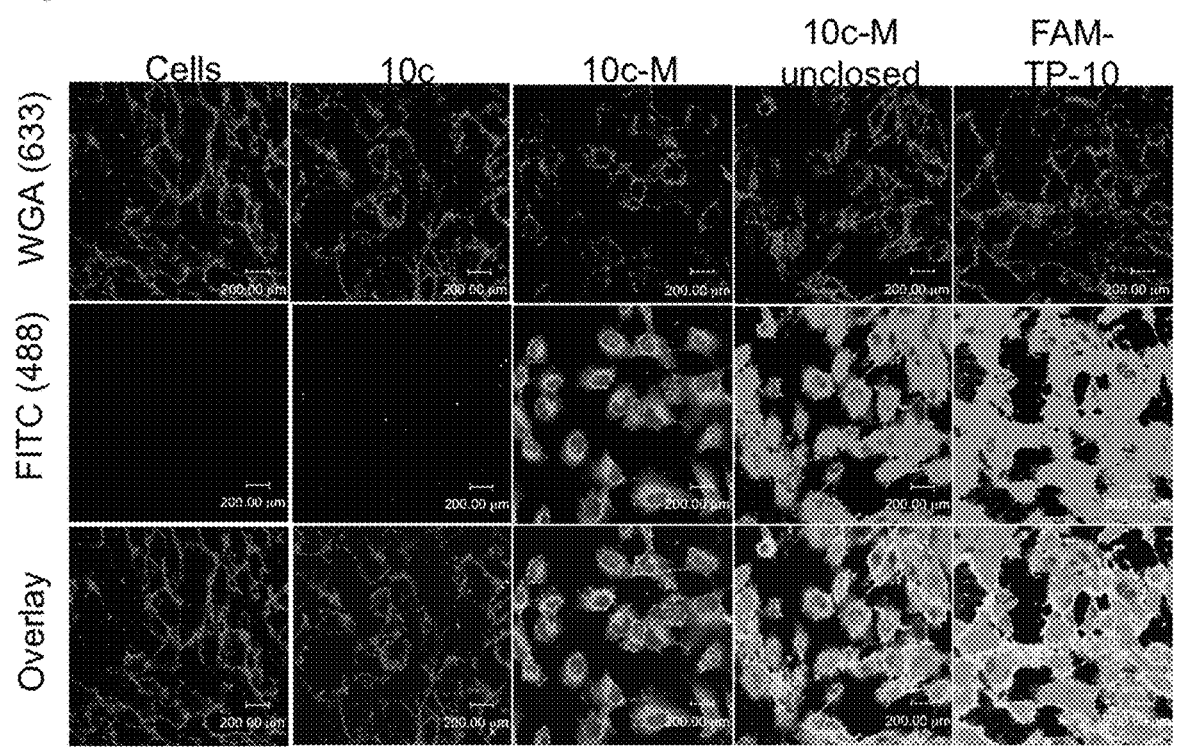
FIG. 99: Confocal imaging of fixed cells shows cytosolic FITC signal for non-canonical peptides in RCM series. Confocal microscopy images of SJSA-1 cells treated with 10 μM FITC-conjugated macrocyclic peptides in the RCM series and their linear controls (FIGS. 3C and 8I). Images were normalized using PMT=470 V in channel 488 corresponding to black image for Cells (0.1% DMSO treated) condition.
Figure 100:
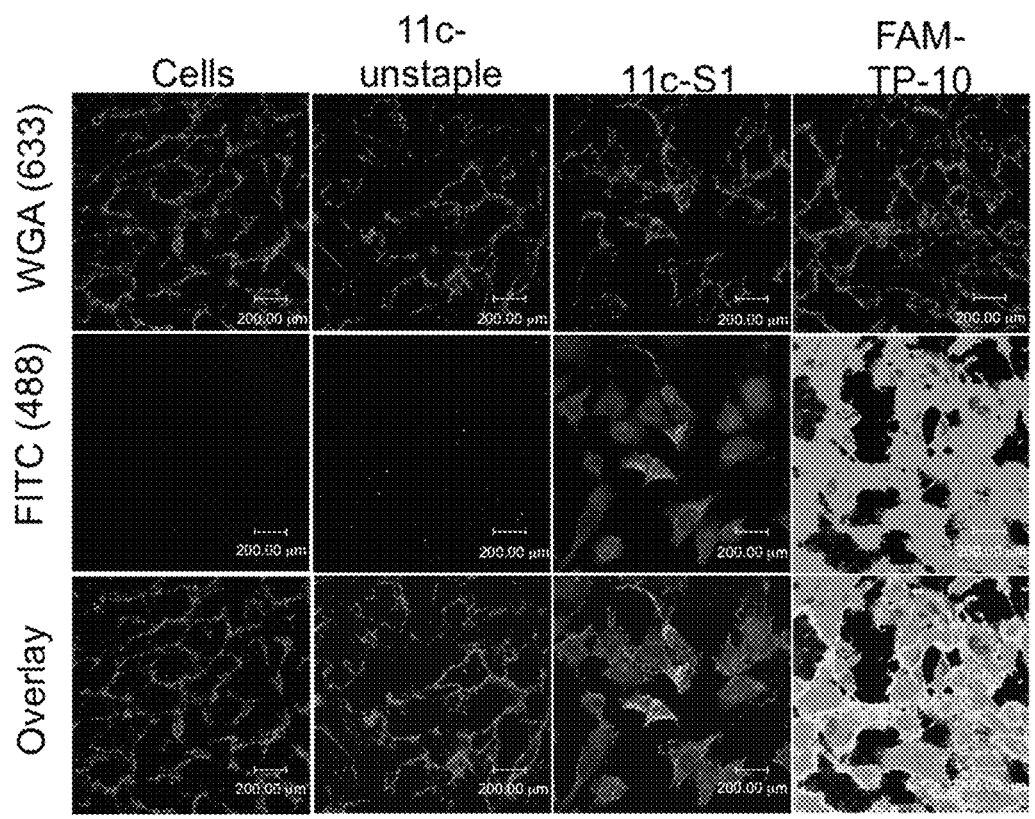
FIG. 100: Confocal imaging of fixed cells shows cytosolic FITC signal for non-canonical macrocyclic peptides in sulfone series. Confocal microscopy images of SJSA-1 cells treated with 10 μM FITC-conjugated macrocyclic peptides in the perfluorosulfone series and their linear controls (FIGS. 3C and 8I). Images were normalized using PMT=470 V in channel 488 corresponding to black image for Cells (0.1% DMSO treated) condition.
Figure 102:
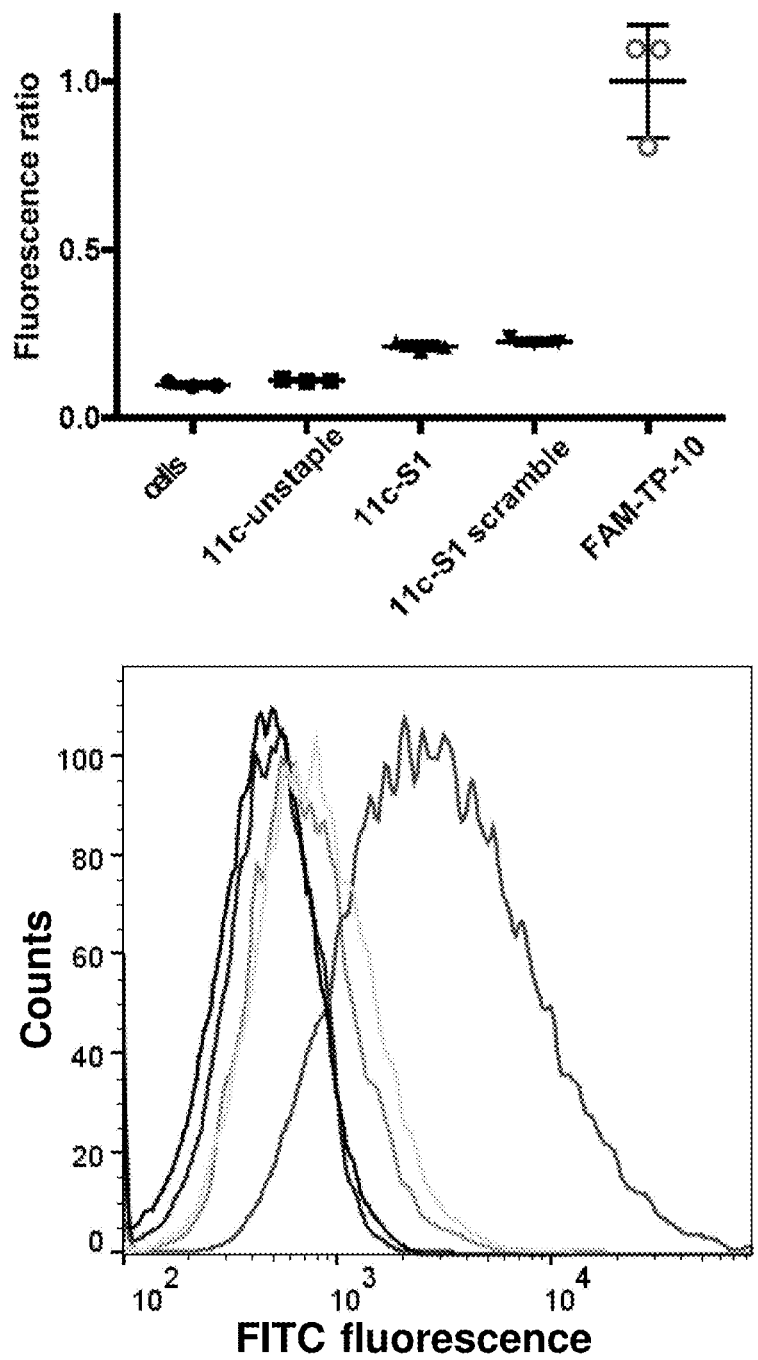
FIG. 102: Flow cytometry analysis confirmed cellular loading with FITC labeled non-canonical peptide in sulfone series. Intracellular loading of perfluorosulfone macrocyclized constructs (10 μM) and controls (FIGS. 3C and 8I) was assessed by FACS. Impermeant trypan blue was used to quench extracellular fluorescence. Mean fluorescence was normalized to FAM-TP-10 a fluorescein labeled cell-penetrating peptide[3]. The horizontal bar represents the mean of three measurements (n=3) within the same experiment. Error bars represent standard deviation of the mean. Each peptide was assayed three times. This experiment was performed one time.
Figure 103:
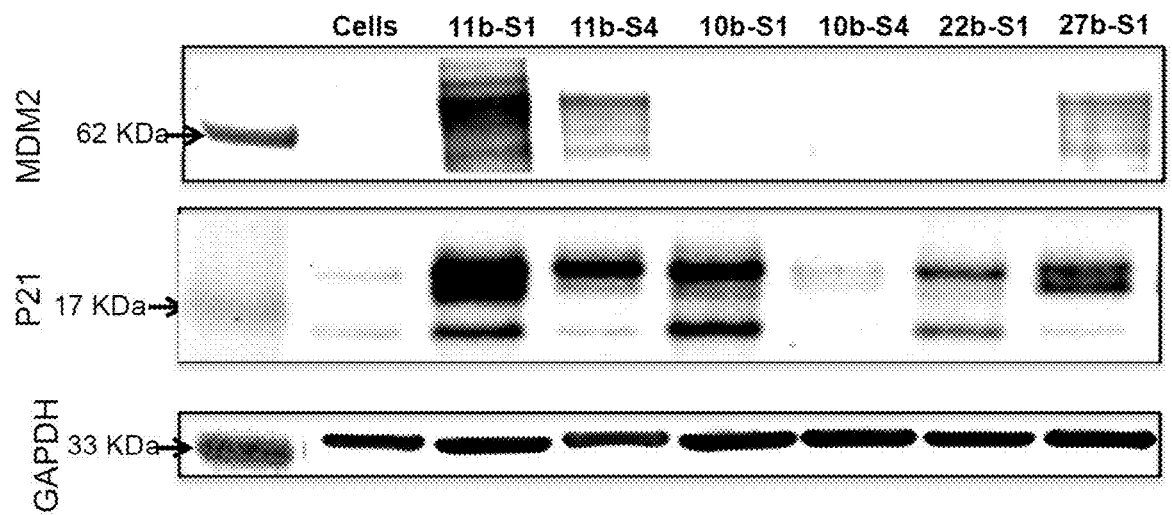
FIG. 103: Low nanomolar 11b-S1 macrocyclic inhibitor substantially upregulated MDM2 and P21. Comparison of perfluorosulfone macrocyclized peptides (FIG. 82) using western blot analysis (10 μM). Peptide 11b-S1 upregulated p53 gene products p21 and MDM2 by contrast to other macrocyclic constructs with weaker affinity or impeded MDM2 or 0.1% DMSO treated control (Cells). This experiment was performed one time, upregulation of MDM2 and p21 for peptide 11b-S1 was confirmed in at least 3 independent experiments.
Figure 104:
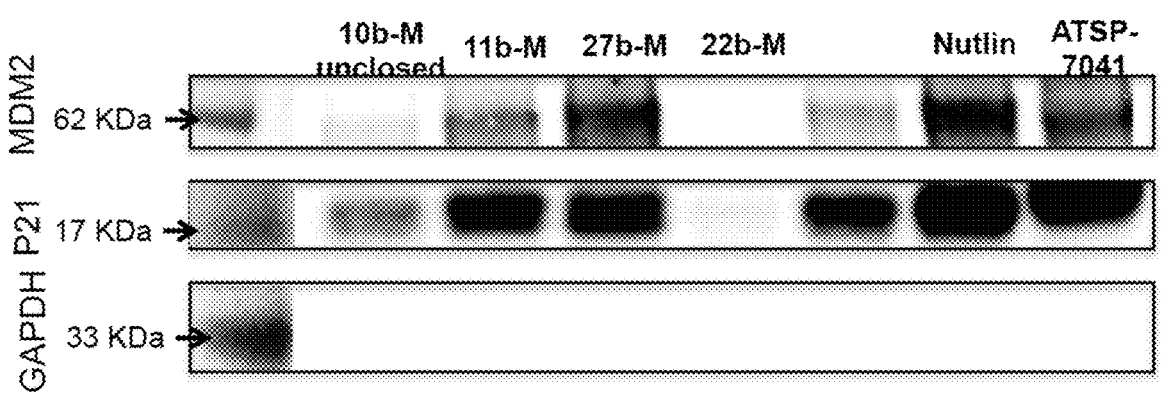
FIG. 104. Low nanomolar 11b-M and 27b-M macrocyclic inhibitors substantially upregulated MDM2 and P21. Comparison of RCM peptides (FIG. 82) using western blot analysis (10 μM). Macrocyclic peptides 11b-M and 27b-M upregulated p21 and MDM2 while lower affinity linear 10b-M unclosed had a more limited effect and 22b-M with impeded binding had no effect. This experiment was performed one time.
Figure 105:
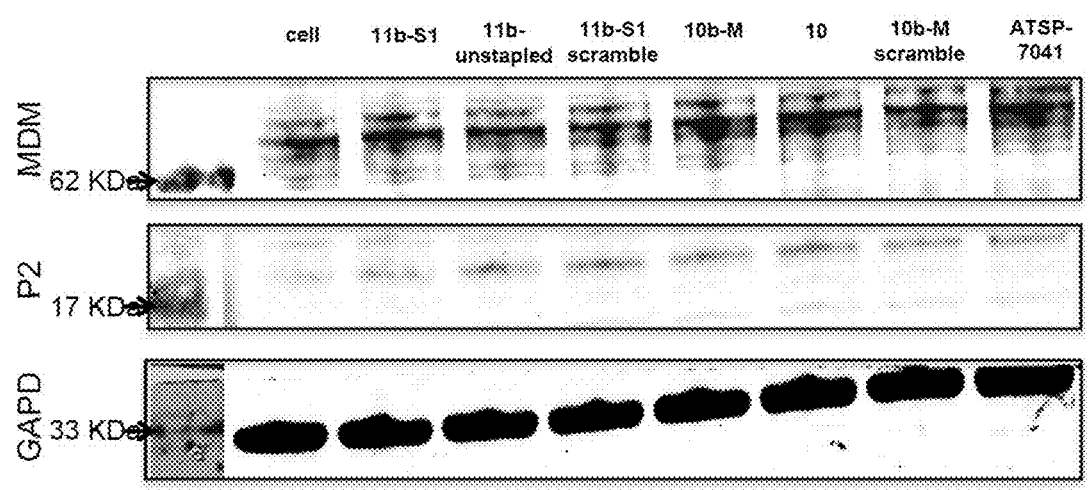
FIG. 105: Upregulation of p21 and MDM2 is specific to p53 positive cells. Absence of upregulation of p21 and MDM2 in p53 null K562 cells for bioactive peptides and their inactive controls (FIG. 82, 10 μM). Absence of upregulation of p21 and MDM2 in p53 null K562 cells for active compounds and their inactive controls was illustrated using western blot analysis (10 μM concentration). This experiment was performed one time.
Figure 106:
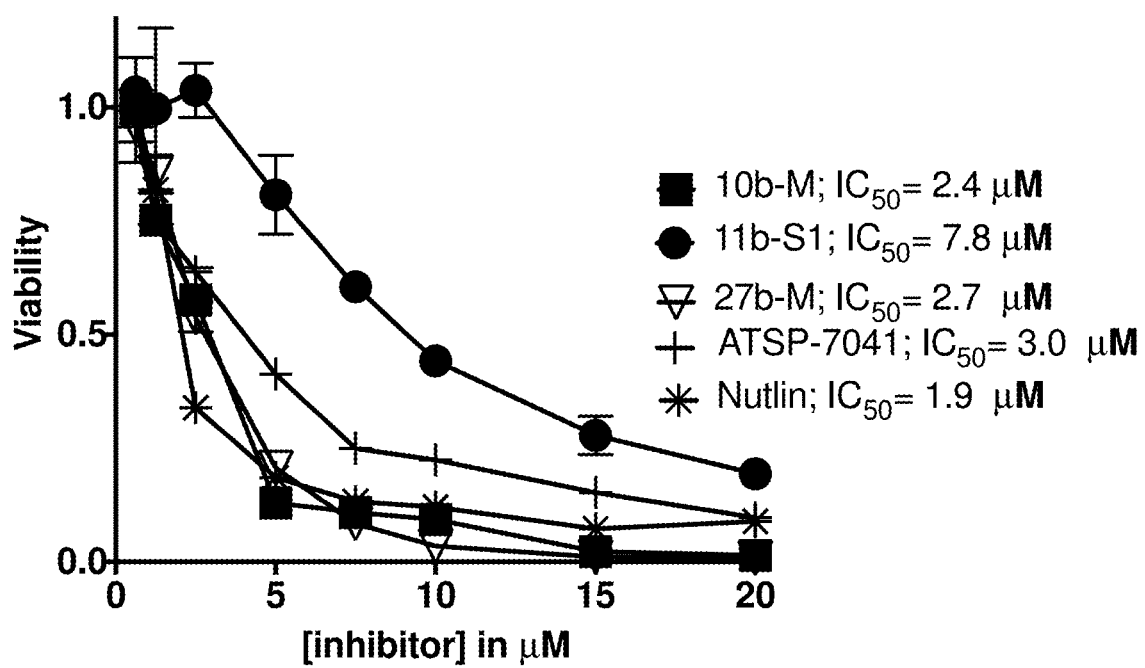
FIG. 106: Active non-canonical macrocyclic inhibitors kill SJSA-1 cells at low micromolar concentrations. Potency comparison for bioactive macrocyclic inhibitors (FIGS. 3E and 104). Non-canonical side chain containing macrocyclic peptides were compared to positive controls ATSP-7041 and Nutlin-3.
Figure 108:
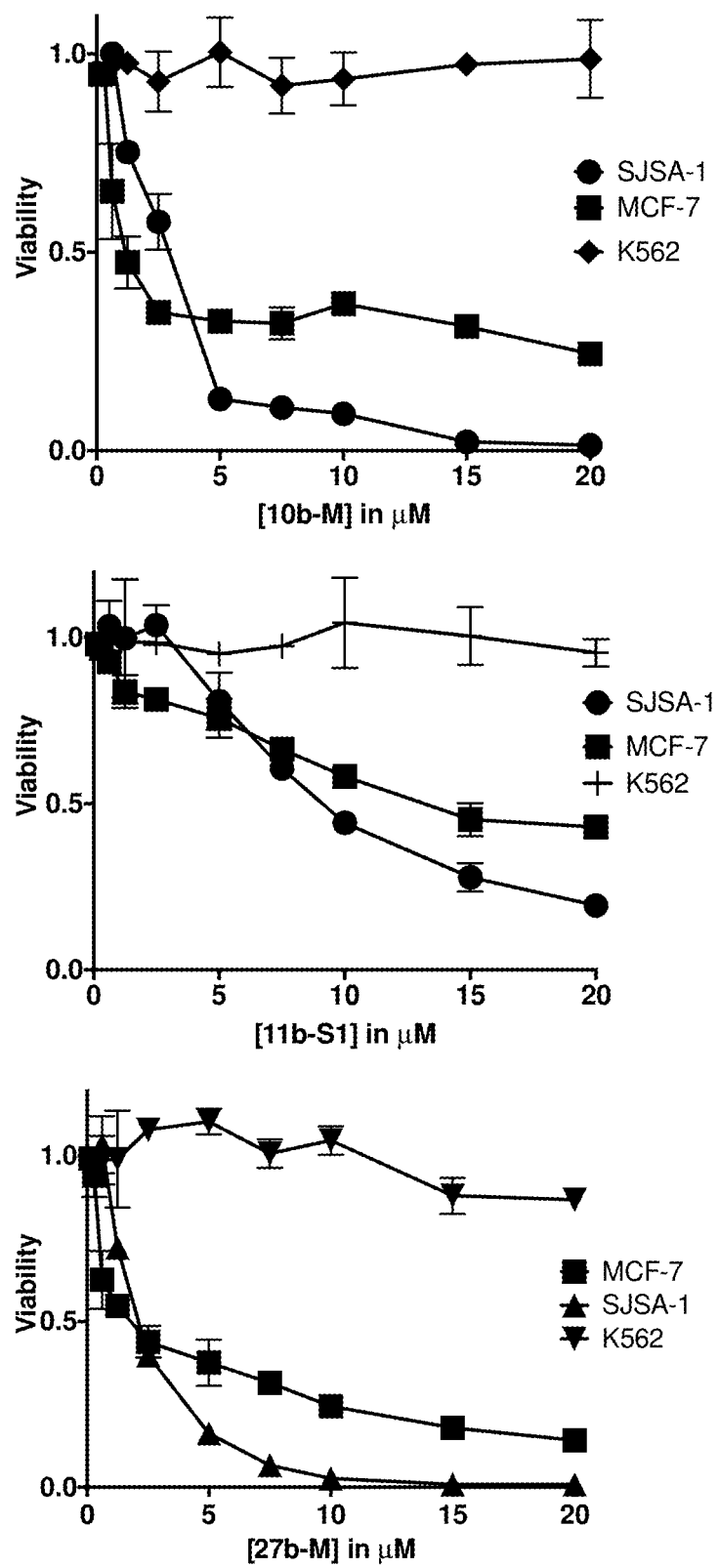
FIG. 108: Active macrocyclic inhibitors killed selectively p53 positive cells at low micromolar concentrations. 10b-M, 11b-S1 and 27b-M non-canonical macrocyclic inhibitors were also tested against MDM2 and MDMX overexpressing cells MCF-7 and p53-null K562 cells. These peptides lowered viability for MCF-7 cells but did not significantly lower K-562 viability, underlining their specific mode of action at the tested concentrations.

The discovered macrocyclic low nanomolar MDM2 binders 10b-M and 11b-S1 were further evaluated along with their controls (FIG. 3C) for their ability to cross cell membranes and lower the viability of MDM2 over expressing cell lines. By contrast to linear controls 10c and 11c-unstapled (FIG. 3C), fluorescein isothiocyanate (FITC) conjugated macrocyclic peptides and linear 10c-M unclosed showed appreciable intracellular loading as evidenced by confocal imaging (FIGS. 3D and 99-100) and confirmed by flow cytometry (FIGS. 101-102). However, only low nanomolar binding macrocyclic inhibitors were found to activate p53 transcription factor to levels comparable to positive controls ATSP-7041 and Nutlin-3a [21](FIGS. 3E and 103-105) as evidenced by western blot analysis of p53 gene products. Remarkably, this feature translates into a potent killing of osteosarcoma SJSA-1 cells for these tight binders while peptides with lower affinity to MDM2 or limited cell penetration did not appreciably diminish the viability of these MDM2 overexpressing cells (FIGS. 3F, 106-107) at low micromolar concentrations. The incubation of these macrocyclic killers with MCF-7, an MDM2 and MDMX overexpressing breast cancer cell line, also led to lowered viability at low micromolar concentrations in contrast to K562 p53-null cells where no dose dependent killing was observed at these concentrations (FIG. 108), underlining the selectivity of their killing mechanism.

Finally, in an effort to extend the discovery of PPI inhibitors to highly attractive [3], and large (>30 mer) non-proteinogenic peptide scaffolds, an all D-configured mini-protein capable of binding MDM2 while exhibiting a folded structure [22] was designed (FIG. 4A). The latter entails a D-configured helical binding loop based on D-PMI-β [5b] sequence, fused on its C-terminal end to a D-configured cystine-stabilized β-sheet domain derived from EETI-II (58) (see, e.g., FIG. 6) knottin [23] (FIG. 4A). To confirm correct folding of this non-natural scaffold, peptide 53-reduced was synthesized and conversion to 53 was demonstrated upon oxidation (FIG. 122). Using a label free approach, the affinity of 53 for MDM2 was also estimated to be about 20 fold lower than 54b the parent DPMI-β based linear binder (FIG. 126). To extend this non-natural structure to non-canonical side chains and discover higher affinity folded mini-protein inhibitors of MDM2, Library 5 was prepared (FIG. 4B). Following a similar strategy to trypsin binding knottin 59 (FIGS. 6, 17, and 19), a diol amino acid was also introduced [24] (FIG. 4B) in this scaffold to allow for in situ oxidative backbone cleavage and sequencing of the affinity selected binders (FIG. 4C). Library 5 was therefore synthesized and folded in solution and its members (~4 KDa) were efficiently resolved from SUMO-$^{25\text{-}109}$ MDM2 (~23 KDa) using HPSEC, therefore allowing for specific selection and sequencing of 18 binders (FIGS. 124-125). These were found to be correctly folded based on the analysis of their mass difference before and after sodium periodate oxidative cleavage (FIG. 125). 10 of these sequences were then selected for resynthesis, folding and validation and determined them to have nanomolar affinities to MDM2 (FIGS. 4D, 126). Surprisingly, 43 like many other validated binders exhibits a flexible alkyl alanine residue as the central hotspot; demonstrating that this flexible side chain is equally efficient in binding MDM2 pocket with high affinity in L and D configurations. By contrast, $^{3}$Trp was completely conserved while $^{10}$Leu was readily replaced by larger hydrophobic side chains paralleling the results for L-configured Library 3 screening.

Taken together, these results demonstrate that the in solution affinity selection platform is particularly suited for the rapid generation, with virtually no false positives (1 false positive for more than 50 resynthesized and validated binders), of novel bioactive chemical matter. In the context of drug discovery these capabilities will prove particularly useful in structure guided approaches where non-canonical side chains may be used both to robustly probe for key binding residues within protein-protein interfaces while allowing for the rapid discovery of highly potent non-canonical inhibitors based on chemical structures of various complexities and sizes. It is envisioned that increasing library sizes (>$10^7$ members) by means of automation coupled to the development of novel scaffolds will dramatically expand the chemical space for structure and function, a powerful prospect to drug the undruggable using this affinity selection platform.

REFERENCES

[1] (a) Wells, J. A.; McClendon, C. L. *Nature* 2007, 450, 7172. (b) Mullard, A. *Nat. Rev. Drug. Discov.* 2012, 1, 11. (c) Scott, D. E.; Bayly, A. R.; Abell C.; Skidmore, J.; *Nat. Rev. Drug. Discov.* 2016, 15, 8. (d) Petta, I.; Lievens, S.; Libert, C.; Tavernier, J.; De Bosscher, K. *Mol. Ther.* 2016, 24, 4.

[2] Modell, A. E.; Blosser, S. L.; Arora, P. S. *Trends Pharmacol. Sci.* 2016, 37, 8.

[3] (a) Pelay-Gimeno, M.; Glas, A.; Koch, O.; Grossmann, T. N. *Angew. Chem. Int. Ed. Engl.* 2015, 27, 54. (b) Milroy, L. G., Grossmann, T. N., Hennig, S.; Brunsveld, L.; Ottmann, C.; *Chem. Rev.* 2014, 14, 114. (c) Cunningham, A. D.; Qvit, N.; Mochly-Rosen, D. *Curr. Opin. Struct. Biol.* 2017, 44. (d) Valeur, E.; Guéret, S. M.; Adihou, H.; Gopalakrishnan, R.; Lemurell, M.; Waldmann, H.; Grossmann, T. N.; Plowright, A. T.; *Angew. Chem. Int. Ed. Engl.* 2017 published online 7/24.

[4] (a) Walensky, L. D.; Kung, A. L.; Escher, I.; Malia, T. J.; Barbuto, S.; Wright, R. D., Wagner, G.; Verdine, G. L.; Korsmeyer, S. *J. Science* 2004, 305, 1466. (b) Grossmann, T. N.; Yeh, J. T. H.; Bowman, B. R.; Chu, Q.; Moellering, R. E.; Verdine, G. L. *Proc. Natl. Acad. Sci.*

U.S.A. 2012, 109, 17942. (c) Spokoyny, A. M.; Zou, Y.; Ling, J. J.; Yu, H.; Lin, Y. S.; Pentelute, B. L. *J. Am. Chem. Soc.* 2013, 135, 16. (d) Lautrette, G., Touti, F.; Lee, H. G.; Dai, P.; Pentelute, B. L. *J. Am. Chem. Soc.* 2016, 138, 27.

[5] (a) Rognan, D.; Scapozza, L.; Folkers, G.; Daser, A. *Proc. Natl. Acad. Sci. U.S.A.* 1995, 92, 3. (b) Zhan, C.; Zhao, L.; Wei, X.; Wu, X.; Chen, X.; Yuan, W.; Lu, W. Y.; Pazgier, M.; Lu, W.; *J. Med. Chem.* 2012, 12, 55. (c) Zhou, H.; Liu, L.; Huang, J.; Bernard, D., Karatas, H.; Navarro, A.; Lei, M.; Wang, S.; *J. Med. Chem.* 2013, 14, 56. (d) Chen, H.; Annis, D. A.; Chang, Y; Aivado, M; Olson, K; Viau, C. J., PCT/US2015/052031

[6] (a) Renfrew, P. D.; Choi, E. J.; Bonneau, R.; Kuhlman, B.; *PLoS One* 2012, 7, 3. (b) Drew, K.; Renfrew, P. D.; Craven, T. W.; Butterfoss, G. L.; Chou, F. C.; Lyskov, S.; Bullock, B. N.; Watkins, A.; Labonte, J. W.; Pacella, M.; Kilambi, K. P.; Leaver-Fay, A.; Kuhlman, B.; Gray, J. J.; Bradley, P.; Kirshenbaum, K.; Arora, P. S.; Das, R.; Bonneau, R.; *PLoS One* 2013, 15, 8. (c) Rooklin, D., Modell, A. E.; Li, H.; Berdan, V.; Arora, P. S.; Zhang, Y. *J. Am. Chem. Soc.* 2017, Published online 8/4.

[7] (a) Ferrer, M; Kapoor, T. M.; Strassmaier, T.; Weissenhorn, W.; Skehel, J. J.; Oprian, D.; Schreiber, S. L.; Wiley, D. C.; Harrison, S. C.; *Nat. Struct. Biol.* 1999, 6, 10. (b) Upadhyaya, P.; Qian, Z.; Selner, N. G.; Clippinger, S. R.; Wu, Z.; Briesewitz, R.; Pei D. *Angew. Chem. Int. Ed. Engl.* 2015, 22, 54. (c) Rezaei, Araghi R.; Ryan, J. A.; Letai, A.; Keating, A. E. *ACS Chem Biol.* 2016, 20, 11.

[8] Passioura, T.; Suga, H.; *Chem. Commun.* 2017, 7, 53.

[9] (a) Chen, X.; Tan, P. H.; Zhang, Y.; Pei, D. *J. Comb. Chem.* 2009 11, 4. (b) Gao, Y.; Amar, S.; Pahwa, S.; Fields, G.; Kodadek, T. *ACS Comb. Sci.* 2015, 17, 1. (c) Mendes, K.; Ndungu, J. M.; Clark, L. F.; Kodadek, T.; *ACS Comb. Sci.* 2015, 17, 9. (d) Brinton, L. T.; Bauknight, D. K.; Dasa, S. S.; Kelly, K. A.; *PLoS One* 2016, 17, 11.

[10] (a) Muckenschnabel, I.; Falchetto, R.; Mayr, L. M.; Filipuzzi, I; *Anal. Biochem.* 2004, 15, 324. (b) O'Connell, T. N.; Ramsay, J.; Rieth, S. F.; Shapiro, M. J.; Stroh, J. G. *Anal. Chem.* 2014, 5, 86.

[11] (a) Zuckermann, R. N.; Kerr, J. M., Siani, M. A.; Banville, S. C.; Santi, D. V.; *Proc. Natl. Acad. Sci. USA.* 1992, 15, 89. (b) Huyer, G.; Kelly, J.; Moffat, J.; Zamboni, R.; Jia, Z.; Gresser, M. J.; Ramachandran, C. *Anal. Biochem.* 1998, 10, 258.

[12] (a) Kussie, P. H.; Gorina, S.; Marechal, V.; Elenbaas, B.; Moreau, J.; Levine, A. J.; Pavletich, N. P. *Science.* 1996, 274, 5289. (b) Vassilev, L. T.; Vu, B. T.; Graves, B.; Carvajal, D.; Podlaski, F.; Filipovic, Z.; Kong, N.; Kammlott, U.; Lukacs, C.; Klein, C.; Fotouhi, N.; Liu, E. A. *Science.* 2004, 303, 5659. (c) Teveroni, E.; Lucá, R.; Pellegrino, M.; Ciolli, G.; Pontecorvi, A.; Moretti, F. *Expert Opin Ther Pat.* 2016, 12. (d) Burgess, A.; Chia, K. M.; Haupt, S.; Thomas, D.; Haupt, Y.; Lim, E. *Front. Oncol.* 2016, 6, 7.

[13] (a) Lin, J.; Chen, J.; Elenbaas, B.; Levine, A. *J. Genes Dev.* 1994, 8, 10. (b) Picksley, S. M.; Vojtesek, B.; Sparks, A.; Lane, D. P. *Oncogene* 1994, 9, 9.

[14] Böttger, A.; Böttger, V.; Garcia-Echeverria, C.; Chéne, P.; Hochkeppel, H. K.; Sampson, W.; Ang, K.; Howard, S. F.; Picksley, S. M.; Lane, D. P. *J. Mol Biol.* 1997, 269, 5.

[15] (a) Li, C.; Pazgier, M.; Li, C.; Yuan, W.; Liu, M.; Wei, G.; Lu, W Y.; Lu, W. *J. Mol. Biol.* 2010, 398, 2. (b) Zondlo, S. C.; Lee, A. E.; Zondlo, N. *J. Biochemistry* 2006, 45, 39.

[16] (a) Furman, J. L.; Chiu, M.; Hunter, M. J. A.A.P.S J. 2015, 17, 1.

[17] (a) Ganser-Pornillos, B. K.; Cheng, A.; Yeager, M. *Cell* 2007, 131, 1. (b) Bartonova, V.; Igonet, S.; Sticht, J.; Glass, B.; Habermann, A.; Vaney, M. C.; Sehr, P.; Lewis, J.; Rey, F. A.; Kraüsslich, H. G. *J. Biol. Chem.* 2008, 283, 46.

[18] Sticht, J.; Humbert, M.; Findlow, S.; Bodem, J.; Müller, B.; Dietrich, U.; Werner, J.; Kräusslich, H. G. *Nat. Struct. Mol. Biol.* 2005, 12, 8.

[19] Adamson, C. S.; Freed, E. O. *Mol. Interv.* 2009, 2.

[20] Zhang, H.; Zhao, Q.; Bhattacharya, S.; Waheed, A. A.; Tong, X.; Hong, A.; Heck, S.; Curreli, F.; Goger, M.; Cowburn, D.; Freed, E. O.; Debnath, A. K. *J. Mol. Biol.* 2008, 378, 3.

[21] (a) Chang, Y. S.; Graves, B.; Guerlavais, V.; Tovar, C.; Packman, K.; To, K. H.; Olson, K. A.; Kesavan, K.; Gangurde, P.; Mukherjee, A.; Baker, T.; Darlak, K.; Elkin, C.; Filipovic, Z.; Qureshi, F. Z.; Cai, H.; Berry, P.; Feyfant, E.; Shi, X. E.; Horstick, J.; Annis, D. A.; Manning, A. M.; Fotouhi, N.; Nash, H., Vassilev, L. T.; Sawyer, T. K. *Proc. Natl. Acad. Sci. U.S.A.* 2013, 110, E3445. (b) Wachter, F.; Morgan, A. M.; Godes, M., Mourtada, R.; Bird, G. H.; Walensky, L. D. *Oncogene.* 2017, 36, 15.

[22] (a) Ji, Y.; Majumder, S.; Millard, M.; Borra, R.; Bi, T.; Elnagar, A. Y.; Neamati, N.; Shekhtman, A.; Camarero, J. A. *J. Am. Chem. Soc.* 2013 135, 31. (b) De Veer, S. J.; Weidmann, J.; Craik, D. *J. Acc Chem Res.* 2017, 50, 7.

[23] Heitz, A.; Le-Nguyen, D.; Chiche, L. *Biochemistry.* 1999, 38, 32.

[24] Rodenko, B.; Toebes, M.; Celie, P. H.; Perrakis, A.; Schumacher, T. N.; Ovaa, H. *J. Am. Chem. Soc.* 2009 131, 34.

Example 2

This example describes materials and methods associated with Example 1, as well as additional materials, methods, and results associated with Example 1.

Materials

H-Rink Amide-ChemMatrix resin was obtained from PCAS BioMatrix Inc. (St-Jean-sur-Richelieu, Quebec, Canada). 1-[Bis(dimethylamino)methylene]-1H-1,2,3-triazolo[4,5-b]pyridinium-3-oxid-hexafluorophosphate (HATU), Fmoc-L-Arg(Pbf)-OH, Fmoc-L-His(Trt)-OH, Fmoc-L-Lys(Boc)-OH, Fmoc-L-Asp(tBu)-OH, Fmoc-L-Glu(tBu)-OH, Fmoc-L-Ser(tBu)-OH, Fmoc-L-Thr(tBu)-OH, Fmoc-L-Asn(Trt)-OH, Fmoc-L-Gln(Trt)-OH, Fmoc-L-Cys(Trt)-OH, Fmoc-L-Gly-OH, Fmoc-L-Ala-OH, Fmoc-L-Val-OH, Fmoc-L-Leu-OH, Fmoc-L-Met-OH, Fmoc-L-Phe-OH, Fmoc-L-Tyr(tBu)-OH, Fmoc-L-Trp(Boc)-OH, Fmoc-3-Ala(9-anthryl)-OH, Fmoc-L-Ala(2-naphthyl)-OH, Fmoc-D-Ala(2-naphthyl)-OH Fmoc-L-Ala(pyrenyl)-OH, Fmoc-Ala(p-cyclobutyl)-OH, Fmoc-s-cyclobutyl-D-Ala-OH, Fmoc-L-Cha-OH, Fmoc-D-Cha-OH Fmoc-L-Phe(4-F)-OH, Fmoc-L-HomoPhe-OH, Fmoc-L-Phe(3,4-Dimethoxy)-OH, Fmoc-L-Phg-OH, L-Phe(4-CN)-OH, L-Phe(4-NO2)-OH, Fmoc-L-Phe(4-NHBoc)-OH, Fmoc-L-Phe(4-CF3)-OH, Fmoc-D-Phe(4-CF3)-OH Fmoc-L-Ala(4,4'-biphenyl)-OH, Fmoc-3,4-difluoro-L-Phe-OH, Fmoc-3,4-difluoro-D-Phe-OH Fmoc-L-Phe(3,4,5-trifluoro)-OH, Fmoc-L-Phe(F)5-OH, Fmoc-D-Phe(F)5-OH, Fmoc-D-HomoLeu-OH, Fmoc-R-Ala-OH, Fmoc-L-Dap(Boc)-OH and FITC isomer I were purchased from Chem-Impex International (Wood Dale, Ill.). Fmoc-Anon(2)-OH, Fmoc-D-Anon(2)-OH and Fmoc-D-Adec(2)-OH were purchased from Watanabe Chemical Industries, Ltd. (Hiroshima, Japan). Fmoc-(R)-2-(7-octenyl)Ala-OH, Fmoc-(S)-2-(4-pentenyl)Ala-OH and Hoveyda- Grubbs Catalyst™ 2nd Generation were obtained from Sigma-Aldrich. Biotin-PEG$_4$-NHS was purchased from ChemPep Inc. (Wellington, Fla.). Peptide synthesis-grade N,N-dimethylformamide (DMF), dichloromethane (DCM), diethyl ether, HPLC-grade acetonitrile, were obtained from VWR International (Philadelphia, Pa.). All reactions were set up on the bench top open to air. Water was deionized and used as is. DMSO-d6 was purchased in sealed ampules from Cambridge Isotopes. Trypsin from bovine pancreas and monoclonal ANTI-FLAG® M2 antibody were purchased from Sigma-Aldrich. Human $^{1-137}$MDMX was purchased from Abcam (ab167947). High performance size exclusion chromatography columns BIO-SEC-3, 7.8×150 mm, 3 μm, 100 Å and BIO-SEC-3, 7.8×50 mm, 3 μm, 100 Å and analytical RP-HPLC columns Zorbax SB C3, 2.1×150 mm, 5 μm were purchased from Agilent technologies. Purification of perfluorosulfone electrophile was performed by silica gel column chromatography purchased from Acros Organics. All other materials and reagents were purchased from commercial sources and used as received. $^1$H and $^3$C NMR spectra were recorded on a Brucker 400 MHz spectrometer and calibration was performed using residual DMSO-d5 (2.54 ppm) as an internal reference. The following abbreviations were used for multiplicities: s=singlet, d=doublet, t=triplet, bs=broad singlet, m=multiplet.

Methods for LC-MS and LC-MS/MS Analysis
LC-MS Chromatograms and Associated Mass Spectra for Affinity Selections were Acquired Using Agilent 6550 ESI-Q-TOF Mass Spectrometer Mobile phases are: 0.1% formic acid in water (solvent A) and 0.1% formic acid in acetonitrile (solvent B).

Method A: LC conditions: Zorbax SB C3 column: 2.1×150 mm, 5 μm, column temperature: 20° C., gradient: 0-2 minutes 1% B, 2-12 minutes 1-65% B, 12-12.1 minutes 65-90% B, 12.1-13.1 90% B. flow rate: 0.5 mL/min.

Method B: LC conditions: Zorbax SB C3 column: 2.1×150 mm, 5 μm, column temperature: 20° C., gradient: 0-1 minutes 1% B, 1-35 minutes 1-65% B, 35-35.1 minutes 65-90% B, 35.1-37 90% B. flow rate: 0.5 mL/min.

LC-MS Chromatograms and Associated Mass Spectra for Purified Peptides were Acquired Using Agilent 6520 ESI-Q-TOF Mass Spectrometer Mobile phases are: 0.1% formic acid in water (solvent A) and 0.1% formic acid in acetonitrile (solvent B).

Method C: LC conditions: Zorbax SB C3 column: 2.1×150 mm, 5 μm, column temperature: 40° C., gradient: 0-2 minutes 1% B, 2-8 minutes 1-30% B, 8-14 minutes 30-60% B, flow rate: 0.8 mL/min.

Method D: LC conditions: Zorbax SB C3 column: 2.1×150 mm, 5 μm, column temperature: 40° C., 0-2 minutes 1% B, 2-8 minutes 1-30% B, 8-13 minutes 30-95% B, flow rate: 0.8 mL/min.

MS/MS Analysis was Performed Using the Above LC Methods with the Following Parameters MS and MS/MS acquisition range: 100-1700 m/z
MS acquisition rate: 2 spectra/s, time: 500 ms/spectrum, transients/spectrum: 2547
MS/MS acquisition rate: 8 spectra/s, time: 125 ms/spectrum, transients/spectrum: 620
Maximum number of precursors per cycle: 12
Absolute MS/MS threshold (precursor ion selection for sequencing): 10 000 counts unless stated otherwise. Corresponded typically to EIC peak areas >50 000 for triply charged peptides Active exclusion: after 10 spectra and release after 0.5 minutes
Mass exclusion range: 100-400 m/z and 600-1700 m/z
Precursor selection: +3
CID collision energies:

Using PEAKS Studio Software from Bioinformatics Solutions Inc. (Waterloo, Canada), MS/MS Spectra were Imported and Refined with the Following Parameters Merge scan: retention time window of 0.2 min and precursor m/z tolerance error 0.01 Da
Correct precursor: mass only
Filter scans: retention times incompatible with library members are discarded
De novo sequencing error tolerance: 15.0 ppm and fragment ion: 0.01 Da
Fixed post-translational modification (PTM) commonly used: Amidation (C-terminus, any residue, −0.98 Da), EETI-II $^1$Gly-$^2$Ser (N-terminus, any residue, 217.0521), $^1$Lys-$^2$Ala (N-terminus, any residue, 199.1302)
Variable post-translational modification (PTM) commonly used: F$_5$f (Phe, 89.9528 Da), F$_3$f (Phe, 53.9717 Da), F$_2$f (Phe, 35.9811 Da), Ff (Phe, 17.9887 Da), CF$_3$f (Phe, 67.9873 Da), NH$_2$f (Phe, 15.0108), NO$_2$f (Phe, 44.985 Da), CNf (Phe, 24.9952 Da), Phg (Phe, −14.0156 Da), Dmf (Phe, 60.0211 Da), Homof (Phe, 14.0156 Da), Phf (Phe, 76.0313 Da), Cha (Leu, 40.0313 Da), Hexa (Leu, 42.047 Da), Hepa (Leu, 56.047 Da), Homol (Leu, 14.0157 Da) Cba (Leu, 12.0 Da), Anta (Phe, 100.0313 Da), Pyra (Phe, 124.0313 Da), Napha (Phe, 50.0156 Da), Methionine sulfoxide (Met, 15.9949), cleaved diol (C-terminus, any residue, 70.0531 Da)

General Methods for Affinity Selection Using HPSEC
High Pressure Size Exclusion Chromatograms were Acquired Using Agilent 1260 HPLC-UV Instrument SEC conditions: unless stated otherwise, high performance size exclusion column BIO-SEC-3, 7.8×150 mm, 3 μm particle size and 100 Å pore size was used. 100 μL of binding mixture containing peptides or peptide libraries and protein target was isocratically eluted in buffered mobile phase (25 mM Tris, 50 mM NaCl, pH 7.5, with or without L-arginine supplementation) at 1 mL/min flow rate for 15 minutes (typical backpressure ~80-90 bars for a brand new column). Generally, mobile phase is also used as the binding buffer for affinity selection experiments, and systematically before each experiment a blank injection is performed consisting in a protein only injection. During affinity selection experiments the breakthrough fraction (protein fraction) was monitored by UV and collected. The latter contained the protein-binder complexes which were dissociated using 0.2% formic acid before characterization using LC-MS or LC-MS/MS analysis.

Maintenance and cleaning: after each affinity selection experiment SEC columns were carefully cleaned with one of the following buffers. Buffer 1: 0.5 M Na$_2$SO$_4$, pH 3.0. Buffer 2: 50 mM phosphate, pH 7.0, 20% acetonitrile. Buffer 3: 6M urea, 25 mM Tris, pH 7.5, mixtures with higher organics content (methanol, isopropanol or acetonitrile) were also used for cleaning purposes.

General Methods for Peptide and Peptide Library Preparation
Peptide Numbering and Nomenclature All synthesized peptides have their C-terminus amidated.
Unless stated otherwise, numbered molecules correspond to peptide-based (linear, macrocyclic or folded) peptides without any molecular labels (Biotin, acetyl or FITC). For example 60 corresponds to the sequence of macrocyclic pDI-sulfone without any further modification.

Xa, corresponds to the modification of sequence number X to allow for the introduction of a biotin label. For example 6a corresponds to the N-terminal modification of 6 with a Biotin-(Peg)$_4$ label.

Xb, corresponds to N-terminal acetylation of sequence number X. For example 6b corresponds to the N-terminal acetylation of 6.

Xc, corresponds to the modification of sequence number X to allow for the introduction of a FITC label. For example 10c corresponds to the N-terminal modification of 10 with a FITC-βAla label.

Manual Solid-Phase Synthesis of Non-Canonical Amino Acid Containing Peptide Sequences Peptide sequences were manually synthesized typically at 0.05 mmol scale on H-Rink Amide-ChemMatrix resin using manual Fmoc-SPPS (Solid phase peptide synthesis). Torviq syringes (10 mL) were utilized as the reactor vessel and the resin was swollen in DMF for a few minutes before starting synthesis. The procedure for canonical amino acid coupling cycle included 10 minutes coupling with 1 mmol (20 equiv.) of Fmoc-protected amino acid, 0.95 mmol (19 equiv.) HATU, and 500 µL of diisopropylethyl amine (DIEA, 100 equiv.) in 2.5 mL of DMF at room temperature. For non-canonical amino acids, 30 minutes of coupling were required with 0.25 mmol (5 equiv.) Fmoc-protected amino acid, 0.237 mmol (4.75 equiv.) HATU and 125 µL of diisopropylethyl amine (DIEA, 25 equiv.) in 625 µL of DMF at room temperature. The resin was then washed (5×) with DMF, deprotected (2×) for 3 minutes with 20% (v/v) piperidine in DMF and finally washed again (5×) with DMF to conclude the cycle. After peptide synthesis completion, the resin was washed with DCM (5×) and dried under reduced pressure.

Automated Fast-Flow Peptide Synthesis[1]

L and D-configured peptide sequences containing usual amino acid side chains were synthesized at 90° C. on H-Rink Amide-ChemMatrix resin with HATU activation using a fully automatic flow-based peptide synthesizer[1]. Amide bond formation was effected in 8 seconds, and Fmoc groups were removed in 8 seconds with 20% (v/v) piperidine in DMF.

Overall cycle times were about 40 seconds. After completion of fast-flow synthesis, the resins were washed with DCM (5×) and dried under reduced pressure.

Solid-Phase Synthesis of Combinatorial Peptide Libraries

Libraries 1 to 6 were synthesized on Tentagel resin (30 microns beads, 0.22 mmol/g, Rapp Polymere) at a typical scale of 0.5 g of resin (~20*10^6 beads) using split and pool technique. Fixed regions were synthesized using manual SPPS. For each randomized residue, resin was equally spitted in separate torviq syringes and for each coupling cycle, Fmoc-protected amino acids (5 equiv. with regard to resin substitution), HATU (4.75 equiv.) and DIEA (25 equiv.) were added for 30 min. The splitted resin was then washed (5×) with DMF and pooled then deprotected (2×) with 20% (v/v) piperidine in DMF and finally washed (5×) with DMF to conclude the split and pool cycle. After synthesis completion, the resins are washed with DCM (5×) and dried under reduced pressure then cleaved and purified using RP-HPLC to remove PEG impurities.

Peptide Cleavage and Deprotection

Peptides were cleaved from the resin and side-chains were simultaneously deprotected by treatment with 2.5% (v/v) 1,2-ethanedithiol (EDT), 5% (v/v) water, 5% (v/v) phenol, 5% (v/v) thioanisole in neat trifluoro acetic acid (TFA) for 8 min at 60° C., 6 ml of cleavage cocktail was used for 0.1 mmol of peptide. The resulting solution was triturated and washed with cold ether (pre-chilled in −80° C. freezer) for linear peptides. In the case of macrocyclic peptides the resulting solution was triturated and washed with cold ether/cold cyclohexane (50/50) (pre-chilled in −80° C. freezer). The trituration was repeated a total of three times. The obtained solids were dissolved in water/acetonitrile (50/50) and lyophilized.

RP-HPLC Purification of Peptides

The crude peptides were dissolved in a water/acetonitrile mixture with 0.1% TFA and purified by semi-preparative RP-HPLC using a Waters 600 HPLC system (Agilent Zorbax SB C3 column: 9.4×250 mm, 5 µm or Agilent Zorbax SB C18 column: 9.4×250 mm, 5 µm, or Agilent Zorbax SB C3 column: 21.2×250 mm, 7 µm). HPLC fractions containing pure product were confirmed by LC-MS analysis, combined, and lyophilized.

General Synthetic Procedures

Synthesis of Fmoc Protected Diol Amino Acid[2]

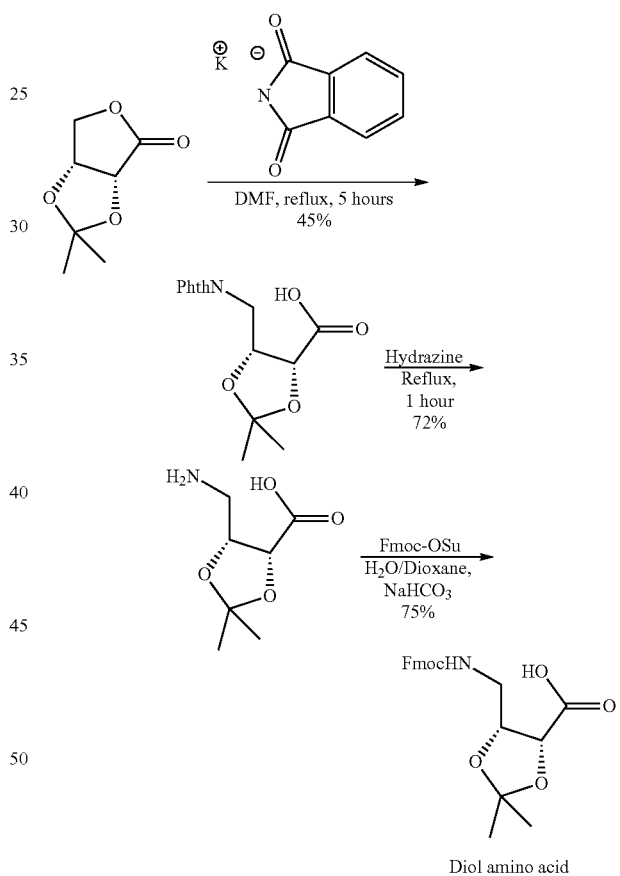

Diol amino acid was synthesized as described[2]. NMR $^1$H spectra matches those reported in literature[2]. $^1$H NMR (400 MHz, DMSO-d6): δ (ppm) 13.00 (bs, 1H), 7.89 (d, J=7.5 Hz, 2H), 7.71 (d, J=7.5 Hz, 2H), 7.46 and 6.97-6.92 (t and m, J=7.4 Hz, 1H, rotamers), 7.42 (t, J=7.5 Hz, 2H), 7.33 (t, J=7.5 Hz, 2H), 4.60 (d, J=6.8 Hz, 1H), 4.40-4.35 (m, 1H), 4.30 (d, J=6.8 Hz, 2H), 4.22 (t, J=6.8 Hz, 1H), 3.31-3.28 and 2.90-2.97 (m, rotamers, 2H), 1.47 (s, 3H), 1.30 (s, 3H). $^{13}$C NMR (100 MHz, DMSO-d6): δ (ppm) 170.75, 156.12, 143.89, 140.74, 127.61, 127.06, 120.11, 125.23, 109.76, 75.42, 74.99, 65.52, 46.69, 41.21, 27.04, 25.57.

Representative Protocol for Peptide Perfluorosulfone Macrocyclization[3]

50 mL conical tube was charged with 10 mL of peptide (1.25 mM stock solution in DMF). 5 mL of DIEA solution (20 equiv. 50 mM stock solution in DMF) was added. The resulting mixture was capped and vortexed for 10 seconds. Then 10 mL of perfluorosulfone[3] (1.25 equiv. 1.56 mM stock solution in DMF) was added. The resulting reaction mixture was capped, vortexed for 10 seconds, and left overnight at room temperature. DMF was removed under reduced pressure and the obtained residue was dissolved in a water/acetonitrile mixture with 0.1% TFA, filtered, then subjected to RP-HPLC purification.

Representative protocol for Peptide RCM Macrocyclization[4, 5]

Ring-closing metathesis was performed on the peptide while still on the solid support. An eppendorf tube was charged with peptidyl resin (30 μmol) to which was added 1 mL of a 6 mM freshly prepared solution of Hoveyda-Grubbs second-generation catalyst (20 mol % with respect to resin substitution) in 1,2-dichloroethane, under slow nitrogen bubbling and gentle agitation for 2 h at 50° C. Completeness of the ring-closing metathesis (RCM) reaction was monitored by LC-MS. Upon completion resin-bound peptide was washed (5×) with DMF and with DCM (5×) and dried under vacuum.

Representative Protocol for Peptide Labeling with Biotin

Peptide labeling with D-biotin was performed on the resin bound protected peptides by treating the protected peptide resin either with a solution of Biotin-PEG$_4$-NHS (ChemPep Inc., 2 equiv.) and DIEA (4 equiv.) dissolved in DMF for 6 hours at room temperature; or with a solution of D-biotin (10 equiv.), HATU (9.5 equiv.) and DIEA (in DMF for 20 minutes at room temperature. Upon completion, the resin was washed with DMF (5×) and DCM (5×) and dried under reduced pressure.

Representative Protocol for Peptide Labeling with FITC

Peptide labeling with FITC was performed on the resin bound protected peptides by treating the N-terminal β-alanine containing protected peptide resin with a solution of fluorescein isothiocyanate isomer I (Chem-Impex International, 6 equiv.) and DIEA (10 equiv.) dissolved in DMF for 3 hours at room temperature in the dark. Upon completion of the reaction resin was washed with DMF (5×) and DCM (5×) and finally dried under reduced pressure.

Representative Protocol for Peptide and Peptide Library Oxidative Folding[6]

Single mini-proteins and Library 5 were folded in the same conditions. Typically to 1-2 mg of crude material was added 50 μL of 20× dissolving buffer (6M Guanidine hydrochloride, 5 mM TCEP hydrochloride, 50 mM Tris, pH 7.7). The obtained suspension was thoroughly vortexed and left to stand for a few minutes before dilution in 950 μL of folding buffer (2 mM cystine, 2 mM cysteine, 50 mM Tris, pH 7.7). The thus obtained solution was thoroughly stirred overnight in the library case and for a few hours under LC-MS monitoring for single mini-proteins. The mixture was either filtered using solid phase extraction (SPE) in the library case or filtered using a 0.22 μm nylon filter followed by RP-HPLC purification for single mini-proteins.

Protocol for the Macrocyclization of Library 6

Decafluorobiphenyl macrocyclization: A 0.6 mL eppendorf tube was charged with 20 μL of Library 6 (1.25 mM stock solution in DMF) and 10 μL of DIEA solution (10 equiv. 25 mM stock in DMF) was added. The resulting mixture was capped and vortexed for 10 seconds followed by addition of 25 μL of decafluorobiphenyl electrophile (1.25 mM stock solution in DMF) and 5 μL of DMF. The reaction mixture was vortexed and left to stand for 5 hours at room temperature before LC-MS analysis.

Figure 18:
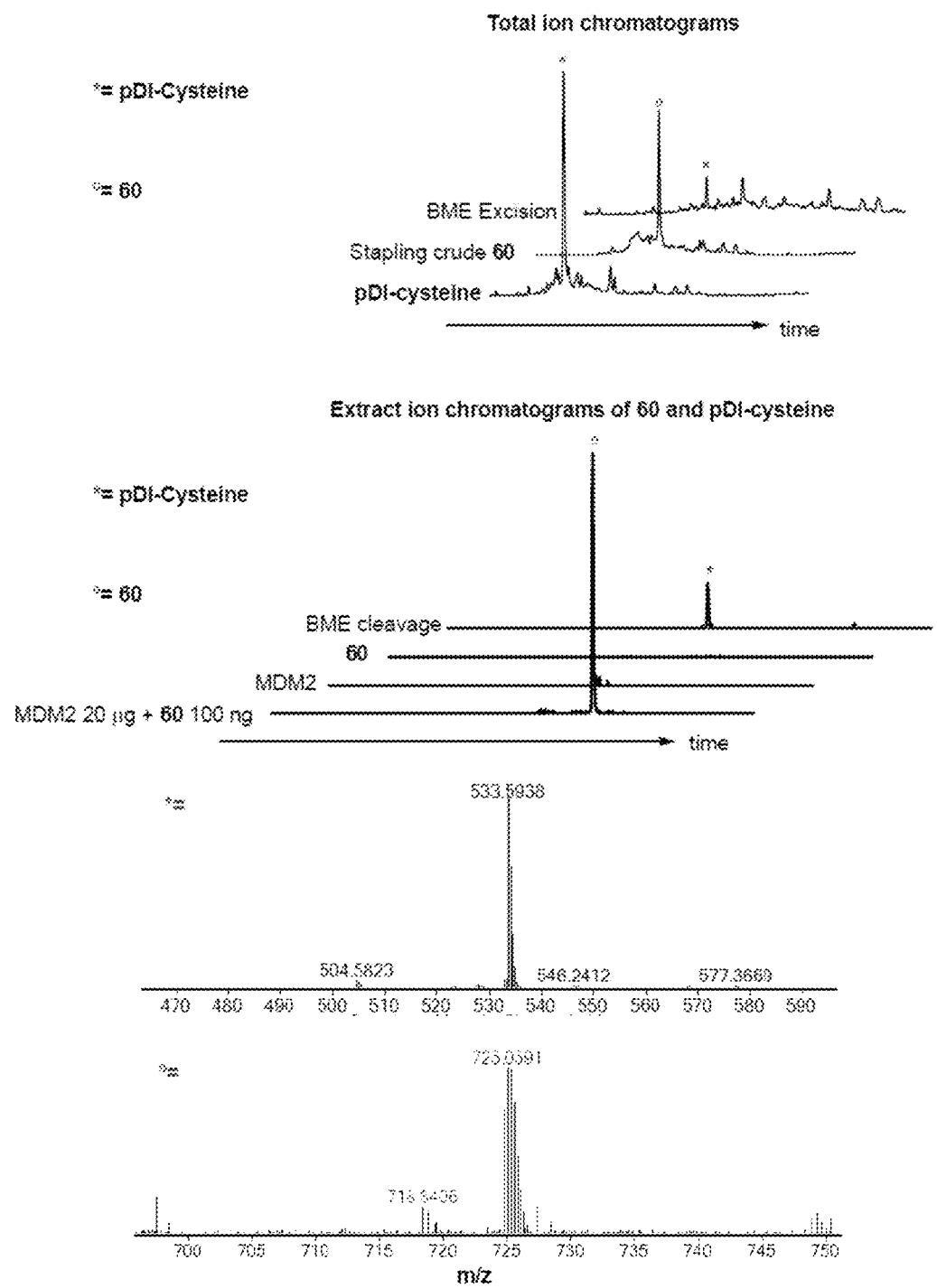
FIG. 18: Affinity selection followed by efficient in situ macrocycle excision of 60 to yield linear pDI-cysteine. Top, total ion chromatogram (TIC, LC-MS method A) demonstrating conversion of crude stapled 60 into pDI-cysteine and other products upon 2-mercaptoethanol (BME) excision. Briefly, to crude 60 (1 μg, 5 μM) in 100 μL of 200 mM CAPS buffer was added 2-mercaptoethanol at a final concentration of 50 mM and pH was adjusted to 10. After vortexing, the mixture was left for 2 hours at room temperature allowing for complete conversion of 60. Middle, extract ion chromatogram (EIC, LC-MS method A) for affinity selection of 60 using MDM2 followed by conversion to linear pDI-cysteine. 60 (100 ng, 500 nM) was added to MDM2 (20 μg, 8.5 μM) in 100 μL final volume of mobile phase supplemented with L-arginine pH 7.5. The solution was mixed by pipetting and left to stand for 1 hour at room temperature before size exclusion chromatography. To the collected protein fraction was added CAPS and 2-mercaptoethanol to a final concentration of 200 mM and 50 mM, respectively. After setting pH to 10 the mixture was vortexed and analyzed by LC-MS. Bottom, MS spectra confirming 60 and pDI-cysteine identities at (*) and (°). Linearization was performed two times on 60 varying the concentration of starting material (10 ng or 1 ug in 100 uL) and afforded the desired pDI-cysteine after 5 minutes or 2 hours of incubation. Linearization was also performed twice after affinity selecting 60 from a Library or using crude 60.

Perfluorosulfone macrocyclization: _A 1.5 mL eppendorf tube was charged with 110 μL of Library 6 (6.25 mM stock solution in DMSO). 10 μL of a TCEP solution (120 μM in 50 mM Tris pH 8.5) was added and the resulting mixture was capped and left at room temperature for 10 minutes. The mixture was then diluted with 400 μL of buffer (50 mM Tris pH 8.5) followed by the addition of 110 μL of perfluorosulfone solution (7.5 mM stock in acetonitrile). The reaction mixture was frequently vortexed and finally spun down after one hour at room temperature. Supernatant was analyzed and found to only contain the desired macrocyclized library. Concurrently, these same conditions were used to staple pDI-cysteine peptide and were shown to equally provide 60 efficiently (FIG. 18).

Protein Expression and Purification[7, 8]

MDM2 protein preparation[7]: SUMO-$^{25-109}$ MDM2 (MW=23 297 Da) was expressed in Rosetta (DE3) pLysS cells. Single transformed colonies were grown in 1 L LB cultures. Upon reaching OD600=0.4 these cultures were induced for 4 hours at 22° C. with 0.4 M IPTG. The cell suspensions were then pelleted at 6000 rpm at 4° C. and frozen at −80° C. Approximately 20 g of cell pellet was resuspended in 100 ml of 50 mM Tris-HCl, 150 mM NaCl, pH 7.5 buffer containing 100 mg lysozyme, 2 mg Roche DNAase 1, and 1 tablet of Roche protease inhibitor cocktail then sonicated (3×) for 20 seconds. The suspension was then centrifuged at 17000 rpm for 40 minutes to clarify the lysate. The latter was loaded into 2× 5 ml HisTrap FF crude Ni-NTA columns (GE Healthcare, UK) and washed with 100 mL of 20 mM Tris-HCl pH 8.5, 150 mM NaCl, and with 40 mM imidazole in 20 mM Tris-HCl pH 8.5, 500 mM NaCl. The crude protein was eluted from the columns using 10 mL 500 mM imidazole in 20 mM Tris-HCl pH 8.5, 500 mM NaCl. The eluted protein was buffer exchanged into 20 mM Tris-HCl pH 8.5, 50 mM NaCl using a HiPrep 26/10 Desalting column (GE Healthcare, UK). Crude protein mixture was purified the same day using 2×5 mL Hi Trap Q HP (GE Healthcare, UK) anion exchange columns with a linear NaCl gradient (50 mM to 500 mM). Pure SUMO-$^{25-109}$ MDM2 was obtained in the early eluting fraction, as evidenced by LC-MS analysis, concentrated using 3000 Da Amicon Ultra-15 Centrifugal Filter Unit (EMD Millipore) and used as is in affinity selection experiments.

C-CA protein preparation[8]: HIV-1 C-terminal capsid domain (SUMO-C-CA, MW=22916 Da) was expressed in BL21 DE3 competent cells. Single transformed colonies were grown in 1 L LB cultures and upon reaching OD600=0.6 these cultures were induced with 0.4 M IPTG and left shaking overnight at 30° C. The cell suspensions were then pelleted at 6000 rpm at 4° C. and frozen at −80° C. About 20 g of cell pellet was resuspended in 50 mL Tris buffer (50 mM Tris, 150 mM NaCl, pH 7.4) containing 100 mg lysozyme, 2 mg DNAse 1, and 1 tablet of Roche protease inhibitor cocktail then sonicated (3×) for 20 seconds. The suspension was then centrifuged at 17,000 rpm for 40 minutes to clarify the lysate. The latter was loaded into 2×5 ml HisTrap FF crude Ni-NTA columns (GE Healthcare, UK) and washed with 100 mL of 20 mM Tris-HCl pH 8.5, 150 mM NaCl, at pH 8.5 and 50 mL of 40 mM imidazole in 20 mM Tris-HCl pH 8.5, 500 mM NaCl. The crude protein was eluted from the columns using 10 mL of 500 mM imidazole in 20 mM Tris-HCl pH 8.5, 500 mM NaCl. The eluted protein was buffer exchanged into 20 mM Tris-HCl pH 8.5, 150 mM NaCl using a HiPrep 26/10 desalting column (GE Healthcare, UK). SUMO-C-CA was concentrated using 3000 Da Amicon Ultra-15 Centrifugal Filter Unit (EMD Millipore), analyzed by LC-MS and used as is in affinity selection experiments.

Bio-Layer Interferometry (BLI) Based Validation Assays[3, 7, 9]

1—Immobilized Binder Kinetic Assay[3, 7]

In vitro binding assays were performed using Fortebio Octet® RED96 Bio-Layer Interferometry system (Octet RED96, ForteBio, CA) at 30° C. and 1000 rpm. Briefly, streptavidin tips were dipped in 200 µL of biotinylated peptide solution (2.5 µM in PBS with 0.05% tween) for the loading step. The tips loaded with peptide were then sampled with SUMO-$^{25-109}$ MDM2 or SUMO-C-CA at various concentrations in PBS with 0.05% tween to obtain the association curve. Buffer only and protein only conditions (at a high sampled protein concentration) were used as references for background substraction. After association, the tips were dipped back into PBS and 0.05% tween to obtain the dissociation curve. The association and dissociation curves were fitted with Fortebio Biosystems (global fitting algorithm) to obtain the dissociation constant ($K_D$).

2—In Solution Competition Assay[7, 9]

A competition binding assay[9] was performed using the same bio-layer interferometry system to estimate the binding affinity of N-terminus acetylated peptides and mini-protein binders of SUMO-$^{25-109}$ MDM2.

Calibration Curve: Streptavidin (SA) sensors were soaked in competition buffer (PBS supplemented with 0.05% Tween-20, and L-arginine pH 7.5) for 10 minutes at 30° C. Modified[15, 29] p53 peptide with an N-terminal Gly-Ser linker (sequence: (Gly-Ser)$_6$-Ser-Gln-Glu-Thr-Phe-Ser-Asp-Leu-Trp-Lys-Leu-Leu-Pro-Glu-Asn) (SEQ ID NO: 137), was fast flow synthesized and labeled with a biotin on its N-terminus. The thus obtained biotinylated 63a (0.5 µM in competition buffer) was loaded on the SA sensor for 10 minutes at 30° C. and 1000 rpm. Then serial dilutions of SUMO-$^{25-109}$ MDM2 in competition buffer were analyzed for binding at 30° C. and 1000 rpm followed by dissociation in competition buffer. A calibration curve corresponding to binding response at equilibrium (in nm)=f(free [MDM2] in nM) was generated using GraphPad Prism 6 software using non-linear regression analysis (see FIG. 5).

Competition assay: various concentrations of acetylated peptides and mini-protein binders were incubated in wells with 100 or 50 nM SUMO-$^{25-109}$ MDM2 in competition buffer at room temperature for 30 minutes. Meanwhile, SA sensors were soaked in competition buffer for 10 minutes at 30° C. Peptide 63a (0.5 µM in competition buffer) was immobilized on the SA sensor surface for 10 minutes and the association and dissociation curves of SUMO-$^{25-109}$ MDM2 pre-incubated samples were then analyzed at 30° C. and 1000 rpm. Based on the binding (nm) values, the concentration of "free" MDM2 was interpolated for each sample using the calibration curve. Non-linear regression analysis was performed using GraphPad Prism 6 software to estimate the Kd value based on the equation: Kd=[peptide][MDM2]/[complex]. The following equation was used to generate fitted curves. $[y]=0.5*[(b-Kd-[X])+(([X]+Kd-b)^2+4b*Kd)^{(0.5)}]$ where y is "free" MDM2 in nM, X is the acetylated peptide inhibitor in nM, Kd is the dissociation constant, and b is ymax (see FIG. 5).

Figure 24:
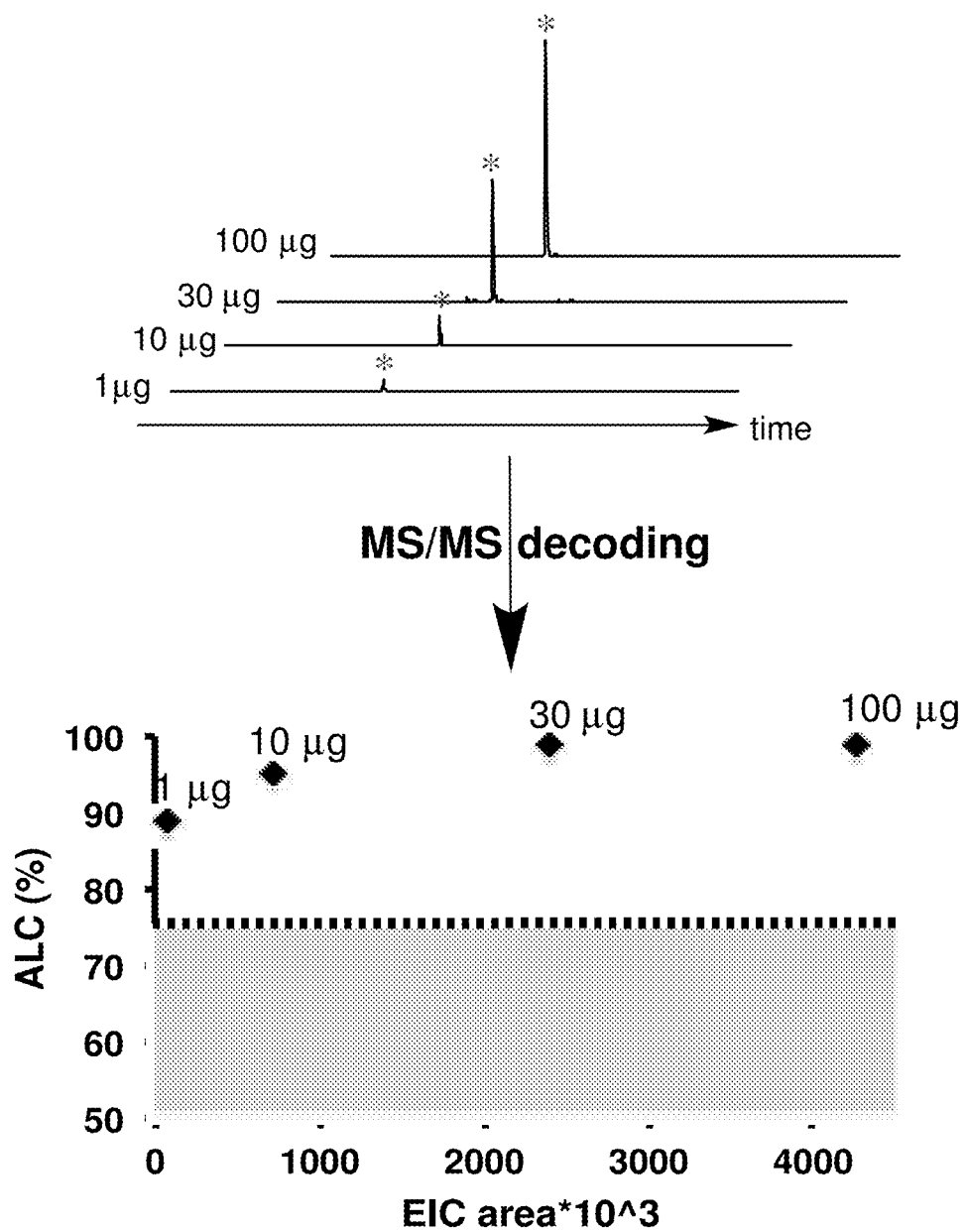
FIG. 24: Efficient MS/MS decoding of affinity selected 6 from Library 2. Top, extract ion chromatogram (EIC, LC-MS method A) for affinity selection of 6 by MDM2 at different amounts of Library 2 (10^3 members). Bottom, exemplary dependence of average local confidence (ALC) score on EIC peak area of affinity selected 6 from Library 2. In the analysis conditions, 6 was affinity selected and sequenced in the library context as efficiently as in the single binder case (down to ~1 ng in Library 2). Therefore in view of the solubility limit of 6 (~10 mg/mL e.g. 1 mg in 100 µL solution) this opens up the possibility of preparing and screening libraries of millions of peptides with this affinity selection assay format.

Solution-Phase Affinity Selection in Model Systems
   HPSEC Selection Assay for Model Binders:
     a) Model binders (see FIG. 6)
     b) Exemplary affinity selection of EETI-II knottin by trypsin in equimolar binding conditions (see FIG. 7)
     c) Affinity selection yield in library relevant conditions (see FIG. 8)
     d) Exemplary HPSEC/LC-MS traces for selection yield determination (see FIGS. 9A-14B)
     e) Illustration of selection yield dependence on protein/peptide amounts in the case of 6 and MDM2 (see FIG. 15)
   2—Sequencing of Affinity Selected Model Binders:
     a) Linear binder MS/MS sequencing (see FIG. 16)
     b) Complex binder decoding (see FIG. 17)
Macrocycle excision of 60 (see FIG. 18)
Backbone cleavage of knottin mini-protein 59 (see FIG. 19)
   2—HPSEC Affinity Selection in the Library Context:
     a) In solution LC-MS library characterization
       (i) Library 1 exemplary purification and characterization (see FIG. 21)
       (ii) Library 2 exemplary characterization (see FIG. 22)
     b) Affinity selection of 6 from Library 2 (see FIG. 23)
     c) Sequencing of affinity selected 6 from Library 2 (see FIG. 24)

Screening of Linear Canonical and Non-Canonical Peptide Libraries
   Combinatorial Mapping of MDM2 Binding Pocket Using Library 1 and Library 2
     a) Mutational tolerance of binder 6 hotspots
       (i) Library 2 screening-usual stringency (see FIG. 25)
       (ii) Library 2 screening-lower stringency (see FIG. 26)
       (iii) Library 2 screening outcome-decoded sequences (see FIG. 27)
       (iv) Library 2 binder validation (see FIGS. 28-34)
     b) Determining 6 binding mode to MDM2
       (i) Library 1 screening (see FIG. 35)
       (ii) Library 1 screening outcome and decoded sequences (see FIG. 36)
       (iii) Library 1 binder validation (see FIGS. 37-40)
   Screening of Linear Canonical and Non-Canonical Peptide Libraries:
     a) Affinity selection with usual stringency
       (i) Resynthesized binders after Library 3 screen in usual stringency conditions (see FIG. 41)
       (ii) Resynthesized binders after Library 3 screen in usual stringency conditions (see FIGS. 42-46)
     b) Affinity selection with higher stringency
       (i) Effect of stringency on EIC peak area of exemplary affinity selected sequences from Library 3 (see FIG. 47)
       (i) Library 3 resynthesized sequences-higher stringency (see FIG. 48)
       (ii) Library 3 binder validation-higher stringency (see FIGS. 49-71)
   3-Discovery of Non-Canonical CAI Based Inhibitors:
List of Library 4 resynthesized binders (see FIG. 72)
Library 4 binder validation (see FIGS. 73-80)
Expanding Non-Canonical Side Chains to the Discovery of Potent Macrocyclic Inhibitors
   1—Macrocyclic Binders Based on Library 3 Non-Canonical Sequences:
     a) Miscellaneous macrocyclic bioactive constructs and controls (see FIG. 81)
     b) Binding and cell-killing activity of macrocyclic inhibitors (see FIG. 82)
     c) Validation of macrocyclic peptides derived from non-canonical Library 4 and 5 (see FIGS. 83-98)
   2—Biological Validations
     a) Cell penetration
     b) Western blot analysis of p53 activation by non-canonical macrocyclic inhibitors c) Cell viability assays
   (i) SJSA-I viability assay for low nanomolar non-canonical macrocyclic inhibitors (see FIG. 106)
   (ii) 10b-M and 11b-S1 macrocyclic inhibitors cell-killing experiments with controls (see FIG. 107)
   (iii) 10b-M and 11b-S1 viability responses for other cell lines (see FIG. 108)

Cell Penetration
Confocal Imaging

SJSA-1 cells were cultured in 24 well plates containing cover slips until they reached 80% confluency. Appropriate amounts of peptides were dissolved in RPMI-1640 supplemented with 10% serum and 1% Pen-Strep and were added to the cells to a final concentration of 10 µM (0.1% DMSO). Cells were incubated with the samples for 4 hours at 37° C. and 5% CO2. After incubation, cells were washed (2×) with HBSS and one more time with PBS then fixed with 4% formaldehyde (Alfa Aesar, Mass.) in DPBS for 10 minutes. Cells were then washed (2×) with PBS and stained with 5 µg/ml wheat germ agglutinin tetramethyl-647 conjugate (Thermo Fisher Scientific, CA) in PBS for 20 minutes. Finally, cells were washed (2×) with PBS and the cover slips were transferred to microscope slides and imaged using scan confocal microscope Leica DMRXE (see FIGS. 99 and 100)

Flow Cytometry

SJSA-1 cells were cultured in triplicate in 24 well plates until they reached 80% confluency. Appropriate amounts of peptides dissolved in RPMI-1640 media supplemented with 10% FBS and 1% Pen-Strep were added to the cells to a final concentration of 10 µM and incubated for 4 hours at 37° C. and 5% C02. Supernatant was removed and trypsin-EDTA 0.25% (0.5 mL) was added to the cells and incubated for 10 minutes at 37° C. and 5% C02. After incubation, cells were recovered by pipetting then transferred to Eppendorf tubes and spun down at 2200 rpm for 3 minutes. The pellets were washed 3 times with PBS then re-suspended in PBS with 2% FBS (v/v) before filtration using Cell Strainer caps. Cells were finally treated with trypan blue$_{10}$ (Thermo Fisher Scientific, CA) and the fluorescence of individual cells was measured on a BD LSRII Flow Cytometer (wavelengths were 488 nm for excitation and 525 nm for detection and 10,000 events were recorded for every experimental conditions) and results analyzed using FlowJo® software (see FIGS. 101 and 102).

Western Blot Analysis of p53 Activation by Non-Canonical Macrocyclic Inhibitors

SJSA-1 and K-562 cells were seeded in 6 well plates at a cell density of 350*10^3 cells/well in RPMI-1640 media supplemented with 10% serum and 1% Pen-Strep and incubated overnight at 37° C. and 5% CO2. The next day cells were treated with peptides and controls at 10 µM for 12 hours. Then cells were harvested and their pellets washed (2×) with PBS and lysed in 100 µL of RIPA buffer supplemented with Roche protease inhibitor cocktail on ice for 30 minutes. The lysates were clarified by brief centrifugation at 4° C. and total protein concentration was determined using the Bio-Rad DC protein assay. Aliquots of the cell lysates were run on 12% Tris-Glycine polyacrylamide gels (Invitrogen). After transfer using Trans-Blot Turbo Transfer system (Biorad), the membrane was blocked at room temperature for 2 hours with LI-COR blocking buffer. The membrane was cut in three and each part was incubated respectively with anti-MDM2 (mouse, SMP14: sc-965, Santa Cruz Biotechnology), anti-p21 (mouse, F-5: sc-6246, Santa Cruz Biotechnology) and anti-GAPDH (rabbit, GAPDH (D16H11) XP®, Cell Signaling Technology) antibodies in TBST overnight at 4° C. The membranes were washed and incubated with the appropriate secondary antibodies in TBST for 1 h at room temperature, washed again, then imaged with the LI-COR Odyssey infrared imaging system (see FIGS. 103-105).

Cell Viability Assays

SJSA-1, K-562 and MCF-7 cells were plated in 96-well plates in RPMI-1640 containing 10% FBS and 1% Pen-Strep and the next day were treated with the indicated concentrations of peptide or vehicle control. Peptide stocks were diluted into RPMI-1640 containing 10% FBS and 1% Pen-Strep to achieve 2× working individual stock solutions that were thoroughly mixed then diluted into the treatment wells. Cell viability was assayed after 72 hours by addition of CellTiter 96® AQueous One Solution Cell Proliferation reagent (MTS). All assays were performed in triplicate, and data was normalized to vehicle treated control and analyzed using Prism software (GraphPad Software).

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

3-Macrocyclization of Non-Canonical C-CA Binding Sequences
See FIGS. 109 and 110-114

4—In Solution Perfluoroaryl Macrocyclization of Peptide Libraries;
   a) Library 6 design (see FIG. 115)
   b) in solution characterization (see FIG. 116)
   c) Affinity selection of 60 from Library 6 (see FIG. 117)
      (i) Affinity selection from perfluoroayl macrocyclized peptide library (see FIG. 18)
      (ii) Validation of resynthesized macrocyclic peptides (see FIGS. 119-121)

Affinity Selection of Non-Canonical Folded Mini-Proteins
1—Peptide 53 Folding, HPSEC Affinity Selection and Decoding
Folding of mini-protein 53 (see FIG. 122)
HPSEC affinity selection of 53 and its decoding (see FIG. 123)

2—Affinity Selection from Folded Library, Decoding and Binder Validation
Affinity selection in the folded library context (see FIG. 124)
Mini-protein binder decoding and folding assessment (see FIGS. 125, 126, and 127-139)

Exemplary LC-MS Spectra of Purified Peptides
See FIGS. 140-153

REFERENCES FOR EXAMPLE 2

1. Mijalis, A. J.; Thomas, D. A.; Simon, M. D.; Adamo, A.; Beaumont, R.; Jensen, K. F.; Pentelute, B. L. *Nat Chem. Biol.* 2017, 13, 5.
2. (a) Rodenko, B.; Toebes, M.; Celie, P. H.; Perrakis, A.; Schumacher, T. N.; Ovaa, H. *J. Am. Chem. Soc.* 2009, 131, 34. (b) Kamiya, T.; Saito, Y.; Seki, H.; Hashimot, M. *Tetrahedron* 1972, 28, 899.
3. Lautrette, G.; Touti F., Lee, H. G.; Dai, P.; Pentelute, B. L. *J. Am. Chem. Soc.* 2016, 138, 27.
4. Kim, Y. W.; Grossmann, T. N.; Verdine, G. L. *Nat. Protoc.* 2011 6, 6.
5. Chang, Y. S.; Graves, B.; Guerlavais, V.; Tovar, C.; Packman, K.; to, K. H.; Olson, K. A.; Kesavan, K.; Gangurde, P.; Mukherjee, A.; Baker, T.; Darlak, K.; Elkin, C.; Filipovic, Z.; Qureshi, F. Z.; Cai, H.; Berry, P.; Feyfant, E.; Shi, X. E.; Horstick, J.; Annis, D. A.; Manning, A. M.; Fotouhi, N.; Nash, H.; Vassilev, L. T.; Sawyer, T. K. Proc. Natl. *Acad. Sci. U.S.A* 2013, 110, E3445.

6. Simon, M. D.; Maki, Y.; Vinogradov, A. A.; Zhang, C.; Yu, H.; Lin, Y. S.; Kajihara, Y.; Pentelute, B. L. *J. Am. Chem. Soc.* 2016 138, 37.
7. Rabideau, A. E.; Liao, X.; Pentelute, B. L. *Chem. Sci.* 2015, 6, 1.
8. Vinogradov, A. A.; Choo, Z. N.; Totaro, K. A.; Pentelute, B. L. *Org Lett.* 2016, 18, 6.
9. Pazgier, M.; Liu, M.; Zou, G.; Yuan, W.; Li, C.; Li, J.; Monbo, J.; Zella, D.; Tarasov, S. G.; Lua, W. *Proc. Natl. Acad. Sci. U.S.A.* 2009, 106, 12.
10. Illien, F.; Rodriguez, N.; Amoura, M.; Joliot, A.; Pallerla, M.; Cribier, S.; Burlina, F.; Sagan, S. *Sci Rep.* 2016, 6, 36938.
11. Spokoyny, A. M.; Zou, Y.; Ling, J. J.; Yu, H.; Lin, Y. S.; Pentelute, B. L. *J. Am. Chem. Soc.* 2013, 135, 16.

EQUIVALENTS AND SCOPE

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A peptide, or a salt thereof, comprising a sequence of formula (I):

$$LTFX_1HX_2WAX_3LTSK \quad (I),$$ (SEQ ID NO: 1)

wherein:
$X_1$ is Gln, Pro, or Glu;
$X_2$ is Phe, Tyr, or Glu; and
$X_3$ is Glu, Gln, Ala, or Leu; or
comprising a sequence of formula (II):

$$LTFEHYWAQX_1TSK \quad (II),$$ (SEQ ID NO: 6)

wherein:
$X_1$ is Phe or Leu; or
comprising a sequence of the formula (III):

$$LTX_1EHYX_2AQX_3TSK \quad (III),$$ (SEQ ID NO: 9)

wherein:
$X_1$ is Ff, $F_2$f, $F_3$f, or Phe;
$X_2$ is Hexa, Trp, Napha, or Anta; and
$X_3$ is Cba, Cha, Ff, $F_2$f, $F_3$f, $F_5$f, Hexa, Homof, or Leu; or
comprising a sequence of formula (V):

$$LTX_1X_2EX_3X_4AX_5(Cba)X_6SAA \quad (V),$$ (SEQ ID NO: 34)

wherein:
- $X_1$ is $F_2f$ or Phe;
- $X_2$ is R8 or Dap or a portion of a cross-link or staple;
- $X_3$ is Tyr or Phe;
- $X^4$ is Hexa, Napha, or Trp;
- $X_5$ is Gln or Glu; and
- $X_6$ is S5 or Dap or a portion of a cross-link or staple; or comprising a sequence of formula (VII):

$$\text{LTFX}_1\text{HYWAQLX}_2\text{SK (VII),} \quad \text{(SEQ ID NO: 47)}$$

wherein:
- $X_1$ is Cys or Cys(ar) or a portion of a cross-link or staple; and
- $X_2$ is Cys or Cys(ar) or a portion of a cross-link or staple.

2. The peptide of claim 1, or a salt thereof, comprising a sequence of formula (I) selected from the group consisting of SEQ ID NOs: 2-5.

3. The peptide of claim 1, or a salt thereof, comprising a sequence of formula (II) selected from the group consisting of SEQ ID NOs: 7 and 8.

4. The peptide of claim 1, or a salt thereof, comprising a sequence of formula (III) selected from the group consisting of SEQ ID NOs: 10-29.

5. The peptide of claim 1, or a salt thereof, wherein the peptide comprises a sequence of formula (V) (SEQ ID NO: 34); and wherein the side chain of $X_2$ and the side chain of $X_6$ are joined together by a linker.

6. The peptide of claim 1, or a salt thereof, comprising a sequence of formula (V) selected from the group consisting of SEQ ID NOs: 35-43.

7. The peptide of claim 1, or a salt thereof, wherein the peptide comprises a sequence of formula (VII) (SEQ ID NO: 47); and wherein the side chain of the first Cys(ar) and the side chain of the second Cys(ar) are joined together by a linker.

8. The peptide of claim 1, or a salt thereof, comprising a sequence of formula (VII) selected from the group consisting of SEQ ID NOs: 48 and 49.

9. A pharmaceutical composition comprising a peptide of claim 1, or a pharmaceutically acceptable salt thereof.

10. The peptide of claim 1, or a salt thereof, comprising a sequence of formula (I):

$$\text{LTFX}_1\text{HX}_2\text{WAX}_3\text{LTSK,} \quad \text{(I) (SEQ ID NO: 1)}$$

wherein:
- $X_1$ is Gln, Pro, or Glu;
- $X_2$ is Phe, Tyr, or Glu; and
- $X_3$ is Glu, Gln, Ala, or Leu.

11. The peptide of claim 1, or a salt thereof, comprising a sequence of formula (II):

$$\text{LTFEHYWAQX}_1\text{TSK,} \quad \text{(II) (SEQ ID NO: 6)}$$

wherein:
- $X_1$ is Phe or Leu.

12. The peptide of claim 1, or a salt thereof, comprising a sequence of formula (III):

$$\text{LTX}_1\text{EHYX}_2\text{AQX}_3\text{TSK,} \quad \text{(III) (SEQ ID NO: 9)}$$

wherein:
- $X_1$ is Ff, $F_2f$, $F_3f$, or Phe;
- $X_2$ is Hexa, Trp, Napha, or Anta; and
- $X_3$ is Cba, Cha, Ff, $F_2f$, $F_3f$, Fsf, Hexa, Homof, or Leu.

13. The peptide of claim 1, or a salt thereof, comprising a sequence of formula (V):

$$\text{LTX}_1\text{X}_2\text{EX}_3\text{X}_4\text{AX}_5(\text{Cba})\text{X}_6\text{SAA,} \quad \text{(V) (SEQ ID NO: 34)}$$

wherein:
- $X_1$ is $F_2f$ or Phe;
- $X_2$ is R8 or Dap or a portion of a cross-link or staple;
- $X_3$ is Tyr or Phe;
- $X_4$ is Hexa, Napha, or Trp;
- $X_5$ is Gln or Glu; and
- $X_6$ is S5 or Dap or a portion of a cross-link or staple.

14. The peptide of claim 1, or a salt thereof, comprising a sequence of formula (VII):

$$\text{LTFX}_1\text{HYWAQLX}_2\text{SK,} \quad \text{(VII) (SEQ ID NO: 47)}$$

wherein:
- $X_1$ is Cys or Cys(ar) or a portion of a cross-link or staple and
- $X_2$ is Cys or Cys(ar) or a portion of a cross-link or staple.

15. A method of treating cancer in a subject in need thereof comprising administering to the subject a peptide of claim 1, or a pharmaceutically acceptable salt thereof, or a pharmaceutical composition thereof.

16. A method of disrupting a p53-MDM2 interaction comprising contacting a MDM2 protein with a peptide of claim 1, or a pharmaceutically acceptable salt thereof, or a pharmaceutical composition of claim 9.

17. A method of treating or preventing HIV in a subject in need thereof comprising administering to the subject a peptide of claim 1, or a pharmaceutically acceptable salt thereof, or a pharmaceutical composition thereof.

18. A method of preventing an HIV capsid from forming comprising contacting an HIV capsid protein with peptide of claim 1, or a pharmaceutically acceptable salt thereof, or a pharmaceutical composition thereof.

19. A peptide, or a salt thereof, comprising a sequence of formula (IV):

$$\text{IT}(F_2f)\text{ED}(\text{Cba})\text{LHX}_1\text{X}_2\text{GP (IV),} \quad \text{(SEQ ID NO: 30)}$$

wherein:
- $X_1$ is Tyr or Dmf; and
- $X_2$ is Tyr or $F_2f$; or comprising a sequence of formula (VI):

$$\text{IT}(F_2f)\text{X}_1\text{DX}_2\text{LX}_3\text{X}_4\text{X}_5\text{GP (VI),} \quad \text{(SEQ ID NO: 44)}$$

wherein:
- $X_1$ is Cys or S5 or a portion of a cross-link or staple;
- $X_2$ is Cba or Leu;
- Xa is Cys or S5 or a portion of a cross-link or staple;
- $X_4$ is Tyr or Dmf; and
- $X_5$ is Tyr or $F_2f$.

20. The peptide of claim 19, or a salt thereof, wherein the C-terminal end of the sequence of formula (IV) is covalently bound to the N-terminal end of a peptide having the sequence $(GS)_nK$ SEQ ID NO: 178), where n is an integer from 0 to 12.

21. The peptide of claim 19, or a salt thereof, comprising a sequence of formula (IV) selected from the group consisting of SEQ ID NOs: 31-33.

22. The peptide of claim 19, or a salt thereof, wherein the peptide comprises a sequence of formula (VI) (SEO ID NO: 44); and wherein the side chain of $X_1$ and the side chain of $X_3$ are joined together by a linker.

23. The peptide of claim 19, or a salt thereof, wherein the C-terminal end of the sequence of formula (VI) is covalently bound to the N-terminal end of a peptide having the sequence $(GS)_nK$ (SEQ ID NO: 178), where n is an integer from 0 to 12.

24. The peptide of claim 19, or a salt thereof, comprising a sequence of formula (VI) selected from the group consisting of SEQ ID NOs: 45 and 46.

25. The peptide of claim 19, or a salt thereof, comprising a sequence of formula (IV):

```
            (IV)                    (SEQ ID NO: 30)
    IT(F2f)ED(Cba)LHX1X2GP,
``` wherein:
$X_1$ is Tyr or Dmf and
$X_2$ is Tyr or $F_2f$.

26. The peptide of claim 19, or a salt thereof, comprising a sequence of formula (VI):

```
            (VI)                    (SEQ ID NO: 44)
    IT(F2f)X1DX2LX3X4X5GP,
``` wherein:
$X_1$ is Cys or S5 or a portion of a cross-link or staple;
$X_2$ is Cba or Leu;
$X_3$ is Cys or S5 or a portion of a cross-link or staple;
$X_4$ is Tyr or Dmf; and
$X_5$ is Tyr or $F_2f$.

27. A pharmaceutical composition comprising a peptide of claim 19, or a pharmaceutically acceptable salt thereof.

28. A method of treating cancer in a subject in need thereof comprising administering to the subject a peptide of claim 19, or a pharmaceutically acceptable salt thereof, or a pharmaceutical composition thereof.

29. A method of disrupting a p53-MDM2 interaction comprising contacting a MDM2 protein with a peptide of claim 19, or a pharmaceutically acceptable salt thereof, or a pharmaceutical composition thereof.

30. A method of treating or preventing HIV in a subject in need thereof comprising administering to the subject a peptide of claim 19, or a pharmaceutically acceptable salt thereof, or a pharmaceutical composition thereof.

31. A method of preventing an HIV capsid from forming comprising contacting an HIV capsid protein with a peptide of claim 19, or a pharmaceutically acceptable salt thereof, or a pharmaceutical composition thereof.

32. A peptide or mini-protein, or a salt thereof, comprising a sequence of formula (VIII):

```
                              (SEQ ID NO: 50)
    KAWYANX1EKLX2R,  (VIII),
``` wherein:
$X_1$ is Hexa, Hepa, Cha, or $CF_3f$; and
$X_2$ is Homol, Cha, Cba, Leu, Hexa, or Trp.

33. The peptide or mini-protein of claim 32, or a salt thereof, wherein all amino acids in the peptide or mini-protein are of the D-configuration.

34. The peptide or mini-protein of claim 32, or a salt thereof, comprising a sequence of formula (VIII) selected from the group consisting of SEQ ID NOs: 51-61.

35. A pharmaceutical composition comprising a peptide or mini-protein of claim 32, or a pharmaceutically acceptable salt thereof.

36. A method of treating cancer in a subject in need thereof comprising administering to the subject a peptide or mini-protein of claim 32, or a pharmaceutically acceptable salt thereof, or a pharmaceutical composition thereof.

37. A method of disrupting a p53-MDM2 interaction comprising contacting a MDM2 protein with a peptide or mini-protein of claim 32, Or a pharmaceutically acceptable salt thereof, or a pharmaceutical composition thereof.

38. A method of treating or preventing HIV in a subject in need thereof comprising administering to the subject a peptide or mini-protein of claim 32, or a pharmaceutically acceptable salt thereof, or a pharmaceutical composition thereof.

39. A method of preventing an HIV capsid from forming comprising contacting an HIV capsid protein with a peptide or mini-protein of claim 32, or a pharmaceutically acceptable salt thereof, or a pharmaceutical composition thereof.

* * * * *

UNITED STATES PATENT AND TRADEMARK OFFICE
CERTIFICATE OF CORRECTION

PATENT NO. : 11,279,734 B2
APPLICATION NO. : 16/206944
DATED : March 22, 2022
INVENTOR(S) : Bradley L. Pentelute et al.

It is certified that error appears in the above-identified patent and that said Letters Patent is hereby corrected as shown below:

In the Claims

Claim 12, Column 215, Line 10, "SEO" should read --SEQ--.

Claim 37, Column 216, Line 36, "Or" should read --or--.

Signed and Sealed this
Fourteenth Day of June, 2022

Katherine Kelly Vidal
*Director of the United States Patent and Trademark Office*